United States Patent
McKinnell et al.

(10) Patent No.: US 10,538,513 B2
(45) Date of Patent: *Jan. 21, 2020

(54) PYRAZOLO AND TRIAZOLO BICYCLIC COMPOUNDS AS JAK KINASE INHIBITORS

(71) Applicant: THERAVANCE BIOPHARMA R&D IP, LLC, South San Francisco, CA (US)

(72) Inventors: Robert Murray McKinnell, Millbrae, CA (US); Erik Fenster, San Bruno, CA (US); Tom M. Lam, San Francisco, CA (US); Jerry Nzerem, South San Francisco, CA (US); Marta Dabros, Foster City, CA (US); Venkat R. Thalladi, Foster City, CA (US); Miroslav Rapta, San Carlos, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/456,179

(22) Filed: Jun. 28, 2019

(65) Prior Publication Data

US 2019/0315724 A1 Oct. 17, 2019

Related U.S. Application Data

(63) Continuation of application No. 16/050,227, filed on Jul. 31, 2018.

(60) Provisional application No. 62/539,642, filed on Aug. 1, 2017.

(51) Int. Cl.
| | |
|---|---|
| *C07D 403/12* | (2006.01) |
| *C07D 471/04* | (2006.01) |
| *A61P 35/00* | (2006.01) |
| *C07D 487/04* | (2006.01) |
| *C07D 413/12* | (2006.01) |
| *A61P 29/00* | (2006.01) |
| *A61P 17/00* | (2006.01) |
| *C07D 401/12* | (2006.01) |
| *A61P 1/00* | (2006.01) |

(52) U.S. Cl.
CPC .............. *C07D 403/12* (2013.01); *A61P 1/00* (2018.01); *A61P 17/00* (2018.01); *A61P 29/00* (2018.01); *A61P 35/00* (2018.01); *C07D 401/12* (2013.01); *C07D 413/12* (2013.01); *C07D 471/04* (2013.01); *C07D 487/04* (2013.01); *C07B 2200/13* (2013.01)

(58) Field of Classification Search
CPC .. C07D 403/12; C07D 401/12; C07D 413/12; C07D 471/04; C07D 487/04; A61P 17/00; A61P 1/00; A61P 29/00; A61P 35/00
USPC ...................................................... 514/261.1
See application file for complete search history.

(56) References Cited

U.S. PATENT DOCUMENTS

| | | | |
|---|---|---|---|
| 8,377,946 B1* | 2/2013 | Chen .................... | C07D 487/04 514/262.1 |
| 8,648,069 B2 | 2/2014 | Akritopoulou-Zanze | |
| 9,163,007 B2 | 10/2015 | Akritopoulou-Zanze et al. | |
| 9,518,052 B2 | 12/2016 | Coe et al. | |
| 9,617,258 B2 | 4/2017 | Thorarensen et al. | |
| 2003/0139427 A1 | 7/2003 | Castelhano et al. | |
| 2007/0104780 A1 | 5/2007 | Lipari et al. | |
| 2012/0238559 A1 | 9/2012 | Baldwin et al. | |
| 2012/0245170 A1 | 9/2012 | Bedjeguelal et al. | |
| 2013/0065894 A1 | 3/2013 | Loehn et al. | |
| 2013/0085128 A1 | 4/2013 | Hachtel et al. | |
| 2013/0150340 A1 | 6/2013 | Plettenburg et al. | |

(Continued)

FOREIGN PATENT DOCUMENTS

| | | |
|---|---|---|
| CN | 105837574 A | 8/2016 |
| EP | 2567959 A1 | 3/2013 |

(Continued)

OTHER PUBLICATIONS

Abcouwer "Angiogenic factors and cytokines in diabetic retinopathy", J Clin Cell Immunol, Supplement 1: 1-12 (2013).

(Continued)

*Primary Examiner* — Daniel R Carcanague
(74) *Attorney, Agent, or Firm* — Jeffrey A. Hagenah

(57) ABSTRACT

The invention provides compounds of formula (I):

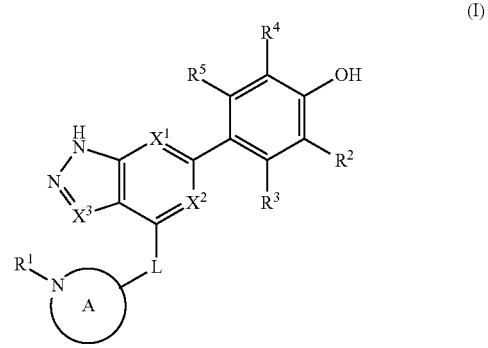

or a pharmaceutically-acceptable salt thereof, wherein the variables are defined in the specification, that are inhibitors of JAK kinases, particularly JAK3. The invention also provides crystalline forms, pharmaceutical compositions comprising such compounds, methods of using such compounds to treat gastrointestinal and other inflammatory diseases, and processes and intermediates useful for preparing such compounds.

16 Claims, 9 Drawing Sheets

(56) References Cited

U.S. PATENT DOCUMENTS

| | | |
|---|---|---|
| 2014/0349998 A1 | 11/2014 | Ahearn et al. |
| 2015/0158864 A1 | 6/2015 | Thorarensen et al. |
| 2015/0329542 A1 | 11/2015 | Coe et al. |
| 2017/0071946 A1 | 3/2017 | Coe et al. |
| 2018/0064621 A1 | 3/2018 | Salce, Jr. et al. |
| 2018/0117148 A1 | 5/2018 | Holman |
| 2019/0040043 A1 | 2/2019 | Fenster et al. |

FOREIGN PATENT DOCUMENTS

| | | |
|---|---|---|
| JP | 2009007342 A | 1/2009 |
| WO | 02/085853 A2 | 10/2002 |
| WO | 03/078403 A2 | 9/2003 |
| WO | 2004/113304 A1 | 12/2004 |
| WO | 2006/040351 A1 | 4/2006 |
| WO | 2007/117995 A2 | 10/2007 |
| WO | 2009/147188 A1 | 12/2009 |
| WO | 2009/147189 A1 | 12/2009 |
| WO | 2009/147190 A1 | 12/2009 |
| WO | 2010/012121 A1 | 2/2010 |
| WO | 2011/031554 A2 | 3/2011 |
| WO | 2011/067365 A1 | 6/2011 |
| WO | 2011/112766 A2 | 9/2011 |
| WO | 2012/061537 A1 | 5/2012 |
| WO | 2013/037390 A1 | 3/2013 |
| WO | 2013/057253 A1 | 4/2013 |
| WO | 2013/149194 A1 | 10/2013 |
| WO | 2013/167403 A1 | 11/2013 |
| WO | 2014/140065 A1 | 9/2014 |
| WO | 2015/083028 A1 | 6/2015 |
| WO | 2015/112445 A1 | 7/2015 |
| WO | 2015/173683 A1 | 11/2015 |
| WO | 2016/011394 A1 | 1/2016 |
| WO | 2016/071293 A2 | 5/2016 |
| WO | 2016/178110 A1 | 11/2016 |
| WO | 2016/179605 A1 | 11/2016 |
| WO | 2017/143014 A1 | 8/2017 |
| WO | 2018/004306 A1 | 1/2018 |
| WO | 2018/075937 A1 | 4/2018 |
| WO | 2019090158 A1 | 5/2019 |
| WO | 2019/132560 A1 | 7/2019 |
| WO | 2019/132561 A1 | 7/2019 |
| WO | 2019/132562 A1 | 7/2019 |

OTHER PUBLICATIONS

Bao et al., "The involvement of the JAK-STAT signaling pathway in chronic inflammatory skin disease atopic dermatitis", JAK-STAT, 2(3): e24137-1-e24137-8 (2013).
Coghill et al., "Effector CD4+ T cells, the cytokines they generate, and GVHD: something old and something new", Bood, 117(12): 3268-3276 (Mar. 24, 2011).
PCT International Search Report and Written Opinion for PCT/US2018/044508 dated Oct. 4, 2018.
Craiglow et al., "Tofacitinib citrate for the treatment of vitiligo: A pathogenesis-directed therapy", JAMA Dermatology, 151: 1110-1112 (2015).
De Nitto et al., "Involvement of interleukin-15 and interleukin-21, two gamma-chain-related cytokines, in celiac disease", World J Gastroenterol, 15(37): 4609-4614 (Oct. 7, 2009).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Forster et al., "Selective JAK3 inhibitors with a covalent reversible binding mode targeting a new induced fit binding pocket", Cell Chemical Biology, 23: 1335-1340 (2016).
Goedken et al., "Tricyclic covalent inhibitors selectively target JAK3 through an active site Thiol", J. Biol. Chem., 290 (8): 4573-4589 (2015).
Horai et al, "Cytokines in autoimmune uveitis", Journal of Interferon & Cytokine Research, 31(10): 733-744 (2011).

Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th11Tc1 mucosal cytokine profile", Molecular Immunology, 55: 355-364 (2013).
Liu et al., "Developing irreversible inhibitors of the protein kinase cysteinome", Chemistry & Biology, 20: 146-159 (2013).
Lynch et al., "Strategic use of conformational bias and structure based design to identify potent JAK3 inhibitors with improved selectivity against the JAK family and the kinome", Bioorganic & Medicinal Chemistry Letters, 23: 2793-2800 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Reimund et al., "Mucosal inflammatory cytokine production by intestinal biopsies in patients with ulcerative colitis and Crohn's disease", Journal of Clinical Immunology, 16(3): 144-150 (1996).
Ritzen et al., "Fragment-based discovery of 6-Arylindazole JAK inhibitors", Acs Medicinal Chemistry Letters, 7: 641-646 (2016).
Scott, "Tofacitinib: A review of its use in adult patients with rheumatoid arthritis", Drugs, 73: 857-874 (2013).
Shchuko et al., "Intraocular cytokines in retinal vein occlusion and its relation to the efficiency of anti-vascular endothelial growth factor therapy", Indian Journal of Ophthalmology, 63: 905-911 (2015).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Soth et al., "3-Amido pyrrolopyrazine JAK kinase inhibitors: Development of a JAK3 vs JAK1 selective inhibitor and evaluation in cellular and in vivo models", Journal of Medicinal Chemistry, 56: 345-356 (2013).
Stallmach et al., "Cytokine/chemokine transcript profiles reflect mucosal inflammation in Crohn's disease", Int J colorectal Dis, 19: 308-315 (2004).
Stevenson et al., "Dry eye disease", Arch Ophthalmol, 130(1): 90-100 (Jan. 2012).
Tan et al., "Development of selective covalent Janus kinase 3 inhibitors", J. Med. Chem., 58: 6589-6606 (2015).
Tanaka et al., "New insight into mechanisms of pruritus from molecular studies on familial primary localized cutaneous amyloidosis", British Journal of Dermatology, 161: 1217-1224 (2009).
Telliez et al., "Discovery of a JAK3-selective inhibitor: Functional differentiation of JAK3-selective inhibition over pan-JAK or JAK1-selective inhibition", ACS Chemical Biology, 11: 3442-3451 (2016).
Thorarensen et al., "Design of a Janus Kinase 3 (JAK3) specific inhibitor 1-((2S,5R)-5-((7H-Pyrrolo[2,3-d] pyrimidin-4-yl)amino)-2-methylpiperidin-1-yl)prop-2-en-1-one (PF-06651600) allowing for the interrogation of JAK3 signaling in humans", Journal of Medicinal Chemistry, 60: 1971-1993 (2017).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).

(56) References Cited

OTHER PUBLICATIONS

Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yano et al., "Ipilimumab augments antitumor activity of bispecific antibody-armed T cells", Journal of Translational Medicine, 12: 191 (2014).
Zhou et al., "Cytokines and Behcet's Disease", Autoimmunity Reviews, 11: 699-704 (2012).

\* cited by examiner

PYRAZOLO AND TRIAZOLO BICYCLIC COMPOUNDS AS JAK KINASE INHIBITORS

CROSS-REFERENCE TO RELATED APPLICATIONS

This application is a continuation application of U.S. Ser. No. 16/050,227, filed on Jul. 31, 2018, now allowed, which application claims the benefit of U.S. Provisional Application No. 62/539,642, filed on Aug. 1, 2017, the disclosures of which are incorporated herein by reference in their entirety.

BACKGROUND OF THE INVENTION

Field of the Invention

The invention is directed to pyrazolo and triazolo bicyclic compounds useful as JAK kinase inhibitors and more particularly as JAK3 inhibitors that are selective for JAK3 over other members of the JAK kinase family such as JAK1, JAK2 and TYK2. The invention is also directed to crystalline forms, pharmaceutical compositions comprising such compounds, methods of using such compounds to treat inflammatory diseases, and processes and intermediates useful for preparing such compounds.

State of the Art

Ulcerative colitis is a chronic inflammatory disease of the colon. The disease is characterized by inflammation and ulceration of the mucosal layer of the rectum and the large intestine. Common symptoms include diarrhea, bloody stools, and abdominal pain.

The clinical course is intermittent, marked by alternating periods of exacerbation and remission. Incidence seems to be greater in developed than in developing countries. An estimated 1.2 million people in major industrialized countries suffer from ulcerative colitis and the numbers are expected to increase along with population growth. Patients with ulcerative colitis are at an increased risk of developing colorectal cancer. (e.g. Danese et al. *N Engl J Med*, 2011, 365, 1713-1725). Although there exists a variety of therapeutic options to promote and maintain remission of ulcerative colitis (UC) in patients, none is ideal. There remains an unmet medical need for an effective therapy to promote and maintain remission of moderate to severe UC without the safety concerns resulting from chronic, systemic immunosuppression.

Although the precise pathogenesis of UC is unclear, it is apparent that proinflammatory cytokines play a pivotal role in the immunological response (Strober et al., *Gastroenterol*, 2011, 140, 1756-1767). Many of the proinflammatory cytokines most commonly elevated in UC (e.g., IL-4, IL-6, IL-13, IL-15, IL-23, IL-24, IFNγ and leptin), rely on the JAK family of tyrosine kinases (i.e., JAK1, JAK2, JAK3 and Tyk2) for signal transduction.

Inhibition of the JAK3 enzyme blocks the signaling of many key pro-inflammatory cytokines. Thus JAK3 inhibitors are likely to be useful in the treatment of ulcerative colitis and other gastrointestinal inflammatory diseases such as Crohn's disease and immune checkpoint inhibitor induced colitis. JAK3 inhibitors are also likely to be useful for the treatment of inflammatory skin diseases such as atopic dermatitis and inflammatory respiratory disorders such as allergic rhinitis, asthma, and chronic obstructive pulmonary disease (COPD). In addition, JAK3 inhibitors may also be useful in the treatment of many ocular diseases for which inflammation plays a prominent role such as uveitis, diabetic retinopathy, diabetic macular edema, dry eye disease, age-related macular degeneration, retinal vein occlusion (RVO) and atopic keratoconjunctivitis.

Selectivity for JAK3 over JAK1 is anticipated to be beneficial as there is evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 also allows sparing of erythropoietin (EPO) and thrombopoietin (TPO) signaling. Therefore, it would be desirable to provide new compounds which are selective JAK3 inhibitors over other members of the JAK kinase family such as JAK1, JAK2 and TYK2.

Finally, due to the modulating effect of the JAK/STAT pathway on the immune system, systemic exposure to JAK inhibitors may have an adverse systemic immunosuppressive effect. It would be desirable, therefore, to provide new JAK3 inhibitors which have their effect at the site of action without significant systemic effects. In particular, for the treatment of gastrointestinal inflammatory diseases, such as ulcerative colitis, it would be desirable to provide new JAK3 inhibitors which can be administered orally and achieve therapeutically relevant exposure in the gastrointestinal tract with minimal systemic exposure. For skin diseases, it would be desirable to provide new JAK3 inhibitors that could be administered topically to the skin with minimal systemic exposure.

Therefore, it would be desirable to provide new compounds which are selective JAK3 inhibitors over other members of the JAK kinase family such as JAK1, JAK2 and TYK2, and have minimal systemic exposure.

SUMMARY OF THE INVENTION

In one aspect, the invention provides novel compounds having activity as JAK kinase inhibitors and more particularly as JAK3 inhibitors.

Accordingly, the invention provides a compound of formula (I):

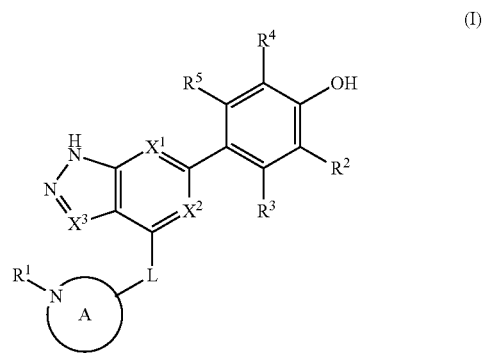

or a pharmaceutically acceptable salt thereof, wherein
$X^1$ and $X^2$ are each independently selected from N and CH;
$X^3$ is selected from the group consisting of N, CH, C—$CH_3$, C—$CF_3$, C—$CHF_2$, C—$CH_2$—O—$CH_3$, C—SMe, C—$NMe_2$, C—NH—$CH_3$, C—Cl, C—CN, and C—OMe;

is selected from the group consisting of

[chemical structures showing various linker groups including O, S, S=O, SO₂, NR^a, NR^b, NR^c, amide with O, O-CR^d R^e, NR^f-CR^g R^h, CR^i R^j, S-CR^l R^m, and O-CR^n R^o]

R^a, R^b, R^c, and R^f are each independently selected from the group consisting of H and $C_{1-3}$ alkyl;

R^d, R^e, R^g, R^h, R^i, R^j, R^l, R^m, R^n and R^o are each independently selected from the group consisting of H and $C_{1-3}$ alkyl wherein the $C_{1-3}$ alkyl group may be optionally substituted with 1 to 3 halogens;

Optionally R^d and R^e may be joined to form a cyclopropyl ring;

A is selected from the group consisting of (a) a 4 to 10 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, and O, wherein L is linked to a carbon atom in A and A is optionally substituted with 1 to 3 R^k groups;

each R^k is independently selected from the group consisting of F, CN, $C_{1-3}$ alkoxy, cyclopropyl, and $C_{1-3}$ alkyl, wherein the $C_{1-3}$ alkyl group may be optionally substituted with OH, OMe or 1 to 3 halogens;

R¹ is selected from the group consisting of

[chemical structures showing acrylate, vinyl sulfonyl, and N-methyl aminomethyl acrylate groups]

-continued

[chemical structures showing propiolate, N-methyl crotonate, pyrrolidine-substituted enone structures, and R^p R^q N-substituted enone]

wherein R^p and R^q are each independently selected from the group consisting of H, $C_{3-5}$ cycloalkyl and $C_{1-6}$ alkyl, wherein the $C_{1-6}$ alkyl group may be optionally substituted with 1 to 3 substituents independently selected from the group consisting of $C_{1-3}$ alkoxy and —S—$C_{1-3}$ alkyl, or R^p and R^q form a 4 to 6 membered monocyclic heterocyclic group containing one nitrogen atom and optionally containing one additional heteroatom selected from N, S, and O, wherein the 4 to 6 membered monocyclic heterocyclic group is optionally substituted with 1 to 3 substituents independently selected from the group consisting of $C_{1-6}$ alkyl, $C_{1-3}$ alkoxy, —S—$C_{1-3}$ alkyl and —$C_{1-3}$ alkyl-$C_{1-3}$ alkoxy;

R² is selected from the group consisting of H, Cl, OMe, Me and F;

R³ is selected from the group consisting of H and F;

R⁴ is selected from the group consisting of H and F; and

R⁵ is selected from the group consisting of H, Me and F.

The disclosure also provides some crystalline forms of certain compounds, Form 1, Form 2, Form 2b, Form 3, and Form 4.

The invention also provides a pharmaceutical composition comprising a compound of the disclosure, or a pharmaceutically acceptable salt thereof, or a crystalline form of the disclosure, and a pharmaceutically-acceptable carrier.

The invention also provides a method of treating gastro-intestinal inflammatory disease, in particular, ulcerative colitis, in a mammal, the method comprising administering to the mammal a compound of the disclosure, or a pharmaceutically acceptable salt thereof, or a crystalline form of the disclosure, or a pharmaceutical composition of the disclosure.

The invention also provides a method of treating inflammatory diseases or disorders of the skin in a mammal, the method comprising applying a compound of the disclosure, or a pharmaceutically acceptable salt thereof, or a pharmaceutical composition of the disclosure to the skin of the mammal.

The invention also provides a method of treating cutaneous T-cell lymphoma in a mammal, the method comprising applying a pharmaceutical composition comprising a compound of the disclosure, or a pharmaceutically acceptable salt thereof, to the skin of the mammal.

In another aspect, the invention also provides a process described herein, which is useful for preparing the compounds of the disclosure.

The invention also provides a compound of the disclosure or a pharmaceutically acceptable salt thereof, as described herein for use in medical therapy, as well as the use of a compound of the disclosure, or a pharmaceutically acceptable salt thereof, or a crystalline form thereof, in the manufacture of a formulation or medicament for treating a gastrointestinal inflammatory disease, or an inflammatory disease of the skin in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
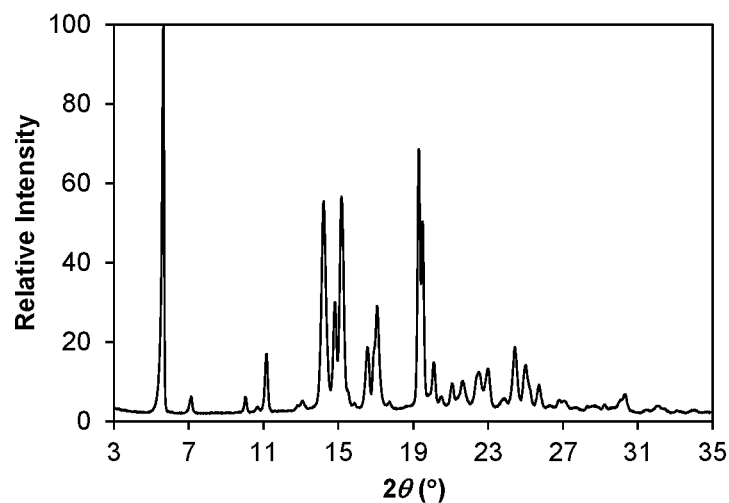
FIG. 1 shows a powder x-ray diffraction (PXRD) pattern of crystalline Form 1 of compound 3 (hereinafter Form 1).

Among other aspects, the invention provides JAK kinase inhibitors of formula (I) which are selective for JAK3 over other members of the JAK kinase family such as JAK1, JAK2 and TYK2, pharmaceutically-acceptable salts thereof, and intermediates for the preparation thereof.

In one aspect, the invention provides novel compounds having activity as JAK kinase inhibitors, particularly as JAK3 kinase inhibitors.

Accordingly, the invention provides a compound of formula (I):

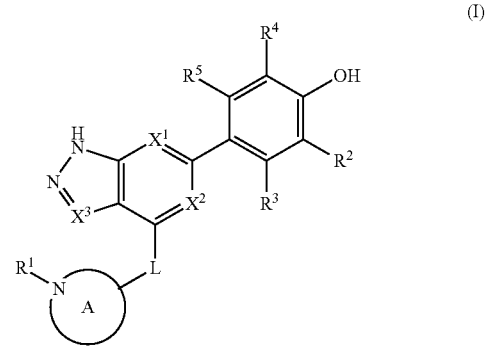

or a pharmaceutically acceptable salt thereof, wherein $X^1$ and $X^2$ are each independently selected from N and CH;

$X^3$ is selected from the group consisting of N, CH, C—CH$_3$, C—CF$_3$, C—CHF$_2$, C—CH$_2$—O—CH$_3$, C—SMe, C—NMe$_2$, C—NH—CH$_3$, C—Cl, C—CN, and C—OMe;

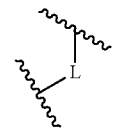

is selected from the group consisting of

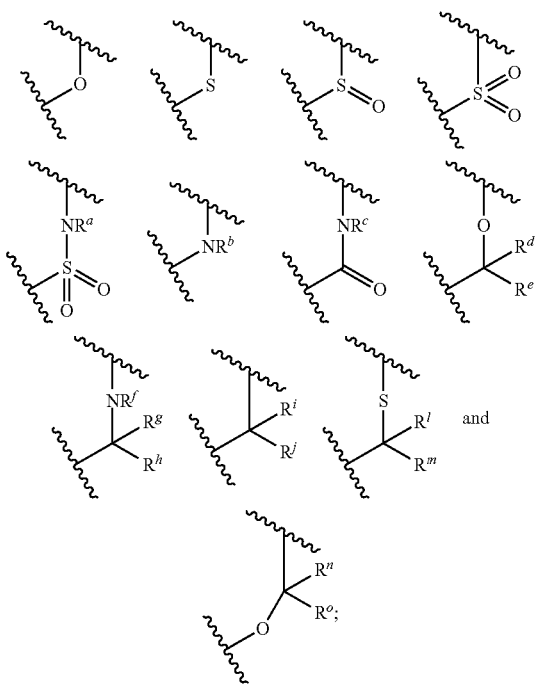

$R^a$, $R^b$, $R^c$, and W are each independently selected from the group consisting of H and $C_{1-3}$ alkyl;

$R^d$, $R^e$, $R^g$, $R^h$, $R^i$, $R^j$, $R^l$, $R^m$, $R^n$ and $R^o$ are each independently selected from the group consisting of H and $C_{1-3}$ alkyl wherein the $C_{1-3}$ alkyl group may be optionally substituted with 1 to 3 halogens; optionally $R^d$ and $R^e$ may be joined to form a cyclopropyl ring;

A is selected from the group consisting of (a) a 4 to 10 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, and O, wherein L is linked to a carbon atom in A and A is optionally substituted with 1 to 3 $R^k$ groups;

each $R^k$ is independently selected from the group consisting of F, CN, $C_{1-3}$ alkoxy, cyclopropyl, and $C_{1-3}$ alkyl, wherein the $C_{1-3}$ alkyl group may be optionally substituted with OH, OMe or 1 to 3 halogens;

$R^1$ is selected from the group consisting of

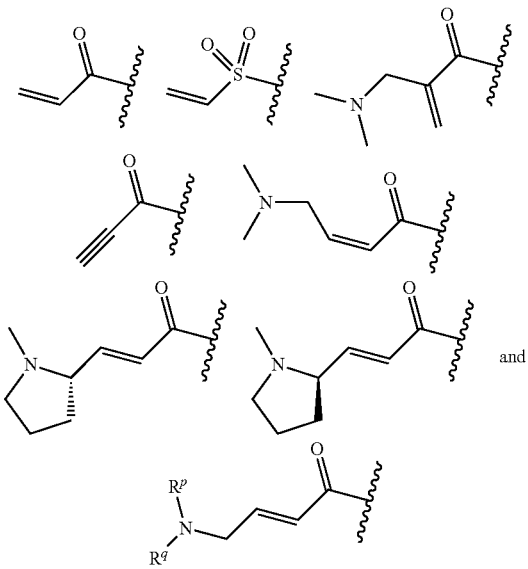

wherein $R^p$ and $R^q$ are each independently selected from the group consisting of H, $C_{3-5}$ cycloalkyl and $C_{1-6}$ alkyl, wherein the $C_{1-6}$ alkyl group may be optionally substituted with 1 to 3 substituents independently selected from the group consisting of $C_{1-3}$ alkoxy and —S—$C_{1-3}$ alkyl, or $R^p$ and $R^q$ form a 4 to 6 membered monocyclic heterocyclic group containing one nitrogen atom and optionally containing one additional heteroatom selected from N, S, and O, wherein the 4 to 6 membered monocyclic heterocyclic group is optionally substituted with 1 to 3 substituents independently selected from the group consisting of $C_{1-6}$ alkyl, $C_{1-3}$ alkoxy, —S—$C_{1-3}$ alkyl and —$C_{1-3}$ alkyl-$C_{1-3}$ alkoxy;

$R^2$ is selected from the group consisting of H, Cl, OMe, Me and F;

$R^3$ is selected from the group consisting of H and F;

$R^4$ is selected from the group consisting of H and F; and $R^5$ is selected from the group consisting of H, Me and F.

In some embodiments, $X^3$ is CH.

In some embodiments, $R^p$ and $R^q$ are each independently selected from the group consisting of H, cyclobutyl and $C_{1-4}$ alkyl, wherein the $C_{1-4}$ alkyl group may be optionally substituted with 1 or 2 substituents independently selected from the group consisting of $C_{1-2}$ alkoxy and —S—$C_{1-2}$ alkyl, or $R^p$ and $R^q$ form a 4 to 6 membered monocyclic heterocyclic group containing one nitrogen atom and optionally containing one additional heteroatom selected from S, and O, wherein the 4 to 6 membered monocyclic heterocyclic group is optionally substituted with 1 or 2 substituents independently selected from the group consisting of $C_{1-3}$ alkyl, $C_{1-2}$ alkoxy, —S—$C_{1-2}$ alkyl and —$C_{1-3}$ alkyl-$C_{1-2}$ alkoxy.

In some embodiments, $R^p$ and $R^q$ are each independently selected from the group consisting of H, cyclobutyl and $C_{1-4}$ alkyl, wherein the $C_{1-4}$ alkyl group may be optionally substituted with 1 or 2 substituents independently selected from the group consisting of OMe and —SEt, or $R^p$ and $R^q$ form a 4 to 6 membered monocyclic heterocyclic group containing one nitrogen atom and optionally containing one additional heteroatom selected from S, and O, wherein the 4 to 6 membered monocyclic heterocyclic group is optionally substituted with 1 or 2 substituents independently selected from the group consisting of Me, OMe, $CH_2OMe$, and —SMe.

In some embodiments, $R^1$ is selected from the group consisting of

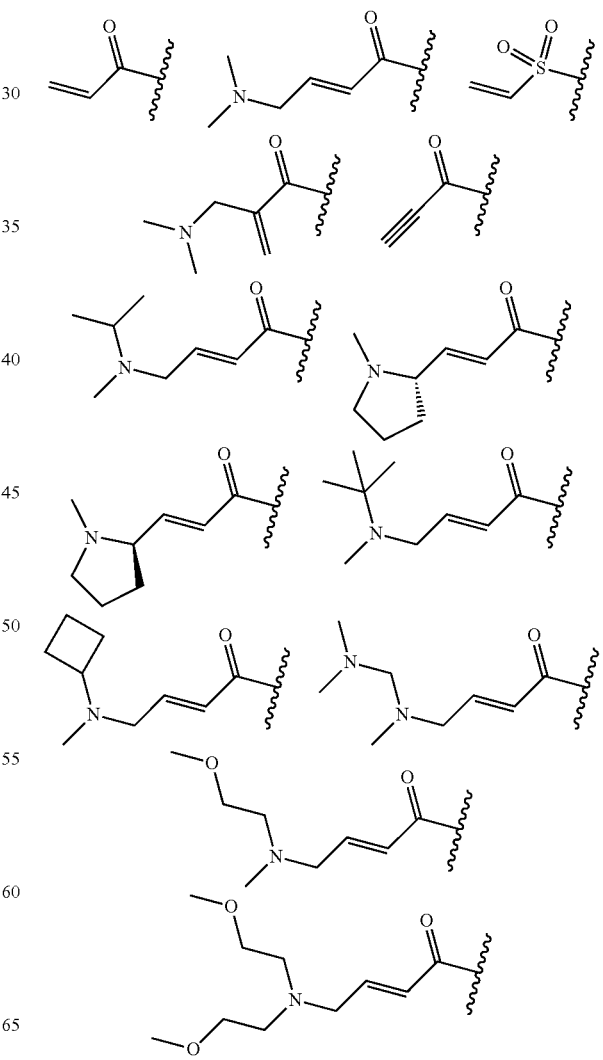

-continued

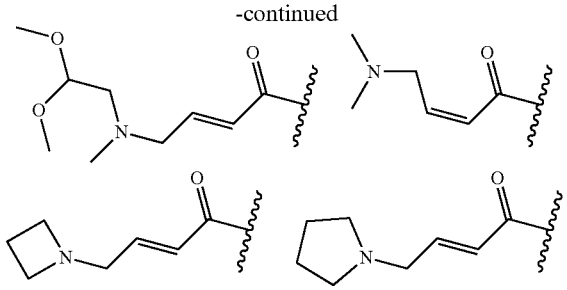

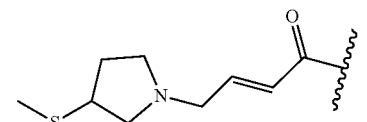

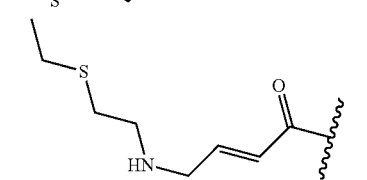

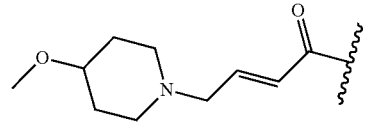

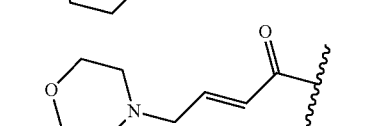

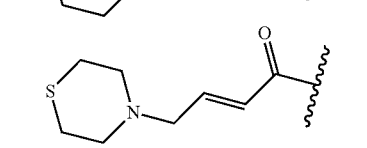

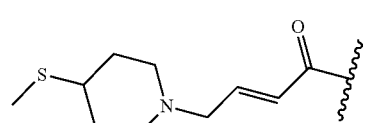

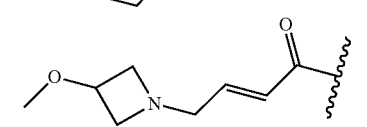

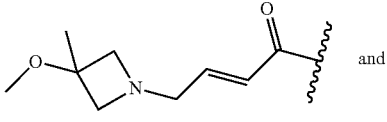

and

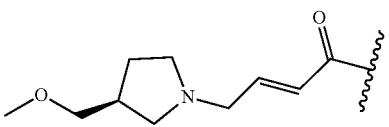

In some embodiments, $R^1$ is

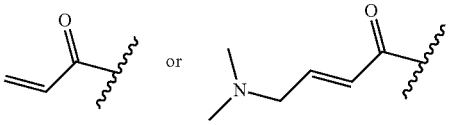

In some embodiments, $R^1$ is

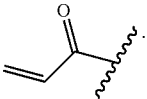

In some embodiments, $R^1$ is

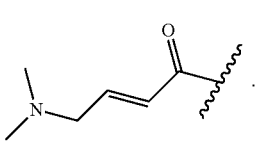 [SMILES: *C(=O)/C=C/CN(C)C]

The 6 to 10 membered multicyclic heterocyclic group may be spiro-cyclic, fused and/or bridged.

In some embodiments, the 6 to 10 membered multicyclic heterocyclic group is a spiro-cyclic heterocyclic group. In some embodiments, the 6 to 10 membered multicyclic heterocyclic group is a fused heterocyclic group. In some embodiments, the 6 to 10 membered multicyclic heterocyclic group is a bridged heterocyclic group.

In some embodiments, A is selected from the group consisting of (a) a 4 to 8 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, and O, wherein L is linked to a carbon atom in A and A is optionally substituted with 1 to 3 $R^k$ groups.

In some embodiments, A is selected from the group consisting of (a) a 4 to 6 membered monocyclic heterocyclic group containing one nitrogen atom and optionally containing one additional heteroatom selected from N, S, $S(O)_2$ and O, and (b) a 6 to 10 membered multicyclic heterocyclic group containing one nitrogen atom and optionally containing one additional heteroatom selected from N, S, and O, wherein L is linked to a carbon atom in A and A is optionally substituted with 1 to 3 $R^k$ groups.

In some embodiments, A is selected from the group consisting of:

(a) a 4 to 6 membered monocyclic heterocyclic group containing one nitrogen atom and optionally containing one additional heteroatom selected from N, S, $S(O)_2$ and O, and (b) a 7 or 8 membered multicyclic heterocyclic group containing one nitrogen atom and optionally containing one additional heteroatom selected from N, S and O, wherein L is linked to a carbon atom in A and A is optionally substituted with 1 to 3 $R^k$ groups.

In some embodiments, A is selected from the group consisting of azetidine, pyrrolidine, piperidine, morpholine, 2-azaspiro[3.3]heptane, thiomorpholine and nortropane.
In some embodiments,
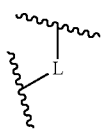
is selected from the group consisting of
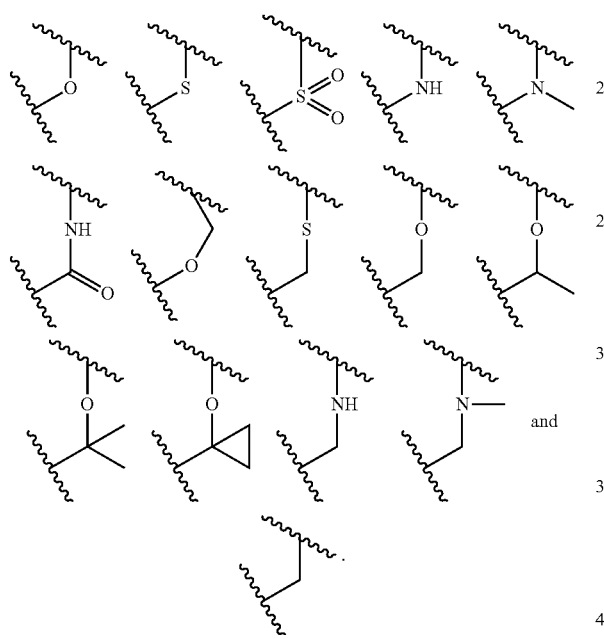
and
.
In some embodiments,
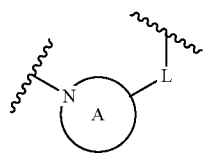
is selected from the group consisting of:
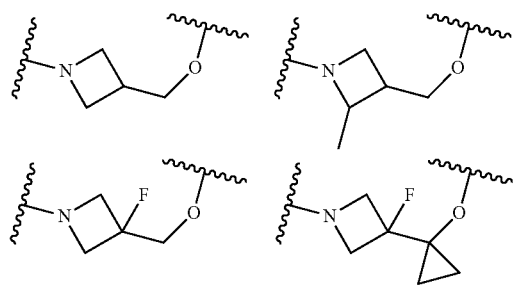
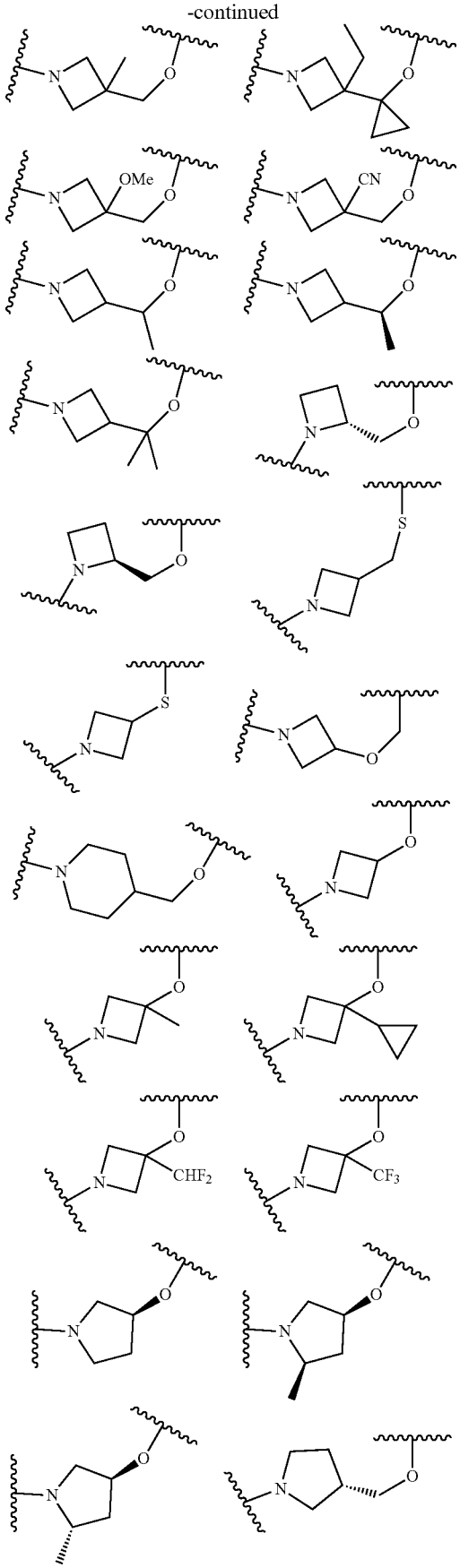

-continued
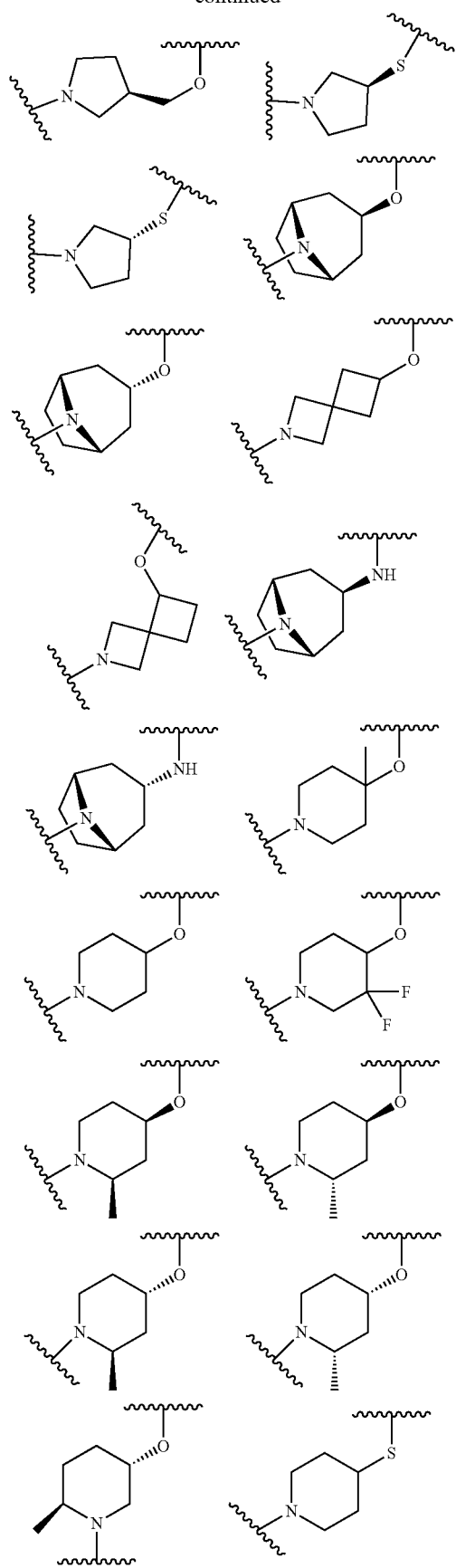
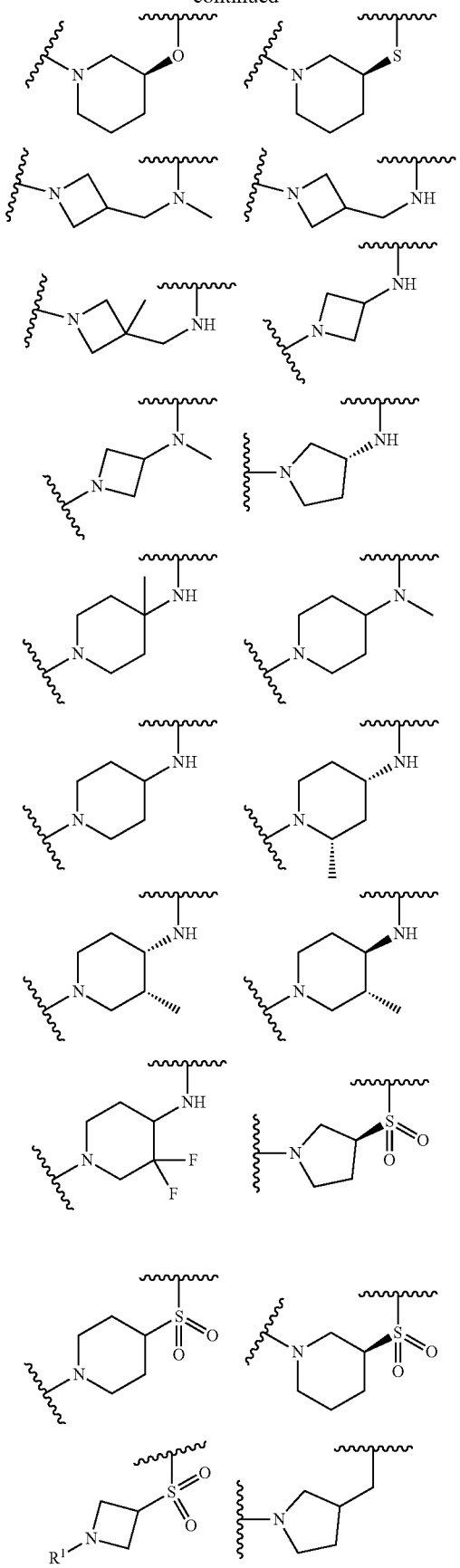

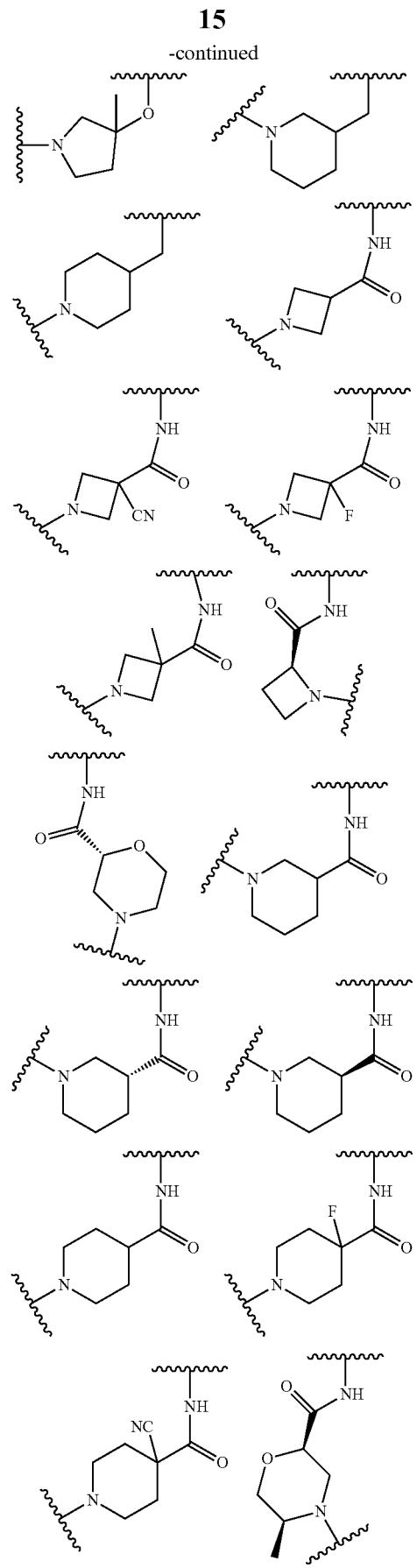
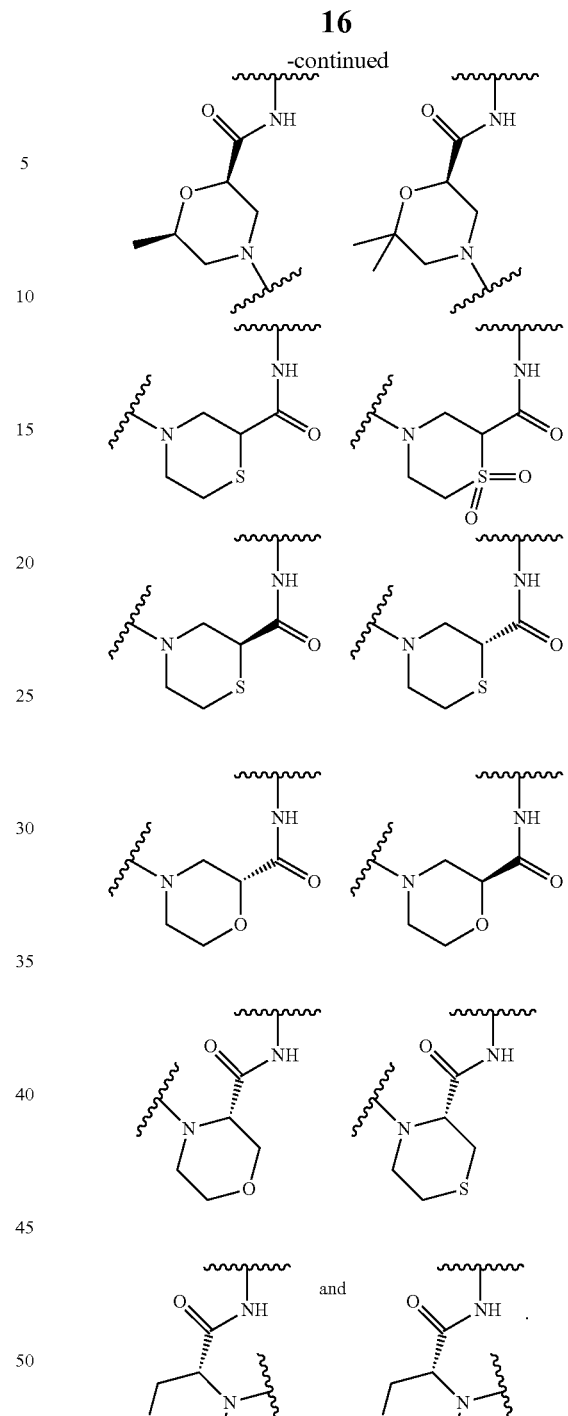

In some embodiments, $X^1$ and $X^2$ are both CH. In some embodiments, $X^1$ is N and $X^2$ is CH. In some embodiments, $X^1$ and $X^2$ are both N. In some embodiments, $X^1$ is CH and $X^2$ is N.

In some embodiments, $R^2$ is H. In some embodiments, $R^2$ is F. In some embodiments, $R^2$ is Cl. In some embodiments, $R^2$ is OMe. In some embodiments, $R^2$ is Me. In some embodiments, $R^3$ is H. In some embodiments, $R^3$ is F. In some embodiments, $R^4$ is H. In some embodiments, $R^4$ is F. In some embodiments, $R^5$ is H. In some embodiments, $R^5$ is F. In some embodiments, $R^5$ is Me.

In some embodiments,

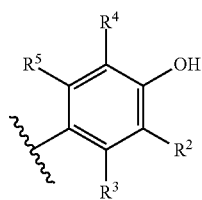

is selected from the group consisting of:

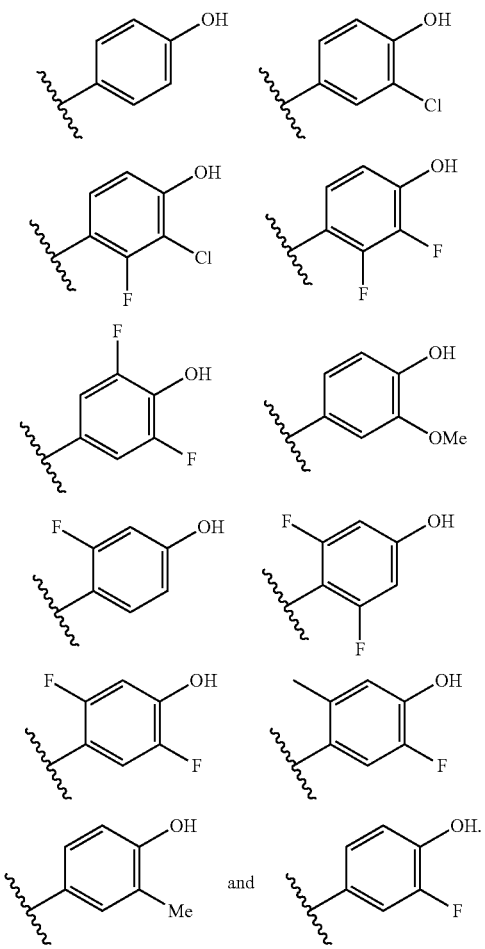

In some embodiments,

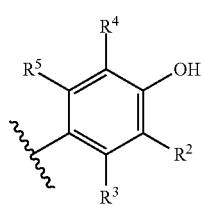

is selected from the group consisting of:

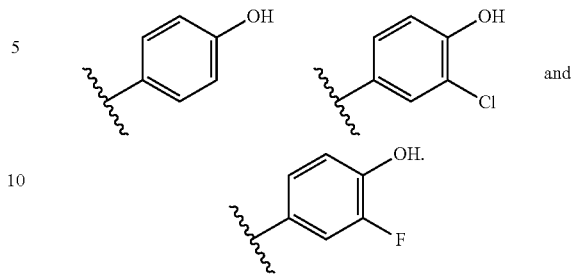

The invention also provides a compound of formula (II):

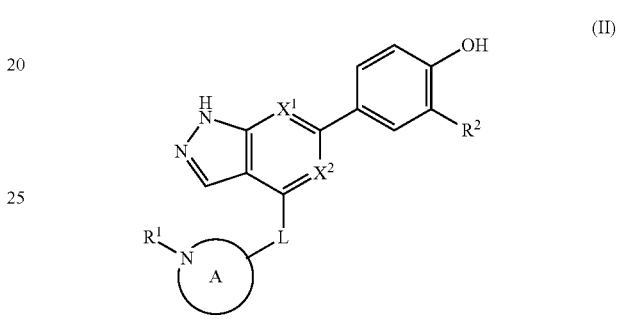

or a pharmaceutically acceptable salt thereof, wherein
$X^1$ and $X^2$ are both CH, or $X^1$ and $X^2$ are both N, or $X^1$ is N and $X^2$ is CH;

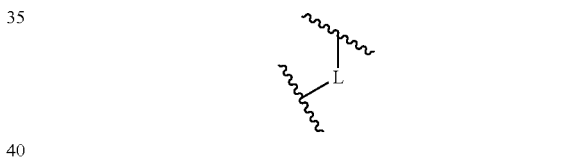

is selected from the group consisting of

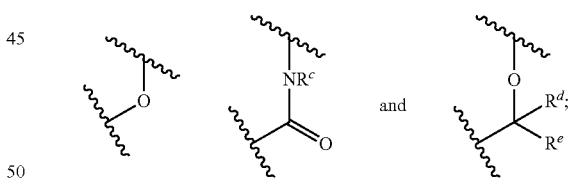

$R^c$, $R^d$, and $R^e$ are each independently selected from the group consisting of H and methyl;
A is selected from the group consisting of azetidine, pyrrolidine, piperidine, and morpholine;
wherein L is linked to a carbon atom in A and A is optionally substituted with 1 to 2 $R^k$ groups;
each $R^k$ is independently selected from the group consisting of F, CN, methyl, ethyl and $C_{1-2}$ haloalkyl;

$R^1$ is 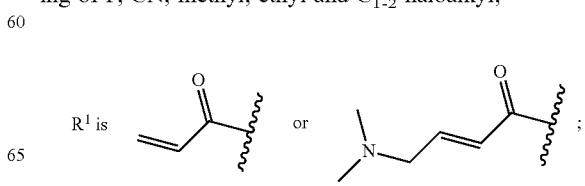

and $R^2$ is selected from the group consisting of H, Cl, and F.

In some embodiments,

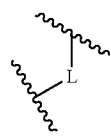

is selected from the group consisting of

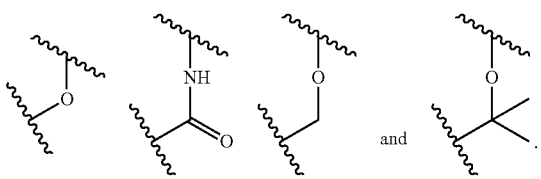

In some embodiments, $R^1$ is

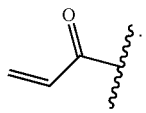

In some embodiments, $R^1$ is

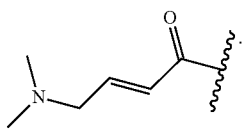 [SMILES: *C(=O)/C=C/CN(C)C]

In some embodiments, the compound has the formula:

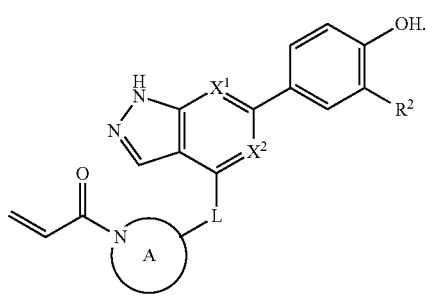

In some embodiments, the compound has the formula:

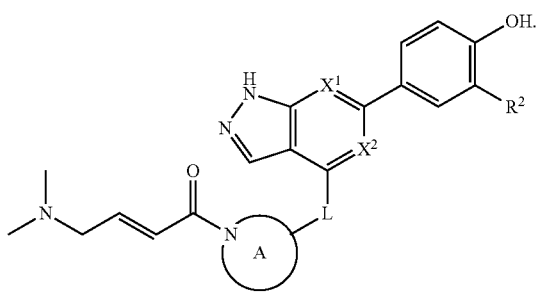

In some embodiments,

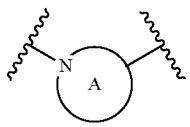

is selected from the group consisting of:

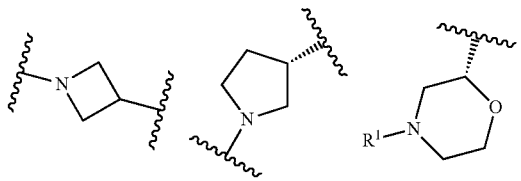

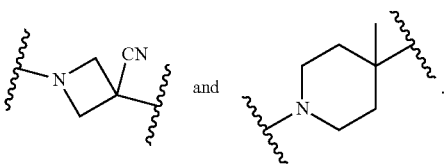

In some embodiments,

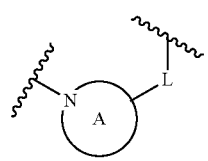

is selected from the group consisting of:

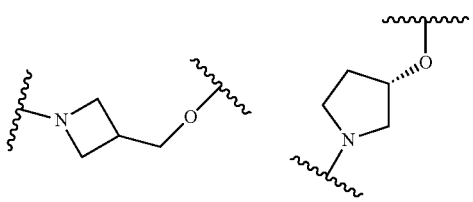

-continued

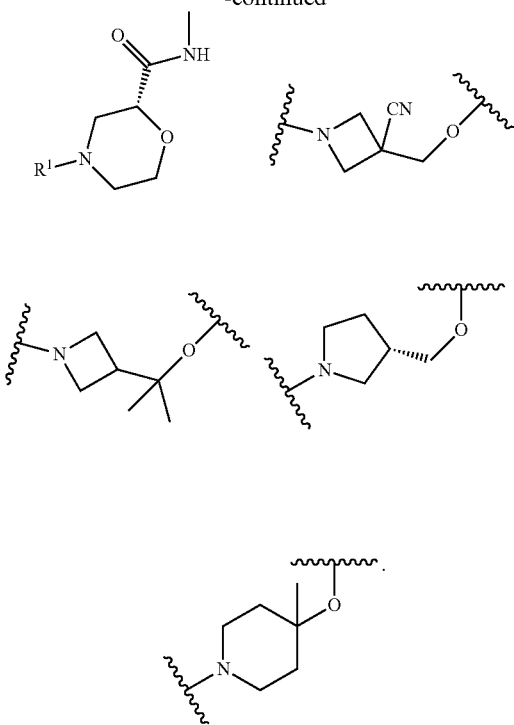

The disclosure also provides a compound, or a pharmaceutically acceptable salt thereof, of the formula (Ia) or (IIa):

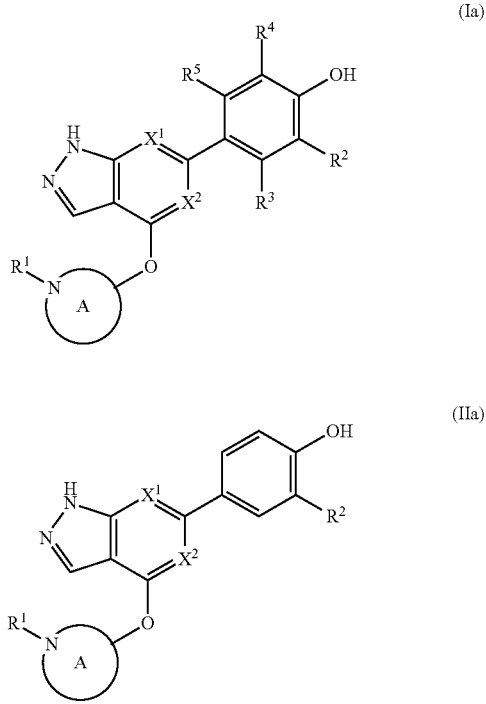

wherein the variables are as defined in the embodiments above.

The disclosure also provides a compound, or a pharmaceutically acceptable salt thereof, of the formula (Ib) or (IIb):

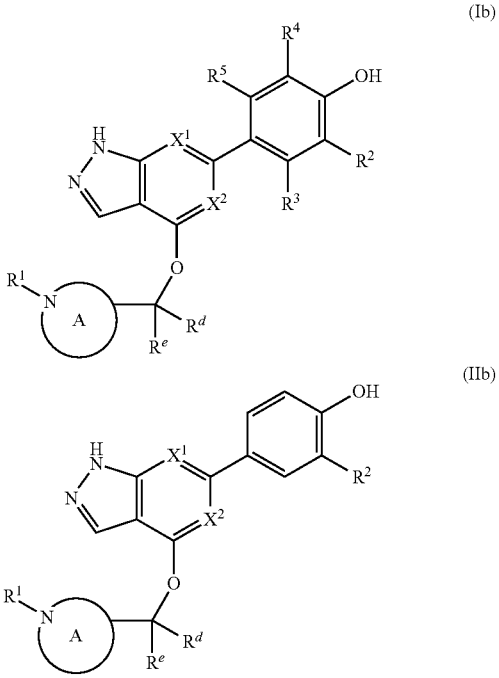

wherein the variables are as defined in the embodiments above.

The disclosure also provides a compound, or a pharmaceutically acceptable salt thereof, of the formula (Ic) or (IIc):

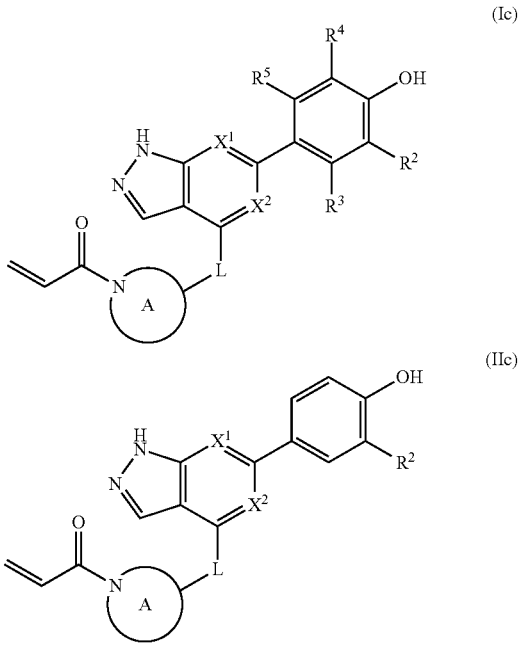

wherein the variables are as defined in the embodiments above.

The disclosure also provides a compound, or a pharmaceutically acceptable salt thereof, of the formula (Id) or (IId):

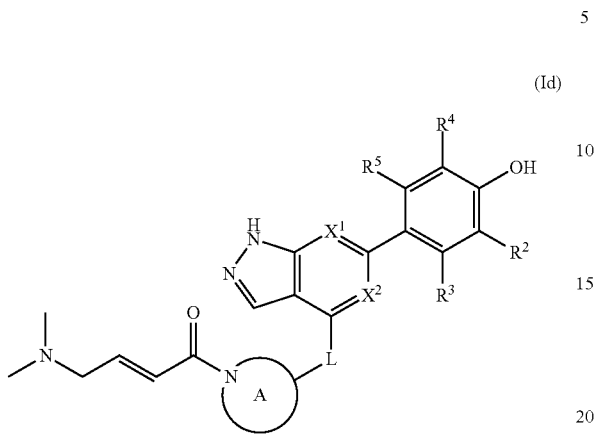

(Id)

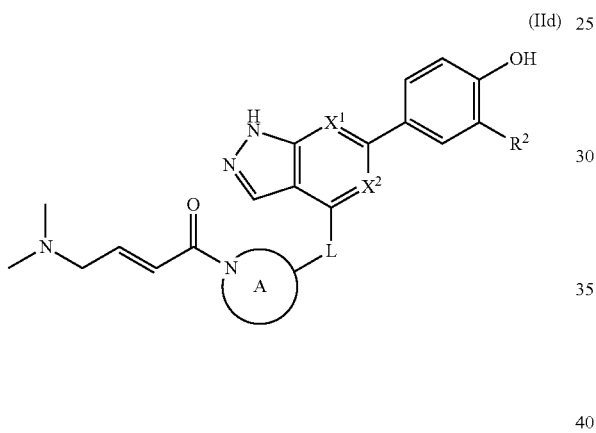

(IId)

wherein the variables are as defined in the embodiments above.

The disclosure also provides a compound, or a pharmaceutically acceptable salt thereof, of the formula (Ie) or (IIe):

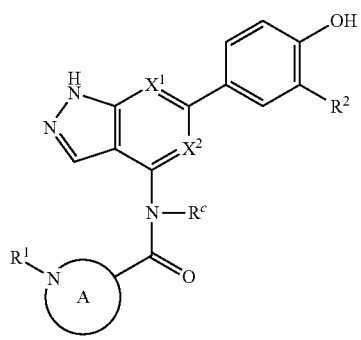

(Ie)

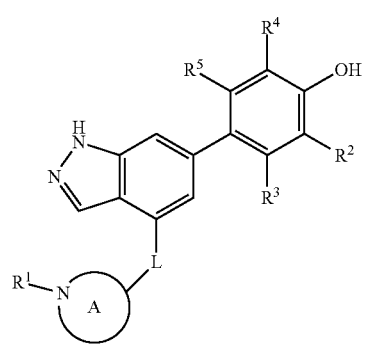

(IIe)

wherein the variables are as defined in the embodiments above.

The disclosure also provides a compound, or a pharmaceutically acceptable salt thereof, of the formula (If), (IIf), (IIIf), (IVf), (Vf), (VIf), (VIIf) or (VIIIf):

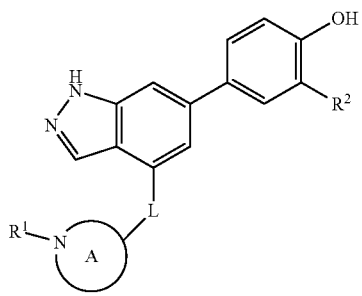

(If)

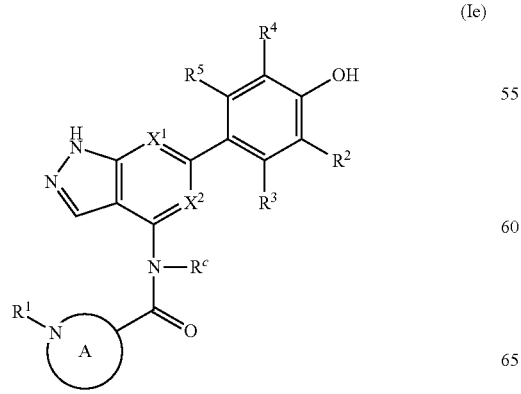

(IIf)

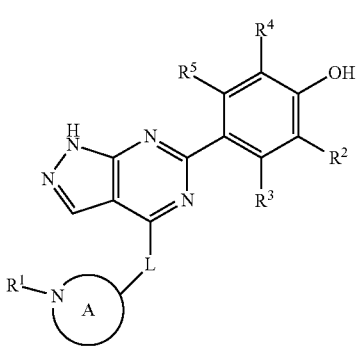

(IIIf)

-continued
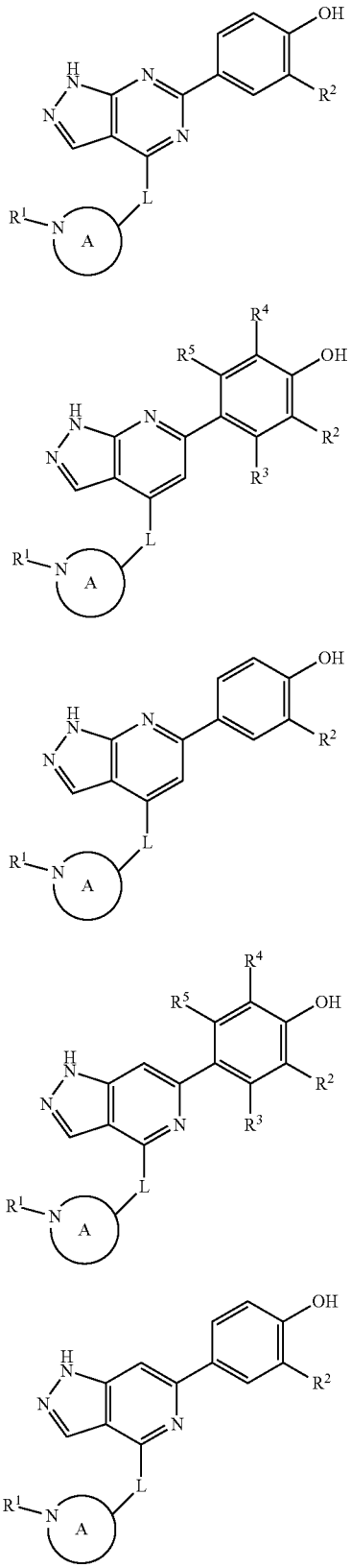
wherein the variables are as defined in the embodiments above.
The invention also provides a compound, or a pharmaceutically acceptable salt thereof, selected from the group consisting of
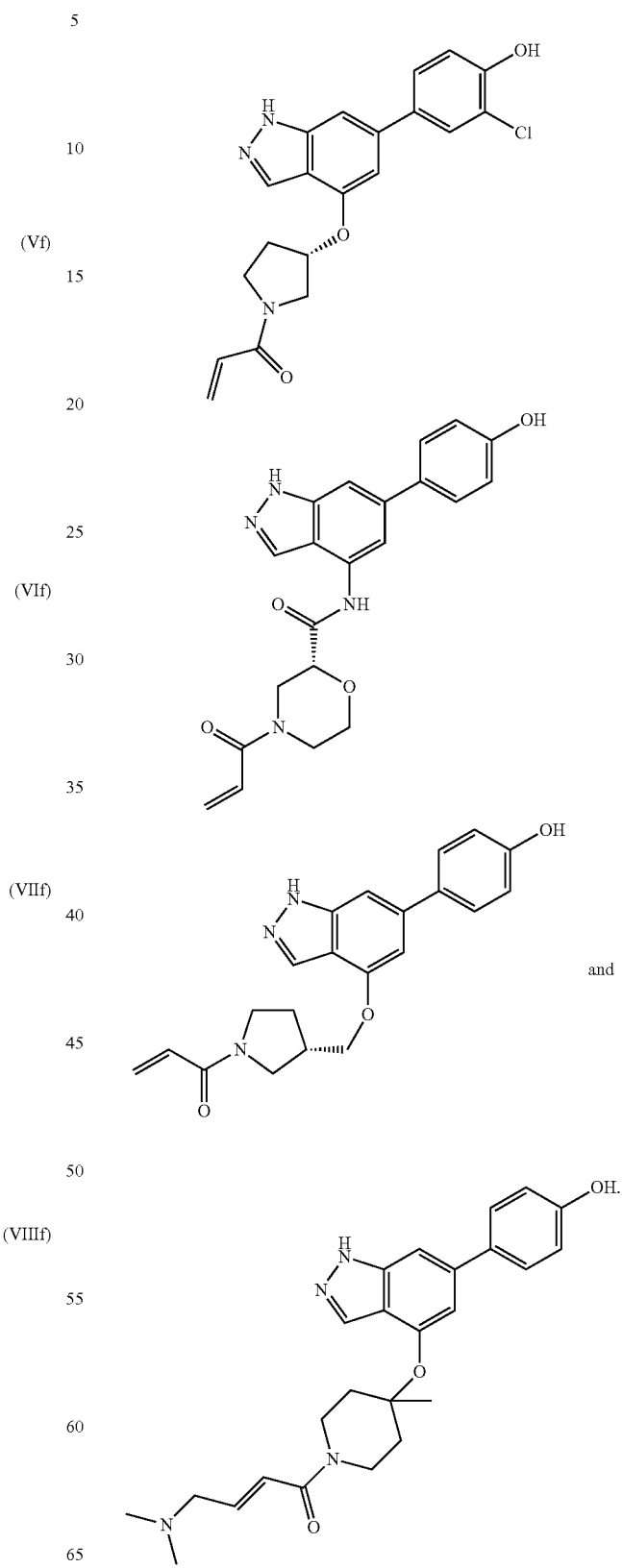

The invention also provides a compound, or a pharmaceutically acceptable salt thereof, having formula (B):

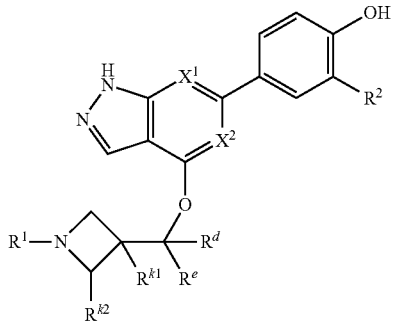
(B)

or a pharmaceutically acceptable salt thereof, wherein
X$^1$ and X$^2$ are each independently selected from N and CH;
R$^d$ and R$^e$ are each independently selected from the group consisting of H and C$_{1-3}$ alkyl; optionally R$^d$ and R$^e$ may be joined to form a cyclopropyl ring;
R$^{k1}$ is selected from the group consisting of H, F, CN, OMe, and C$_{1-3}$ alkyl;
R$^{k2}$ is selected from the group consisting of H and methyl;

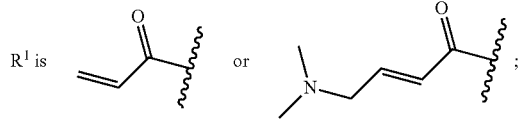

and
R$^2$ is selected from the group consisting of H, Cl, and F.
In some embodiments, R$^d$ and R$^e$ are each independently selected from the group consisting of H and methyl; optionally R$^d$ and R$^e$ may be joined to form a cyclopropyl ring; and R$^{k1}$ is selected from the group consisting of H, F, CN, OMe, methyl and ethyl.

The invention also provides a compound, or a pharmaceutically acceptable salt thereof, having formula (C):

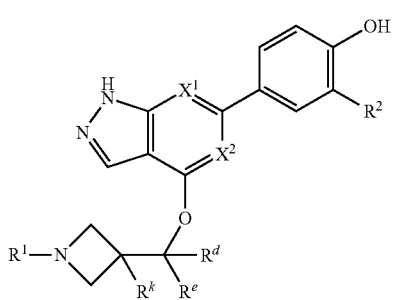
(C)

or a pharmaceutically acceptable salt thereof, wherein
X$^1$ and X$^2$ are both CH, or X$^1$ and X$^2$ are both N, or X$^1$ is N and X$^2$ is CH;
R$^d$ and R$^e$ are each independently selected from the group consisting of H and methyl;
R$^k$ is selected from the group consisting of H, CN, methyl and ethyl;

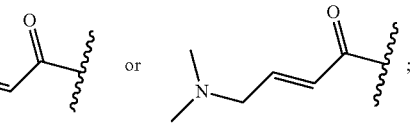

and
R$^2$ is selected from the group consisting of H, Cl, and F.

In some embodiments, the compound or a pharmaceutically acceptable salt thereof, is selected from the group consisting of:

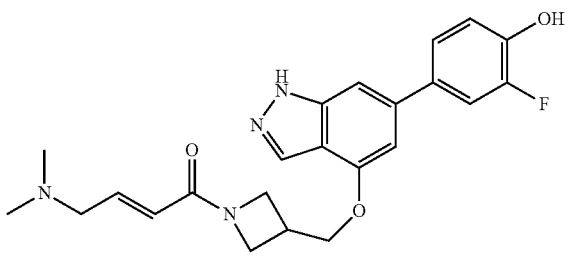

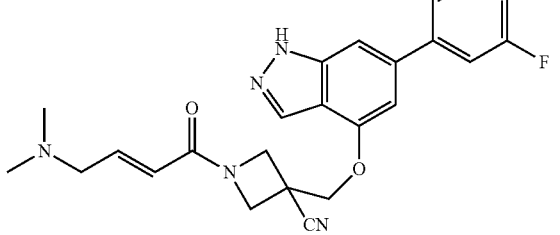

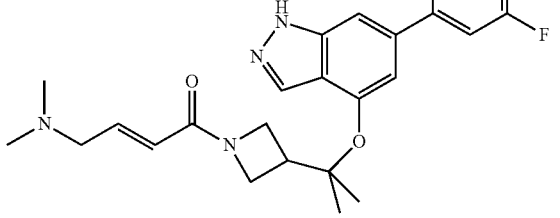

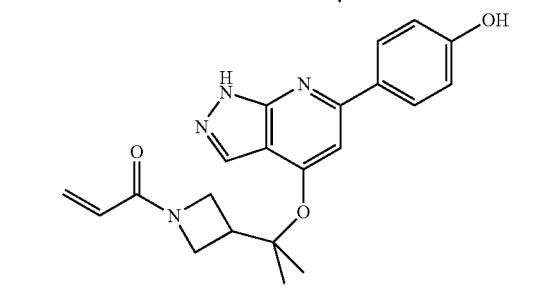

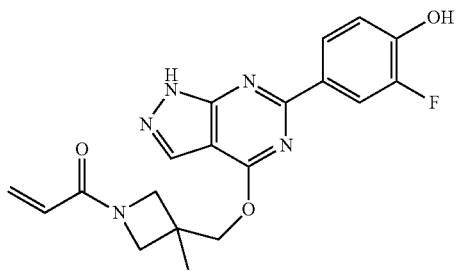

and

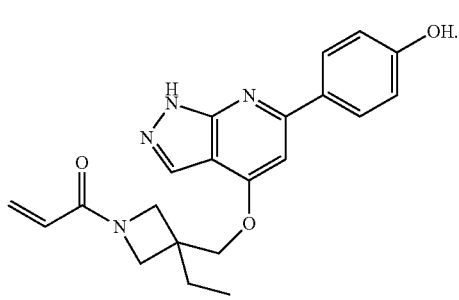

The invention also provides a compound, or a pharmaceutically acceptable salt thereof, having the formula:

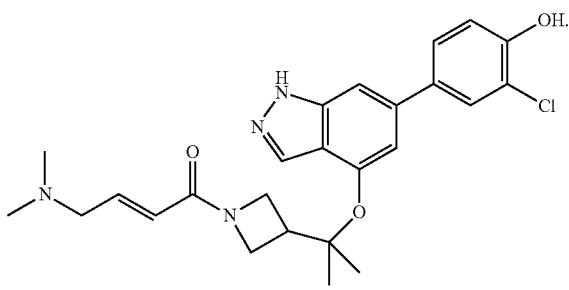 [SMILES: CN(C)C/C=C/C(=O)N1CC(C(C)(C)Oc2cc(-c3ccc(O)c(Cl)c3)cc3[nH]ncc23)C1]

The invention also provides a compound, or a pharmaceutically acceptable salt thereof, having the formula:

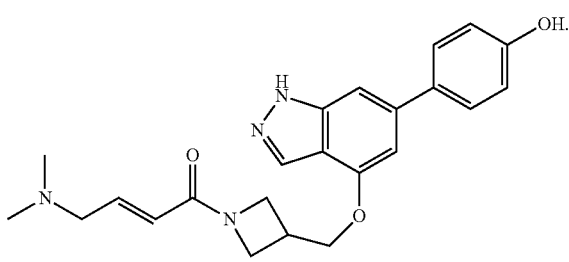 [SMILES: CN(C)C/C=C/C(=O)N1CC(COc2cc(-c3ccc(O)cc3)cc3[nH]ncc23)C1]

The invention also provides a compound, or a pharmaceutically acceptable salt thereof, having the formula:

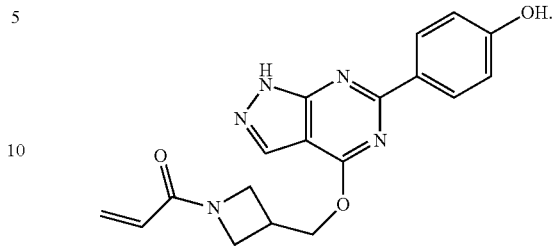

The invention also provides a pharmaceutical composition comprising a compound of the disclosure, or a pharmaceutically acceptable salt thereof, or a crystalline form thereof, and a pharmaceutically-acceptable carrier. In some embodiments, the pharmaceutical composition further comprises one or more other therapeutic agents. In some embodiments, the one or more other therapeutic agent is useful for treating a gastrointestinal inflammatory disease, an inflammatory disease of the skin, an inflammatory disease of the lungs or an inflammatory disease of the eye. In some embodiments, the one or more other therapeutic agent is useful for treating a gastrointestinal inflammatory disease. In some embodiments the gastrointestinal inflammatory disease is ulcerative colitis. In some embodiments the gastrointestinal inflammatory disease is Crohn's disease.

Furthermore, some compounds may sometimes exist in tautomeric forms. It will be understood that although structures are shown, or named, in a particular form, the invention also includes the tautomer thereof.

The compounds of the invention may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

This invention also includes isotopically-labeled compounds of the disclosure, for example isotopically-labeled compounds of formula (I), (II), (B), (C), compound 1, compound 3, compound 4, i.e., compounds of the disclosure and compounds of formula (I), (II), (B), (C), compound 1, compound 3, compound 4 where an atom has been replaced or enriched with an atom having the same atomic number but an atomic mass different from the atomic mass that predominates in nature. Examples of isotopes that may be incorporated into a compounds of the disclosure and a compound of formula (I), (II), (B), (C), compound 1, compound 3, compound 4, include, but are not limited to, $^2$H, $^3$H, $^{11}$C, $^{13}$C, $^{14}$C, $^{13}$N, $^{15}$N, $^{15}$O, $^{17}$O, $^{18}$O, $^{35}$S, and $^{18}$F. Of particular interest are compounds of the disclosure and compounds of formula (I), (II), (B), (C), compound 1, compound 3, and compound 4, enriched in tritium or carbon-14, which compounds can be used, for example, in tissue distribution studies. Also of particular interest are compounds of the disclosure and compounds of formula (I), (II), (B), (C), compound 1, compound 3, compound 4 enriched in deuterium especially at a site of metabolism, which compounds are expected to have greater metabolic stability. Additionally, of particular interest are compounds of the disclosure and compounds of formula (I), (II), (B), (C), compound 1, compound 3, compound 4, enriched in a positron emitting isotope, such as $^{11}C$, $^{18}F$, $^{15}O$ and $^{13}N$, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "haloalkyl" refers to an alkyl group, as defined above, that is substituted by one or more halogen, e.g., trifluoromethyl, difluoromethyl, trichloromethyl, 2,2,2 trifluoroethyl, 1,2 difluoroethyl, 3 bromo 2 fluoropropyl, 1,2 dibromoethyl, and the like.

When a specific number of carbon atoms are intended for a particular term, the number of carbon atoms is shown preceding the term. For example, the term "$C_{1-3}$alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused, spiro or bridged). When the heterocyclic group is multicyclic, at least one but not necessarily all of the cyclic groups contains a heteroatom. Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "therapeutically effective amount" means an amount sufficient to effect treatment when administered to a patient in need of treatment.

The term "treatment" as used herein means the treatment of a disease, disorder, or medical condition (such as a gastrointestinal inflammatory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), triisopropylsilyl (TIPS), tert-butyldimethylsilyl (TBS or TBDMS), [2-(trimethylsilyl)-ethoxy]methyl (SEM); and the like. Numerous protecting groups, and their introduction and removal, are described in T. W. Greene and P. G. M. Wuts, *Protecting Groups in Organic Synthesis*, Third Edition, Wiley, New York General Synthetic Procedures Compounds of this disclosure, and intermediates thereof, can be prepared according to the following general methods and procedures using commercially-available or routinely-prepared starting materials and reagents. The substituents and variables (e.g., A, $X^1$, $X^2$, $R^1$, $R^2$, $R^3$, $R^a$, $R^b$ etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials known to those skilled in the art. In particular, it will be appreciated that compounds of the disclosure may be prepared by a variety of process routes in which reactants are combined in different orders to provide different intermediates en route to producing final products.

A general method of preparing final compounds of the disclosure wherein L is selected from:

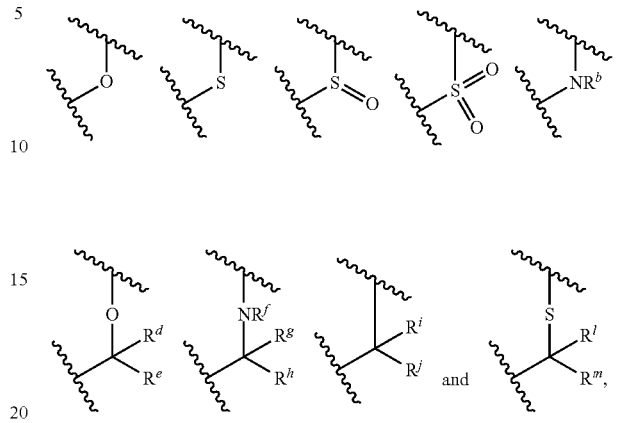

is illustrated in Scheme 1.

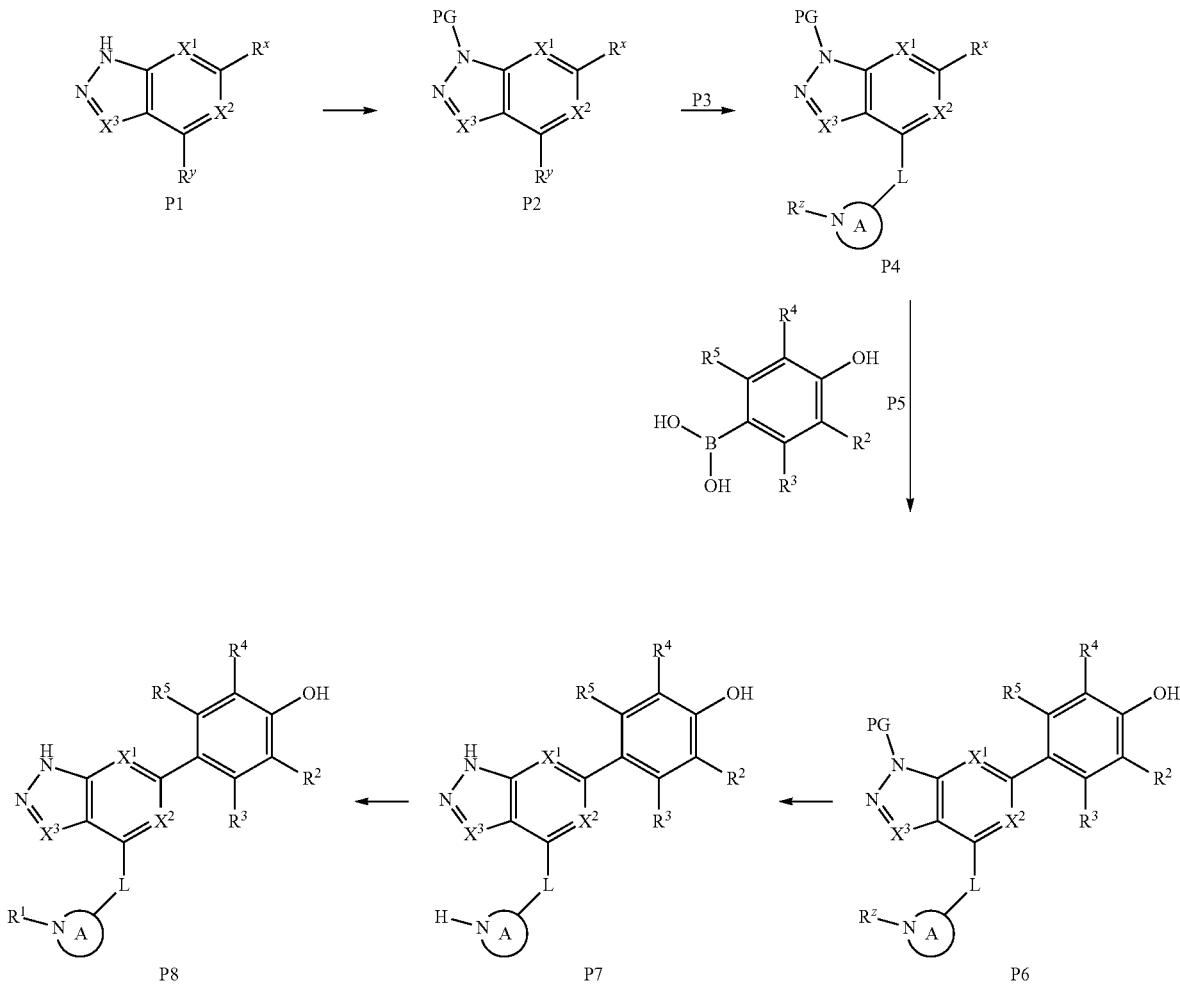

Starting material P1, where $R^x$ and $R^y$ are halogens which may be the same or different, is protected with a protected group PG such as tetrahydropyran to give P2. P2 is then reacted with P3 to give P4.

P3 may be:

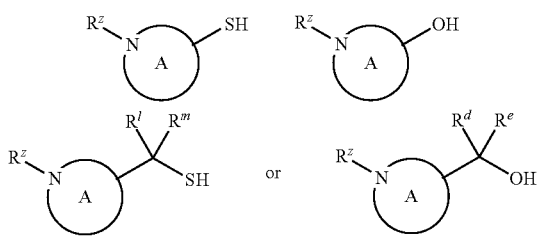

where $R^z$ is a second protecting group, for example Boc. In this case, P3 is deprotonated with a base such as NaH and reacted with P2 to give P4.

Alternatively, P3 may be:

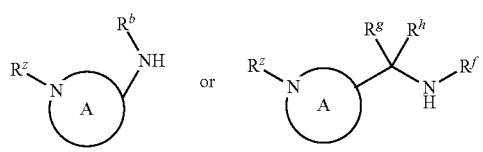

where $R^z$ is a second protecting group, for example Boc. In this case, P3 is reacted with P2 under Buchwald coupling conditions such as in the presence of Pd(0) and a base to give P4. Alternatively, P3 is reacted with P2 in presence of a base such as DIPEA to give P4.

Alternatively, P3 may be:

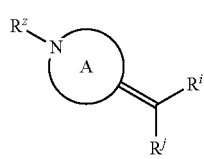

where $R^z$ is a second protecting group, for example Boc. In this case, P3 is reacted with P2 in presence of Pd(0), 9-BBN and a base to form P4.

P4 is coupled with boronic acid P5 (Suzuki coupling) in presence of Pd(0) and a base to give P6. P6 is deprotected to give P7 (when PG is tetrahydropyran and $R^z$ is Boc, simultaneous deprotection of the amines occur in presence of a strong acid such as TFA or HCl). Finally, P7 is derivatized into an amide by amide coupling (reaction with an acid in presence of a coupling agent such as HATU or hydroxybenzotriazole (HOBT)) or reaction with an acyl chloride in presence of a base such as Hunig's base.

In this reaction scheme, the order of the reactions may be modified. For example the Suzuki coupling may be conducted before the introduction of the portion containing the A ring. This can for example be the case when the portion containing the A ring is introduced through a Buchwald coupling.

In this reaction scheme, protection of one or both of the amino groups is optional. The same synthetic scheme may be used without amino protection for one or both amino groups but may provide lower yields.

The sulfonyl linker can be obtained by oxidizing the corresponding sulfide, for example with oxone and basic alumina.

Accordingly, in a method aspect, the invention provides a method for preparing a compound of formula (I) or a pharmaceutically acceptable salt thereof,

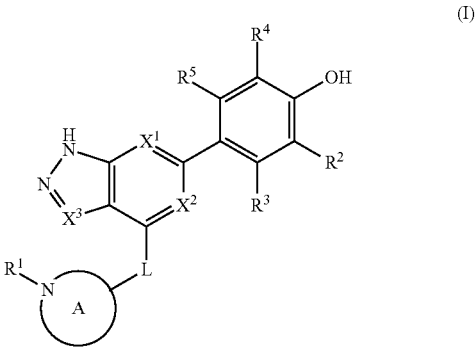

(I)

the method comprising:
reacting a compound of formula (III):

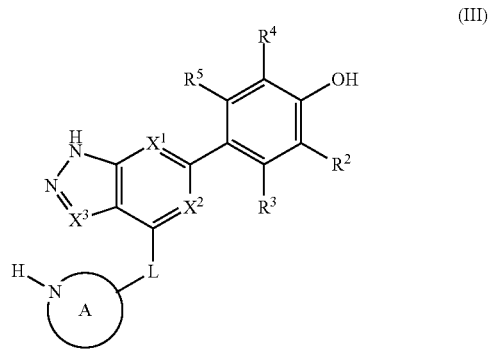

(III)

with
(i) Cl—$R^1$, or
(ii) HO—$R^1$ wherein $R^1$, $R^2$, $R^3$, $R^4$, $X^1$, $X^2$, L and A are as defined above, and optionally forming a pharmaceutically-acceptable salt to provide a compound of formula (I), or a pharmaceutically acceptable salt thereof.

In separate and distinct aspects, the invention provides a compound of formula (III) wherein the variables take any of the values described above.

Crystalline Forms

In one aspect, the invention provides a crystalline form of the compound of formula:

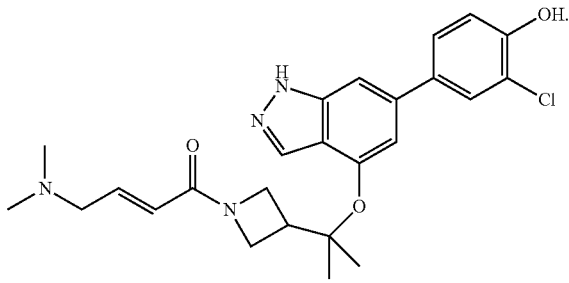 [SMILES: CN(C)C/C=C/C(=O)N1CC(C(C)(C)Oc2cc(-c3ccc(O)c(Cl)c3)cc3[nH]ncc23)C1]

Form 1

Crystalline Form 1 of the invention is a crystalline anhydrous free form of compound 3. In one aspect, Form 1 is characterized by a powder X-ray diffraction (PXRD) pattern having significant diffraction peaks, among other peaks, at 2θ values of 5.65±0.20, 14.22±0.20, 15.16±0.20, and 19.31±0.20. Form 1 may be further characterized by a PXRD pattern having additional diffraction peaks at 2θ values of 7.12±0.20, 10.02±0.20, 11.16±0.20, 17.06±0.20, and 24.43±0.20. Form 1 may be further characterized by a PXRD pattern having two or more additional diffraction peaks, including three or more and four or more additional diffraction peaks at 2θ values selected from 13.10±0.20, 14.82±0.20, 16.55±0.20, 20.08±0.20, 21.08±0.20, 21.65±0.20, 22.51±0.20, 22.98±0.20, 25.02±0.20, 25.72±0.20, 26.80±0.20, 27.06±0.20, 28.31±0.20, 30.08±0.20, 30.31±0.20 and 32.08±0.20. Form 1 is characterized by a PXRD pattern having three, four, five, or six diffraction peaks at 2θ values selected from 5.65±0.20, 7.12±0.20, 10.02±0.20, 11.16±0.20, 14.22±0.20, 15.16±0.20, 17.06±0.20, 19.31±0.20 and 24.43±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 1 is characterized by a powder x-ray diffraction pattern in which the peak positions are substantially in accordance with those shown in FIG. 1.

In another aspect, crystalline Form 1 is characterized by its behavior when exposed to high temperature. As demonstrated in FIG. 2, the differential scanning calorimetry (DSC) trace recorded at a heating rate of 10° C. per minute exhibits a peak in endothermic heat flow, identified as a melt transition, with an onset at about 154.9° C. and a peak at about 162.9° C. Melting was followed immediately by decomposition.

The crystalline form is characterized by a differential scanning calorimetry trace recorded at a heating rate of 10° C. per minute which shows a maximum in endothermic heat flow with a peak at about 162.9° C. The crystalline form is characterized by a differential scanning calorimetry trace recorded at a heating rate of 10° C. per minute which shows a maximum in endothermic heat flow with a peak at 162.9±3° C.

The crystalline form is characterized by a differential scanning calorimetry trace recorded at a heating rate of 10° C. per minute which shows a maximum in endothermic heat flow at a temperature between about 154.9° C. and about 171° C., or between 158° C. and 167° C.

Figure 3:
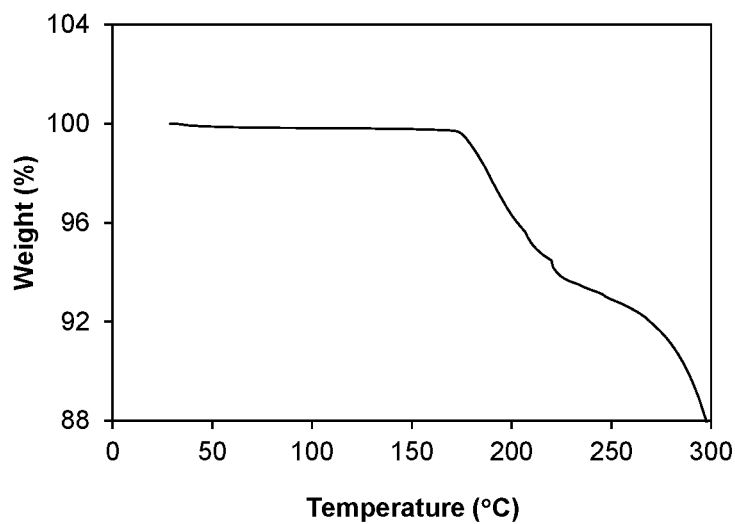
FIG. 3 shows a thermal gravimetric analysis (TGA) plot of crystalline Form 1.

A representative TGA trace of the Form 1 crystalline free form is shown in FIG. 3. The thermal gravimetric analysis (TGA) trace shows a small weight loss of about 0.14% at 100° C. The compound decomposes at an onset temperature of about 175° C.

Figure 4:
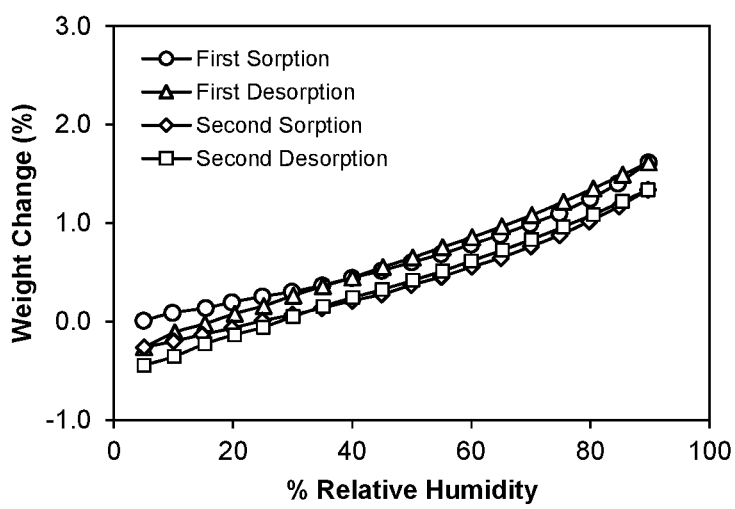
FIG. 4 shows a dynamic moisture sorption (DMS) isotherm of crystalline Form 1 observed at a temperature of about 25° C.

A representative DMS trace for the Form 1 crystalline free form is shown in FIG. 4. Form 1 demonstrated about 1.62% weight gain in the humidity range of 5% to 90% relative humidity. Form 1 is considered to be slightly hygroscopic.

Form 1 may be prepared by dissolving compound 3 as an amorphous form in ethanol followed by stirring at a temperature of between about 20° C. and about 25° C. followed by filtration and drying to give Form 1. Optionally, the solid can be washed with ethanol before drying.

Form 1 may be prepared by adding acetone to the compound in an amorphous form and stirring at a temperature of between about 20° C. and about 25° C. followed by the addition of seeds. The resulting slurry is filtered and dried to give Form 1.

Form 2

Crystalline Form 2 of the invention is a crystalline hydrate free form of compound 3. In one aspect, Form 2 is characterized by a powder X-ray diffraction (PXRD) pattern having significant diffraction peaks, among other peaks, at 2θ values of 6.90±0.20, 9.15±0.20, 10.00±0.20, and 18.31±0.20. Form 2 may be further characterized by a PXRD pattern having additional diffraction peaks at 2θ values of 11.18±0.20, 15.51±0.20, and 20.90±0.20. Form 2 may be further characterized by a PXRD pattern having two or more additional diffraction peaks, including three or more and four or more additional diffraction peaks at 2θ values selected from 12.76±0.20, 13.33±0.20, 13.82±0.20, 14.43±0.20, 16.04±0.20, 17.00±0.20, 17.90±0.20, 22.06±0.20, 22.51±0.20, 25.00±0.20, 26.92±0.20, 27.26±0.20, 27.61±0.20, 29.37±0.20, 30.53±0.20, and 30.92±0.20. Form 2 is characterized by a PXRD pattern having three, four, five, or six diffraction peaks at 2θ values selected from 6.90±0.20, 9.15±0.20, 10.00±0.20, 11.18±0.20, 15.51±0.20, 18.31±0.20, and 20.90±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 2 is characterized by a powder x-ray diffraction pattern in which the peak positions are substantially in accordance with those shown in FIG. 5.

In another aspect, crystalline Form 2 is characterized by its behavior when exposed to high temperature. As demonstrated in FIG. 6, the differential scanning calorimetry (DSC) trace recorded at a heating rate of 10° C. per minute exhibits a desolvation endotherm with an onset at about 52.7° C. and a peak at about 84.4° C., and a melting endotherm with an onset at about 160.0° C. and a peak at about 167.6° C. Melting was followed immediately by decomposition.

Figure 7:
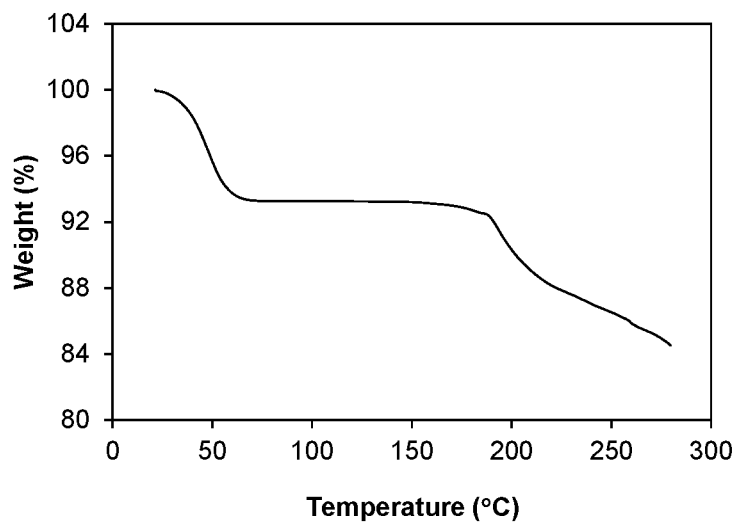
FIG. 7 shows a thermal gravimetric analysis (TGA) plot of crystalline Form 2.

A representative TGA trace of the Form 2 crystalline free form of the invention is shown in FIG. 7. The thermal gravimetric analysis (TGA) trace of FIG. 7 shows a weight loss of about 6.73% at 75° C. The compound desolvates at an onset temperature of about 25° C. The compound decomposes at an onset temperature of about 185° C.

Figure 8:
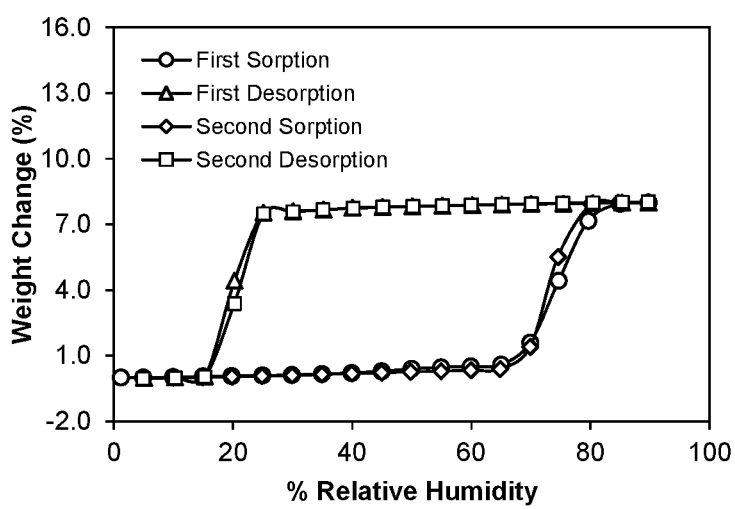
FIG. 8 shows a dynamic moisture sorption (DMS) isotherm of crystalline Form 2 observed at a temperature of about 25° C.

A representative DMS trace for the Form 2 crystalline free form of the invention is shown in FIG. 8. Form 2 converts to a hydrate (Form 2b) at RH above 65%. The dehydration occurs at RH below 15%. The total moisture uptake between 5%-90% RH is 7.99%.

Form 2 may be prepared by dissolving compound 3 in amorphous form in methanol followed by the addition of an anti-solvent such as water, in a ratio of about 1:2 methanol:water. Optionally, the mixture is sonicated. The mixture is then stirred at a temperature of between about 20° C. and about 25° C. for about 12 to 24 hours. Form 2 is then isolated by filtration and drying. Optionally, the solid can be washed with methanol.

Form 2 can also be prepared by dissolution in ethanol and water or methanol and water by complete dissolution in about 10 volumes of alcohol followed by slow addition of about 8-10 volumes of water until cloud point. Seeds of Form 2 are added to form a slurry slowly over time. More water is added slowly (about 10 volumes) to provide a solid which can be filtered and dried to give Form 2.

Form 2b

Crystalline Form 2b of the invention is a crystalline dehydrated free form of compound 3. In one aspect, Form 2b is characterized by a powder X-ray diffraction (PXRD) pattern having significant diffraction peaks, among other peaks, at 2θ values of 7.61±0.20, 16.76±0.20, 17.90±0.20, and 20.67±0.20. Form 2b may be further characterized by a PXRD pattern having additional diffraction peaks at 2θ values of 10.33±0.20, 11.25±0.20, 12.71±0.20, 15.88±0.20. Form 2b may be further characterized by a PXRD pattern having two or more additional diffraction peaks, including three or more and four or more additional diffraction peaks at 2θ values selected from 13.23±0.20, 13.66±0.20, 13.90±0.20, 15.02±0.20, 15.27±0.20, 16.33±0.20, 18.26±0.20, 21.37±0.20, 21.92±0.20, 22.31±0.20, 22.90±0.20, 23.22±0.20, 23.61±0.20, 24.74±0.20, 25.78±0.20, 26.23±0.20, 26.73±0.20, 27.57±0.20, 29.10±0.20, 29.39±0.20, 30.72±0.20, 30.94±0.20, 31.69±0.20, 32.06±0.20, 33.76±0.20, and 34.35±0.20. Form 2b is characterized by a PXRD pattern having three, four, five, or six diffraction peaks at 2θ values selected from 7.61±0.20, 10.33±0.20, 11.25±0.20, 12.71±0.20, 15.88±0.20, 16.76±0.20, 17.90±0.20, and 20.67±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 2b is characterized by a powder x-ray diffraction pattern in which the peak positions are substantially in accordance with those shown in FIG. 17.

In another aspect, the invention provides a crystalline form of the compound of formula:

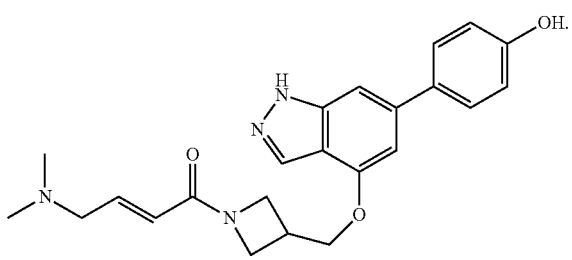 [SMILES: CN(C)C/C=C/C(=O)N1CC(COc2cc(-c3ccc(O)cc3)cc3[nH]ncc23)C1]

Form 3

Crystalline Form 3 of the invention is a crystalline anhydrous free form of compound 1. In one aspect, Form 3 is characterized by a powder X-ray diffraction (PXRD) pattern having significant diffraction peaks, among other peaks, at 2θ values of 9.67±0.20, 11.61±0.20, 17.61±0.20, 18.88±0.20, and 23.33±0.20. Form 3 may be further characterized by a PXRD pattern having additional diffraction peaks at 2θ values of 4.82±0.20, 15.69±0.20, and 16.19±0.20. Form 3 may be further characterized by a PXRD pattern having two or more additional diffraction peaks, including three or more and four or more additional diffraction peaks at 2θ values selected from 11.92±0.20, 12.98±0.20, 13.23±0.20, 16.45±0.20, 16.67±0.20, 19.39±0.20, 19.96±0.20, 20.14±0.20, 22.14±0.20, 23.84±0.20, 24.06±0.20, 24.29±0.20, 25.31±0.20, 25.63±0.20, 27.06±0.20, 27.31±0.20, 30.10±0.20, and 30.53±0.20. Form 3 is characterized by a PXRD pattern having three, four, five, or six diffraction peaks at 2θ values selected from 4.82±0.20, 9.67±0.20, 11.61±0.20, 15.69±0.20, 16.19±0.20, 17.61±0.20, 18.88±0.20, and 23.33±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 3 is characterized by a powder x-ray diffraction pattern in which the peak positions are substantially in accordance with those shown in FIG. 9.

In another aspect, crystalline Form 3 is characterized by its behavior when exposed to high temperature. As demonstrated in FIG. 10, the differential scanning calorimetry (DSC) trace recorded at a heating rate of 10° C. per minute exhibits a peak in endothermic heat flow, identified as a melt transition, with an onset at about 197.7° C. and a peak at about 201.3° C. Melting was followed immediately by decomposition.

The crystalline form is characterized by a differential scanning calorimetry trace recorded at a heating rate of 10° C. per minute which shows a maximum in endothermic heat flow with a peak at 201.3° C.±2° C.

The crystalline form is characterized by a differential scanning calorimetry trace recorded at a heating rate of 10° C. per minute which shows a maximum in endothermic heat flow at a temperature between 198° C. and 204° C.

Figure 11:
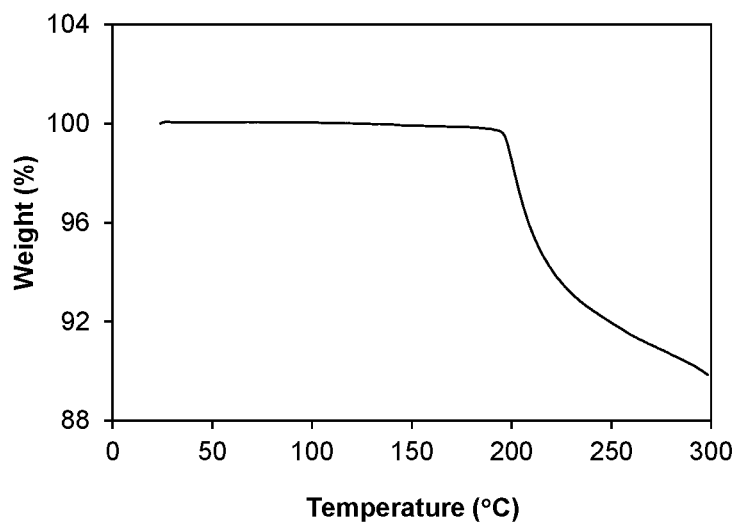
FIG. 11 shows a thermal gravimetric analysis (TGA) plot of crystalline Form 3.

A representative TGA trace of the Form 3 crystalline free form of the invention is shown in FIG. 11. The thermal gravimetric analysis (TGA) trace of FIG. 11 shows no significant weight loss at temperatures below the onset of decomposition at about 195° C.

Figure 12:
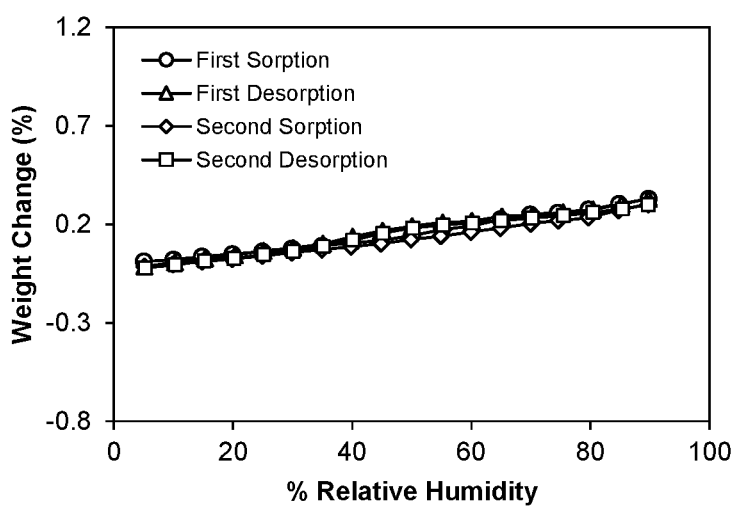
FIG. 12 shows a dynamic moisture sorption (DMS) isotherm of crystalline Form 3 observed at a temperature of about 25° C.

A representative DMS trace for the Form 3 crystalline free form of the invention is shown in FIG. 12. Form 3 demonstrated about 0.33% weight gain in the humidity range of 5% to 90% relative humidity. Form 3 is considered to be non-hygroscopic.

Form 3 may be prepared by suspending compound 1 in an amorphous form in a 1:1 mixture of acetonitrile and isopropanol. The resulting suspension is stirred for about 1 day at about 50° C., filtered, optionally washed with a 1:1 mixture of acetonitrile and isopropanol and dried for a few hours to provide Form 3.

Form 3 may be prepared by dissolving compound 1 as an amorphous free base in IPA at a temperature of between about 20° C. and about 25° C. An equal amount of acetonitrile is added. More compound can be added until a saturated solution is formed. Seeds are added and the mixture is stirred overnight. The developing white slurry formed is filtered and dried to yield Form 3.

Form 4

Crystalline Form 4 of the invention is a crystalline hydrate free form of compound 1. In one aspect, Form 4 is characterized by a powder X-ray diffraction (PXRD) pattern having significant diffraction peaks, among other peaks, at 2θ values of 6.26±0.20, 16.55±0.20, 16.94±0.20, 18.33±0.20, 23.61±0.20, and 24.24±0.20. Form 4 may be further characterized by a PXRD pattern having additional diffraction peaks at 2θ values of 11.86±0.20, 12.51±0.20, 13.16±0.20, and 14.98±0.20. Form 4 may be further characterized by a PXRD pattern having two or more additional diffraction peaks, including three or more and four or more additional diffraction peaks at 2θ values selected from 17.61±0.20, 18.78±0.20, 19.39±0.20, 19.57±0.20, 19.84±0.20, 21.45±0.20, 21.82±0.20, 22.57±0.20, 24.67±0.20, 25.10±0.20, 25.39±0.20, 27.19±0.20, 27.39±0.20, 28.55±0.20, and 31.51±0.20. Form 4 is characterized by a PXRD pattern having three, four, five, or six diffraction peaks at 2θ values selected from 6.26±0.20, 11.86±0.20, 12.51±0.20, 13.16±0.20, 14.98±0.20, 16.55±0.20, 16.94±0.20, 18.33±0.20, 23.61±0.20, and 24.24±0.20.

As is well known in the field of powder X-ray diffraction, peak positions of PXRD pattern are relatively less sensitive to experimental details, such as details of sample preparation and instrument geometry, than are the relative peak heights. Thus, in one aspect, the crystalline Form 4 is characterized by a powder x-ray diffraction pattern in which the peak positions are substantially in accordance with those shown in FIG. 13.

In another aspect, crystalline Form 4 is characterized by its behavior when exposed to high temperature. As demonstrated in FIG. 14, the differential scanning calorimetry (DSC) trace recorded at a heating rate of 10° C. per minute exhibits a desolvation endotherm with an onset at about 60.9° C. and a peak at about 103.6° C., and a melting endotherm characterized by an onset at about 167.3° C. The compound decomposes at melting and the melting endotherm and the decomposition exotherm overlap.

Figure 15:
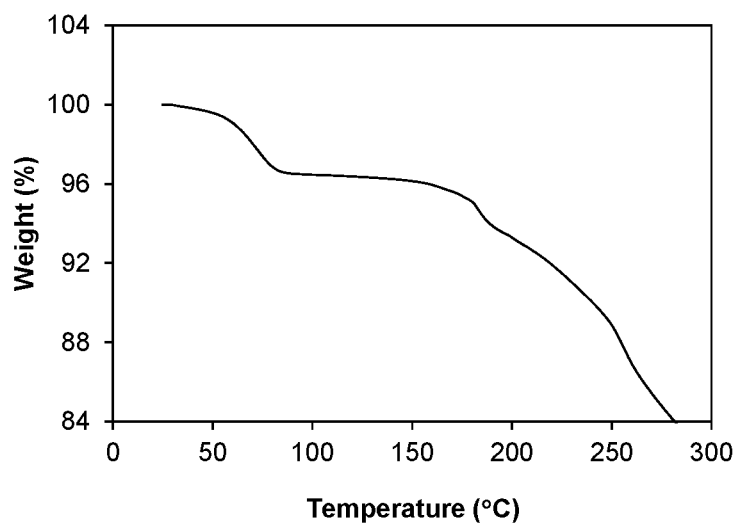
FIG. 15 shows a thermal gravimetric analysis (TGA) plot of crystalline Form 4.

A representative TGA trace of the Form 4 crystalline free form of the invention is shown in FIG. 15. The thermal gravimetric analysis (TGA) trace of FIG. 15 shows a weight loss of about 3.54% at 100° C. The compound desolvates at an onset temperature of about 50° C. The compound decomposes at an onset temperature of about 165° C.

Figure 16:
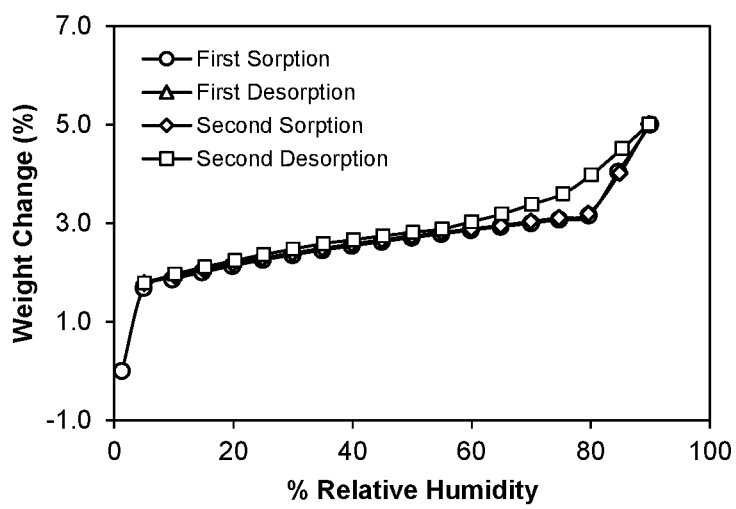
FIG. 16 shows a dynamic moisture sorption (DMS) isotherm of crystalline Form 4 observed at a temperature of about 25° C.

A representative DMS trace for the Form 4 crystalline free form of the invention is shown in FIG. 16. Form 4 demonstrated about 5.01% weight gain in the humidity range of 5% to 90% relative humidity. Form 4 is considered to be moderately hygroscopic.

Form 4 may be prepared by suspending compound 1 in water. The resulting suspension is stirred for about 1 to 2 days at about 50° C., filtered, optionally washed with water, and dried at a temperature of between about 20° C. and about 25° C. for about 2-6 hours to provide Form 4.

Alternatively, Form 4 may be prepared by dissolving compound 1 in ethanol and water or methanol and water by complete dissolution in about 10 volumes of alcohol followed by slow addition of about 8-10 volumes of water until cloud point. Seeds of Form 4 are added and a resulting slurry develops slowly over time. Then more water is added slowly (about 10 volumes) and the solid is filtered and dried to give Form 4.

Pharmaceutical Compositions

The compounds of the disclosure and pharmaceutically-acceptable salts thereof are typically used in the form of a pharmaceutical composition or formulation. Such pharmaceutical compositions may be administered to a patient by any acceptable route of administration including, but not limited to, oral, topical (including transdermal), rectal, nasal, inhaled, and parenteral modes of administration.

Accordingly, in one of its composition aspects, the invention is directed to a pharmaceutical composition comprising a pharmaceutically-acceptable carrier or excipient and a compound of formula (I), (II), (B), (C), compound 1, compound 3, or compound 4 or a pharmaceutically-acceptable salt thereof. Optionally, such pharmaceutical compositions may contain other therapeutic and/or formulating agents if desired. When discussing compositions and uses thereof, the "compound of the invention" or "compound of the disclosure" may also be referred to herein as the "active agent". As used herein, the term "compound(s) of the disclosure" is intended to include all compounds encompassed by formula (I), (II), (B), (C), (Ia), (IIa), (Ib), (IIb), (Ic), (IIc), (Id), (IId), (Ie), (IIe), (If), (IIf), (IVf), (Vf), (VIf), (VIIf), and (VIIIf), and pharmaceutically-acceptable salts thereof.

The pharmaceutical compositions of the disclosure typically contain a therapeutically effective amount of a compound of the disclosure. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; including from about 5 to about 70% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the disclosure are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the disclosure are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the disclosure will typically comprise the active agent and one or more pharmaceutically-acceptable carriers. Optionally, such solid dosage forms may comprise: fillers or extenders, such as starches, microcrystalline cellulose, lactose, dicalcium phosphate, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as croscarmellose sodium, agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the disclosure. Examples of pharmaceutically-acceptable antioxidants include: water-soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid, methacrylic acid ester copolymers, cellulose acetate trimellitate, carboxymethyl ethyl cellulose, hydroxypropyl methyl cellulose acetate succinate, and the like.

Pharmaceutical compositions of the disclosure may also be formulated to provide slow or controlled release of the active agent using, by way of example, hydroxypropyl methylcellulose in varying proportions; or other polymer matrices, liposomes and/or microspheres. In addition, the pharmaceutical compositions of the disclosure may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof. Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this disclosure, or a pharmaceutically acceptable salt thereof, can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more antioxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the disclosure and a powder suitable for use in a powder inhaler. Suitable powder bases include, by way of example, lactose or starch.

The compounds of the disclosure, or a pharmaceutically acceptable salt thereof, may also be formulated for topical administration to the skin as an ointment or cream. Ointment formulations are semisolid preparations having a base of an oily or greasy material that is typically clear. Suitable oily materials for use in ointment formulations include petrolatum (petroleum jelly), beeswax, cocoa butter, shea butter, and cetyl alcohol. Ointments may optionally additionally include emollients and penetration enhancers, if desired.

Cream formulations may be prepared as emulsions comprising an oil phase and aqueous phase, typically including purified water. Components of cream formulations may include: oil bases, such as petrolatum, mineral oils, vegetable and animal oils, and triglycerides; cream bases, such as lanolin alcohols, stearic acid, and cetostearyl alcohol; a gel base, such as polyvinyl alcohol; solvents, such as, propylene glycol and polyethylene glycol; emulsifiers, such as polysorbates, stearates, such as glyceryl stearate, octylhydroxystearate, polyoxyl stearate, PEG stearyl ethers, isopropyl palmitate, and sorbitan monostearate; stabilizers, such as polysaccharides and sodium sulfite; emollients (i.e. moisturizers), such as medium chain triglycerides, isopropyl myristate, and dimethicone; stiffening agents, such as cetyl alcohol and stearyl alcohol; antimicrobial agents, such as methylparaben, propylparaben, phenoxyethanol, sorbic acid, diazolidinyl urea, and butylated hydroxyanisole; penetration enhancers, such as N-methylpyrrolidone, propylene glycol, polyethylene glycol monolaurate, and the like; and chelating agents, such as edetate disodium.

The following non-limiting examples illustrate representative pharmaceutical compositions of the present invention.

Tablet Oral Solid Dosage Form

A compound of the disclosure or a pharmaceutically-acceptable salt thereof is dry blended with microcrystalline cellulose, polyvinyl pyrrolidone, and croscarmellose sodium in a ratio of 4:5:1:1 and compressed into tablets to provide a unit dosage of, for example, 5 mg, 20 mg or 40 mg active agent per tablet.

Capsule Oral Solid Dosage Form

A compound of the disclosure or a pharmaceutically-acceptable salt thereof is combined with microcrystalline cellulose, polyvinyl pyrrolidone, and croscarmellose sodium in a ratio of 4:5:1:1 by wet granulation and loaded into gelatin or hydroxypropyl methylcellulose capsules to provide a unit dosage of, for example, 5 mg, 20 mg or 40 mg active agent per capsule.

Liquid Formulation

A liquid formulation comprising a compound of the disclosure (0.1%), water (98.9%) and ascorbic acid (1.0%) is formed by adding a compound of the disclosure to a mixture of water and ascorbic acid.

Enteric Coated Oral Dosage Form

A compound of the disclosure is dissolved in an aqueous solution containing polyvinyl pyrrolidone and spray coated onto microcrystalline cellulose or sugar beads in a ratio of 1:5 w/w active agent:beads and then an approximately 5% weight gain of an enteric coating comprising an acrylic copolymer, for example a combination of acrylic copolymers available under the trade names Eudragit-L® and Eudragit-S®, or hydroxypropyl methylcellulose acetate succinate is applied. The enteric coated beads are loaded into gelatin or hydroxypropyl methylcellulose capsules to provide a unit dosage of, for example, 30 mg active agent per capsule.

Enteric Coated Oral Dosage Form

An enteric coating comprising a combination of Eudragit-L® and Eudragit-S®, or hydroxypropyl methylcellulose acetate succinate is applied to a tablet oral dosage form or a capsule oral dosage form described above.

Ointment Formulation for Topical Administration

A compound of the disclosure is combined with petrolatum, $C_8$-$C_{10}$ triglyceride, octylhydroxystearate, and N-methylpyrrolidone in a ratio to provide a composition containing 0.05% to 5% active agent by weight.

Ointment Formulation for Topical Administration

A compound of the disclosure is combined with white petrolatum, propylene glycol, mono- and di-glycerides, paraffin, butylated hydroxytoluene, and edetate calcium disodium in a ratio to provide a composition containing 0.05% to 5% active agent by weight.

Ointment Formulation for Topical Administration

A compound of the disclosure is combined with mineral oil, paraffin, propylene carbonate, white petrolatum and white wax to provide a composition containing 0.05% to 5% active agent by weight.

Cream Formulation for Topical Administration

Mineral oil is combined with a compound of the disclosure, propylene glycol, isopropyl palmitate, polysorbate 60, cetyl alcohol, sorbitan monostearate, polyoxyl 40 stearate, sorbic acid, methylparaben and propylparaben to form an oil phase, which is combined with purified water by shear blending to provide a composition containing 0.05% to 5% active agent by weight.

Cream Formulation for Topical Administration

A cream formulation comprising a compound of the disclosure, benzyl alcohol, cetyl alcohol, citric acid anhydrous, mono and di-glycerides, oleyl alcohol, propylene glycol, sodium cetostearyl sulphate, sodium hydroxide, stearyl alcohol, triglycerides, and water contains 0.05% to 5% active agent by weight.

Cream Formulation for Topical Administration

A cream formulation comprising a compound of the disclosure, cetostearyl alcohol, isopropyl myristate, propylene glycol, cetomacrogol 1000, dimethicone 360, citric acid, sodium citrate, and purified water, with imidurea, methylparaben, and propylparaben, as preservatives, contains 0.05% to 5% active agent by weight.

Utility

Inhibition of JAK3 blocks the signaling of many key pro-inflammatory cytokines. Thus the compounds of the disclosure are expected to be useful in the treatment of inflammatory diseases.

The compounds of the disclosure have been designed to be selective for JAK3 over JAK1, JAK2 and TYK2. Selectivity for JAK3 over JAK1 is anticipated to be beneficial as there is some evidence that JAK3 selectivity allows sparing of potentially beneficial cytokines such as IL-10 which has been involved in mucosal healing, IL-22 which is involved in mucus barrier protection and epithelial regeneration, and IL-6 which is involved in the proliferation of intestinal epithelial cells. Selectivity for JAK3 over JAK2 allows sparing of erythropoietin (EPO) and thrombopoietin (TPO) signaling.

Without being limited by this theory, the compounds of the disclosure possess an electrophilic portion which may form a covalent bond with the cysteine (Cys909) present in JAK3, a residue replaced by a serine in the other three JAK isoforms (Goedken et al., *J Biol Chem.*, 2015, 290, 8, 4573-89). Such covalent binding to JAK3 could be beneficial by providing an extended target engagement which may translate in better efficacy. As described in the experimental part, co-crystal structures of compounds 1, 3 and 4 covalently bound to human JAK3 have been obtained which confirms the irreversible binding nature for each of these ligands to JAK3.

Some compounds of the disclosure have been designed to have their effect at the site of action without significant systemic effects, thereby avoiding the potential adverse systemic immunosuppressive effects.

Gastrointestinal Inflammatory Disease

In addition to providing potent inhibition of JAK3, some compounds of the disclosure have been designed to be poorly absorbed to minimize systemic exposure. These compounds are designed to have their effect at the site of action, for example, in the colon. As described in Assay 6, certain compounds exhibit low permeabilities with $K_p$ values less than about $5\times10^{-6}$ cm/sec which is considered favorable to minimize systemic exposure and target the colon. Certain compounds have a $K_p$ value less than about $10\times10^{-6}$ cm/sec which may also be sufficient to minimize systemic exposure and target the colon. As described in Assay 7 below, compounds 1, 2, 3, 4, 6, 7, 8, 21 and 22 exhibited a ratio of exposure in the colon to exposure in plasma upon oral administration greater than about 1250. Compounds 9, 5, 19, and 20 exhibited a colon to plasma ratio in excess of about 200.

Oxazolone-induced colitis is an experimental model that has a histological resemblance to human ulcerative colitis. As described in Assay 8, the compounds 1, 2, 3, 4, 5, 6, 7, 8, 3-11, 5-10, 19, 15-1, 3-55, 3-34, 15-3, 21, 3-80, 3-81, 3-72, 3-57, 3-113 and 3-74 demonstrated activity in the oxazolone-induced colitis model in mice. Further, when tested in Assay 9, an immunosuppression model in mice, which probes systemic functional activity, splenic NK cell counts were unaffected by compounds 1, 2, 4, 5, and 8 at the same or higher doses required to demonstrate efficacy in the oxazolone model.

Finally, compounds 1, 2, 3, 4, 5, 6, 7, and 8 were shown to demonstrate lack of systemic activity in a murine model of IL-2 induced pSTAT5 induction in the thymus.

Thus these compounds demonstrated anti-colitic activity without exhibiting systemic effects in preclinical models.

It is expected that a high colon to plasma ratio will provide robust, luminally-driven anti-inflammatory activity without associated, systemically-driven, adverse effects. Such compounds may be useful for a variety of gastrointestinal inflammatory indications that include, but are not limited to, inflammatory bowel disease, ulcerative colitis (proctosigmoiditis, pancolitis, ulcerative proctitis and left-sided colitis), Crohn's disease, collagenous colitis, lymphocytic colitis, Behcet's disease, celiac disease, immune checkpoint inhibitor induced colitis, ileitis, eosinophilic esophagitis, graft versus host disease-related colitis, and infectious colitis. Ulcerative colitis (Reimund et al., *J Clin Immunology*, 1996, 16, 144-150), Crohn's disease (Woywodt et al., *Eur J Gastroenterology Hepatology*, 1999, 11, 267-276), collagenous colitis (Kumawat et al., *Mol Immunology*, 2013, 55, 355-364), lymphocytic colitis (Kumawat et al., 2013), eosinophilic esophagitis (Weinbrand-Goichberg et al., *Immunol Res*, 2013, 56, 249-260), graft versus host disease-related colitis (Coghill et al., *Blood*, 2001, 117, 3268-3276), infectious colitis (Stallmach et al., *Int J Colorectal Dis*, 2004, 19, 308-315), Behcet's disease (Zhou et al., *Autoimmun Rev*, 2012, 11, 699-704), celiac disease (de Nitto et al., *World J Gastroenterol*, 2009, 15, 4609-4614), immune checkpoint inhibitor induced colitis (e.g., CTLA-4 inhibitor-induced colitis; (Yano et al., *J Translation Med*, 2014, 12, 191), PD-1- or PD-L1-inhibitor-induced colitis), and ileitis (Yamamoto et al., *Dig Liver Dis*, 2008, 40, 253-259) are characterized by elevation of certain pro-inflammatory cytokine levels. As many pro-inflammatory cytokines signal via JAK activation, compounds described in this application may be able to alleviate the inflammation and provide symptom relief.

In particular, the compounds of the disclosure may be useful for the induction and maintenance of remission of ulcerative colitis, and for the treatment of Crohn's disease, immune checkpoint inhibitor induced colitis, and the gastrointestinal adverse effects in graft versus host disease.

In one aspect, therefore, the invention provides a method of treating a gastrointestinal inflammatory disease in a mammal (e.g., a human), the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof.

The invention further provides a method of treating ulcerative colitis in a mammal, the method comprising administering to the mammal a compound of the disclosure, or a pharmaceutically acceptable salt thereof, or a pharmaceutical composition comprising a pharmaceutically-acceptable carrier and a compound of the disclosure, or a pharmaceutically acceptable salt thereof.

When used to treat ulcerative colitis, the compounds of the disclosure, or a pharmaceutically acceptable salt thereof will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating ulcerative colitis and other gastrointestinal inflammatory disorders are expected to range from about 1 to about 400 mg/day of active agent, including from about 5 to about 300 mg/day and from about 20 to about 70 mg per day of active agent for an average 70 kg human.

Combination Therapy

Compounds of the disclosure or a pharmaceutically acceptable salt thereof may also be used in combination with one or more agents which act by the same mechanism or by different mechanisms to effect treatment of gastrointestinal inflammatory disorders. The different agents may be administered sequentially or simultaneously (in separate compositions or in the same composition). Useful classes of agents for combination therapy include, but are not limited to, aminosalicylates, steroids, systemic immunosuppressants, anti-TNFα antibodies, TNF alpha ligand inhibitor, TNF binding agent, anti-VLA-4 antibodies, anti-integrin $\alpha_4\beta_7$ antibodies, anti-bacterial agents, Glucocorticoid agonists, Nuclear factor kappa B inhibitors, 5-Lipoxygenase inhibitors, integrin alpha-4/beta-7 antagonist, Cyclooxygenase inhibitors, IL-23 antagonists, Leukotriene BLT receptor antagonist, IL-6 antagonists, IL-8 antagonists, integrin antagonists, nicotinic acetylcholine receptor agonists, PPAR gamma agonists, sphingosine-1-phosphate receptor-1 modulators, B-lymphocyte antigen CD20 inhibitors, calcineurin inhibitors, CD3 antagonist, cell adhesion molecule inhibitors, eosinophil peroxidase inhibitors, heparin agonists, ICAM1 gene inhibitors, IL-13 antagonists, IL-2 receptor alpha subunit inhibitors, insulin sensitizers, interferon beta ligands, interferon gamma receptor antagonists, interleukin-1 beta ligand modulators, MAdCAM inhibitors, PDE 4 inhibitors, sphingosine-1-phosphate receptor-1 agonists, TLR-9 agonists, acetylcholinesterase inhibitors, ACTH receptor agonists, activin receptor antagonists, CCR5 chemokine antagonists, CCR9 chemokine antagonists, and anti-diarrheal medicines.

Aminosalicylates that may be used in combination with the present JAK inhibitor compounds include, but are not limited to, mesalamine, olsalazine and sulfasalazine. Examples of steroids include, but are not limited to, prednisone, prednisolone, hydrocortisone, budesonide, beclomethasone, and fluticasone. Systemic immunosuppressants useful for treatment of inflammatory disorders include, but are not limited to cyclosporine, azathioprine, methotrexate, 6-mercaptopurine, and tacrolimus. Further, anti-TNFα antibodies, which include, but are not limited to, infliximab, adalimumab, golimumab, and certolizumab, may be used in combination therapy. Useful compounds acting by other mechanisms include anti-VLA-4 antibodies, such as natalizumab, anti-integrin $\alpha_4\beta_7$ antibodies, such as vedolizumab, anti-bacterial agents, such as rifaximin, and anti-diarrheal medicines, such as loperamide. (Mozaffari et al. *Expert Opin. Biol. Ther.* 2014, 14, 583-600; Danese, *Gut,* 2012, 61, 918-932; Lam et al., *Immunotherapy,* 2014, 6, 963-971.)

Other compounds that may be used in combination with the present JAK inhibitor compounds include, but are not limited to opaganib, abatacept, mongersen, filgotinib, LYC-30937, BI-655130, mirikizumab, adalimumab, tacrolimus, rituximab, GSK-2982772, andecaliximab, naltrexone, risankizumab, QBECO, alicaforsen, etrolizumab, foralumab, ocrelizumab, vedolizumab, amiselimod, ozanimod, dolcanatide, catridecacog, budesonide, STNM-01, cannabidiol, telotristat etiprate, SHP-647, carotegrast methyl, peg-ilodecakin, TOP-1288, iberogast N, PF-06480605, peficitinib, beclomethasone, recombinant interferon beta-1a, infliximab, golimumab, tralokinumab, ustekinumab, certolizumab pegol, thalidomide, upadacitinib, apremilast, natalizumab, interferon beta-1a, rifaximin, RBX-2660, etrasimod, zileuton, fingolimod, cobitolimod, ropivacaine, ABX-464, PF-06700841, prednisolone, GLPG-0974, valganciclovir, ciclosporin, VB-201, tulinercept, MDGN-002, PTG-100, dexamethasone, GED-0507-34-Levo, bertilimumab, brazikumab, KHK-4083, rosiglitazone, mocravimod, sotrastaurin, KAG-308, PUR-0110, E-6007, balsalazide, basiliximab, LP-02, ASP-3291, *Trichuris suis* ova, K(D)PT, midismase, DNVX-078, vatelizumab, alequel, low molecular weight heparin, metenkefalin, tridecactide, HMPL-004, SB-012, olsalazine, balsalazide, propionyl-L-carnitine, *Clostridium butyricum*, beclomethasone and acemannan.

In another aspect, therefore, the invention provides a therapeutic combination for use in the treatment of gastrointestinal inflammatory disorders, the combination comprising a compound of the disclosure, or a pharmaceutically acceptable salt thereof, and one or more other therapeutic agents useful for treating gastrointestinal inflammatory disorders, such as the ones illustrated above. For example, the invention provides a combination comprising a compound of the disclosure, or a pharmaceutically acceptable salt thereof, and one or more agents selected from aminosalicylates, steroids, systemic immunosuppressants, anti-TNFα antibodies, anti-VLA-4 antibodies, anti-integrin $\alpha_4\beta_7$ antibodies, anti-bacterial agents, and anti-diarrheal medicines. Secondary agent(s), when included, are present in a therapeutically effective amount, i.e. in any amount that produces a therapeutically beneficial effect when co-administered with a compound of the disclosure or a pharmaceutically acceptable salt thereof.

Also provided, therefore, is a pharmaceutical composition comprising a compound of the disclosure, or a pharmaceutically acceptable salt thereof, or a crystalline form thereof, and one or more other therapeutic agents useful for treating gastrointestinal inflammatory disorders.

Further, in a method aspect, the invention provides a method of treating gastrointestinal inflammatory disorders, the method comprising administering to the mammal a compound of the disclosure, or a pharmaceutically acceptable salt thereof, or a crystalline form thereof, and one or more other therapeutic agents useful for treating gastrointestinal inflammatory disorders.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Inflammatory Skin Disease

Atopic dermatitis and other inflammatory skin diseases have been associated with elevation of proinflammatory cytokines that rely on the JAK-STAT pathway. Therefore, the compounds of the disclosure, or a pharmaceutically acceptable salt thereof, or a crystalline form thereof, may be beneficial in a number of dermal inflammatory or pruritic conditions that include, but are not limited to atopic dermatitis, alopecia areata, vitiligo, psoriasis, dermatomyositis, cutaneous T cell lymphoma (Netchiporouk et al., *Cell Cycle.* 2014; 13, 3331-3335) and subtypes (Sezary syndrome, mycosis fungoides, pagetoid reticulosis, granulomatous slack skin, lymphomatoid papulosis, pityriasis lichenoides chronica, pityriasis lichenoides et varioliformis acuta, CD30+ cutaneous T-cell lymphoma, secondary cutaneous CD30+ large cell lymphoma, non-mycosis fungoides CD30– cutaneous large T-cell lymphoma, pleomorphic T-cell lymphoma, Lennert lymphoma, subcutaneous T-cell lymphoma, angiocentric lymphoma, blastic NK-cell lymphoma), prurigo nodularis, lichen planus, primary localized cutaneous amyloidosis, bullous pemphigoid, skin manifestations of graft versus host disease, pemphigoid, discoid lupus, granuloma annulare, lichen simplex chronicus, vulvar/scrotal/perianal pruritus, lichen sclerosus, post herpetic neuralgia itch, lichen planopilaris, and foliculitis decalvans. In particular, atopic dermatitis (Bao et al., *JAK-STAT,* 2013, 2, e24137), alopecia areata (Xing et al., *Nat Med.* 2014, 20, 1043-1049), vitiligo (Craiglow et al, *JAMA Dermatol.* 2015, 151, 1110-1112), prurigo nodularis (Sonkoly et al., *J Allergy Clin Immunol.* 2006, 117, 411-417), lichen planus (Welz-Kubiak et al., *J Immunol Res.* 2015, ID:854747), primary localized cutaneous amyloidosis (Tanaka et al., *Br J Dermatol.* 2009, 161, 1217-1224), bullous pemphigoid (Feliciani et al., *Int J Immunopathol Pharmacol.* 1999, 12, 55-61), and dermal manifestations of graft versus host disease (Okiyama et al., *J Invest Dermatol.* 2014, 134, 992-1000) are characterized by elevation of certain cytokines that signal via JAK activation. Accordingly, compounds of the disclosure, or a pharmaceutically acceptable salt thereof, or a crystalline form thereof, may be able to alleviate associated dermal inflammation or pruritus driven by these cytokines. In particular, compounds of the disclosure, or a pharmaceutically acceptable salt thereof, or a crystalline form thereof, may be expected to be useful for the treatment of atopic dermatitis and other inflammatory skin diseases.

In one aspect, therefore, the invention provides a method of treating an inflammatory skin disease in a mammal (e.g., a human), the method comprising applying a pharmaceutical composition comprising a compound of the disclosure, or a pharmaceutically acceptable salt thereof, or a crystalline form thereof, and a pharmaceutical carrier to the skin of the mammal. In one aspect, the inflammatory skin disease is atopic dermatitis.

Compounds of the disclosure, or a pharmaceutically acceptable salt thereof, or a crystalline form thereof, may also be used in combination with one or more compound useful to treat inflammatory skin diseases. In some embodiments, the one or more compound is a steroid, Histamine H1 receptor antagonist, calcineurin inhibitor, IL-13 antagonist, PDE 4 inhibitor, G-protein coupled receptor-44 antagonist, IL-4 antagonist, 5-HT 1a receptor antagonist, 5-HT 2b receptor antagonist, Alpha 2 adrenoceptor agonist, cannabinoid CB1 receptor antagonist, CCR3 chemokine, antagonist, collagenase inhibitor, cytosolic phospholipase A2 inhibitor, eotaxin ligand inhibitor, GATA 3 transcription factor inhibitor, Histamine H4 receptor antagonist, IL-10 antagonist, IL-12 antagonist, IL-17 antagonist, IL-2 antagonist, IL-23 antagonist, IL-4 receptor modulator, IL-5 antagonist, immunoglobulin E antagonist, immunoglobulin E modulator, interferon gamma receptor antagonist, Interleukin 33 ligand inhibitor, Interleukin-31 receptor antagonist, Leukotriene antagonist, Liver X receptor agonist, Liver X receptor beta agonist, nuclear factor kappa B inhibitor, OX-40 receptor antagonist, PGD2 antagonist, phospholipase A2 inhibitor, SH2 domain inositol phosphatase 1 stimulator, thymic stromal lymphoprotein ligand inhibitor, TLR modulator, TNF alpha ligand modulator, or vanilloid VR1 antagonist. In some embodiments, the one or more compound is a gram positive antibiotic, such as mupirocin or fusidic acid. In some embodiments, the one or more compound is tranilast, tacrolimus, epinastine, SB-011, AM-1030, ZPL-521, MM-36, FB-825, PG-102, viromed, GBR-830, AVX-001, AMG-0101, E-6005, DMT-210, AX-1602, bertilimumab, rosiptor acetate, Q-301, ANB-020, VTP-38543, ZPL-389, lebrikizumab, tezepelumab, fexofenadine, pimecrolimus, bepotastine, crisaborole, tralokinumab, fevipiprant, doxycycline, desloratadine, ALX-101, nemolizumab, asivatrep, ciclosporin, mepolizumab, dupilumab, secukinumab, timapiprant, or ustekinumab.

In one aspect, therefore, the invention provides a method of treating an inflammatory skin disease in a mammal, the method comprising applying a compound of the disclosure, or a pharmaceutically acceptable salt thereof, or a crystalline form thereof, and a gram positive antibiotic to the skin of the mammal. In another aspect, the invention provides a pharmaceutical composition comprising a compound of the disclosure, or a pharmaceutically acceptable salt thereof, or a crystalline form thereof, a gram positive antibiotic, and a pharmaceutically-acceptable carrier.

Respiratory Diseases

Cytokines which signal through the JAK-STAT pathway, in particular IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF) have also been implicated in asthma inflammation and in other inflammatory respiratory diseases. As described above, the compounds of the disclosure have been shown to be potent inhibitors of JAK3 and have also demonstrated potent inhibition of IL-2 pro-inflammatory cytokines in cellular assays.

The anti-inflammatory activity of JAK inhibitors has been robustly demonstrated in preclinical models of asthma (Malaviya et al., *Int Immunopharmacol*, 2010, 10, 829-836; Matsunaga et al., *Biochem and Biophys Res Commun*, 2011, 404, 261-267; Kudlacz et al., *Eur J Pharmacol*, 2008, 582, 154-161.) Accordingly, the compounds of the disclosure, or a pharmaceutically acceptable salt thereof, or a crystalline form thereof, may be useful for the treatment of inflammatory respiratory disorders such as asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. The compounds of the disclosure, or a pharmaceutically acceptable salt thereof, therefore, may be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, and sarcoidosis.

In one aspect, therefore, the disclosure provides a method of treating a respiratory disease in a mammal (e.g., a human), the method comprising administering to the mammal a compound of the disclosure or a pharmaceutically-acceptable salt thereof, or a crystalline form thereof.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, bronchiolitis obliterans, bronchiolitis obliterans organizing pneumonia (also termed COS), primary Graft Dysfunction (PGD), organizing pneumonia (OP), acute rejection (AR), lymphocytic bronchiolitis (LB), chronic Lung Allograft Dysfunction (CLAD), restrictive CLAD (rCLAD or RAS), neutrophilic allograft dysfunction, allergic rhinitis or sarcoidosis. In another aspect, the respiratory disease is asthma or chronic obstructive pulmonary disease.

In a further aspect, the respiratory disease is a lung infection, a helminthic infection, pulmonary arterial hypertension, sarcoidosis, lymphangioleiomyomatosis, bronchiectasis, or an infiltrative pulmonary disease. In yet another aspect, the respiratory disease is drug-induced pneumonitis, fungal induced pneumonitis, allergic bronchopulmonary aspergillosis, hypersensitivity pneumonitis, eosinophilic granulomatosis with polyangiitis, idiopathic acute eosinophilic pneumonia, idiopathic chronic eosinophilic pneumonia, hypereosinophilic syndrome, Löffler syndrome, bronchiolitis obliterans organizing pneumonia, or immune-checkpoint-inhibitor induced pneumonitis.

The disclosure further provides a method of treating a respiratory disease, the method comprising administering to the mammal a pharmaceutical composition comprising a compound of the disclosure or a pharmaceutically-acceptable salt thereof, or a crystalline form thereof, and a pharmaceutically-acceptable carrier.

Compounds of the disclosure, or a pharmaceutically acceptable salt thereof, or a crystalline form thereof, may also be used in combination with one or more compound useful to respiratory diseases.

Ocular Diseases

Many ocular diseases have been shown to be associated with elevations of proinflammatory cytokines that rely on the JAK-STAT pathway.

The compounds of the disclosure, or a pharmaceutically acceptable salt thereof, or a crystalline form thereof, therefore, may be useful for the treatment of a number of ocular diseases that include, but are not limited to, uveitis, diabetic retinopathy, diabetic macular edema, dry eye disease, age-related macular degeneration, retinal vein occlusion (RVO) and atopic keratoconjunctivitis.

In particular, uveitis (Horai and Caspi, *J Interferon Cytokine Res*, 2011, 31, 733-744), diabetic retinopathy (Abcouwer, *J Clin Cell Immunol*, 2013, Suppl 1, 1-12), diabetic macular edema (Sohn et al., *American Journal of Opthamology*, 2011, 152, 686-694), dry eye disease (Stevenson et al, *Arch Ophthalmol*, 2012, 130, 90-100), retinal vein occlusion (Shchuko et al, *Indian Journal of Ophthalmology*, 2015, 63(12), 905-911) and age-related macular degeneration (Knickelbein et al, *Int Ophthalmol Clin*, 2015, 55(3), 63-78) are characterized by elevation of certain pro-inflammatory cytokines that signal via the JAK-STAT pathway. Accordingly, compounds of the disclosure, or a pharmaceutically acceptable salt thereof, may be able to alleviate the associated ocular inflammation and reverse disease progression or provide symptom relief.

In one aspect, therefore, the disclosure provides a method of treating an ocular disease in a mammal, the method comprising administering a pharmaceutical composition comprising a compound of the disclosure, or a pharmaceutically-acceptable salt thereof, or a crystalline form thereof, and a pharmaceutical carrier to the eye of the mammal. In one aspect, the ocular disease is uveitis, diabetic retinopathy, diabetic macular edema, dry eye disease, age-related macular degeneration, retinal vein occlusion or atopic keratoconjunctivitis. In one aspect, the method comprises administering the compound of the disclosure, or a pharmaceutically acceptable salt thereof, or a crystalline form thereof, by intravitreal injection.

Compounds of the disclosure, or a pharmaceutically acceptable salt thereof, or a crystalline form thereof, may also be used in combination with one or more compound useful to ocular diseases.

Other Diseases

The compounds of the disclosure, or a pharmaceutically acceptable salt thereof, or a crystalline form thereof, may also be useful to treat other diseases such as other inflammatory diseases, autoimmune diseases or cancers.

The compounds of the disclosure, or a pharmaceutically acceptable salt thereof, or a crystalline form thereof, may be useful to treat one or more of arthritis, rheumatoid arthritis, juvenile rheumatoid arthritis, transplant rejection, xerophthalmia, psoriatic arthritis, diabetes, insulin dependent diabetes, motor neurone disease, myelodysplastic syndrome, pain, sarcopenia, cachexia, septic shock, systemic lupus erythematosus, leukemia, chronic lymphocytic leukemia, chronic myelocytic leukemia, acute lymphoblastic leukemia, acute myelogenous leukemia, ankylosing spondylitis, myelofibrosis, B-cell lymphoma, hepatocellular carcinoma, Hodgkins disease, breast cancer, Multiple myeloma, melanoma, non-Hodgkin lymphoma, non-small-cell lung cancer, ovarian clear cell carcinoma, ovary tumor, pancreas tumor, polycythemia vera, Sjoegrens syndrome, soft tissue sarcoma, sarcoma, splenomegaly, T-cell lymphoma, and thalassemia major.

Compounds of the disclosure have been demonstrated to be potent inhibitors of the JAK3 enzyme and to be selective for JAK3 over JAK1, JAK2 and TYK2 in enzyme binding assays and to have potent functional activity for JAK3 in a cellular assay as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
Calcd=calculated
Boc=tert-Butyloxycarbonyl
d=day(s)
DIPEA=N,N-diisopropylethylamine
DMF=N,N-dimethylformamide
DMSO=dimethyl sulfoxide
EtOAc=ethyl acetate
EtOH=ethyl alcohol
h=hour(s)
HATU=N,N,N',N'-tetramethyl-O-(7-azabenzotriazol-1-yl)uronium hexafluorophosphate
IPA=isopropyl alcohol
MeOH=methanol
min=minute(s)
RT or rt=room temperature
SiG=Silica gel
TEA=triethylamine
THF=tetrahydrofuran
THP=tetrahydropyran
TFA=trifluoroacetic acid Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as $CD_3OD$, $CDCl_3$, or $d_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Unless otherwise indicated the following conditions were used for preparative HPLC purifications.
Column: C18, 5 µm 21.2×150 mm or C18, 5 µm 21×250 mm or C14, 5 µm 21×150 mm
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions
Method A
Column: LUNA C18 (2), 150×4.60 mm, 3 µm
Column temperature: 37° C.
Flow rate: 1.0 mL/min
Injection volume: 5 µL
Sample preparation: Dissolve in 1:1 ACN:water
Mobile Phases: A=Water:ACN:TFA (98:2:0.05)
    B=Water:ACN:TFA (2:98:0.05)
Detector wavelength: 250 nm
Gradient: 32 min total (time (min)/% B): 0/2, 10/20, 24/90, 29/90, 30/2, 32/2
Method B
Column: LUNA C18 (2), 150×4.60 mm, 3 µm
Column temperature: 37° C.
Flow rate: 1.0 mL/min
Injection volume: 10 µL
Sample preparation: Dissolve in 1:1 ACN:water
Mobile Phases: A=Water:ACN:TFA (98:2:0.05)
    B=Water:ACN:TFA (10:90:0.05)
Detector wavelength: 254 nm
Gradient: 35 min total (time (min)/% B): 0/2, 20/25, 23/90, 26/90, 27/2, 35/2

Powder X-ray diffraction patterns were obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 35° in 2θ with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle.

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 300° C.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300-350° C. The balance and furnace chambers were purged with nitrogen flow during use.

Dynamic moisture sorption (DMS) measurements were performed using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of an initial drying step (0% RH) for 120 minutes, followed by two cycles of sorption and desorption with a scan rate of 5% RH/step over the humidity range of 5% RH to 90% RH. The DMS run was performed isothermally at 25° C.

Preparation 1: 6-bromo-4-fluoro-1-(tetrahydro-2H-pyran-2-yl)-1H-indazole

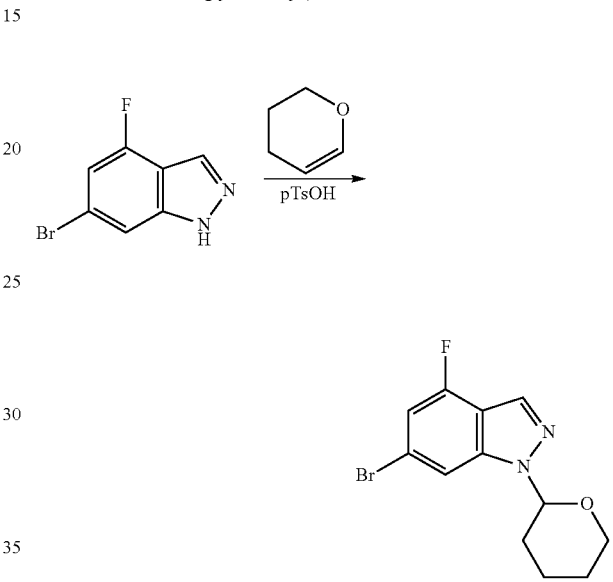

A mixture of 6-bromo-4-fluoro-1h-indazole (5 g, 23.25 mmol), 3,4-dihydro-2H-pyran (6.38 ml, 69.8 mmol) and p-toluenesulfonic acid monohydrate (0.442 g, 2.325 mmol) in DCM (76 ml) was stirred at rt overnight. The reaction was concentrated and the resulting residue was purified by flash column chromatography using a 0-60% EtOAc/Hexanes gradient to yield the desired product (6.08 g, 87% yield).

Preparation 2: tert-butyl 3-(((6-bromo-1-(tetrahydro-2H-pyran-2-yl)-1H-indazol-4-yl)oxy)methyl)azetidine-1-carboxylate

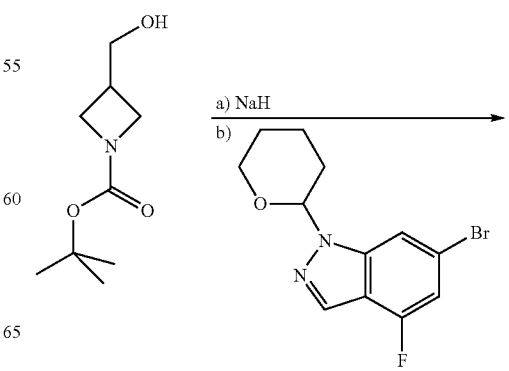

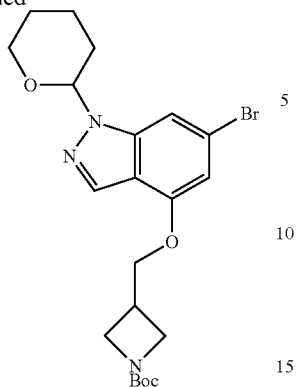

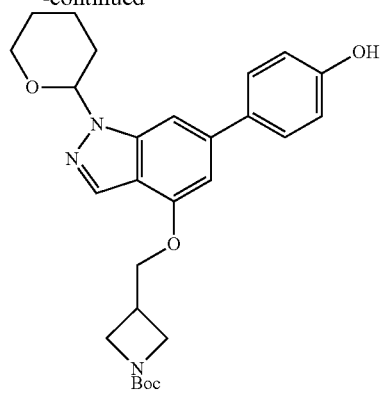

Sodium hydride (1.003 g, 41.8 mmol) was slowly added to a stirring solution of 1-Boc-Azetidine-3-yl-methanol (6.89 g, 36.8 mmol) in DMF (60 mL) under an atmosphere of $N_2$ at 0° C. and the reaction was allowed to warm to rt. The frothy reaction mixture was stirred for 30 minutes at rt before being cooled once again to 0° C. A solution of 6-bromo-4-fluoro-1-(tetrahydro-2H-pyran-2-yl)-1H-indazole (5.00 g, 16.71 mmol) in DMF (20 mL) was slowly cannulated into the reaction mixture, the reaction was warmed to rt and stirred for 2 hours at rt. The reaction was quenched with the slow addition of $H_2O$ (150 mL) and EtOAc (100 mL) and allowed to stir for 5 minutes. Additional water (100 mL) was added and the biphasic mixture was extracted with EtOAc (3×100 mL). The combined organic fractions were then washed with 1:1 $H_2O$:brine (3×100 mL) and dried over $Na_2SO_4$. The resulting clear slightly pink oil was purified by flash column chromatography using a 0-100% EtOAc/hexanes gradient to yield the desired product as a clear, colorless, viscous oil (7.34 g, 15.74 mmol, 94% yield). (m/z): [M+H]$^+$ calcd for $C_{21}H_{28}BrN_3O_4$ 466.13 found 466.1.

Preparation 3: tert-butyl 3-(((6-(4-hydroxyphenyl)-1-(tetrahydro-2H-pyran-2-yl)-1H-indazol-4-yl)oxy)methyl)azetidine-1-carboxylate

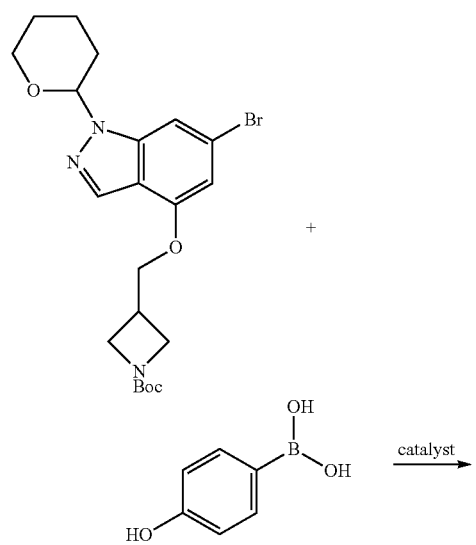

Dichloro[1,1'-bis(diphenylphosphino)ferrocene]palladium(II) dichloromethane adduct (1.93 g, 2.36 mmol) was added to a solution of 4-hydroxybenzeneboronic acid (3.26 g, 23.61 mmol), tert-butyl 3-(((6-bromo-1-(tetrahydro-2H-pyran-2-yl)-1H-indazol-4-yl)oxy)methyl)azetidine-1-carboxylate (7.34 g, 15.74 mmol), and potassium phosphate (10.02 g, 47.2 mmol) in 1,4-dioxane (63.0 ml) and water (15.74 ml). The reaction mixture was degassed with $N_2$ for 10 minutes and then stirred at 110° C. for 2 hours. The reaction mixture was concentrated in vacuo to a volume of about 5 mL. A saturated aqueous solution of ammonium chloride (20 mL) was added and the mixture was extracted with methylene chloride (3×20 mL). The methylene chloride extracts were combined, dried over sodium sulfate and concentrated in vacuo to yield a brown liquid. The crude liquid was purified via flash column chromatography using 50% ethyl acetate in hexanes to yield tert-butyl 3-(((6-(4-hydroxyphenyl)-1-(tetrahydro-2H-pyran-2-yl)-1H-indazol-4-yl)oxy)methyl)azetidine-1-carboxylate (7.55 g, 15.74 mmol, 100% yield). (m/z): [M+H]$^+$ calcd for $C_{27}H_{33}N_3O_5$ 480.24 found 480.1.

Preparation 4: 4-(4-(azetidin-3-ylmethoxy)-1H-indazol-6-yl)phenol

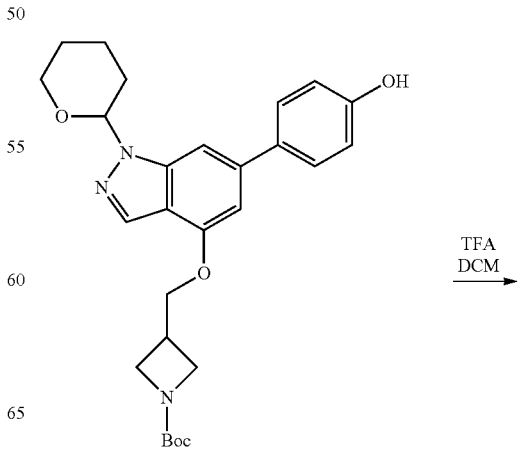

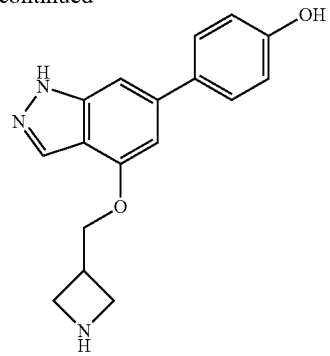

TFA (10.90 ml) was slowly added to a solution of tert-butyl 3-(((6-(4-hydroxyphenyl)-1-(tetrahydro-2H-pyran-2-yl)-1H-indazol-4-yl)oxy)methyl)azetidine-1-carboxylate (7.84 g, 16.35 mmol) in dichloromethane (21.80 ml). The clear solution was stirred at rt for 5 hours. The reaction was concentrated in vacuo to yield 4-(4-(azetidin-3-ylmethoxy)-1H-indazol-6-yl)phenol as a TFA salt (6.69 g, 16.35 mmol, 100% yield). (m/z): [M+H]$^+$ calcd for $C_{17}H_{17}N_3O_2$ 296.13 found 296.1.

Example 1A: (E)-4-(dimethylamino)-1-(3-(((6-(4-hydroxyphenyl)-1H-indazol-4-yl)oxy)methyl)azetidin-1-yl)but-2-en-1-one

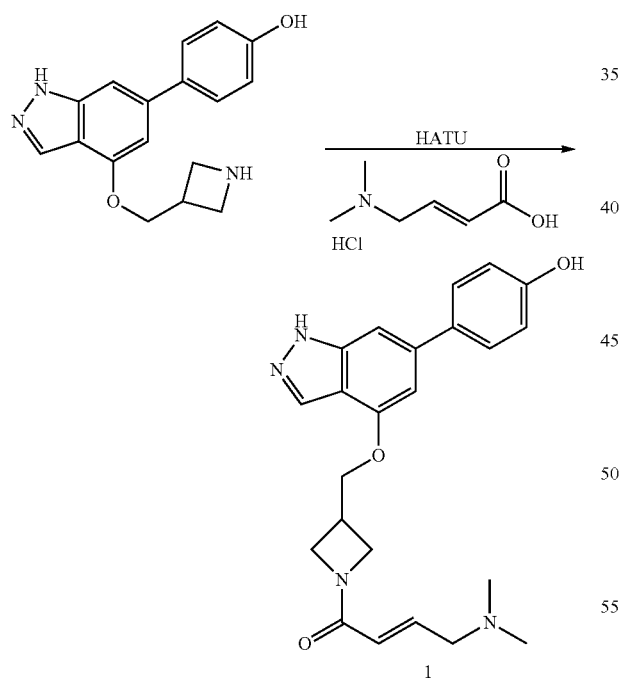

HATU (2-(7-aza-1H-benzotriazole-1-yl)-1,1,3,3-tetramethyluronium hexafluorophosphate, 817 mg, 2.150 mmol) was added to a solution of (E)-4-(dimethylamino)but-2-enoic acid hydrochloride (405 mg, 2.44 mmol) in DMF (2.00 mL) and the reaction mixture was stirred at rt for 5 minutes. 4-(4-(azetidin-3-ylmethoxy)-1H-indazol-6-yl)phenol TFA salt (800 mg, 1.954 mmol) was added, followed by DIPEA (1.707 ml, 9.77 mmol) and the reaction mixture was stirred at rt for 15 minutes and then concentrated in vacuo to yield a yellow liquid. The crude liquid was purified via preparatory scale C18 column chromatography using a gradient of 20-80% acetonitrile in water with 0.05% trifluoroacetic acid to yield (E)-4-(dimethylamino)-1-(3-(((6-(4-hydroxyphenyl)-1H-indazol-4-yl)oxy)methyl)azetidin-1-yl)but-2-en-1-one as a TFA salt (235.0 mg, 0.578 mmol, 29.6% yield). (m/z): [M+H]$^+$ calcd for $C_{23}H_{26}N_4O_3$ 407.20 found 407.2. 1H NMR (400 MHz, DMSO-d6) δ 13.07 (s, 1H), 10.33 (s, 1H), 7.93 (s, 1H), 7.55 (d, J=7.9 Hz, 2H), 7.21 (S, 1H), 6.86 (d, J=8.6 Hz, 2H), 6.79 (s, 1H), 6.66-6.58 (m, 1H), 6.45 (d, J=15.5 Hz, 1H), 4.45-4.36 (m, 2H), 4.17-4.07 (m, 2H), 3.91-3.83 (m, 3H), 3.22-3.10 (m, 2H), 2.75 (s, 6H).

Example 1B: Crystalline (E)-4-(dimethylamino)-1-(3-((((6-(4-hydroxyphenyl)-1H-indazol-4-yl)oxy)methyl)azetidin-1-yl)but-2-en-1-one Form 4

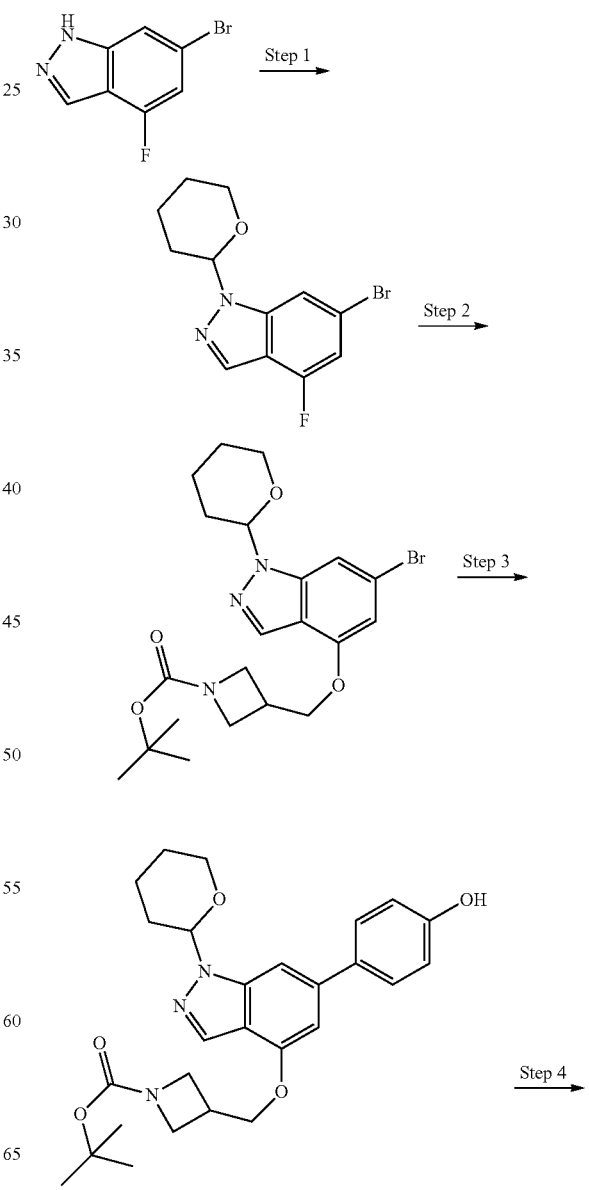

-continued

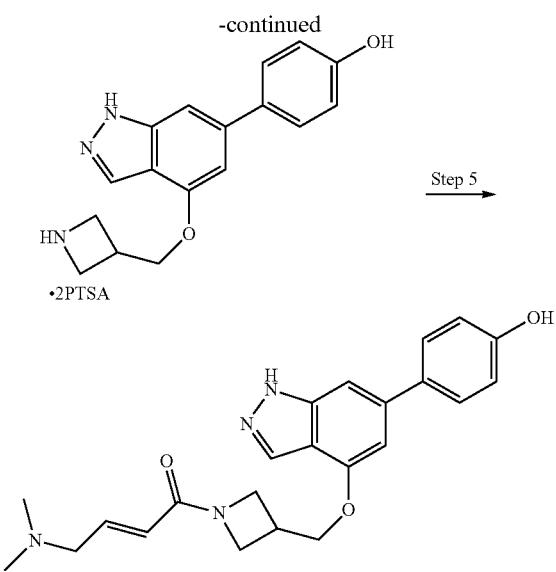

Step 1

To a suspension of 6-bromo-4-fluoro-1H-indazole (20.0 g, 93 mmol) in 200 ml of DCM, was added p-toluenesulfonic acid monohydrate (1.769 g, 9.30 mmol). The reaction mixture remained a suspension. 3,4-dihydro-2H-pyran (16.97 ml, 186 mmol) was then added. A complete dissolution of solids was observed after 5 minutes. The reaction mixture was stirred at RT overnight to form a dark solution. 200 mL of aqueous bicarbonate were added, the phases were separated and the organic layer was washed by 200 ml of brine and dried with sodium sulfate. The solution was filtered through silica plug to remove the dark color and the silica was washed with 300 ml of DCM. The solvent was evaporated to give 25 g of product as an off-white solid.

Step 2A

In a 500 ml round-bottomed flask was added tert-butyl 3-(hydroxymethyl)azetidine-1-carboxylate (22.53 g, 120 mmol) and 100 ml of dimethylacetamide (DMAc). The flask was purged with nitrogen. Cesium carbonate (39.2 g, 120 mmol) was added. 6-Bromo-4-fluoro-1-(tetrahydro-2H-pyran-2-yl)-1H-indazole (24 g, 80 mmol) was added and the reaction mixture was stirred at 70° C. for 2 days. An additional 0.5 eq of tert-butyl 3-(hydroxymethyl)azetidine-1-carboxylate and cesium carbonate were added and the reaction was heated at 70° C. overnight to provide full conversion. The reaction mixture was cooled to RT and then slowly poured into stirred ice-cold water (700 ml). The resulting slurry was stirred for 20 minutes and then filtered and dried to yield 32 g of product. The product was crystallized from methanol-water by adding water slowly as antisolvent until cloudiness. A white slurry developed over time. The solid was filtered and dried to yield 28 g of material over 98% pure.

Step 2B

Alternatively, potassium t-butoxide was added to a solution of tert-butyl 3-(hydroxymethyl)azetidine-1-carboxylate in DMAc at 0° C. After 60 minutes, 6-Bromo-4-fluoro-1-(tetrahydro-2H-pyran-2-yl)-1H-indazole was added at 0° C. and the reaction mixture was warmed up to room temperature giving clean complete conversion in less than 6 hours.

Step 3

In a 250 mL Schlenk flast was added tert-butyl 3-(((6-bromo-1-(tetrahydro-2H-pyran-2-yl)-1H-indazol-4-yl)oxy)methyl)azetidine-1-carboxylate (10.0 g, 21.44 mmol) and 80 ml of dioxane. (4-Hydroxyphenyl)boronic acid (4.44 g, 32.2 mmol) was added. Potassium phosphate tribasic anhydrous (13.65 g, 64.3 mmol) was added with 20 ml of water and the reaction mixture was purged with nitrogen. $PdCl_2(dppf)$-$CH_2Cl_2$ adduct (0.876 g, 1.072 mmol) was added and the flask with a condenser was re-filled with nitrogen three times. The reaction mixture was heated at 110° C. for 2 h and 30 minutes to show complete conversion by HPLC. The reaction mixture was cooled to RT followed by removal of most of the dioxane. 150 ml of saturated ammonium chloride was added followed by 150 ml of ethyl acetate. The pH was adjusted to neutral with 1M aq HCl. The phases were separated and the organic layer was dried with sodium sulfate followed by solvent removal. The crude product was dissolved in 150 ml of DCM and loaded on 300 g SiG column, eluted with 20-50% ethyl acetate in hexanes. The pure fractions were combined and the solvent was evaporated. 100 ml of MeTHF was added, followed by addition of crystalline seeds. A slurry developed over time. 100 ml of DIIPE was added and the slurry was stirred overnight. Filtration and drying yielded 7.9 g of pure material (>99%).

Step 4

In a 50 mL round-bottomed flask was added tert-butyl 3-(((6-(4-hydroxyphenyl)-1-(tetrahydro-2H-pyran-2-yl)-1H-indazol-4-yl)oxy)methyl)azetidine-1-carboxylate (85 g, 177 mmol) in 400 ml of methanol. p-Toluenesulfonic acid monohydrate (101 g, 532 mmol) was added and the reaction mixture was stirred at RT to give about 90% conversion after 2 days. The reaction mixture was stirred for another 24 hours at room temperature to give about 96% conversion. 400 ml of diisopropyl ether was added and the resulting slurry was stirred at room temperature overnight and formed a crystalline salt overnight. Filtration and drying under nitrogen yielded 100 g of >99% pure material as a bis PTSA salt.

Step 5

In a 100 mL round-bottomed flask was added (E)-4-(dimethylamino)but-2-enoic acid, HCl (1.899 g, 11.46 mmol) and 20 ml of DMF. HCTU o-(1h-6-chlorobenzotriazole-1-yl)-1,1,3,3-tetramethyluronium hexafluorophosphate (4.91 g, 11.46 mmol) was added and the reaction mixture was stirred at RT for 20 minutes. In a separate flask was added 4-(4-(azetidin-3-ylmethoxy)-1H-indazol-6-yl)phenol, 2TFA (5.0 g, 9.55 mmol) and 20 ml of DMF. The resulting solution was cooled to 0° C., followed by a slow addition of DIPEA (5 ml, 38.2 mmol, 3 eq). The above solution was added (over 5 minutes) to the pre-activated acid reaction mixture and the reaction mixture was stirred at room temperature for 15 minutes. One additional equivalent of DIPEA was added dropwise. Complete conversion was observed by HPLC after 20 minutes at room temperature. The reaction mixture was poured into 200 ml of stirred water. Sticky solids precipitated out at pH around 7. The pH was carefully adjusted to about 8 with aqueous ammonia. The solution was extracted three times with 100 ml of MeTHF. The combined organic layers were dried with sodium sulfate followed by solvent removal. The crude free base product was dissolved in 25 ml of 10% methanol in DCM, loaded on 125 g silica gel column and eluted with isocratic 10% methanol in DCM containing 0.5% aqueous ammonia. The pure fractions were combined and the solvent was evaporated. Recrystallization from acetone yielded >98% pure material (50% yield).

25 mg of compound 1 was suspended in 1 mL of water. The resulting suspension was stirred for 2 days at 50° C., filtered, washed with 2 mL of water and dried under ambient conditions for a few hours to provide Form 4.

Alternatively, compound 1 was dissolved in ethanol and water or methanol and water by complete dissolution in 10 volumes of alcohol followed by slow addition of approximately 8-10 volumes of water until cloud point. Seeds of Form 4 were added and a slurry developed slowly over time. Then more water was added slowly (about 10 volumes) and the solid was filtered and dried to give Form 4.

Example 1C: Crystalline (E)-4-(dimethylamino)-1-(3-(((6-(4-hydroxyphenyl)-1H-indazol-4-yl)oxy)methyl)azetidin-1-yl)but-2-en-1-one Form 3

Form 3 is an anhydrous free base crystalline form of compound 1.

150 mg of compound 1 was suspended in 2 mL of a 1:1 mixture of acetonitrile and isopropanol. The resulting suspension was stirred for 1 day at 50° C., filtered, washed with 2 mL of a 1:1 mixture of acetonitrile and isopropanol and dried under ambient conditions for a few hours to provide Form 3, which was determined to be a crystalline anhydrous free base.

Alternatively, 200 mg of compound 1 as an amorphous free base was dissolved in 2 ml of IPA at RT. An equal amount of acetonitrile was added. More compound (0.5 g total) was added until a saturated solution formed. Seeds were added and the mixture was stirred overnight. A white slurry developed over time. Filtration and drying yielded 400 mg of product as Form 3, which was determined to be an anhydrous free base.

Example 1D: Characterization of Form 3

Figure 9:
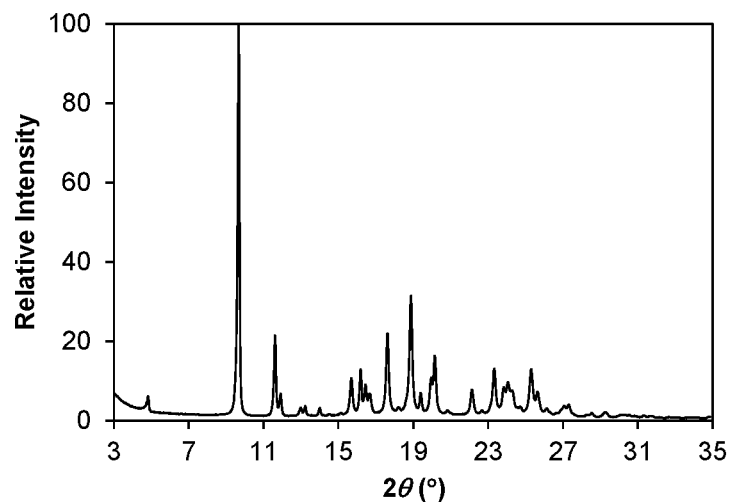
FIG. 9 shows a powder x-ray diffraction (PXRD) pattern of crystalline Form 3 of compound 1 (hereinafter Form 3).

Samples of Form 3 were analyzed by powder X-ray diffraction (PXRD), differential scanning calorimetry (DSC), thermogravimetric analysis (TGA), and dynamic moisture sorption (DMS).
Powder X-Ray Diffraction
The powder X-ray diffraction pattern of Form 3 is shown in FIG. 9.
Observed PXRD two-theta peak positions and d-spacings are shown below.

| 2-Theta | d(Å) | Area | A % |
|---|---|---|---|
| 4.82 | 18.32 | 16367 | 2.7 |
| 9.67 | 9.14 | 610151 | 100.0 |
| 11.61 | 7.61 | 140214 | 23.0 |
| 11.92 | 7.42 | 49009 | 8.0 |
| 12.98 | 6.81 | 21804 | 3.6 |
| 13.23 | 6.69 | 21840 | 3.6 |
| 15.69 | 5.64 | 88944 | 14.6 |
| 16.19 | 5.47 | 89861 | 14.7 |
| 16.45 | 5.38 | 74091 | 12.1 |
| 16.67 | 5.31 | 57780 | 9.5 |
| 17.61 | 5.03 | 158810 | 26.0 |
| 18.88 | 4.70 | 261799 | 42.9 |
| 19.39 | 4.57 | 26844 | 4.4 |
| 19.96 | 4.45 | 164339 | 26.9 |
| 20.14 | 4.40 | 125226 | 20.5 |
| 22.14 | 4.01 | 52100 | 8.5 |
| 23.33 | 3.81 | 74095 | 12.1 |
| 23.84 | 3.73 | 166452 | 27.3 |
| 24.06 | 3.70 | 200590 | 32.9 |
| 24.29 | 3.66 | 79151 | 13.0 |
| 25.31 | 3.52 | 119197 | 19.5 |
| 25.63 | 3.47 | 88838 | 14.6 |
| 27.06 | 3.29 | 62513 | 10.2 |
| 27.31 | 3.26 | 47507 | 7.8 |
| 30.10 | 2.97 | 18475 | 3.0 |
| 30.53 | 2.93 | 16406 | 2.7 |

Thermal Analysis

Figure 10:
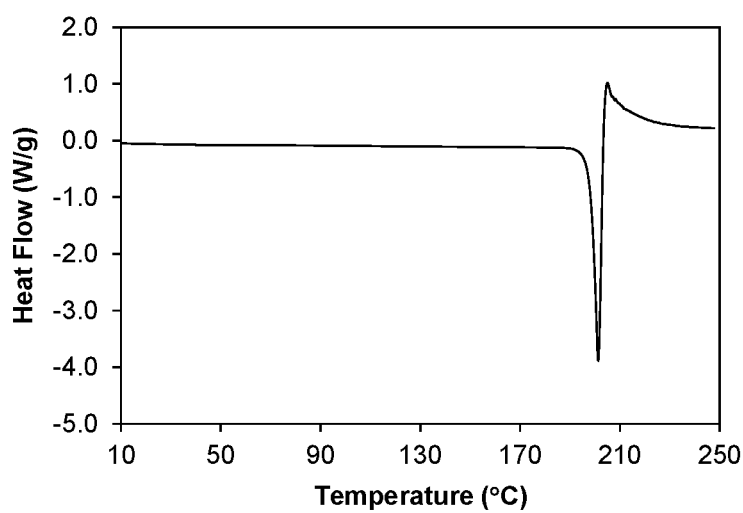
FIG. 10 shows a differential scanning calorimetry (DSC) thermogram of crystalline Form 3.

A representative DSC thermogram of the Form 3 crystalline free form of the invention is shown in FIG. 10. The differential scanning calorimetry (DSC) trace recorded at a heating rate of 10° C. per minute exhibits a peak in endothermic heat flow, identified as a melt transition, with an onset at about 197.7° C. and a peak at about 201.3° C. Melting was followed immediately by decomposition.

The crystalline form is characterized by a differential scanning calorimetry trace recorded at a heating rate of 10° C. per minute which shows a maximum in endothermic heat flow with a peak at about 201.3° C.

The crystalline form is characterized by a differential scanning calorimetry trace recorded at a heating rate of 10° C. per minute which shows a maximum in endothermic heat flow at a temperature between about 197.7° C. and about 204° C.

A representative TGA trace of the Form 3 crystalline free form of the invention is shown in FIG. 11. The thermal gravimetric analysis (TGA) trace of FIG. 11 shows no significant weight loss at temperatures below the onset of decomposition at about 195° C.
Dynamic Moisture Sorption Assessment A representative DMS trace for the Form 3 crystalline free form of the invention is shown in FIG. 12.

Form 3 demonstrated about 0.33% weight gain in the humidity range of 5% to 90% relative humidity. Form 3 is considered to be non-hygroscopic.

Example 1E: Characterization of Form 4

Figure 13:
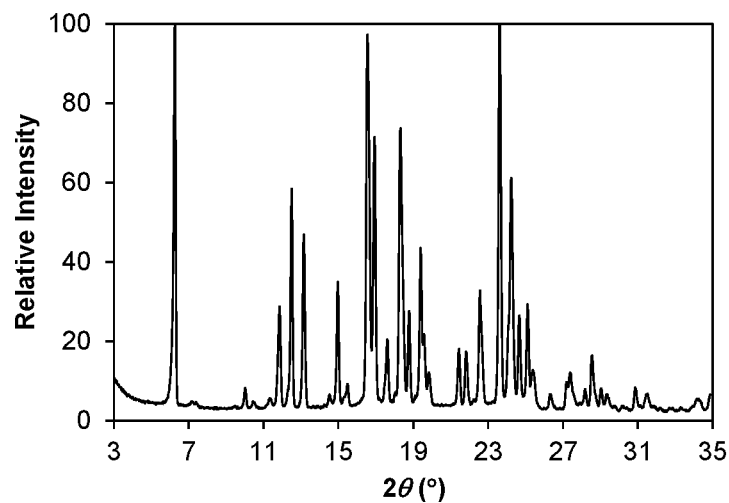
FIG. 13 shows a powder x-ray diffraction (PXRD) pattern of crystalline Form 4 of compound 1 (hereinafter Form 4).

Samples of Form 4 were analyzed by powder X-ray diffraction (PXRD), differential scanning calorimetry (DSC), thermogravimetric analysis (TGA), and dynamic moisture sorption (DMS).
Powder X-Ray Diffraction
The powder X-ray diffraction pattern of Form 4 is shown in FIG. 13.
Observed PXRD two-theta peak positions and d-spacings are shown below.

| 2-Theta | d(Å) | Area | A % |
|---|---|---|---|
| 6.26 | 14.10 | 161835 | 73.90 |
| 11.86 | 7.46 | 51703 | 23.60 |
| 12.51 | 7.07 | 82712 | 37.80 |
| 13.16 | 6.72 | 72445 | 33.10 |
| 14.98 | 5.91 | 53903 | 24.60 |
| 16.55 | 5.35 | 218849 | 100.00 |
| 16.94 | 5.23 | 133498 | 61.00 |
| 17.61 | 5.03 | 28496 | 13.00 |
| 18.33 | 4.84 | 170874 | 78.10 |
| 18.78 | 4.72 | 35644 | 16.30 |
| 19.39 | 4.57 | 92940 | 42.50 |
| 19.57 | 4.53 | 86983 | 39.70 |
| 19.84 | 4.47 | 19121 | 8.70 |
| 21.45 | 4.14 | 22435 | 10.30 |
| 21.82 | 4.07 | 22934 | 10.50 |
| 22.57 | 3.94 | 62931 | 28.80 |
| 23.61 | 3.76 | 162063 | 74.10 |
| 24.24 | 3.67 | 135952 | 62.10 |
| 24.67 | 3.61 | 38471 | 17.60 |
| 25.10 | 3.54 | 55236 | 25.20 |
| 25.39 | 3.51 | 32363 | 14.80 |
| 27.19 | 3.28 | 27010 | 12.30 |
| 27.39 | 3.25 | 32148 | 14.70 |
| 28.55 | 3.12 | 24879 | 11.40 |
| 31.51 | 2.84 | 18975 | 8.70 |

Thermal Analysis

Figure 14:
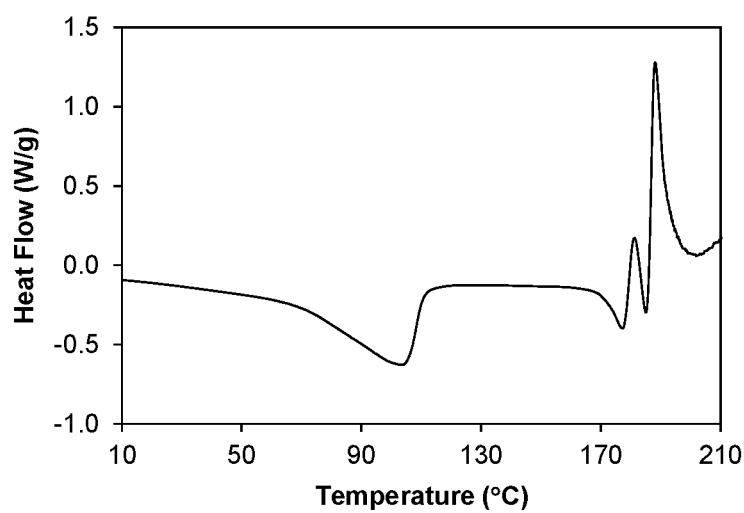
FIG. 14 shows a differential scanning calorimetry (DSC) thermogram of crystalline Form 4.

A representative DSC thermogram of the Form 4 crystalline free form is shown in FIG. 14. The differential scanning calorimetry (DSC) trace recorded at a heating rate of 10° C. per minute exhibits a desolvation endotherm with an onset at about 60.9° C. and a peak at about 103.6° C., and a melting endotherm characterized by an onset at about 167.3° C. The compound decomposes at melting and the melting endotherm and the decomposition exotherm overlap.

A representative TGA trace of the Form 4 crystalline free form is shown in FIG. 15. The thermal gravimetric analysis (TGA) trace of FIG. 15 shows a weight loss of about 3.54% at 100° C. The compound desolvates at an onset temperature of about 50° C. The compound decomposes at an onset temperature of about 165° C.

Dynamic Moisture Sorption Assessment

A representative DMS trace for the Form 4 crystalline free form is shown in FIG. 16.

Form 4 demonstrated about 5.01% weight gain in the humidity range of 5% to 90% relative humidity. Form 4 is considered to be moderately hygroscopic.

Preparation 5: tert-butyl (3S)-3-((6-bromo-1-(tetrahydro-2H-pyran-2-yl)-1H-indazol-4-yl)oxy)pyrrolidine-1-carboxylate

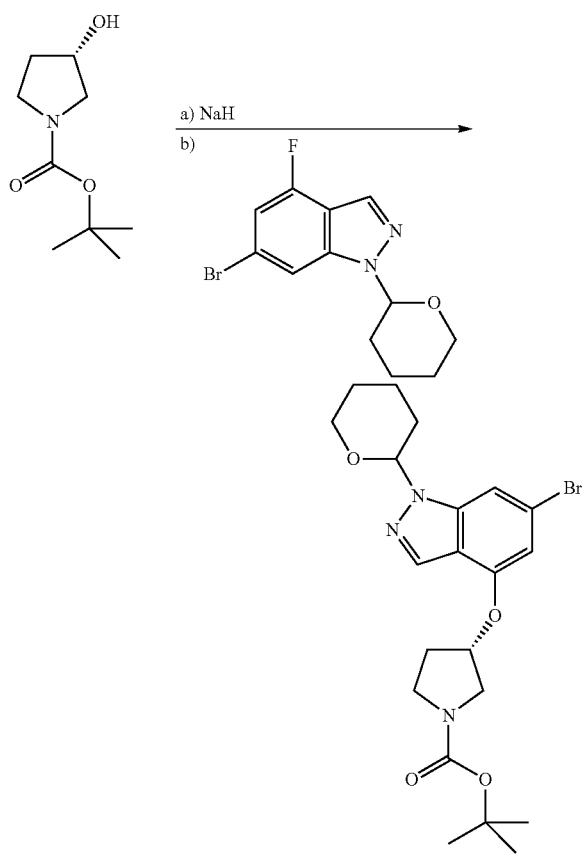

Sodium hydride (0.201 g, 8.36 mmol) was added to a solution of (S)—N-boc-3-pyridinol (1.25 g, 6.69 mmol) in DMF (12 ml) under an atmosphere of N$_2$ at 0° C. and the reaction mixture was stirred at rt for 20 minutes. 6-bromo-4-fluoro-1-(tetrahydro-2H-pyran-2-yl)-1H-indazole (1.0 g, 3.34 mmol) was added and the reaction mixture was stirred at rt for 1 hour. Water (1 mL) was added and the reaction was concentrated in vacuo. The crude material was purified via flash column chromatography using 40% ethyl acetate in hexanes to yield tert-butyl (3S)-3-((6-bromo-1-(tetrahydro-2H-pyran-2-yl)-1H-indazol-4-yl)oxy)pyrrolidine-1-carboxylate (1.40 g, 3.00 mmol, 90% yield). (m/z): [M+H]$^+$ calcd for C$_{21}$H$_{28}$BrN$_3$O$_4$ 466.13 found 466.1.

Preparation 6: tert-butyl (3S)-3-((6-(3-chloro-4-hydroxyphenyl)-1-(tetrahydro-2H-pyran-2-yl)-1H-indazol-4-yl)oxy)pyrrolidine-1-carboxylate

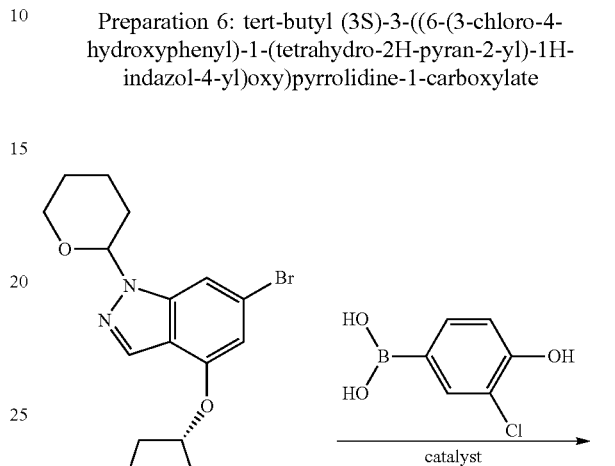

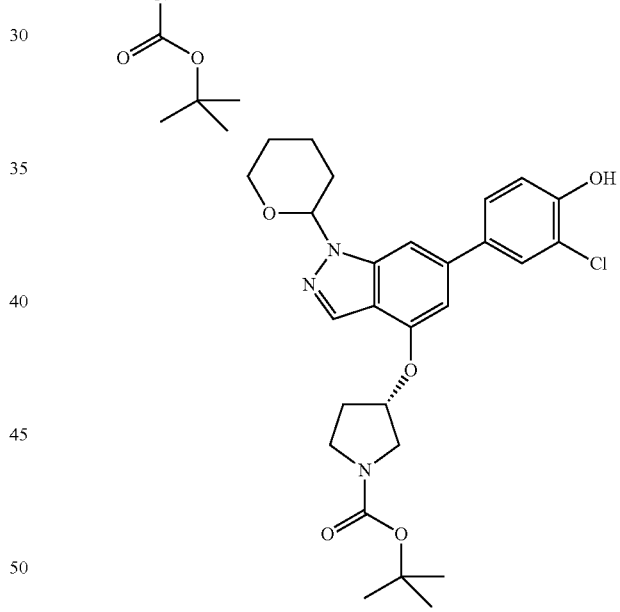

Palladium acetate (0.135 g, 0.600 mmol) was added to a solution of 3-chloro-4-hydroxyphenylboronic acid (0.776 g, 4.50 mmol), tert-butyl (3S)-3-((6-bromo-1-(tetrahydro-2H-pyran-2-yl)-1H-indazol-4-yl)oxy)pyrrolidine-1-carboxylate (1.40 g, 3.00 mmol), 1,1'-bis(di-t-butylphosphino)ferrocene (0.285 g, 0.600 mmol) and potassium phosphate (1.912 g, 9.01 mmol) in 1,4-dioxane (12 ml) and water (3.00 ml). The reaction mixture was degassed with nitrogen for 10 minutes and then stirred at 110° C. for 2 hours. The reaction mixture was concentrated in vacuo to a volume of about 5 mL. A saturated aqueous solution of ammonium chloride (20 mL) was added and the mixture was extracted with methylene chloride (3×20 mL). The methylene chloride extracts were combined, dried over sodium sulfate and concentrated in vacuo to yield a brown liquid. The crude liquid was purified via flash column chromatography using 50% ethyl acetate in hexanes to yield tert-butyl (3S)-3-((6-(3-chloro-4-hydroxyphenyl)-1-(tetrahydro-2H-pyran-2-yl)-1H-indazol-4-yl)oxy)pyrrolidine-1-carboxylate (1.35 g, 2.63 mmol, 87% yield) as a clear yellow liquid. (m/z): [M+H]+ calcd for C27H32ClN3O5 514.20 found 514.2.

Preparation 7: (S)-2-chloro-4-(4-(pyrrolidin-3-yloxy)-1H-indazol-6-yl)phenol

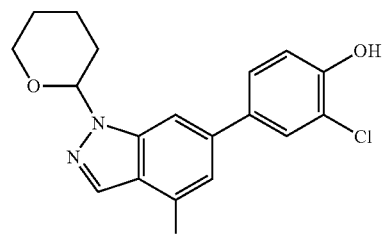

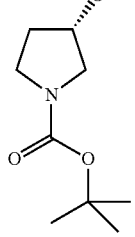

4.0N HCl in dioxane (13.13 ml, 52.5 mmol) was added to a solution of tert-butyl (3S)-3-((6-(3-chloro-4-hydroxyphenyl)-1-(tetrahydro-2H-pyran-2-yl)-1H-indazol-4-yl)oxy)pyrrolidine-1-carboxylate (1.35 g, 2.63 mmol) in dioxane (6 ml), and the reaction mixture was stirred at 60° C. for 30 minutes. The reaction mixture was concentrated in vacuo to yield (S)-2-chloro-4-(4-(pyrrolidin-3-yloxy)-1H-indazol-6-yl)phenol as an HCl salt (0.962 g, 2.63 mmol, 100% yield). (m/z): [M+H]+ calcd for C17H16ClN3O2 330.09 found 330.2.

Example 2: (S)-1-(3-((6-(3-chloro-4-hydroxyphenyl)-1H-indazol-4-yl)oxy)pyrrolidin-1-yl)prop-2-en-1-one

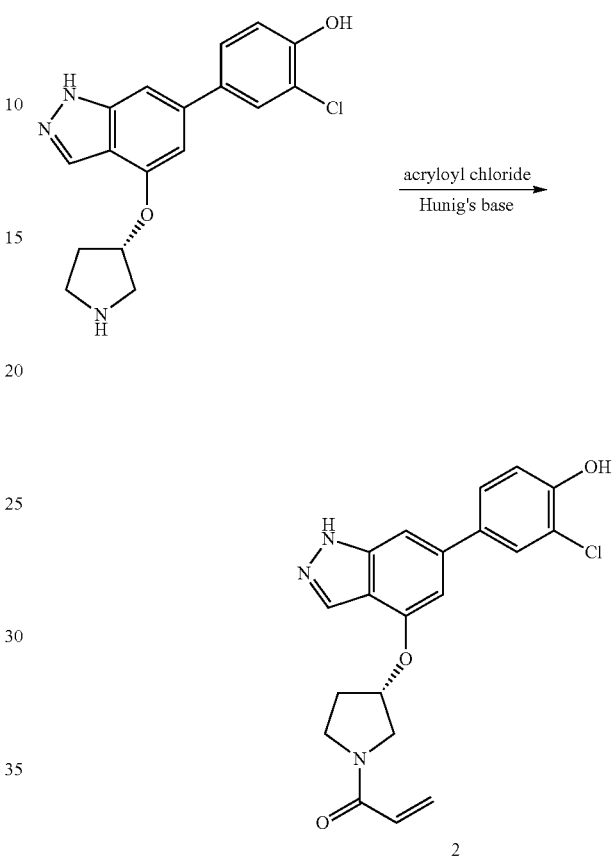

N,N-Diisopropylethylamine (4.59 ml, 26.3 mmol) was added to a solution of (S)-2-chloro-4-(4-(pyrrolidin-3-yloxy)-1H-indazol-6-yl)phenol HCl salt (0.962 g, 2.63 mmol) in DMF (13.0 ml) at 0° C., followed by acryloyl chloride (0.277 ml, 3.41 mmol). The reaction mixture was stirred at rt for 15 minutes then concentrated to a volume of about 2 mL. The crude liquid was purified via preparatory scale C18 column chromatography using a gradient of 20-80% acetonitrile in water with 0.05% trifluoroacetic acid to yield (S)-1-(3-((6-(3-chloro-4-hydroxyphenyl)-1H-indazol-4-yl)oxy)pyrrolidin-1-yl)prop-2-en-1-one as a TFA salt (344 mg, 0.691 mmol, 26.3% yield). (m/z): [M+H]+ calcd for C20H18ClN3O3 384.10 found 384.1. 1H NMR (400 MHz, DMSO-d6) δ 13.03 (s, 1H), 10.33 (s, 1H), 7.98 (s, 1H), 7.74-7.67 (m, 1H), 7.57-7.49 (m, 1H), 7.24 (s, 1H), 7.07 (d, J=0.5 Hz, 1H), 6.80 (s, 1H), 6.69-6.56 (m, 1H), 6.18-6.11 (m, 1H), 5.71-5.62 (m, 1H), 4.01-3.60 (m, 5H), 2.35-2.14 (m, 2H).

Preparation 8: tert-butyl 3-(2-((6-bromo-1-(tetrahydro-2H-pyran-2-yl)-1H-indazol-4-yl)oxy)propan-2-yl)azetidine-1-carboxylate

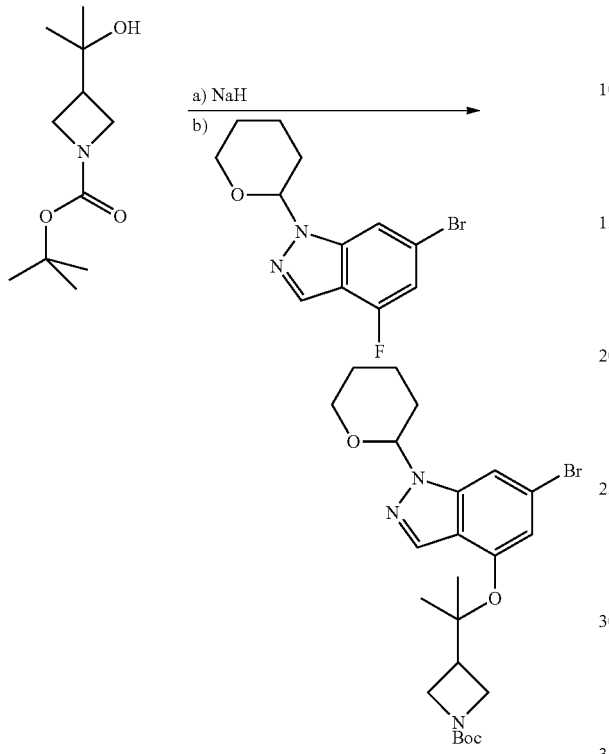

To a dry scintillation vial purged with N₂, tert-butyl 3-(2-hydroxypropan-2-yl)azetidine-1-carboxylate (374 mg, 1.74 mmol) was added, dissolved in 2.4 mL DMF and the solution was cooled to 0° C. 60% by weight sodium hydride in mineral oil (134 mg, 3.34 mmol) was slowly added to the stirring solution and the reaction was allowed to warm to rt following the addition. The frothy reaction was stirred for 30 minutes before being cooled once again to 0° C. A solution of 6-bromo-4-fluoro-1-(tetrahydro-2H-pyran-2-yl)-1H-indazole (400 mg, 1.34 mmol) in 1 mL DMF was slowly added into the scintillation vial containing the organosodium solution. Following the addition, the reaction was warmed to rt and stirred for 2 hours upon which LCMS indicated full conversion of the starting material to the desired product. The reaction was quenched with the slow addition of 1 mL H₂O and 1 mL EtOAc, which was allowed to stir for 5 minutes. The biphasic solution was then transferred to a separatory funnel and an additional 5 mL H₂O were added. The mixture was extracted with 3 times 10 mL of EtOAc and the aqueous layer was discarded. The combined organic fractions were then washed with 3×10 mL 1:1 H₂O:brine to remove residual DMF. The organic was then dried over Na₂SO₄, filtered, and concentrated to a lightly yellow oil. The oil was then purified by flash column chromatography using a 0-40% EtOAc:hexanes gradient. The product was isolated pure as a clear, colorless, viscous oil (288 mg, 44% yield).

Preparation 9: tert-butyl 3-(2-((6-bromo-1-(tetrahydro-2H-pyran-2-yl)-1H-indazol-4-yl)oxy)propan-2-yl)azetidine-1-carboxylate

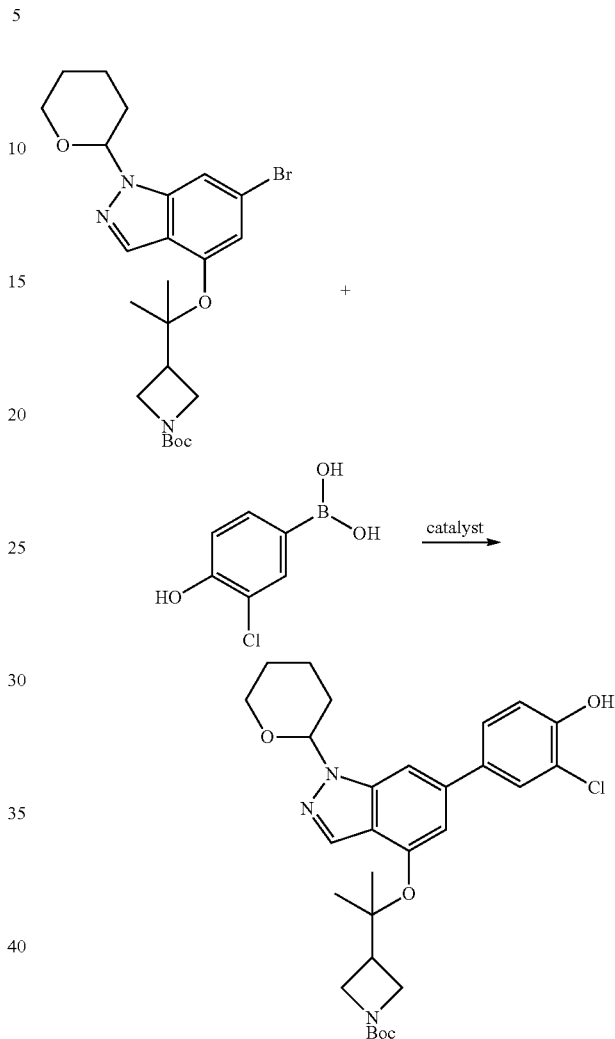

A 1:1 mixture of Palladium acetate (26.2 mg, 0.116 mmol) and 1,1'-Bis(di-t-butylphosphino)ferrocene (55.3 mg, 0.116 mmol) was added to a solution of 3-chloro-4-hydroxybenzeneboronic acid (151 mg, 0.874 mmol), tert-butyl 3-(2-((6-bromo-1-(tetrahydro-2H-pyran-2-yl)-1H-indazol-4-yl)oxy)propan-2-yl)azetidine-1-carboxylate (288 mg, 0.582 mmol), and potassium phosphate (371 mg, 1.747 mmol) in 1,4-dioxane (2.0 ml) and water (0.50 ml). The reaction mixture was degassed with nitrogen for 10 minutes and then stirred at 110° C. for 2 hours. The reaction mixture was concentrated in vacuo to a volume of about 5 mL. A saturated aqueous solution of ammonium chloride (5 mL) was added and the mixture was extracted with ethyl acetate (2×5 mL). The ethyl acetate extracts were combined, dried over sodium sulfate and concentrated in vacuo to yield a brown liquid. The crude liquid was purified via flash column chromatography using 40% ethyl acetate in hexanes to yield tert-butyl 3-(2-((6-bromo-1-(tetrahydro-2H-pyran-2-yl)-1H-indazol-4-yl)oxy)propan-2-yl)azetidine-1-carboxylate (230 mg, 0.424 mmol, 73% yield). (m/z): $[M+H]^+$ calcd for $C_{29}H_{36}N_3O_5$ 542.24 found 542.3.

Preparation 10: 4-(4-((2-azetidin-3-yl)propan-2-yl)oxy)-1-H-indazole-6-yl)-2-chlorophenol

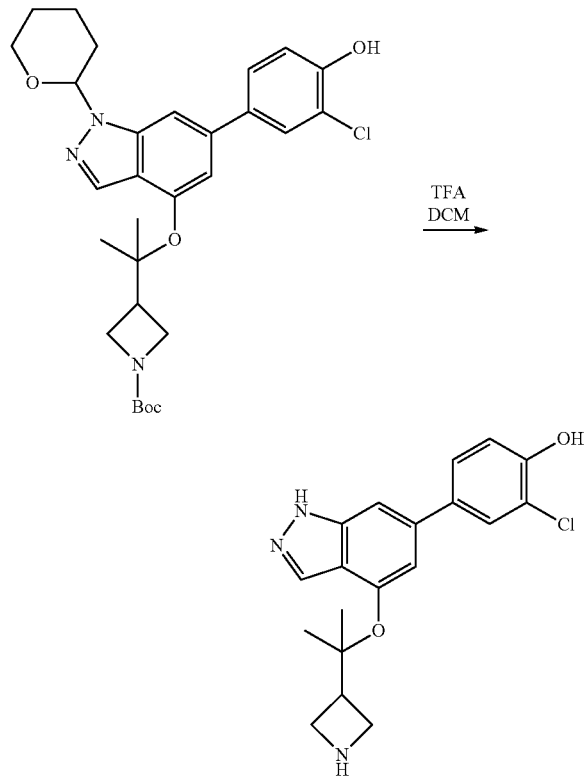

Tert-butyl 3-(2-((6-bromo-1-(tetrahydro-2H-pyran-2-yl)-1H-indazol-4-yl)oxy)propan-2-yl)azetidine-1-carboxylate (230 mg, 0.424 mmol) was dissolved in dichloromethane (1 ml) and TFA (1 ml) was slowly added. The clear solution was stirred at rt for 5 hours upon which LCMS indicated good conversion to the desired product. The reaction was concentrated down to provide 4-(4-((2-azetidin-3-yl)propan-2-yl)oxy)-1-H-indazole-6-yl)-2-chlorophenol as a TFA salt (100% yield). (m/z): [M+H]$^+$ calcd for $C_{19}H_{20}N_3O_2$ 358.13 found 358.1.

Example 3A: (E)-1-(3-(2-((6-(3-chloro-4-hydroxyphenyl)-1H-indazol-4-yl)oxy)propan-2-yl)azetidin-1-yl)-4-(dimethylamino)but-2-en-1-one

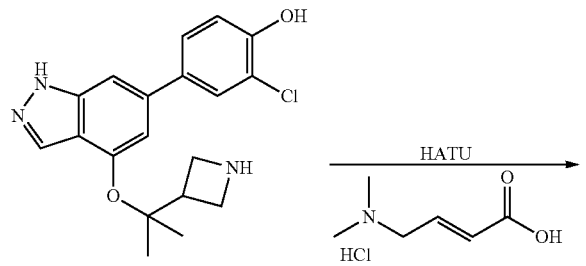

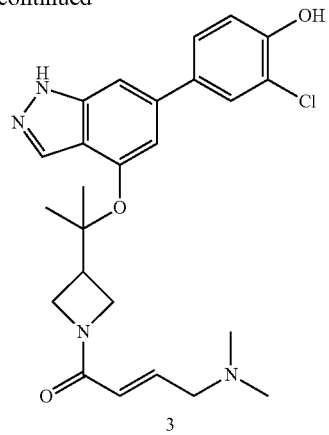

HATU (2-(7-aza-1H-benzotriazole-1-yl)-1,1,3,3-tetramethyluronium hexafluorophosphate, 100 mg, 0.263 mmol) was added to a solution of (E)-4-(dimethylamino)but-2-enoic acid hydrochloride (34 mg, 0.263 mmol) in DMF (1 mL). The reaction mixture was stirred at rt for 5 minutes then 4-(4-((2-azetidin-3-yl)propan-2-yl)oxy)-1-H-indazole-6-yl)-2-chlorophenol TFA salt (118 mg, 0.251 mmol) was added, followed by DIPEA (0.438 ml, 2.507 mmol). The reaction mixture was stirred at rt for 15 minutes and then concentrated in vacuo to yield a yellow liquid. The crude liquid was purified via preparatory scale SFC (supercritical fluid chromatography) using methanol with liquid carbon dioxide to yield (E)-1-(3-(2-((6-(3-chloro-4-hydroxyphenyl)-1H-indazol-4-yl)oxy)propan-2-yl)azetidin-1-yl)-4-(dimethylamino)but-2-en-1-one (41.3 mg, 0.084 mmol, 33% yield). (m/z): [M+H]$^+$ calcd for $C_{25}H_{29}ClN_4O_3$ 469.20 found 469.2. $^1$H NMR (400 MHz, DMSO-d$_6$) δ 13.07 (s, 1H), 10.33 (s, 1H), 7.95 (s, 1H), 7.62 (d, J=2.3 Hz, 1H), 7.47 (dd, J=8.5, 2.3 Hz, 1H), 7.34 (S, 1H), 7.04 (d, J=8.5 Hz, 1H), 6.85 (d, J=1.1 Hz, 1H), 6.63-6.53 (m, 1H), 6.39 (d, J=15.3 Hz, 1H), 4.37-4.23 (m, 2H), 4.11-3.91 (m, 2H), 3.69 (d, J=6.4 Hz, 2H), 3.02-2.90 (m, 1H), 2.62 (s, 9H), 1.32 (S, 9H).

Example 3B: Crystalline (E)-1-(3-(2-((6-(3-chloro-4-hydroxyphenyl)-1H-indazol-4-yl)oxy)propan-2-yl)azetidin-1-yl)-4-(dimethylamino)but-2-en-1-one
Form 1

Form 1 is an anhydrous freebase crystalline form of compound 3.

80 mg of compound 3 as an amorphous freebase was dissolved in 0.5 mL of ethanol. The resulting mixture was stirred for one day at room temperature and yielded a precipitate. The solid was isolated by filtration, washed with 1 mL of ethanol and dried under ambient conditions for a few hours to give Form 1.

Alternatively, in a 50 mL round-bottomed flask, was added compound 3 which had been purified by SiG (1.3 g, 2.77 mmol). 10 ml of acetone was added and the mixture was stirred at RT. Seeds of crystalline free base Form 1 were added. A thick white slurry developed over time. Filtration and drying yielded 1 g of crystalline free base Form 1 with >98% purity.

Example 3B: Crystalline (E)-1-(3-(2-((6-(3-chloro-4-hydroxyphenyl)-1H-indazol-4-yl)oxy)propan-2-yl)azetidin-1-yl)-4-(dimethylamino)but-2-en-1-one
Form 2

Form 2 is a freebase hydrate crystalline form of compound 3.

55 mg of amorphous freebase of compound 3 was dissolved in 0.25 mL of methanol. At this stage, water was added as an antisolvent in a ratio of about 1:2 methanol:water. The resulting mixture was sonicated for several minutes at room temperature to yield a precipitate. The resulting suspension was stirred for 1 day at room temperature, filtered, washed with 1 mL of methanol and dried to provide Form 2.

Alternatively, compound 3 was dissolved in ethanol and water or methanol and water by complete dissolution in 10 volumes of alcohol followed by slow addition of approximately 8-10 volumes of water until cloud point. Seeds of Form 2 were added and a slurry developed slowly over time. Then more water was added slowly (about 10 volumes) and the resulting solid was filtered and dried to give Form 2.

Example 3C: Characterization of Form 1

Samples of Form 1 were analyzed by powder X-ray diffraction (PXRD), differential scanning calorimetry (DSC), thermogravimetric analysis (TGA), and dynamic moisture sorption (DMS).
Powder X-Ray Diffraction
The powder X-ray diffraction pattern of Form 1 is shown in FIG. 1.
Observed PXRD two-theta peak positions and d-spacings are shown below.

| 2-Theta | d(Å) | Area | A % |
|---|---|---|---|
| 5.65 | 15.63 | 343682 | 100.0 |
| 7.12 | 12.40 | 17888 | 5.2 |
| 10.02 | 8.82 | 13064 | 3.8 |
| 11.16 | 7.92 | 60848 | 17.7 |
| 13.10 | 6.75 | 13327 | 3.9 |
| 14.22 | 6.22 | 343837 | 100.0 |
| 14.82 | 5.97 | 158470 | 46.1 |
| 15.16 | 5.84 | 338146 | 98.3 |
| 16.55 | 5.35 | 84525 | 24.6 |
| 17.06 | 5.19 | 188182 | 54.7 |
| 19.31 | 4.59 | 251362 | 73.1 |
| 20.08 | 4.42 | 57430 | 16.7 |
| 21.08 | 4.21 | 29843 | 8.7 |
| 21.65 | 4.10 | 45528 | 13.2 |
| 22.51 | 3.95 | 88807 | 25.8 |
| 22.98 | 3.87 | 75161 | 21.9 |
| 24.43 | 3.64 | 95427 | 27.8 |
| 25.02 | 3.56 | 74549 | 21.7 |
| 25.72 | 3.46 | 24251 | 7.1 |
| 26.80 | 3.32 | 23046 | 6.7 |
| 27.06 | 3.29 | 26069 | 7.6 |
| 28.31 | 3.15 | 10766 | 3.1 |
| 30.08 | 2.97 | 45168 | 13.1 |
| 30.31 | 2.95 | 38502 | 11.2 |
| 32.08 | 2.79 | 22050 | 6.4 |

Figure 2:
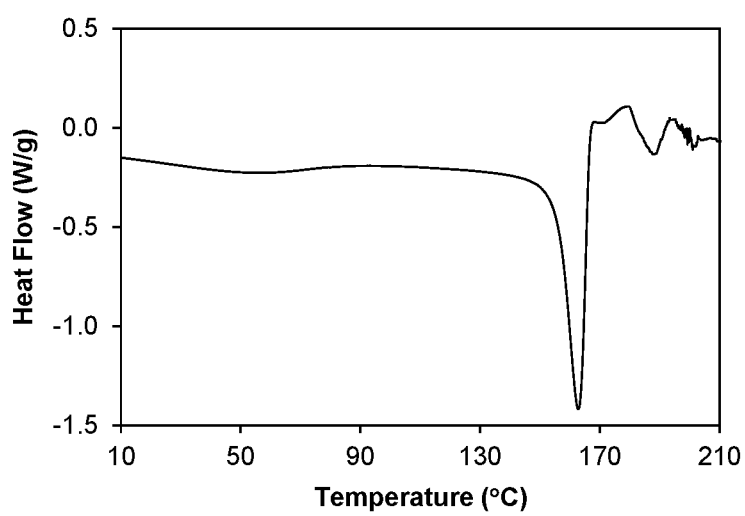
FIG. 2 shows a differential scanning calorimetry (DSC) thermogram of crystalline Form 1.

Thermal Analysis
A representative DSC thermogram of the Form 1 crystalline free form of the invention is shown in FIG. 2. The differential scanning calorimetry (DSC) trace recorded at a heating rate of 10° C. per minute exhibits a peak in endothermic heat flow, identified as a melt transition, with an onset at about 154.9° C. and a peak at about 162.9° C. Melting was followed immediately by decomposition.

The crystalline form is characterized by a differential scanning calorimetry trace recorded at a heating rate of 10° C. per minute which shows a maximum in endothermic heat flow with a peak at about 162.9° C. The crystalline form is characterized by a differential scanning calorimetry trace recorded at a heating rate of 10° C. per minute which shows a maximum in endothermic heat flow with a peak at 162.9±3° C.

The crystalline form is characterized by a differential scanning calorimetry trace recorded at a heating rate of 10° C. per minute which shows a maximum in endothermic heat flow at a temperature between about 154.9° C. and about 171° C.

A representative TGA trace of the Form 1 crystalline free form is shown in FIG. 3. The thermal gravimetric analysis (TGA) trace of FIG. 3 shows a small weight loss of about 0.14% at 100° C. The compound decomposes at an onset temperature of about 175° C.
Dynamic Moisture Sorption Assessment
A representative DMS trace for the Form 1 crystalline free form is shown in FIG. 4.

Form 1 demonstrated about 1.62% weight gain in the humidity range of 5% to 90% relative humidity. Form 1 is considered to be slightly hygroscopic.

Example 3D: Characterization of Form 2

Figure 5:
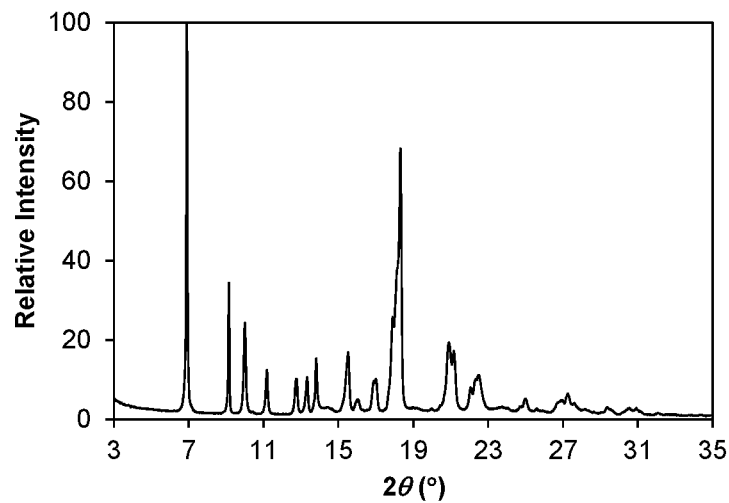
FIG. 5 shows a powder x-ray diffraction (PXRD) pattern of crystalline Form 2 of compound 3 (hereinafter Form 2).

Samples of Form 2 were analyzed by powder X-ray diffraction (PXRD), differential scanning calorimetry (DSC), thermogravimetric analysis (TGA), and dynamic moisture sorption (DMS).
Powder X-Ray Diffraction
The powder X-ray diffraction pattern of Form 2 is shown in FIG. 5.
Observed PXRD two-theta peak positions and d-spacings are shown below.

| 2-Theta | d(Å) | Area | A % |
|---|---|---|---|
| 6.90 | 12.80 | 248788 | 52.1 |
| 9.15 | 9.66 | 73363 | 15.4 |
| 10.00 | 8.84 | 92849 | 19.4 |
| 11.18 | 7.91 | 42354 | 8.9 |
| 12.76 | 6.93 | 34590 | 7.2 |
| 13.33 | 6.64 | 33198 | 6.9 |
| 13.82 | 6.40 | 75603 | 15.8 |
| 14.43 | 6.13 | 20656 | 4.3 |
| 15.51 | 5.71 | 93338 | 19.5 |
| 16.04 | 5.52 | 19890 | 4.2 |
| 17.00 | 5.21 | 58922 | 12.3 |
| 17.90 | 4.95 | 339924 | 71.1 |
| 18.31 | 4.84 | 477815 | 100.0 |
| 20.90 | 4.25 | 169039 | 35.4 |
| 22.06 | 4.03 | 68934 | 14.4 |
| 22.51 | 3.95 | 110745 | 23.2 |
| 25.00 | 3.56 | 23916 | 5.0 |
| 26.92 | 3.31 | 52661 | 11.0 |
| 27.26 | 3.27 | 63506 | 13.3 |
| 27.61 | 3.23 | 22650 | 4.7 |
| 29.37 | 3.04 | 15298 | 3.2 |
| 30.53 | 2.93 | 24930 | 5.2 |
| 30.92 | 2.89 | 22089 | 4.6 |

Figure 6:
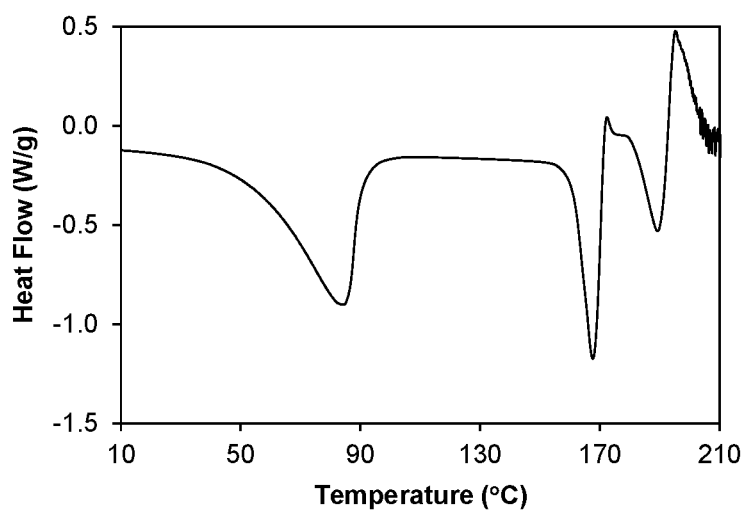
FIG. 6 shows a differential scanning calorimetry (DSC) thermogram of crystalline Form 2.

Thermal Analysis
A representative DSC thermogram of the Form 2 crystalline free form is shown in FIG. 6. The differential scanning calorimetry (DSC) trace recorded at a heating rate of 10° C. per minute exhibits a desolvation endotherm with an onset at about 52.7° C. and a peak at about 84.4° C., and a melting endotherm with an onset at about 160.0° C. and a peak at about 167.6° C. Melting was followed immediately by decomposition.

A representative TGA trace of the Form 2 crystalline free form of the invention is shown in FIG. 7. The thermal gravimetric analysis (TGA) trace of FIG. 7 shows a weight loss of about 6.73% at 75° C. The compound desolvates at an onset temperature of about 25° C. The compound decomposes at an onset temperature of about 185° C.

Dynamic Moisture Sorption Assessment

A representative DMS trace for the Form 2 crystalline free form of the invention is shown in FIG. 8. Form 2 converts to a hydrate (Form 2b) at RH above 65%. The dehydration occurs at RH below 15%. The total moisture uptake between 5%-90% RH is 7.99%.

Example 3E: Characterization of Form 2b

Samples of Form 2b were analyzed by powder X-ray diffraction (PXRD).

Powder X-Ray Diffraction

Figure 17:
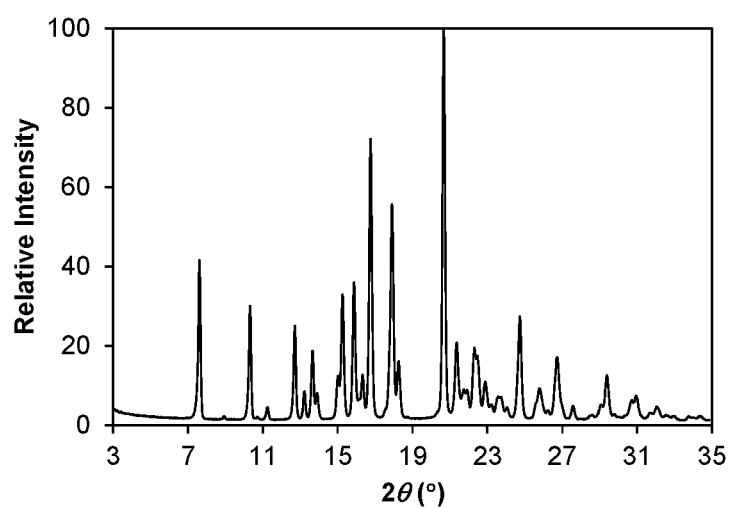
FIG. 17 shows a powder x-ray diffraction (PXRD) pattern of a dehydrated crystalline form of compound 3 (hereinafter Form 2b).

The powder X-ray diffraction pattern of Form 2b is shown in FIG. 17.

Observed PXRD two-theta peak positions and d-spacings are shown below.

| 2-Theta | d(Å) | Area | A % |
|---|---|---|---|
| 7.61 | 11.60 | 182433 | 39.1 |
| 10.33 | 8.56 | 128795 | 27.6 |
| 11.25 | 7.86 | 13807 | 3 |
| 12.71 | 6.96 | 102263 | 21.9 |
| 13.23 | 6.69 | 34318 | 7.4 |
| 13.66 | 6.48 | 86861 | 18.6 |
| 13.90 | 6.37 | 60997 | 13.1 |
| 15.02 | 5.89 | 53064 | 11.4 |
| 15.27 | 5.80 | 166039 | 35.6 |
| 15.88 | 5.58 | 163970 | 35.2 |
| 16.33 | 5.42 | 87102 | 18.7 |
| 16.76 | 5.29 | 364312 | 78.2 |
| 17.90 | 4.95 | 346920 | 74.4 |
| 18.26 | 4.85 | 105152 | 22.6 |
| 20.67 | 4.29 | 465993 | 100 |
| 21.37 | 4.16 | 104882 | 22.5 |
| 21.92 | 4.05 | 69905 | 15 |
| 22.31 | 3.98 | 133265 | 28.6 |
| 22.90 | 3.88 | 42178 | 9.1 |
| 23.22 | 3.83 | 20810 | 4.5 |
| 23.61 | 3.76 | 39278 | 8.4 |
| 24.74 | 3.60 | 160353 | 34.4 |
| 25.78 | 3.45 | 67865 | 14.6 |
| 26.23 | 3.40 | 30059 | 6.5 |
| 26.73 | 3.33 | 120802 | 25.9 |
| 27.57 | 3.23 | 17553 | 3.8 |
| 29.10 | 3.07 | 75111 | 16.1 |
| 29.39 | 3.04 | 97911 | 21 |
| 30.72 | 2.91 | 66141 | 14.2 |
| 30.94 | 2.89 | 71606 | 15.4 |
| 31.69 | 2.82 | 14912 | 3.2 |
| 32.06 | 2.79 | 33582 | 7.2 |
| 33.76 | 2.65 | 16247 | 3.5 |
| 34.35 | 2.61 | 18479 | 4 |

Preparation 11: 4,6-dichloro-1-(tetrahydro-2H-pyran-2-yl)-1H-pyrazolo[3,4-d]pyrimidine

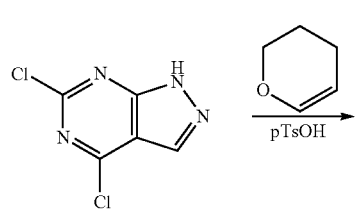

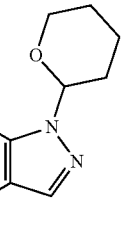

4,6-dichloro-1H-pyrazolo[3,4-d]pyrimidine (2.50 g, 13.23 mmol) was added to a flask and dissolved in 1,4-dioxane (52.9 ml). p-Toluenesulfonic acid monohydrate (pTsOH, 0.25 g, 1.32 mmol) was then added to the clear, pale yellow solution followed by 3,4-dihydro-2h-pyran (1.8 ml, 19.84 mmol) and the reaction was heated to 40° C. and stirred overnight. The resulting mixture was then cooled and concentrated in vacuo. The crude was purified by flash column chromatography using a 0-100% EtOAc:hexanes gradient to yield 4,6-dichloro-1-(tetrahydro-2H-pyran-2-yl)-1H-pyrazolo[3,4-d]pyrimidine (2.6 g, 9.52 mmol, 72.0% yield). (m/z): $[M+H]^+$ calculated for $C_{10}H_{10}Cl_2N_4O$ 274.0 found 188.9 (loss of THP fragment).

Preparation 12: tert-butyl 3-(((6-chloro-1-(tetrahydro-2H-pyran-2-yl)-1H-pyrazolo[3,4-d]pyrimidin-4-yl)oxy)methyl)azetidine-1-carboxylate

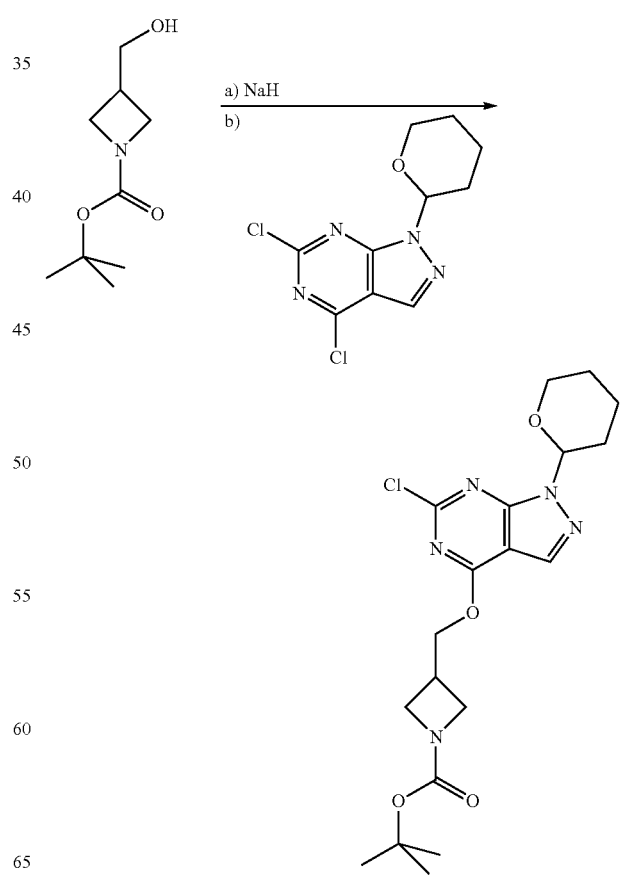

To a dry round bottom flask, 1-boc-azetidine-3-yl-methanol (1.96 g, 10.47 mmol) was added and dissolved in DMF (20.0 mL). The stirring solution was cooled to 0° C. and sodium hydride (0.762 g, 19.04 mmol) was then added. The reaction was warmed to room temperature and stirred for 30 minutes, resulting in a pale pink frothy mixture. The mixture was cooled to 0° C. and a solution of 4,6-dichloro-1-(tetrahydro-2H-pyran-2-yl)-1H-pyrazolo[3,4-d]pyrimidine (2.6 g, 9.52 mmol) in DMF (10 mL) was added via cannula. The reaction was warmed to room temperature and stirred for 3 hours. The reaction was then quenched with 120 mL H$_2$O and extracted 3 times with 30 mL EtOAc. The organic solution was then washed 3 times with 100 mL brine:H$_2$O solution (1:1). The organic was dried over Na$_2$SO$_4$, filtered, and concentrated to a pale yellow oil. The crude was purified by flash column chromatography using a 0-50% EtOAc:hexanes gradient to yield tert-butyl 3-(((6-chloro-1-(tetrahydro-2H-pyran-2-yl)-1H-pyrazolo[3,4-d]pyrimidin-4-yl)oxy)methyl)azetidine-1-carboxylate (1.95 g, 4.60 mmol, 48% yield).

Preparation 13: tert-butyl 3-(((6-(4-hydroxyphenyl)-1-(tetrahydro-2H-pyran-2-yl)-1H-pyrazolo[3,4-d]pyrimidin-4-yl)oxy)methyl)azetidine-1-carboxylate

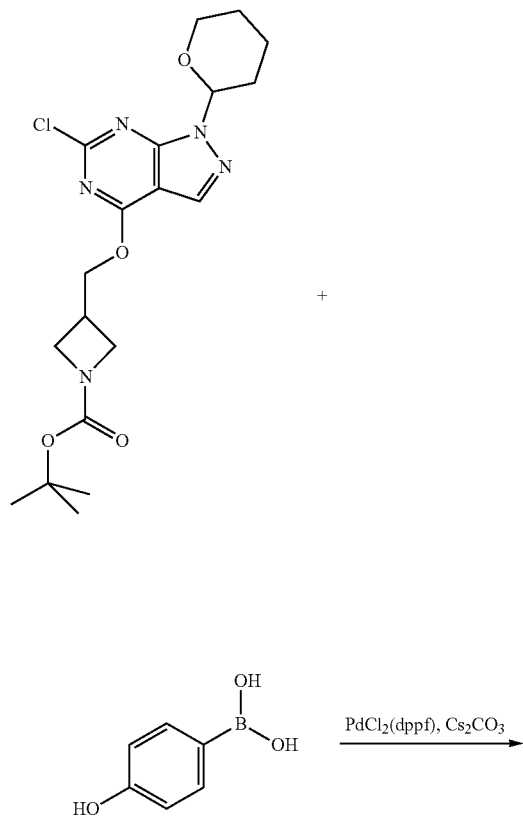

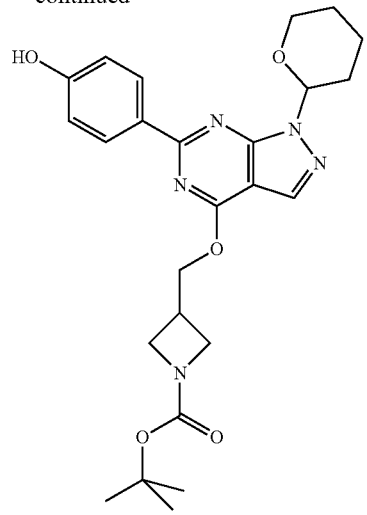

In a round bottom flask, tert-butyl 3-(((6-chloro-1-(tetrahydro-2H-pyran-2-yl)-1H-pyrazolo[3,4-d]pyrimidin-4-yl)oxy)methyl)azetidine-1-carboxylate (1.95 g, 4.60 mmol) was dissolved in 1,4-dioxane (23.0 ml). 4-hydroxyphenylboronic acid (0.95 g, 6.90 mmol) was added followed by water (7.7 ml). Dichloro[1,1'-bis(diphenylphosphino)ferrocene]palladium (0.56 g, 0.69 mmol) was added and the flask was equipped with a reflux condenser, set under nitrogen, heated to 110° C., and stirred overnight. The reaction was then cooled to room temperature and the organic solvent was removed in vacuo. H$_2$O (20 mL) was added to the residue and was extracted three times with DCM (30 mL). The organic was dried over Na$_2$SO$_4$, filtered, and concentrated to a black oil. The crude was purified by flash column chromatography using a 0-100% EtOAc:hexanes gradient to yield tert-butyl 3-(((6-(4-hydroxyphenyl)-1-(tetrahydro-2H-pyran-2-yl)-1H-pyrazolo[3,4-d]pyrimidin-4-yl)oxy)methyl)azetidine-1-carboxylate (2.03 g, 4.22 mmol, 92% yield) as a yellow/orange oil. (m/z): [M+H]$^+$ calculated for C$_{25}$H$_{31}$N$_5$O$_5$ 482.2 found 482.2.

Preparation 14: 4-(4-(azetidin-3-ylmethoxy)-1H-pyrazolo[3,4-d]pyrimidin-6-yl)phenol

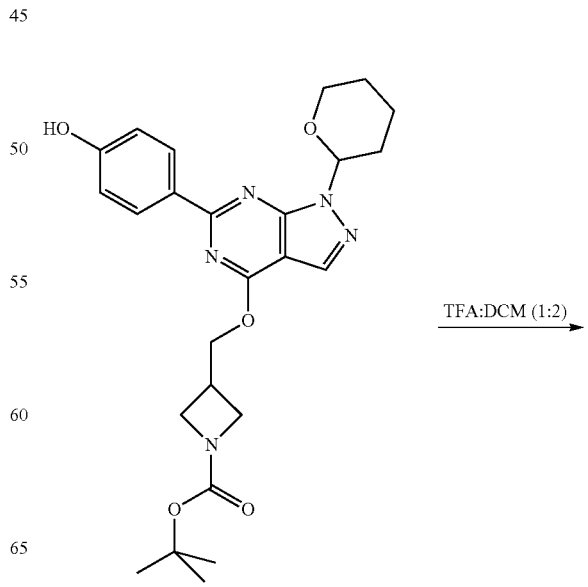

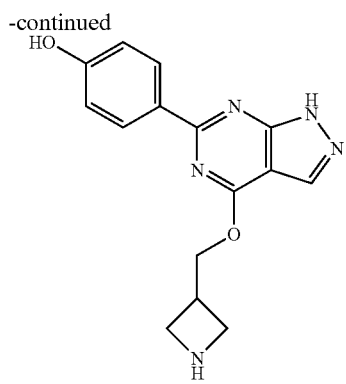

In a round bottom flask, tert-butyl 3-(((6-(4-hydroxyphenyl)-1-(tetrahydro-2H-pyran-2-yl)-1H-pyrazolo[3,4-d]pyrimidin-4-yl)oxy)methyl)azetidine-1-carboxylate (2.03 g, 4.22 mmol) was dissolved in DCM (10.0 ml) and TFA (5.0 ml) was slowly added at room temperature. The reaction was stirred for 18 hours to yield an orange/purple solution. The reaction was concentrated in vacuo to yield a grey/orange solid. The title compound was isolated as the TFA salt in 100% yield (1.25 g, 4.22 mmol). (m/z): [M+H]$^+$ calculated for $C_{15}H_{15}N_5O_2$ 298.1 found 298.3.

Example 4: 1-(3-(((6-(4-hydroxyphenyl)-1H-pyrazolo[3,4-d]pyrimidin-4-yl)oxy)methyl)azetidin-1-yl)prop-2-en-1-one

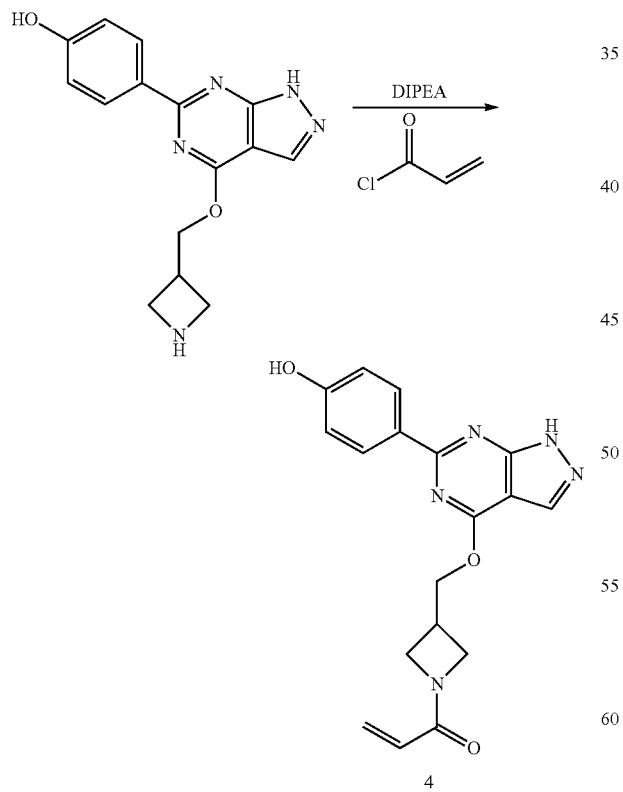

In a round bottom flask, 4-(4-(azetidin-3-ylmethoxy)-1H-pyrazolo[3,4-d]pyrimidin-6-yl)phenol trifluoroacetic acid (1.25 g, 4.20 mmol) was dissolved in DMF (21.0 ml) and diisopropylethylamine (3.67 ml, 21.0 mmol) was added. The reaction was cooled to 0° C. and stirred for 5 minutes before the slow addition of acryloyl chloride (0.273 ml, 3.36 mmol), it was then stirred for 15 minutes at 0° C. The reaction was warmed to room temperature and concentrated in vacuo. The crude was dissolved in 1:1 MeCN:H$_2$O and purified by reverse phase preparatory HPLC using a 20-80% MeCN:H$_2$O gradient. The desired fractions were combined and lyophilized to give the title compound (434 mg, 1.235 mmol, 29% yield). (m/z): [M+H]$^+$ calculated for $C_{18}H_{17}N_5O_3$ 352.1 found 352.2. $^1$H NMR (400 MHz, DMSO-d$_6$) δ 8.32-8.23 (d appt, 2H), 8.07 (s, 1H), 6.89-6.81 (d appt, 2H), 6.30 (dd, J=17.0, 10.3 Hz, 1H), 6.07 (dd, J=17.0, 2.3 Hz, 1H), 5.63 (dd, J=10.3, 2.3 Hz, 1H), 4.81 (d, J=6.5 Hz, 2H), 4.36 (t, J=8.6 Hz, 1H), 4.12 (dd, J=8.6, 5.4 Hz, 1H), 4.06 (t, 1H), 3.82 (dd, J=10.2, 5.5 Hz, 1H), 3.24-3.10 (m, 1H).

Preparation 15: tert-butyl 3-(((6-bromo-1-(tetrahydro-2H-pyran-2-yl)-1H-indazol-4-yl)oxy)methyl)azetidine-1-carboxylate

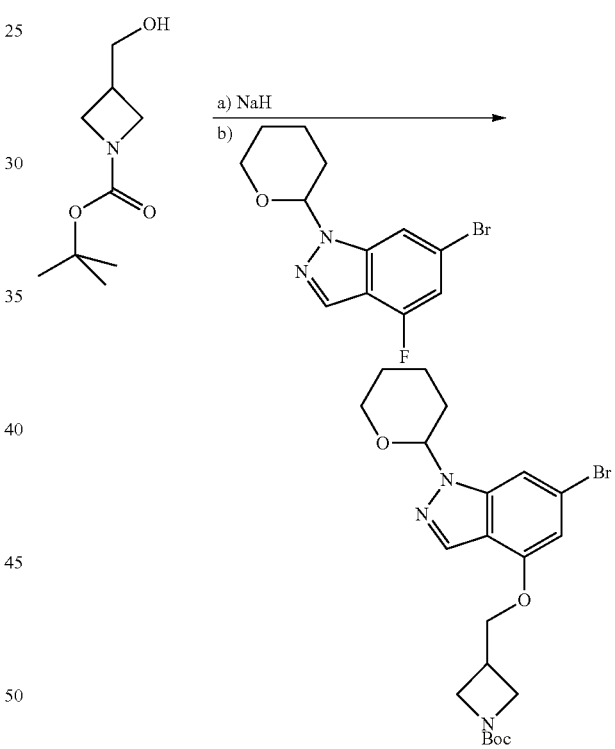

1-Boc-azetidine-3-yl-methanol (3.44 g, 18.39 mmol) was added to an oven dried flask and dissolved in DMF (41.8 ml). The solution was cooled to 0° C. and stirred for 10 minutes before the addition of sodium hydride (0.50 g, 20.89 mmol). The frothy mixture was warmed to room temperature and stirred for 30 minutes. The reaction was then cooled to 0° C. and a solution of 6-bromo-4-fluoro-1-(tetrahydro-2H-pyran-2-yl)-1H-indazole (2.5 g, 8.36 mmol) in DMF (10 mL) was added via cannula. The reaction was warmed to room temperature and stirred for 1.5 hours. The reaction was quenched by the addition of 120 mL H$_2$O and extracted 3 times with 50 mL EtOAc. The organic phase was combined and washed 3 times with 100 mL brine:H$_2$O solution (1:1). The organic phase was then collected and dried over Na$_2$SO$_4$, filtered, and concentrated to a clear, pale yellow oil (3.9 g, 8.36 mmol). The crude product was used without any further purification. (m/z): [M+H]$^+$ calculated for C$_{21}$H$_{28}$BrN$_3$O$_4$ 466.14 found 466.1.

Preparation 16: tert-butyl 3-(((6-(3-fluoro-4-hydroxyphenyl)-1-(tetrahydro-2H-pyran-2-yl)-1H-indazol-4-yl)oxy)methyl)azetidine-1-carboxylate

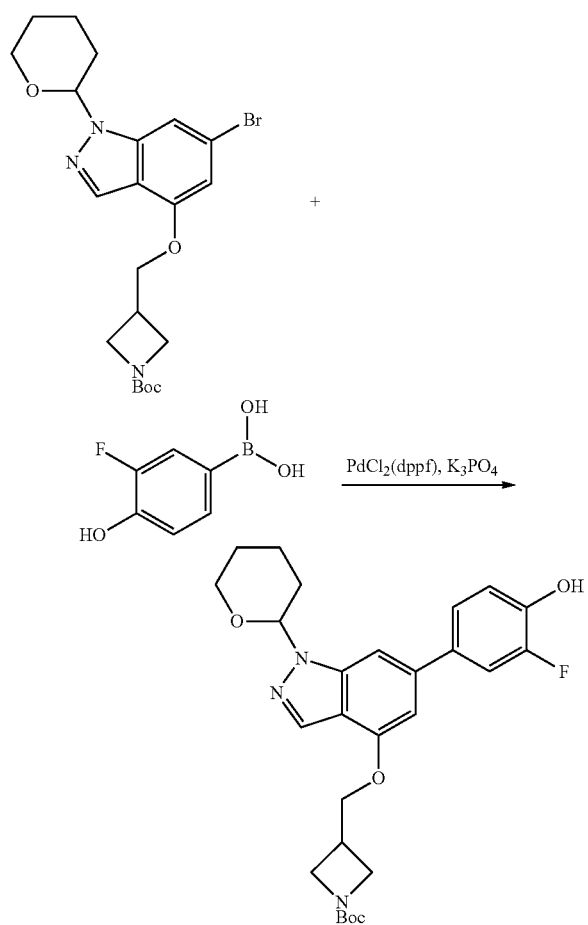

Tert-butyl 3-(((6-bromo-1-(tetrahydro-2H-pyran-2-yl)-1H-indazol-4-yl)oxy)methyl)azetidine-1-carboxylate (3.9 g, 8.36 mmol) was added to a flask and dissolved in 1,4-dioxane (44.6 ml). 3-fluoro-4-hydroxyphenylboronic acid (1.96 g, 12.54 mmol) was added followed by water (11.2 ml) and potassium phosphate, tribasic (5.33 g, 25.09 mmol). Dichloro[1,1'-bis(diphenylphosphino)ferrocene]palladium (1.02 g, 1.25 mmol) was added and the flask was equipped with a reflux condenser and placed under a nitrogen atmosphere. The reaction was heated to 110° C. and stirred for 18 hours. Once cooled to room temperature, the organic solvent was removed in vacuo to yield a black oil. To the oil, 10 mL H$_2$O was added and the solution was extracted 3 times with 40 mL DCM. The organic was collected and dried over Na$_2$SO$_4$, filtered, and concentrated to a black oil. The oil was purified via flash column chromatography using a 0-100% EtOAc:Hex gradient to yield tert-butyl 3-(((6-(3-fluoro-4-hydroxyphenyl)-1-(tetrahydro-2H-pyran-2-yl)-1H-indazol-4-yl)oxy)methyl)azetidine-1-carboxylate (2.58 g, 5.19 mmol, 62% yield) as a clear yellow oil. (m/z): [M+H]$^+$ calculated for C$_{27}$H$_{32}$FN$_3$O$_5$ 498.2 found 498.2.

Preparation 17: 4-(4-(azetidin-3-ylmethoxy)-1H-indazol-6-yl)-2-fluorophenol

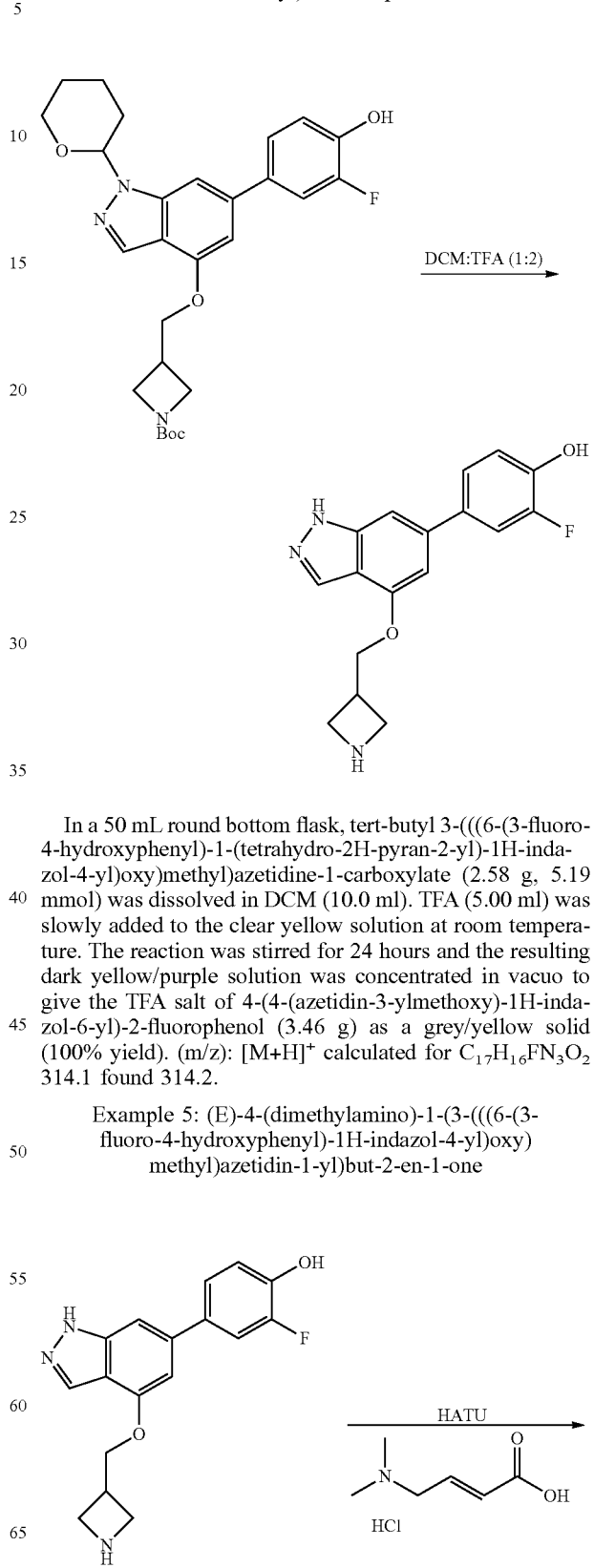

In a 50 mL round bottom flask, tert-butyl 3-(((6-(3-fluoro-4-hydroxyphenyl)-1-(tetrahydro-2H-pyran-2-yl)-1H-indazol-4-yl)oxy)methyl)azetidine-1-carboxylate (2.58 g, 5.19 mmol) was dissolved in DCM (10.0 ml). TFA (5.00 ml) was slowly added to the clear yellow solution at room temperature. The reaction was stirred for 24 hours and the resulting dark yellow/purple solution was concentrated in vacuo to give the TFA salt of 4-(4-(azetidin-3-ylmethoxy)-1H-indazol-6-yl)-2-fluorophenol (3.46 g) as a grey/yellow solid (100% yield). (m/z): [M+H]$^+$ calculated for C$_{17}$H$_{16}$FN$_3$O$_2$ 314.1 found 314.2.

Example 5: (E)-4-(dimethylamino)-1-(3-(((6-(3-fluoro-4-hydroxyphenyl)-1H-indazol-4-yl)oxy)methyl)azetidin-1-yl)but-2-en-1-one

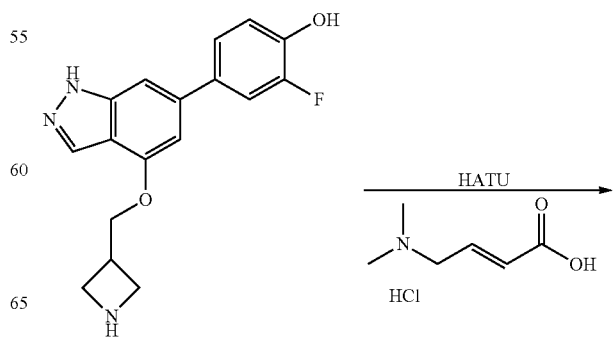

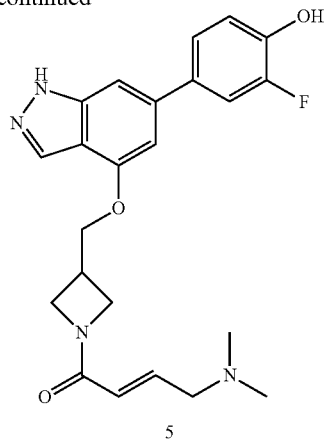

(2E)-4-(dimethylamino)but-2-enoic acid (464 mg, 2.80 mmol) and HATU (976 mg, 2.57 mmol) were added to a round bottom flask, dissolved in DMF (5.5 mL) and stirred for 15 minutes. A solution of 4-(4-(azetidin-3-ylmethoxy)-1H-indazol-6-yl)-2-fluorophenol (1.0 g, 2.34 mmol) in DMF (5.5 mL) was then slowly added to the stirring reaction followed by diisopropylethylamine (2.0 ml, 11.70 mmol). The reaction was stirred for 24 hours and was then concentrated in vacuo. The crude was dissolved in 1:1 MeCN:H$_2$O and purified by reverse phase preparatory HPLC using a 20-80% MeCN:H$_2$O gradient. The desired fractions were combined and lyophilized to give the TFA salt of the title compound (271 mg, 0.50 mmol, 21% yield). (m/z): [M+H]$^+$ calculated for C$_{23}$H$_{25}$FN$_4$O$_3$ 425.2 found 425.2. $^1$H NMR (400 MHz, MeOD-d$_4$) δ 7.94 (d, J=0.8 Hz, 1H), 7.39 (dd, J=12.5, 2.2 Hz, 1H), 7.35-7.28 (m, 1H), 7.24 (t, J=1.0 Hz, 1H), 7.03-6.93 (m, 1H), 6.80-6.68 (m, 2H), 6.53 (dt, J=15.2, 1.1 Hz, 1H), 4.53 (t, J=8.7 Hz, 1H), 4.47-4.34 (m, 2H), 4.35-4.22 (m, 2H), 4.09 (dd, J=10.8, 5.6 Hz, 1H), 3.93 (dd, J=7.2, 1.1 Hz, 2H), 3.27-3.19 (m, 1H), 2.88 (s, 6H).

Preparation 18: 6-Bromo-4-nitro-1-(tetrahydro-2H-pyran-2-yl)-1H-indazole

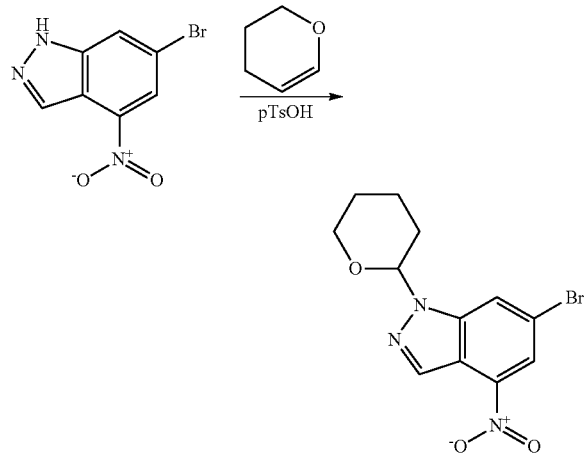

A mixture of 6-bromo-4-nitro-1H-indazole (3.00 g, 12.4 mmol), 3,4-dihydro-2H-pyran, 97% (3.40 ml, 37.2 mmol) and p-toluenesulfonic acid monohydrate (pTsOH, 0.236 g, 1.24 mmol) in DCM (41.3 ml) was stirred at rt overnight. The reaction was filtered through a pad of celite and concentrated. The reaction was assumed to be 100% conversion (4.05 g) and was carried into the subsequent reaction without further purification.

Preparation 19: 6-(4-((tert-Butyldimethylsilyl)oxy)phenyl)-4-nitro-1-(tetrahydro-2H-pyran-2-yl)-1H-indazole

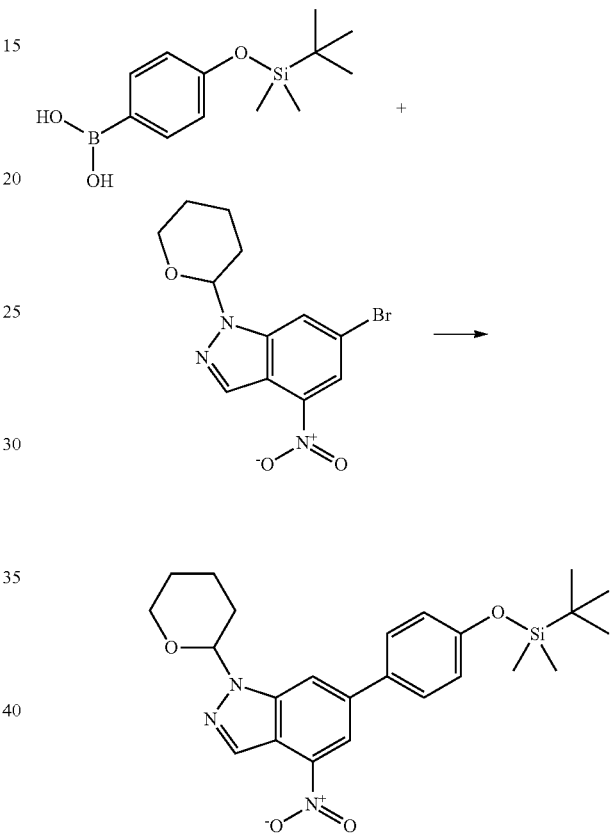

A mixture of 6-(4-((tert-butyldimethylsilyl)oxy)phenyl)-4-nitro-1-(tetrahydro-2H-pyran-2-yl)-1H-indazole (1.00 g, 3.07 mmol), 4-(tert-butyldimethylsilyloxy)phenylboronic acid (1.16 g, 4.60 mmol), and potassium phosphate tribasic (1.30 g, 6.13 mmol) in dioxane (14.9 mL) and H$_2$O (4.98 mL) was purged with N$_2$ for 10 mins. [1,1'-bis(diphenylphosphine)ferrocene]dichloropalladium(II) (0.224 g, 0.307 mmol) was then added, after which the flask was sealed. The reaction was heated to 110° C. and stirred for 1 hr. After confirmed full conversion to the desired product via LCMS, the reaction was quenched with 20 mL H$_2$O and 20 mL EtOAc. Both layers were filtered through a pad of celite and transferred to a separatory funnel. The mixture was extracted 3 times with 20 mL EtOAc, and the aqueous layer was discarded. The combined organic fractions were concentrated and subsequently purified by flash column chromatography using a 0-10% EtOAc:hexanes gradient. The product was isolated pure as a pale-yellow oil (1.03 g, 74.4% yield). (m/z): [M+H]$^+$ calcd for C$_{24}$H$_{31}$N$_3$O$_4$Si 454.61 found 454.3.

Preparation 20: 6-(4-((tert-butyldimethylsilyl)oxy)phenyl)-1-(tetrahydro-2H-pyran-2-yl)-1H-indazol-4-amine

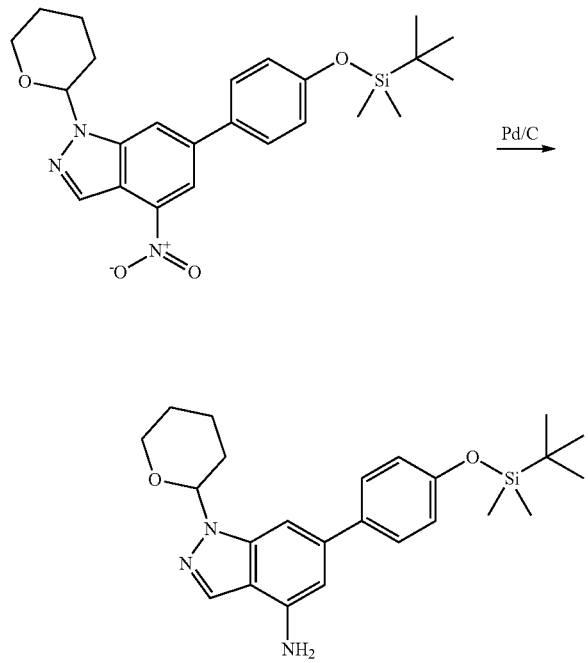

6-(4-((tert-butyldimethylsilyl)oxy)phenyl)-4-nitro-1-(tetrahydro-2H-pyran-2-yl)-1H-indazole (0.980 g, 2.16 mmol) and palladium 10% wt on carbon (wet) (0.980 g) were dissolved in THF (2.8 mL) and isopropyl alcohol (11.2 mL). The reaction vessel was back-filled with $N_2$ for 5 mins, afterwhich it was sealed and placed under a hydrogen atmosphere. The reaction mixture was left to stir at room temperature for 3 hrs. After LCMS indicated full conversion to the desired product, the reaction mixture with filtered. The filter was then washed with additional THF. After concentrating and purifying by flash column chromatography (40 g) using a 0-25% EtOAC:hexanes gradient, the product was isolated (0.562 g, 61.5% yield). (m/z): [M+H]$^+$ calcd for $C_{24}H_{33}N_3O_2Si$ 424.63 found 424.4.

Preparation 21: tert-butyl (2R)-2-((6-(4-((tert-butyldimethylsilyl)oxy)phenyl)-1-(tetrahydro-2H-pyran-2-yl)-1H-indazol-4-yl)carbamoyl)morpholine-4-carboxylate

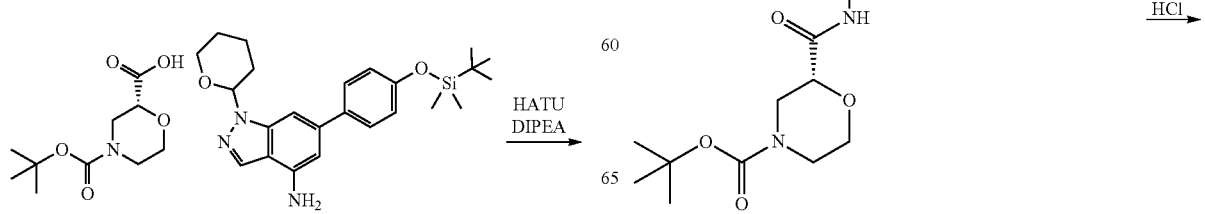

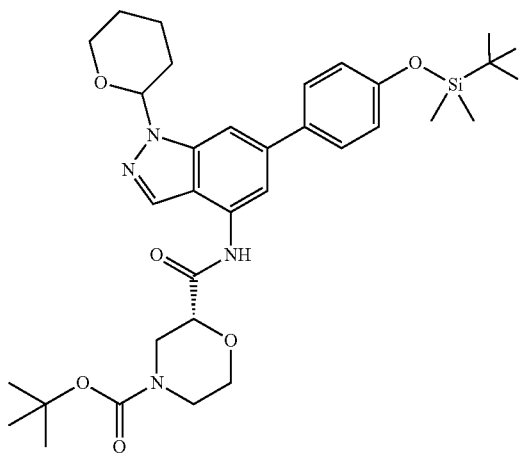

(R)—N-boc-2-morpholinecarboxylic acid (0.819 g, 3.54 mmol) and 1-[bis(dimethylamino)methylene]-1H-1,2,3-triazolo[4,5-b]pyridinium 3-oxide hexafluorophosphate (HATU, 2.69 g, 7.08 mmol) were dissolved in DMF (11.8 mL) and left to stir at room temperature for 5 mins. 6-(4-((tert-Butyldimethylsilyl)oxy)phenyl)-1-(tetrahydro-2H-pyran-2-yl)-1H-indazol-4-amine (1.00 g, 2.36 mmol) was then added, and the reaction mixture was left to stir at room temperature for 2 hrs. LCMS indicated full conversion to the desired product. The reaction was quenched with 10 mL $H_2O$ and 10 mL DCM. After transferring to a separatory funnel, the mixture was extracted three times with 10 mL DCM, and the aqueous layer was discarded. Combined organic fractions were concentrated and subsequently purified by flash column chromatography (40 g) using a 0-45% EtOAc:hexanes gradient. The products was isolated as a pale-yellow oil (1.01 g, 67% yield). (m/z): [M+H]$^+$ calcd for $C_{34}H_{48}N_4O_6Si$ 637.87 found 637.6.

Preparation 22: (R)—N-(6-(4-hydroxyphenyl)-1H-indazol-4-yl)morpholine-2-carboxamide

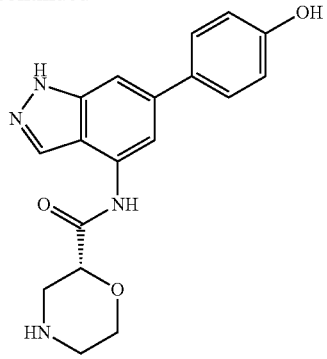

tert-Butyl (2R)-2-((6-(4-((tert-butyldimethylsilyl)oxy)phenyl)-1-(tetrahydro-2H-pyran-2-yl)-1H-indazol-4-yl)carbamoyl)morpholine-4-carboxylate (1.00 g, 1.58 mmol) was dissolved in MeOH (2.0 mL). While stirring, an HCl solution in 4.0M dioxane (12.1 mL, 48.5 mmol) was added slowly. The reaction mixture was heated to 60° C. and stirred for 30 mins, after which LCMS indicated full conversion to the desired product. The mixture was concentrated to give the product as an orange oil. The reaction was assumed to be 100% conversion (0.533 g) and was carried into the subsequent reaction without further purification.

Example 6: (R)-4-acryloyl-N-(6-(4-hydroxyphenyl)-1H-indazol-4-yl)morpholine-2-carboxamide

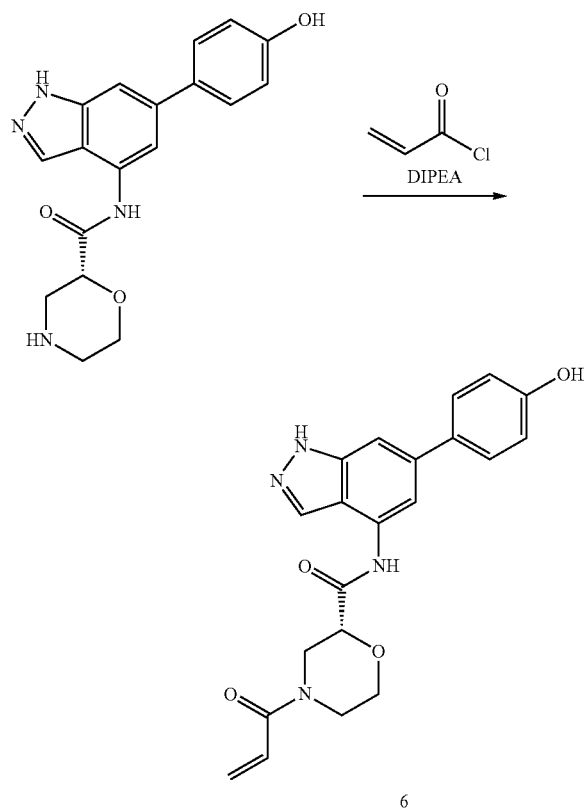

6

(R)—N-(6-(4-hydroxyphenyl)-1H-indazol-4-yl)morpholine-2-carboxamide (0.533 g, 1.58 mmol) was dissolved in DMF (7.9 mL). N,N-diisopropylethylamine (DIPEA, 2.75 mL, 15.8 mmol) was added, followed by slow addition of acryloyl chloride (0.0900 mL, 1.10 mmol). The reaction was stirred at room temperature for 10 mins before conversion was monitored by LCMS. After full conversion was indicated via LCMS, the reaction mixture was concentrated and purified via reverse-phase HPLC prep using a 10-50% ACN:H$_2$O gradient. Fractions of the desired product were collected and concentrated via lyophilization. The product was isolated (130 mg, 21% yield). (m/z): [M+H]$^+$ calcd for C$_{21}$H$_{20}$N$_4$O$_4$ 393.42 found 393.4. $^1$H NMR (400 MHz, Methanol-d$_4$) δ 8.13 (s, 1H), 7.74 (d, J=16.3 Hz, 1H), 7.56 (d, J=6.0 Hz, 2H), 7.51 (s, 1H), 6.91 (dd, J=8.7, 2.9 Hz, 3H), 6.30 (dt, J=16.8, 2.3 Hz, 1H), 5.84 (d, J=10.6 Hz, 1H), 4.45-4.25 (m, 2H), 4.21 (d, J=11.8 Hz, 1H), 4.12-4.02 (m, 1H), 3.78 (t, J=11.5 Hz, 1H), 3.53 (m, 1H), 3.29-2.99 (m, 1H).

Preparation 23: tert-butyl (3S)-3-(((6-bromo-1-(tetrahydro-2H-pyran-2-yl)-1H-indazol-4-yl)oxy)methyl)pyrrolidine-1-carboxylate

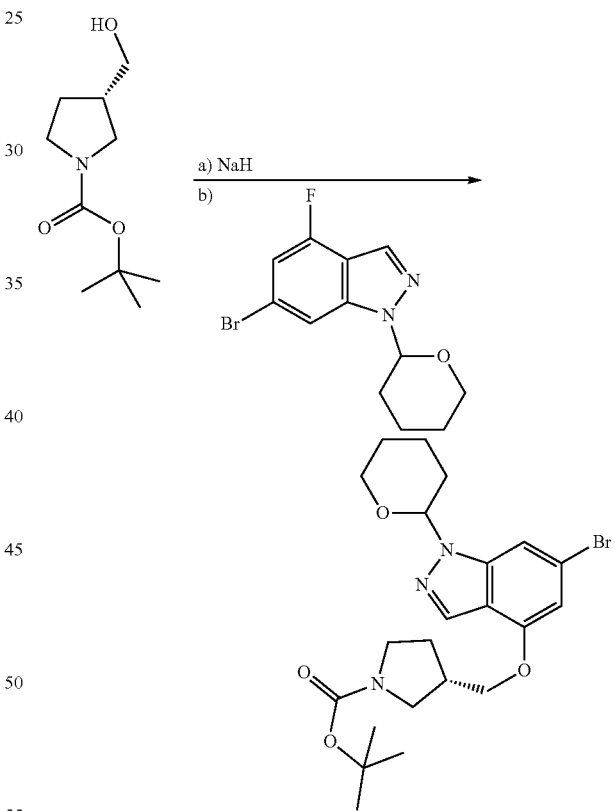

Sodium hydride (0.072 g, 3.01 mmol) was added to a solution of (Ss)-N-boc-pyrrolidine-3-methanol (0.444 g, 2.21 mmol) in DMF (6 ml) under an atmosphere of N$_2$ at 0° C. and the reaction mixture was stirred at rt for 20 minutes. 6-bromo-4-fluoro-1-(tetrahydro-2H-pyran-2-yl)-1H-indazole (0.600 g, 2.01 mmol) was added and the reaction mixture was stirred at rt for 1 hour. Water (1 mL) was added and the reaction was concentrated in vacuo. The crude material was purified via flash column chromatography using 40% ethyl acetate in hexanes to yield tert-butyl (3S)-3-(((6-bromo-1-(tetrahydro-2H-pyran-2-yl)-1H-inda- Preparation 24: tert-butyl (3S)-3-(((6-(4-hydroxyphenyl)-1-(tetrahydro-2H-pyran-2-yl)-1H-indazol-4-yl)oxy)methyl)pyrrolidine-1-carboxylate

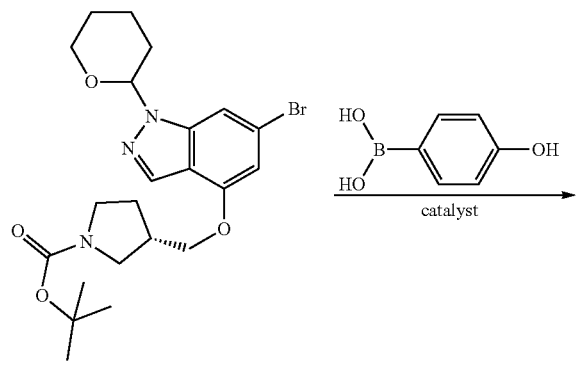

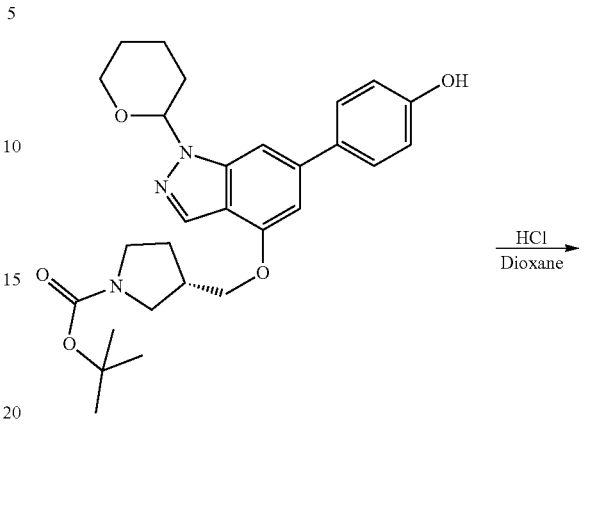

Palladium acetate (0.084 g, 0.375 mmol) was added to a solution of 4-hydroxyphenylboronic acid (0.388 g, 2.81 mmol), tert-butyl (3S)-3-(((6-bromo-1-(tetrahydro-2H-pyran-2-yl)-1H-indazol-4-yl)oxy)methyl)pyrrolidine-1-carboxylate (0.900 g, 1.87 mmol), 1,1'-bis(di-t-butylphosphino)ferrocene (0.178 g, 0.375 mmol) and potassium phosphate (1.193 g, 5.62 mmol) in 1,4-dioxane (12 ml) and water (3.00 ml). The reaction mixture was degassed with nitrogen for 10 minutes and then stirred at 110° C. for 2 hours. The reaction mixture was concentrated in vacuo to a volume of about 5 mL. A saturated aqueous solution of ammonium chloride (10 mL) was added and the mixture was extracted with methylene chloride (3×10 mL). The methylene chloride extracts were combined, dried over sodium sulfate and concentrated in vacuo to yield a brown liquid. The crude liquid was purified via flash column chromatography using 50% ethyl acetate in hexanes to yield tert-butyl (3S)-3-(((6-(4-hydroxyphenyl)-1-(tetrahydro-2H-pyran-2-yl)-1H-indazol-4-yl)oxy)methyl)pyrrolidine-1-carboxylate (0.800 g, 1.62 mmol, 87% yield) as a clear yellow liquid. (m/z): [M+H]$^+$ calcd for $C_{28}H_{35}N_3O_5$ 494.27 found 494.2.

Preparation 25: (S)-4-(4-(pyrrolidin-3-ylmethoxy)-1H-indazol-6-yl)phenol 4.0N HCl in dioxane (8.10 ml, 32.4 mmol) was added to a solution of tert-butyl (3S)-3-(((6-(4-hydroxyphenyl)-1-(tetrahydro-2H-pyran-2-yl)-1H-indazol-4-yl)oxy)methyl)pyrrolidine-1-carboxylate (0.800 g, 1.62 mmol) in dioxane (6 ml), and the reaction mixture was stirred at 60° C. for 30 minutes. The reaction mixture was concentrated in vacuo to yield ((S)-4-(4-(pyrrolidin-3-ylmethoxy)-1H-indazol-6-yl)phenol as an HCl salt (0.501 g, 1.62 mmol, 100% yield). (m/z): [M+H]$^+$ calcd for $C_{18}H_{19}N_3O_2$ 310.16 found 310.3.

Example 7: (S)-1-(3-((6-(3-chloro-4-hydroxyphenyl)-1H-indazol-4-yl)oxy)pyrrolidin-1-yl)prop-2-en-1-one

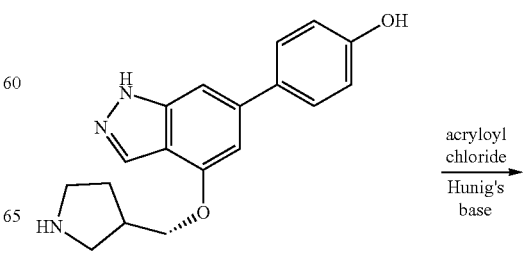

-continued

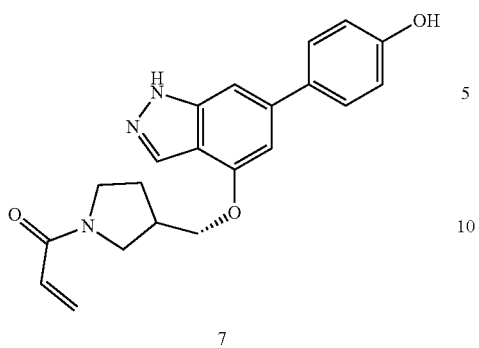

7

N,N-Diisopropylethylamine (2.83 ml, 16.2 mmol) was added to a solution of (S)-4-(4-(pyrrolidin-3-ylmethoxy)-1H-indazol-6-yl)phenol HCl salt (0.560 g, 1.62 mmol) in DMF (5 ml) at 0° C., followed by acryloyl chloride (0.171 ml, 2.11 mmol). The reaction mixture was stirred at rt for 15 minutes then concentrated to a volume of about 2 mL. The crude liquid was purified via preparatory scale C18 column chromatography using a gradient of 30-90% acetonitrile in water with 0.05% trifluoroacetic acid to yield (S)-1-(3-(((6-(4-hydroxyphenyl)-1H-indazol-4-yl)oxy)methyl)pyrrolidin-1-yl)prop-2-en-1-one as a TFA salt (226 mg, 0.473 mmol, 29.2% yield). (m/z): [M+H]$^+$ calcd for $C_{21}H_{21}N_3O_3$ 364.17 found 364.2. 1H NMR (400 MHz, DMSO-d6) δ 13.00 (s, 1H), 10.31 (s, 1H), 8.04-7.94 (m, 1H), 7.59-7.48 (m, 1H), 7.18 (s, 1H), 6.89-6.79 (m, 1H), 6.76-6.70 (m, 1H), 6.65-6.54 (m, 1H), 6.13 (dd, J=16.6, 1.7 Hz, 1H), 5.69-5.62 (m, 1H), 4.25-3.78 (m, 4H), 3.76-3.28 (m, 2H), 2.88-2.63 (m, 1H), 2.22-1.72 (m, 2H).

Preparation 26: tert-butyl 3-(2-((6-bromo-1-(tetrahydro-2H-pyran-2-yl)-1H-indazol-4-yl)oxy)propan-2-yl)azetidine-1-carboxylate

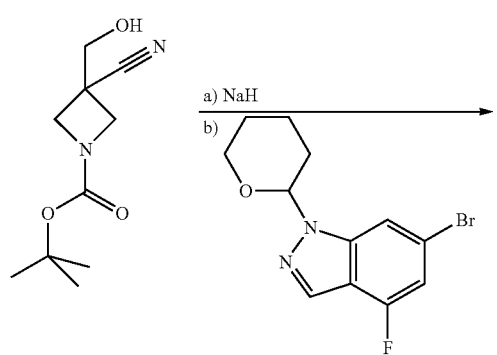

-continued

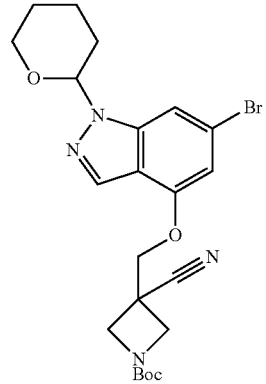

To a dry scintillation vial purged with N$_2$, tert-butyl 3-cyano-3-(hydroxymethyl)azetidine-1-carboxylate (851 mg, 4.01 mmol) was added, dissolved in 5 mL DMF and the solution was cooled to 0° C. 60% by weight sodium hydride in mineral oil (267 mg, 6.69 mmol) was slowly added to the stirring solution and the reaction was allowed to warm to rt following the addition. The frothy reaction was stirred for 30 minutes before being cooled once again to 0° C. A solution of 6-bromo-4-fluoro-1-(tetrahydro-2H-pyran-2-yl)-1H-indazole (800 mg, 2.67 mmol) in 2 mL DMF was slowly added into the scintillation vial containing the organosodium solution. Following the addition, the reaction was warmed to rt and stirred for 2 hours upon which LCMS indicated full conversion of the starting material to the desired product. The reaction was quenched with the slow addition of 2 mL H$_2$O and 2 mL EtOAc, which was allowed to stir for 5 minutes. The biphasic solution was then transferred to a separatory funnel and an additional 10 mL H$_2$O were added. The mixture was extracted with 3 times 20 mL of EtOAc and the aqueous layer was discarded. The combined organic fractions were then washed with 3×10 mL 1:1 H$_2$O:brine to remove residual DMF. The organic was then dried over Na$_2$SO4, filtered, and concentrated to a lightly yellow oil. The oil was then purified by flash column chromatography using a 0-40% EtOAc:hexanes gradient. The product was isolated pure as a clear, colorless, viscous oil (1.096 g, 83% yield). (m/z): [M+H]$^+$ calcd for $C_{22}H_{27}BrN_4O_4$ 491.13 found 491.1.

Preparation 27: tert-butyl 3-cyano-3-(((6-(3-fluoro-4-hydroxyphenyl)-1-(tetrahydro-2H-pyran-2-yl)-1H-indazol-4-yl)oxy)methyl)azetidine-1-carboxylate

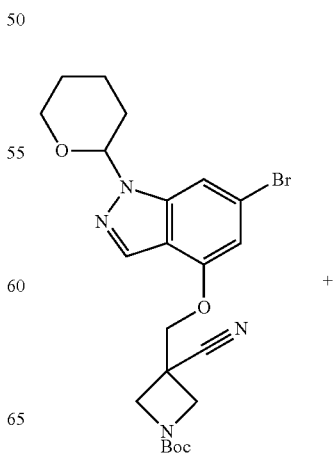

+

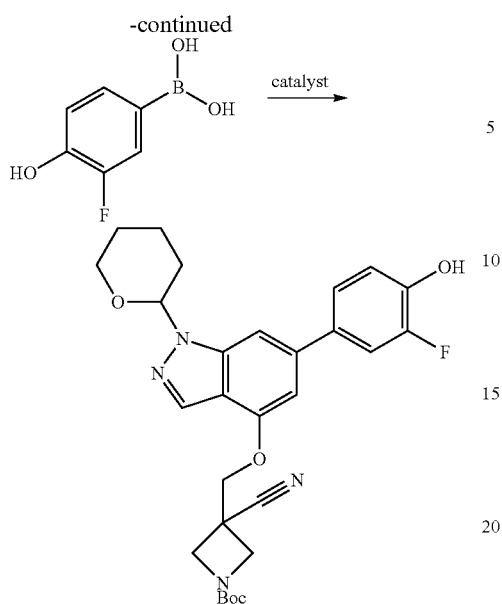

A 1:1 mixture of Palladium acetate (25.1 mg, 0.112 mmol) and 1,1'-Bis(di-t-butylphosphino)ferrocene 98% (53.1 mg, 0.112 mmol) was added to a solution of 3-fluoro-4-hydroxybenzeneboronic acid (262 mg, 1.679 mmol), tert-butyl 3-(2-(((6-bromo-1-(tetrahydro-2H-pyran-2-yl)-1H-indazol-4-yl)oxy)propan-2-yl)azetidine-1-carboxylate (550 mg, 1.119 mmol), and potassium phosphate (713 mg, 3.36 mmol) in 1,4-dioxane (4.5 ml) and water (1 ml). The reaction mixture was degassed with nitrogen for 10 minutes and then stirred at 110° C. for 2 hours. The reaction mixture was concentrated in vacuo. A saturated aqueous solution of ammonium chloride (5 mL) was added and the mixture was extracted with ethyl acetate (2×5 mL). The ethyl acetate extracts were combined, dried over sodium sulfate and concentrated in vacuo to yield a brown liquid. The crude liquid was purified via flash column chromatography using 40% ethyl acetate in hexanes to yield tert-butyl 3-cyano-3-(((6-(3-fluoro-4-hydroxyphenyl)-1-(tetrahydro-2H-pyran-2-yl)-1H-indazol-4-yl)oxy)methyl)azetidine-1-carboxylate (267 mg, 0.511 mmol, 46% yield). (m/z): [M+H]+ calcd for $C_{28}H_{31}FN_4O_5$ 523.24 found 523.4.

Preparation 28: 3-(((6-(3-fluoro-4-hydroxyphenyl)-1H-indazol-4-yl)oxy)methyl)azetidine-3-carbonitrile

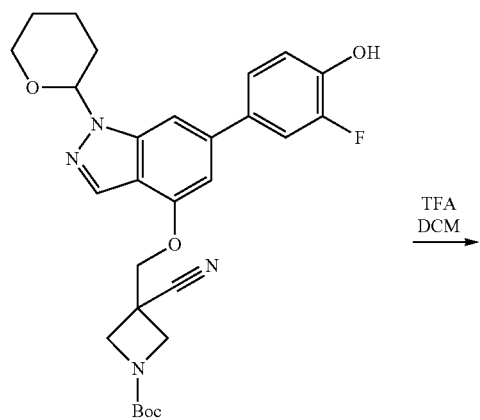

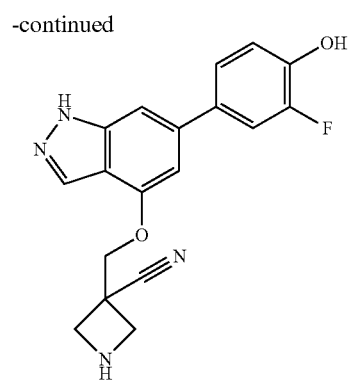

Tert-butyl 3-cyano-3-(((6-(3-fluoro-4-hydroxyphenyl)-1-(tetrahydro-2H-pyran-2-yl)-1H-indazol-4-yl)oxy)methyl)azetidine-1-carboxylate (267 mg, 0.511 mmol) was dissolved in dichloromethane (1 ml) and TFA (1 ml) was slowly added. The clear solution was stirred at rt for 5 hours upon which LCMS indicated good conversion to the desired product. The reaction was concentrated down to provide 3-(((6-(3-fluoro-4-hydroxyphenyl)-1H-indazol-4-yl)oxy)methyl)azetidine-3-carbonitrile as a TFA salt (100% yield). (m/z): [M+H]+ calcd for $C_{18}H_{15}FN_4O_2$ 339.13 found 339.2.

Example 8: (E)-1-(4-(dimethylamino)but-2-enoyl)-3-(((6-(3-fluoro-4-hydroxyphenyl)-1Hindazol-4-yl)oxy)methyl)azetidine-3-carbonitrile

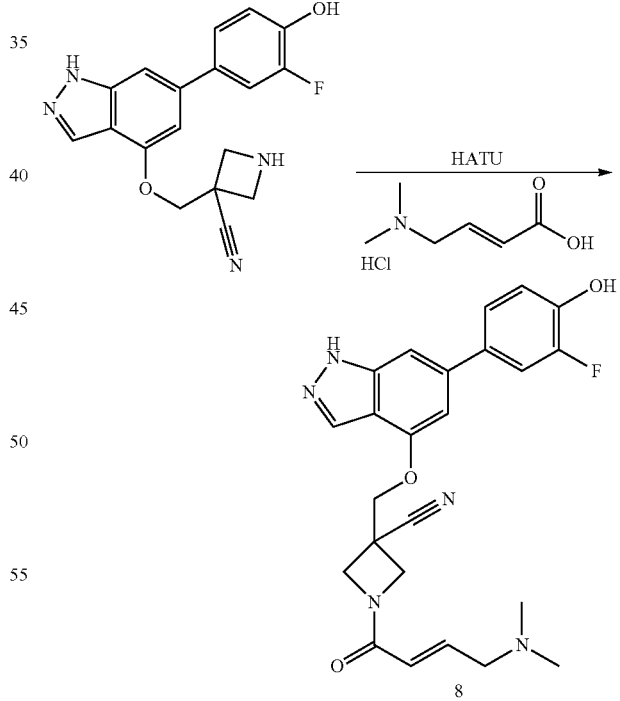

HATU (2-(7-aza-1H-benzotriazole-1-yl)-1,1,3,3-tetramethyluronium, 121 mg, 0.318 mmol) was added to a solution of (E)-4-(dimethylamino)but-2-enoic acid hydrochloride (41.1 mg, 0.318 mmol) in DMF (2 mL). The reaction mixture was stirred at rt for 5 minutes then 3-(((6-(3-fluoro-4-hydroxyphenyl)-1H-indazol-4-yl)oxy)methyl)azetidine- 3-carbonitrile TFA salt (160 mg, 0.354 mmol) was added, followed by DIPEA (0.618 ml, 3.54 mmol). The reaction mixture was stirred at rt for 15 minutes and then concentrated in vacuo to yield a yellow liquid. The crude liquid was purified via preparatory scale Zorbax Bonus-RP (2.1×30 mm, 1.8 micron) column chromatography using 15-75% acetonitrile in water with 0.05% trifluoroacetic acid to yield (E)-1-(4-(dimethylamino)but-2-enoyl)-3-(((6-(3-fluoro-4-hydroxyphenyl)-1Hindazol-4-yl)oxy)methyl)azetidine-3-carbonitrile (56.2 mg, 0.121 mmol, 34% yield). (m/z): [M+H]$^+$ calcd for $C_{24}H_{24}FN_5O_3$ 450.19 found 450.0. $^1$H NMR (400 MHz, DMSO-d$_6$) δ 9.94 (s, 1H), 9.77 (s, 1H), 7.85 (s, 1H), 7.47 (dd, J=12.8, 2.2 Hz, 1H), 7.31 (dd, J=8.4, 1.7 Hz, 1H), 7.22 (S, 1H), 6.99-6.90 (m, 1H), 6.78 (s, 1H), 6.59-6.48 (m, 1H), 6.31 (d, J=15.4 Hz, 1H), 4.67-4.60 (m, 3H), 4.40 (d, J=9.1 Hz, 1H), 4.27 (d, J=10.5 Hz, 1H), 4.12 (d, J=10.4 Hz, 1H), 3.78 (d, J=6.8 Hz, 2H), 2.66 (S, 6H).

Preparation 29: tert-butyl 4-((6-bromo-1-(tetrahydro-2H-pyran-2-yl)-1H-indazol-4-yl)oxy)-4-methylpiperidine-1-carboxylate

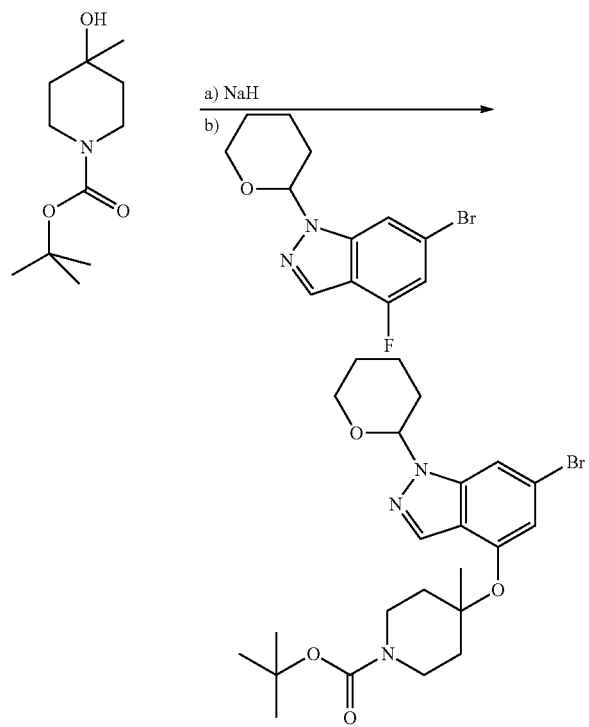

To a dry scintillation vial purged with N$_2$, 1-boc-4-methylpiperidin-4-ol (567 mg, 2.63 mmol) was added, dissolved in 3 mL DMF and the solution was cooled to 0° C. 60% by weight sodium hydride in mineral oil (175 mg, 4.39 mmol) was slowly added to the stirring solution and the reaction was allowed to warm to rt following the addition. The frothy reaction was stirred for 30 minutes before being cooled once again to 0° C. A solution of 6-bromo-4-fluoro-1-(tetrahydro-2H-pyran-2-yl)-1H-indazole (525 mg, 1.755 mmol) in 1 mL DMF was slowly added into the scintillation vial containing the organosodium solution. Following the addition, the reaction was warmed to rt and stirred for 2 hours upon which LCMS indicated full conversion of the starting material to the desired product. The reaction was quenched with the slow addition of 2 mL H$_2$O and 2 mL EtOAc, which was allowed to stir for 5 minutes. The biphasic solution was then transferred to a separatory funnel and an additional 10 mL H$_2$O were added. The mixture was extracted with 3 times 20 mL of EtOAc and the aqueous layer was discarded. The combined organic fractions were then washed with 3×10 mL 1:1 H$_2$O:brine to remove residual DMF. The organic was then dried over Na$_2$SO$_4$, filtered, and concentrated to a lightly yellow oil. The oil was then purified by flash column chromatography using a 0-40% EtOAc:hexanes gradient. The product was isolated pure as a clear, colorless, viscous oil (389 mg, 45% yield). (m/z): [M+H]$^+$ calcd for $C_{23}H_{32}BrN_3O_4$ 494.17 found 494.4.

Preparation 30: tert-butyl 4-((6-(4-hydroxyphenyl)-1-(tetrahydro-2H-pyran-2-yl)-1H-indazol-4-yl)oxy)-4-methylpiperidine-1-carboxylate

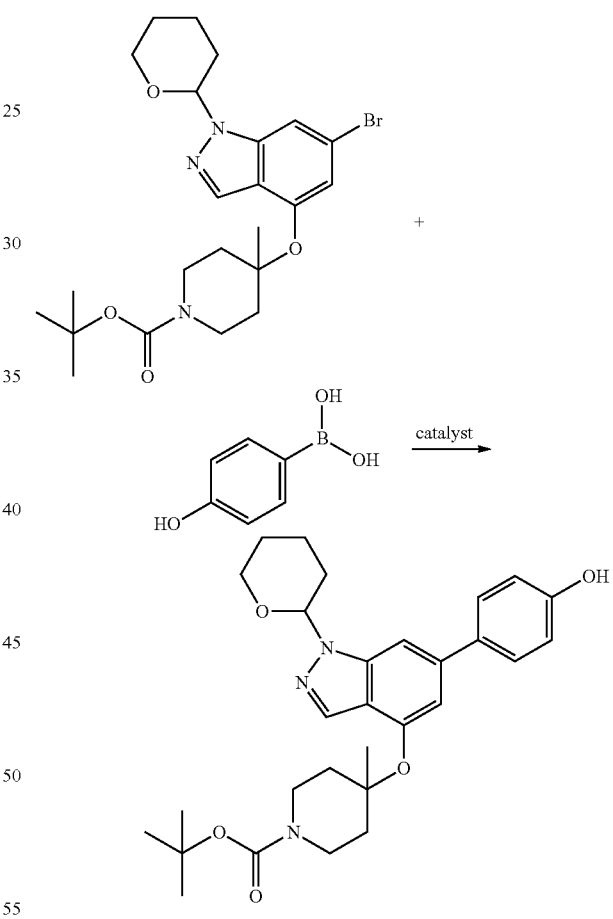

A 1:1 mixture of Palladium acetate (9.1 mg, 0.040 mmol) and 1,1'-Bis(di-t-butylphosphino)ferrocene 98% (19.2 mg, 0.040 mmol) was added to a solution of 4-hydroxybenzeneboronic acid (42 mg, 0.30 mmol), tert-butyl 4-((6-bromo-1-(tetrahydro-2H-pyran-2-yl)-1H-indazol-4-yl)oxy)-4-methylpiperidine-1-carboxylate (100 mg, 0.202 mmol), and Potassium phosphate, tribasic, 97%, anhydrous (129 mg, 0.607 mmol) in 1,4-Dioxane (2 ml) and Water (0.5 ml). The reaction mixture was degassed with nitrogen for 10 minutes and then stirred at 110° C. for 2 hours. The reaction mixture was concentrated in vacuo. A saturated aqueous solution of ammonium chloride (5 mL) was added and the mixture was extracted with ethyl acetate (2×5 mL). The ethyl acetate extracts were combined, dried over sodium sulfate and concentrated in vacuo to yield a brown liquid. The crude liquid was purified via combiflash column chromatography (12 g) using 40% ethyl acetate in hexanes to yield tert-butyl 4-((6-(4-hydroxyphenyl)-1-(tetrahydro-2H-pyran-2-yl)-1H-indazol-4-yl)oxy)-4-methylpiperidine-1-carboxylate (96 mg, 0.189 mmol, 94% yield). (m/z): [M+H]$^+$ calcd for $C_{29}H_{37}N_3O_5$ 5098.28 found 508.3.

Preparation 31: 4-(4-((4-methylpiperidin-4-yl)oxy)-1H-indazol-6-yl)phenol

Example 9: (E)-4-(dimethylamino)-1-(4-((6-(4-hydroxyphenyl)-1H-indazol-4-yl)oxy)-4-methylpiperidin-1-yl)but-2-en-1-one

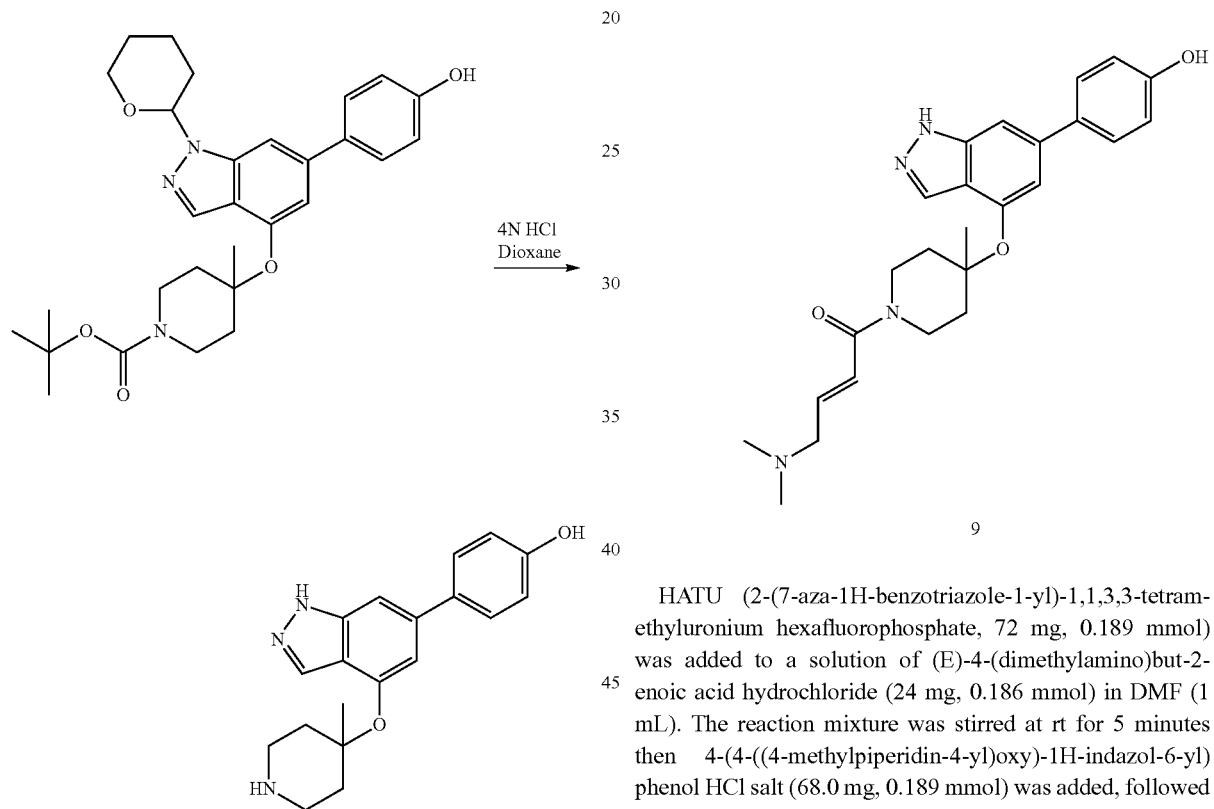

Tert-butyl 4-((6-(4-hydroxyphenyl)-1-(tetrahydro-2H-pyran-2-yl)-1H-indazol-4-yl)oxy)-4-methylpiperidine-1-carboxylate (96 mg, 0.189 mmol) was dissolved in 1,4-dioxane (1 ml) and 4N HCl in 1,4-dioxane (1.18 ml, 4.73 mmol) was slowly added. The clear solution was stirred at rt for 5 hours upon which LCMS indicated good conversion to the desired product. The reaction was concentrated down to provide 4-(4-((4-methylpiperidin-4-yl)oxy)-1H-indazol-6-yl)phenol as an HCl salt (100% yield). (m/z): [M+H]$^+$ calcd for $C_{19}H21N_3O_2$ 324.17 found 324.3.

HATU (2-(7-aza-1H-benzotriazole-1-yl)-1,1,3,3-tetramethyluronium hexafluorophosphate, 72 mg, 0.189 mmol) was added to a solution of (E)-4-(dimethylamino)but-2-enoic acid hydrochloride (24 mg, 0.186 mmol) in DMF (1 mL). The reaction mixture was stirred at rt for 5 minutes then 4-(4-((4-methylpiperidin-4-yl)oxy)-1H-indazol-6-yl)phenol HCl salt (68.0 mg, 0.189 mmol) was added, followed by DIPEA (0.330 ml, 1.890 mmol). The reaction mixture was stirred at rt for 15 minutes and then concentrated in vacuo to yield a yellow liquid. The crude liquid was purified via preparatory scale Zorbax Bonus-RP (2.1×30 mm, 1.8 micron) column chromatography using 5-65% acetonitrile in water with 0.05% trifluoroacetic acid to yield (E)-4-(dimethylamino)-1-(4-((6-(4-hydroxyphenyl)-1H-indazol-4-yl)oxy)-4-methylpiperidin-1-yl)but-2-en-1-one (39.0 mg, 0.063 mmol, 34% yield). (m/z): [M+H]$^+$ calcd for $C_{25}H_{30}FN_4O_3$ 435.24 found 435.2. $^1$H NMR (400 MHz, DMSO-$d_6$) δ 12.99 (s, 1H), 9.66 (s, 1H), 8.02 (d, J=0.9 Hz, 1H), 7.52-7.44 (m, 2H), 7.27 (s, 1H), 6.90 (d, J=15.0 Hz, 1H), 6.86-6.78 (m, 3H), 6.58-6.47 (m, 1H), 3.99-3.86 (m, 1H), 3.83 (d, J=7.2 Hz, 2H), 3.78-3.55 (m, 2H), 2.74 (s, 6H), 1.40 (s, 3H).

Preparation 32: 4,6-dichloro-1-(tetrahydro-2H-pyran-2-yl)-1H-pyrazolo[3,4-b]pyridine

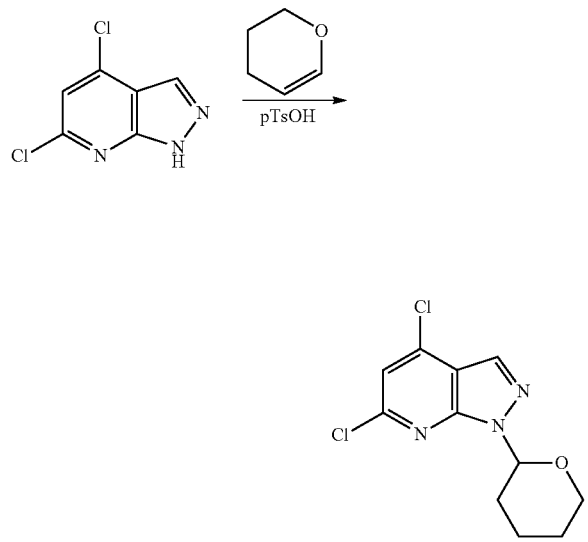

3,4-Dihydro-2h-pyran (2.0 g, 24.07 mmol) was added to a solution of 4,6-dichloro-1H-pyrazolo[3,4-b]pyridine (2.50 g, 13.23 mmol) in methylene chloride (30 mL), followed by p-toluenesulfonic acid monohydrate (0.275 g, 1.60 mmol), and the reaction mixture was stirred at rt for 1 h. Water (50 mL) was added and the mixture was extracted with methylene chloride (3×50 mL). The methylene chloride extracts were combined, washed with brine (1×50 mL), dried over sodium sulfate and concentrated to yield a clear yellow liquid. The crude liquid was purified via flash column chromatography using 10% EtOAc in hexanes to yield 4,6-dichloro-1-(tetrahydro-2H-pyran-2-yl)-1H-pyrazolo[3,4-b]pyridine (3.0 g, 11.1 mmol, 67% yield). (m/z): [M+H]+ calculated for $C_{11}H_{11}Cl_2N_3O$ 272.04 found 272.21.

Preparation 33: tert-butyl 3-(((6-chloro-1-(tetrahydro-2H-pyran-2-yl)-1H-pyrazolo[3,4-b]pyridin-4-yl)oxy)methyl)azetidine-1-carboxylate

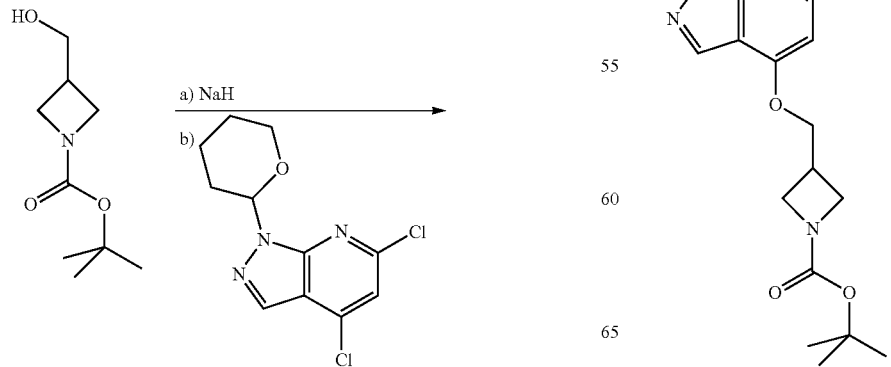

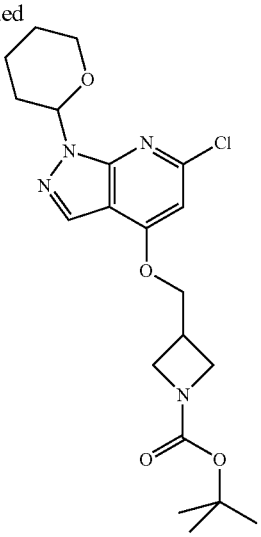

NaH (60% dispersion in mineral oil, 160 mg, 4.0 mmol) was added to a solution of 1-boc-azetidine-3-yl-methanol (760 mg, 4.0 mmol) in DMF (5 mL) and diethyl ether (5 mL) at 0° C. and the reaction mixture was stirred at 0° C. for 15 minutes. 4,6-Dichloro-1-(tetrahydro-2H-pyran-2-yl)-1H-pyrazolo[3,4-b]pyridine (1.0 g, 3.7 mmol) was added and the reaction mixture was stirred at rt for 1 h. Water (10 mL) was added and the reaction mixture was extracted with methylene chloride (3×10 mL). The methylene chloride extracts were combined, washed with brine (1×10 mL), dried over sodium sulfate and concentrated in vacuo to yield a clear yellow liquid. The crude liquid was purified via flash column chromatography using 30% EtOAc in hexanes to yield tert-butyl 3-(((6-chloro-1-(tetrahydro-2H-pyran-2-yl)-1H-pyrazolo[3,4-b]pyridin-4-yl)oxy)methyl)azetidine-1-carboxylate (1.1 g, 2.60 mmol, 70% yield). (m/z): [M+H]+ calculated for $C_{20}H_{27}ClN_4O_4$ 423.18 found 423.25.

Preparation 34: tert-butyl 3-(((6-(4-hydroxyphenyl)-1-(tetrahydro-2H-pyran-2-yl)-1H-pyrazolo[3,4-b]pyridin-4-yl)oxy)methyl)azetidine-1-carboxylate

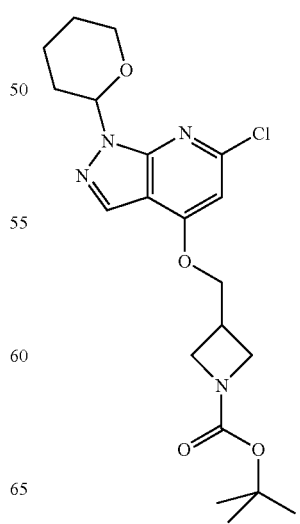

+

101

-continued

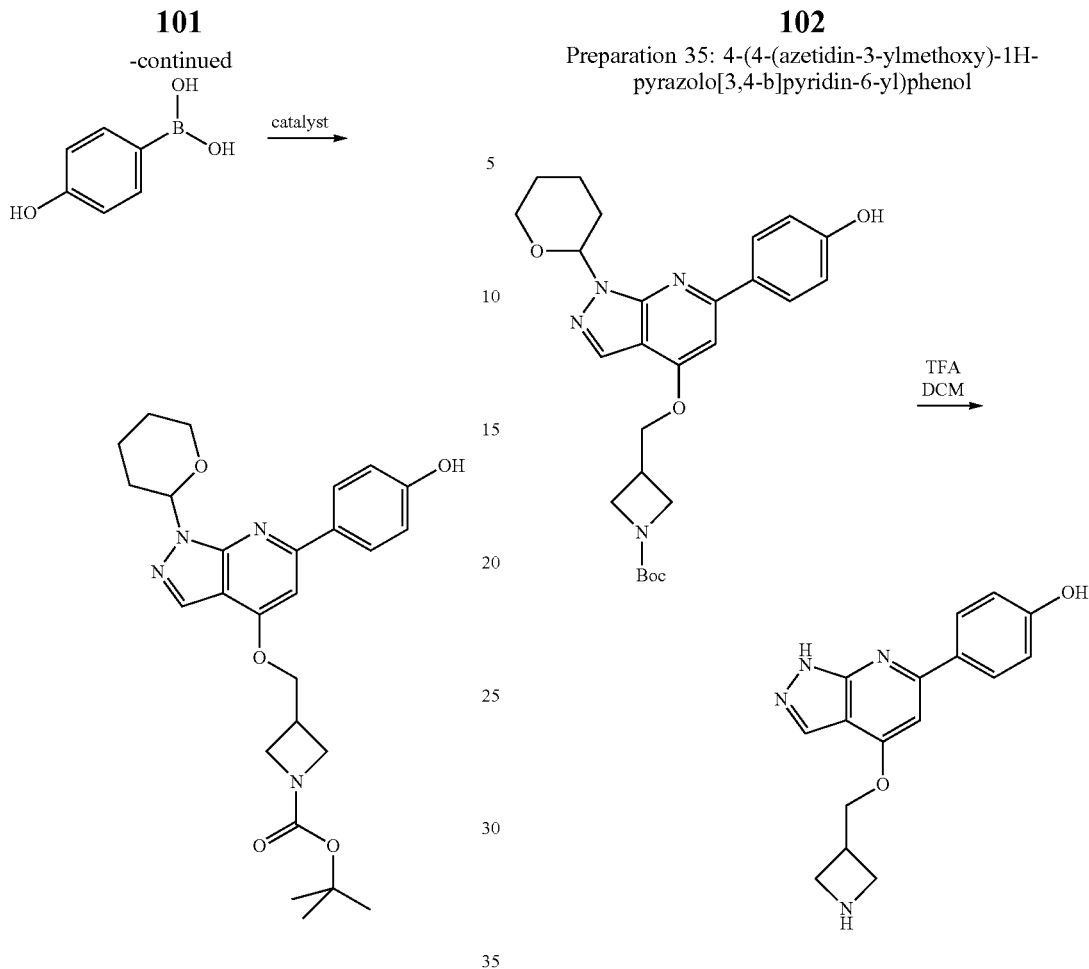

Preparation 35: 4-(4-(azetidin-3-ylmethoxy)-1H-pyrazolo[3,4-b]pyridin-6-yl)phenol A solution of sodium carbonate (500 mg, 4.72 mmol) in water (4 mL) was added to 4-hydroxyphenylboronic acid (392 mg, 2.84 mmol) and tert-butyl 3-(((6-chloro-1-(tetrahydro-2H-pyran-2-yl)-1H-pyrazolo[3,4-b]pyridin-4-yl)oxy)methyl)azetidine-1-carboxylate (1.0 g, 2.36 mmol) in dioxane (20 mL) and the reaction mixture was degassed with nitrogen for 10 minutes. PdCl$_2$(dppf).DCM (196 mg, 0.24 mmol) was added and the reaction mixture was degassed further for 5 minutes and then stirred at 110° C. for 4 hours. The reaction mixture was cooled to rt and then filtered through a bed of Celite. The filtered material was washed with methylene chloride and the filtrates were combined and washed with water (1×10 mL), brine (1×10 mL), dried over sodium sulfate and concentrated in vacuo to yield a clear brown liquid. The crude liquid was purified via flash column chromatography using 50% EtOAc in hexanes to yield tert-butyl 3-(((6-(4-hydroxyphenyl)-1-(tetrahydro-2H-pyran-2-yl)-1H-pyrazolo[3,4-b]pyridin-4-yl)oxy)methyl)azetidine-1-carboxylate (1.02 g, 2.12 mmol, 76% yield). (m/z): [M+H]$^+$ calculated for C$_{26}$H$_{32}$N$_4$O$_5$ 481.25 found 481.65.

TFA (4.0 ml) was added slowly to a solution of tert-butyl 3-(((6-(4-hydroxyphenyl)-1-(tetrahydro-2H-pyran-2-yl)-1H-pyrazolo[3,4-b]pyridin-4-yl)oxy)methyl)azetidine-1-carboxylate (500 mg, 1.04 mmol) in methylene chloride (10 mL) at 0° C. and the reaction mixture was stirred at rt for 3 hours. The reaction mixture was concentrated in vacuo and the resulting solid was triturated with 5% methanol:methylene chloride to yield the title compound as the TFA salt (330 mg, 0.804 mmol, 77% yield). (m/z): [M+H]+ calculated for C$_{16}$H$_{16}$N$_4$O$_2$ 297.14 found 297.15.

Example 10: 1-(3-(((6-(4-hydroxyphenyl)-1H-pyrazolo[3,4-b]pyridin-4-yl)oxy)methyl)azetidin-1-yl)prop-2-en-1-one

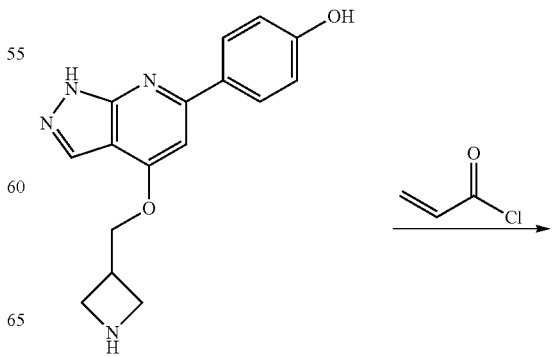

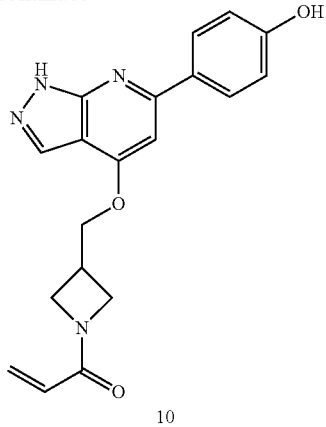

To a solution of 4-(4-(azetidin-3-ylmethoxy)-1H-pyrazolo[3,4-b]pyridin-6-yl)phenol TFA salt (35.5 mg, 0.087 mmol) in DMF (1 mL) was added DIPEA (0.151 ml, 0.865 mmol), followed by the addition of acryloyl chloride (7.0 uL, 0.087 mmol). The reaction mixture was stirred at rt for 15 minutes and then concentrated in vacuo to yield a yellow liquid. The crude liquid was purified via preparatory scale Zorbax Bonus-RP (2.1×30 mm, 1.8 micron) column chromatography using 5-75% acetonitrile in water with 0.05% trifluoroacetic acid to yield 1-(3-(((6-(4-hydroxyphenyl)-1H-pyrazolo[3,4-b]pyridin-4-yl)oxy)methyl)azetidin-1-yl)prop-2-en-1-one (13.4 mg, 0.028 mmol, 33% yield). (m/z): [M+H]$^+$ calcd for $C_{19}H_{28}N_4O_3$ 351.15 found 351.1. $^1$H NMR (400 MHz, DMSO-d$_6$) δ 13.02 (s, 1H), 9.80 (s, 1H), 7.98 (d, J=8.9 Hz, 3H), 7.13 (s, 1H), 6.85 (d, J=8.7 Hz, 2H), 6.32 (dd, J=17.0, 10.3 Hz, 1H), 6.09 (dd, J=17.0, 2.3 Hz, 1H), 5.64 (dd, J=10.3, 2.3 Hz, 1H), 4.55 (d, J=6.7 Hz, 1H), 4.38 (t, J=8.5 Hz, 1H), 4.15-4.02 (m, 2H), 3.80 (dd, J=10.0. 5.4 Hz, 2H), 3.22-3.07 (m, 1H).

Preparation 36: 6-bromo-4-chloro-1-(tetrahydro-2H-pyran-2-yl)-1H-indazole

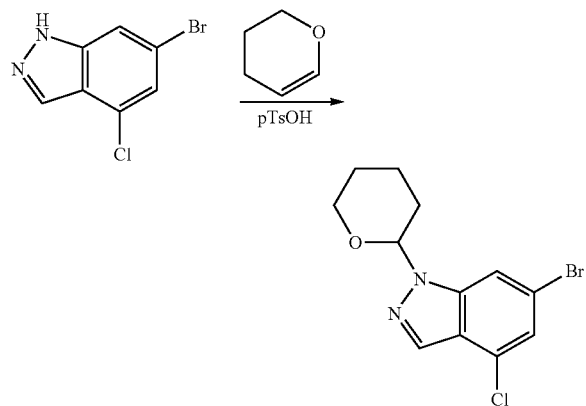

3,4-Dihydro-2h-pyran (19.79 mL, 216.5 mmol) was added to a solution of 6-bromo-4-chloro-1H-indazole (10.0 g, 43.3 mmol) in ethyl acetate (200 mL) at 0° C., followed by p-toluenesulfonic acid monohydrate (1.64 g, 8.66 mmol), and the reaction mixture was stirred at 50° C. for 4 h. Saturated aqueous sodium bicarbonate (100 mL) was added and the mixture was extracted with ethyl acetate (3×100 mL). Ethyl acetate extracts were combined, washed with water (1×100 mL), brine (1×100 mL), dried over sodium sulfate and concentrated to yield a yellow solid. The crude liquid was purified via trituration in n-pentane to yield 6-bromo-4-chloro-1-(tetrahydro-2H-pyran-2-yl)-1H-indazole (13.0 g, 41.2 mmol, 95% yield). (m/z): [M+H]$^+$ calculated for $C_{12}H_{12}BrClN_2O$ 314.99 found 314.93.

Preparation 37: 4-(4-chloro-1-(tetrahydro-2H-pyran-2-yl)-1H-indazol-6-yl)phenol

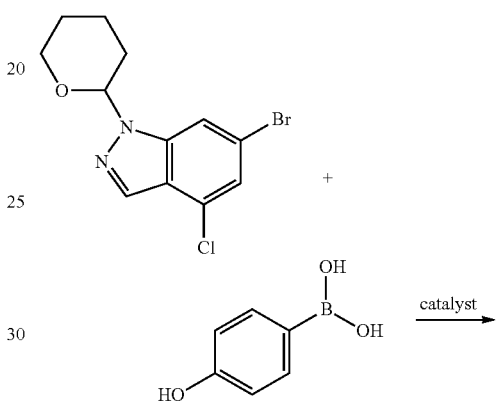

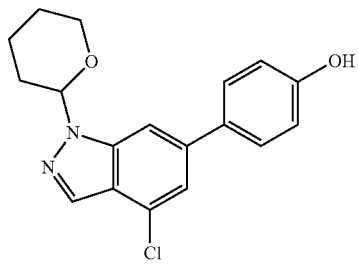

A solution of sodium carbonate (8.77 g, 82.8 mmol), 4-hydroxyphenylboronic acid (6.85 g, 49.7 mmol) and 6-bromo-4-chloro-1-(tetrahydro-2H-pyran-2-yl)-1H-indazole (13.0 g, 41.4 mmol) in dioxane (200 mL) and water (50 mL) was degassed with nitrogen for 15 minutes. PdCl$_2$(dppf).DCM (3.37 g, 4.14 mmol) was added and the reaction mixture was degassed further for 5 minutes and then stirred at 125° C. for 2 hours. The reaction mixture was cooled to rt, ethyl acetate was added and the reaction mixture was filtered through a bed of Celite. Water was added (100 mL) and the mixture was extracted with ethyl acetate. The ethyl acetate extracts were combined, dried over sodium sulfate and concentrated in vacuo to yield a clear brown liquid. The crude liquid was purified via flash column chromatography using a 0-30% EtOAc in hexanes gradient to yield 4-(4-chloro-1-(tetrahydro-2H-pyran-2-yl)-1H-indazol-6-yl)phenol (7.5 g, 22.9 mmol, 55% yield). (m/z): [M+H]$^+$ calculated for $C_{18}H_{17}ClN_2O_2$ 329.11 found 329.08.

Preparation 38: tert-butyl 3-(((6-(4-hydroxyphenyl)-1-(tetrahydro-2H-pyran-2-yl)-1H-indazol-4-yl)(methyl)amino)methyl)azetidine-1-carboxylate

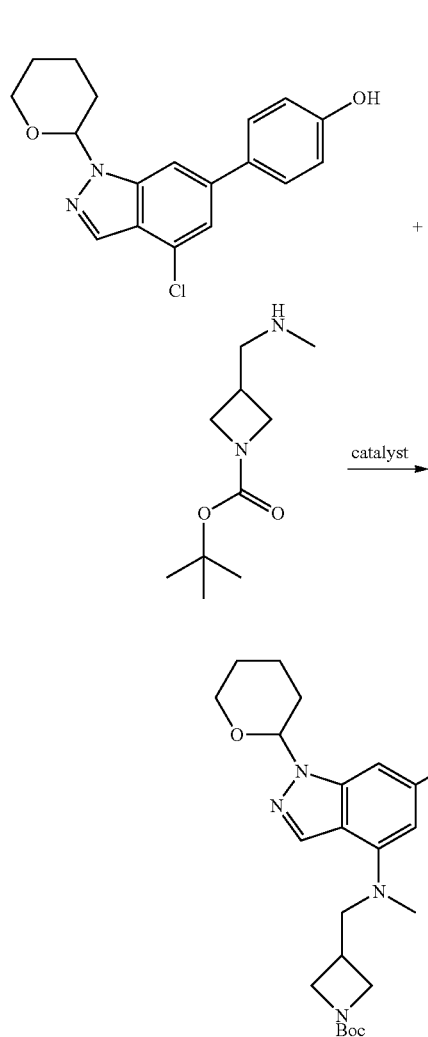

A 1:2 mixture of palladium acetate (68.3 mg, 0.304 mmol) and 2-(di-t-butylphosphino)biphenyl (182.0 mg, 0.608 mmol) was added to a solution of 4-(4-chloro-1-(tetrahydro-2H-pyran-2-yl)-1H-indazol-6-yl)phenol (500 mg, 1.521 mmol), tert-butyl 3-((methylamino)methyl)azetidine-1-carboxylate (457 mg, 2.281 mmol), and sodium tert-butoxide, >99.9% (731 mg, 7.60 mmol) in toluene (15 ml). The reaction mixture was degassed with nitrogen for 10 minutes and then stirred at 110° C. for 16 hours. The reaction mixture was concentrated in vacuo to a volume of about 5 mL. A saturated aqueous solution of ammonium chloride (5 mL) was added and the mixture was extracted with ethyl acetate (2×5 mL). The ethyl acetate extracts were combined, dried over sodium sulfate and concentrated in vacuo to yield a brown liquid. The crude liquid was purified via combiflash column chromatography (24 g) using 50% ethyl acetate in hexanes to yield tert-butyl 3-(((6-(4-hydroxyphenyl)-1-(tetrahydro-2H-pyran-2-yl)-1H-indazol-4-yl)(methyl)amino)methyl)azetidine-1-carboxylate (368 mg, 0.747 mmol, 49% yield). (m/z): [M+H]+ calcd for $C_{28}H_{36}N_4O_4$ 493.28 found 493.4.

Preparation 39: 4-(4-((azetidin-3-ylmethyl)(methyl)amino)-1H-indazol-6-yl)phenol

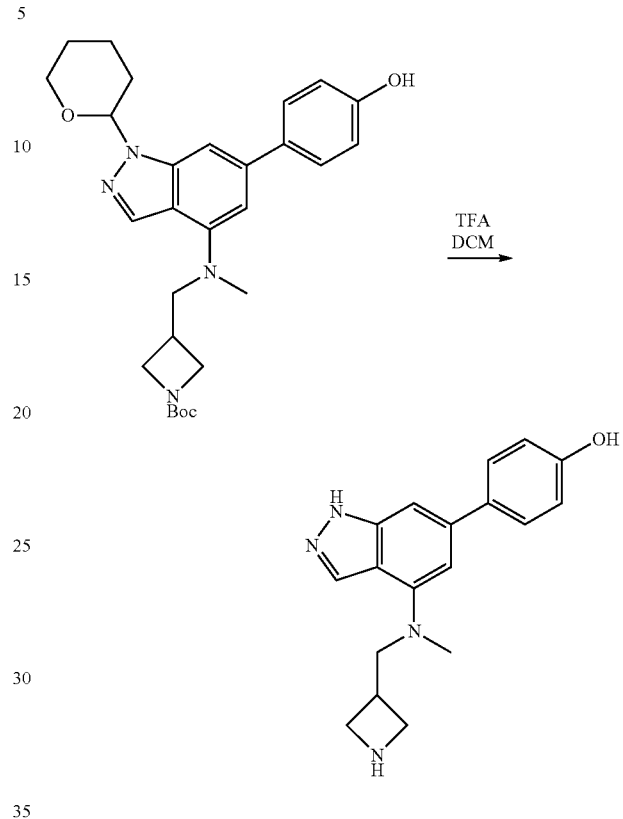

Tert-butyl 3-(((6-(4-hydroxyphenyl)-1-(tetrahydro-2H-pyran-2-yl)-1H-indazol-4-yl)(methyl)amino)methyl)azetidine-1-carboxylate (368 mg, 0.747 mmol) was dissolved in Dichloromethane (1.5 ml) and TFA (1.5 ml) was slowly added. The clear solution was stirred at rt for 5 hours upon which LCMS indicated good conversion to the desired product. The reaction was concentrated down to provide 4-(4-((azetidin-3-ylmethyl)(methyl)amino)-1H-indazol-6-yl)phenol as a TFA salt (100% yield). (m/z): [M+H]+ calcd for $C_{18}H_{20}N_4O$ 309.17 found 309.2.

Example 11: (E)-4-(dimethylamino)-1-(3-(((6-(4-hydroxyphenyl)-1H-indazol-4-yl)(methyl)amino)methyl)azetidin-1-yl)but-2-en-1-one

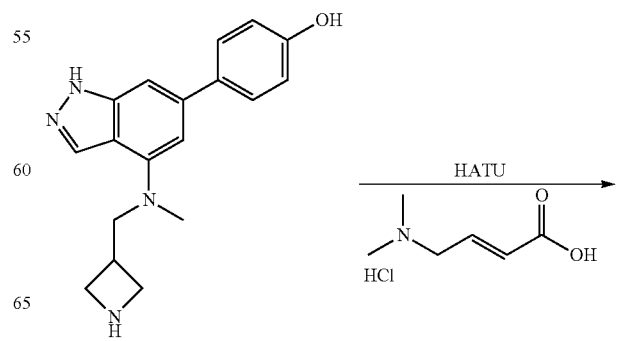

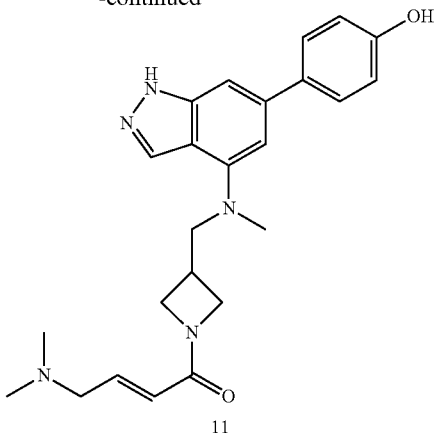

HATU (2-(7-aza-1H-benzotriazole-1-yl)-1,1,3,3-tetramethyluronium hexafluorophosphate, 59.5 mg, 0.157 mmol) was added to a solution of (E)-4-(dimethylamino)but-2-enoic acid hydrochloride (34 mg, 0.263 mmol) in DMF (1 mL). The reaction mixture was stirred at rt for 5 minutes then 4-(4-((azetidin-3-ylmethyl)(methyl)amino)-1H-indazol-6-yl)phenol TFA salt (63 mg, 0.149 mmol) was added, followed by DIPEA (0.260 ml, 1.491 mmol). The reaction mixture was stirred at rt for 15 minutes and then concentrated in vacuo to yield a yellow liquid. The crude liquid was purified via preparatory scale Zorbax Bonus-RP (2.1×30 mm, 1.8 micron) column chromatography using 5-65% acetonitrile in water with 0.05% trifluoroacetic acid to yield (E)-4-(dimethylamino)-1-(3-(((6-(4-hydroxyphenyl)-1H-indazol-4-yl)(methyl)amino)methyl)azetidin-1-yl)but-2-en-1-one (47.6 mg, 0.086 mmol, 96% yield). (m/z): [M+H]+ calcd for $C_{24}H_{29}N_5O_2$ 420.24 found 420.2.

Preparation 40: tert-butyl (3S)-3-((6-(4-hydroxyphenyl)-1-(tetrahydro-2H-pyran-2-yl)-1H-indazol-4-yl)thio)pyrrolidine-1-carboxylate

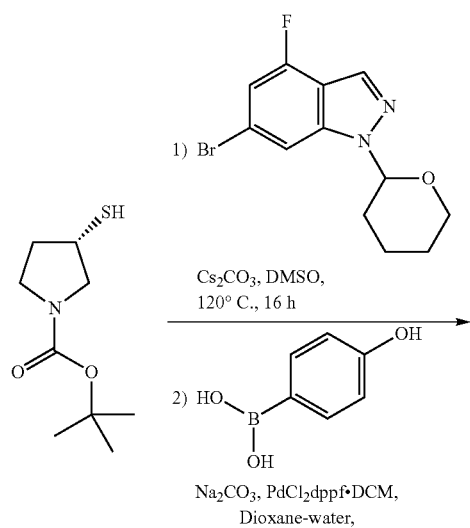

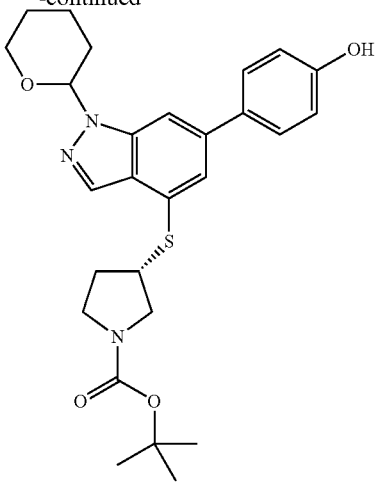

To a stirred solution of 6-bromo-4-fluoro-1-(tetrahydro-2H-pyran-2-yl)-1H-indazole (600 mg, 2.0 mmol) and tert-butyl (S)-3-mercaptopyrrolidine-1-carboxylate (488 mg, 2.20 mmol) in DMSO (5 mL) was added $Cs_2CO_3$ (1.30 mg, 4.0 mmol). The reaction mixture was stirred at 120° C. for 16 hours. Water was added and the reaction mixture was extracted with EtOAc (3×50 ml). The EtOAc extracts were combined, washed with water followed by brine, dried over anhydrous sodium sulphate, filtered and concentrated in vacuo to get the crude intermediate product as clear viscous liquid.

To a stirred solution of the crude intermediate in dioxane (20 mL) and water (4 ml) was added 4-hydroxyphenylboronic acid (240 mg, 1.74 mmol) and $Na_2CO_3$ (461 mg, 4.35 mmol) and the reaction mixture was degassed with nitrogen for 15 minutes. Pd(dppf)Cl$_2$.DCM (118 mg, 0.0145 mmol) was added and the reaction mixture was degassed further for 5 minutes and then stirred at 110° C. for 4 hours. The reaction mixture was cooled to rt, water was added and the reaction mixture was extracted with ethyl acetate (3×50 mL). The ethyl acetate extracts were combined, dried over sodium sulfate and concentrated in vacuo to yield a clear brown liquid. The crude liquid was purified via flash column chromatography using a 30-50% EtOAc in hexanes gradient to yield tert-butyl(3S)-3-((6-(4-hydroxyphenyl)-1-(tetrahydro-2H-pyran-2-yl)-1H-indazol-4-yl)thio)pyrrolidine-1-carboxylate (600 mg, 1.21 mmol, 61%). (m/z): [M+H]+ calculated for $C_{27}H_{33}ClN_3O_4S$ 496.23 found 496.42.

Preparation 41: (S)-4-(4-(pyrrolidin-3-ylthio)-1H-indazol-6-yl)phenol

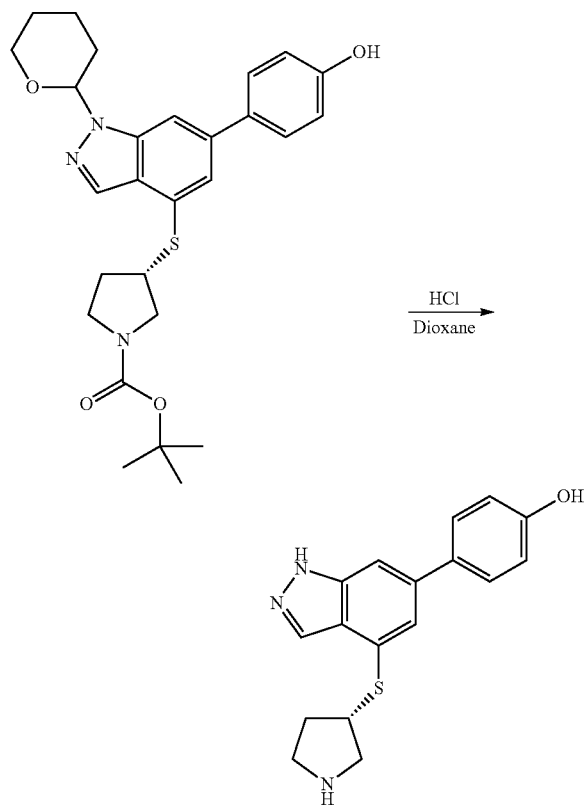

HCl / Dioxane 4.0N HCl in dioxane (10.0 ml, 40.0 mmol) was added to a solution of tert-butyl (3S)-3-((6-(4-hydroxyphenyl)-1-(tetrahydro-2H-pyran-2-yl)-1H-indazol-4-yl)thio)pyrrolidine-1-carboxylate (400 mg, 0.808 mmol) in methanol (6 ml), and the reaction mixture was stirred at 40° C. for 16 h. The reaction mixture was concentrated in vacuo and the resulting residue was purified via preparatory scale C18 column chromatography using a gradient of 20-80% acetonitrile in water with 0.05% trifluoroacetic acid to yield (S)-4-(4-(pyrrolidin-3-ylthio)-1H-indazol-6-yl)phenol as an TFA salt (175 mg, 0.411 mmol, 51% yield). (m/z): [M+H]$^+$ calcd for $C_{17}H_{17}N_3OS$ 312.12 found 312.22.

Example 12: (S)-1-(3-((6-(4-hydroxyphenyl)-1H-indazol-4-yl)thio)pyrrolidin-1-yl)prop-2-en-1-one

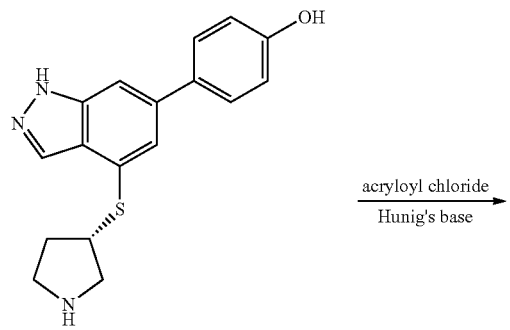

acryloyl chloride / Hunig's base

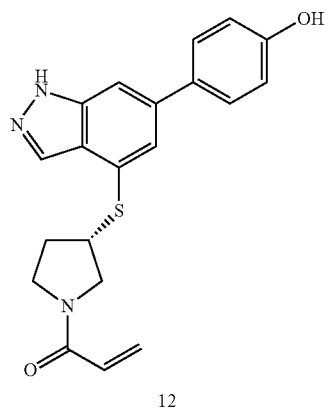

N,N-Diisopropylethylamine (0.079 ml, 0.450 mmol) was added to a solution of (S)-4-(4-(pyrrolidin-3-ylthio)-1H-indazol-6-yl)phenol TFA salt (38.5 mg, 0.091 mmol) in DMF (0.2 ml) at 0° C., followed by acryloyl chloride (8.0 µL, 0.099 mmol). The reaction mixture was stirred at rt for 15 minutes and the crude liquid was purified via preparatory scale C18 column chromatography using a gradient of acetonitrile in water with 0.05% trifluoroacetic acid to yield (S)-1-(3-((6-(4-hydroxyphenyl)-1H-indazol-4-yl)thio)pyrrolidin-1-yl)prop-2-en-1-one as a TFA salt (17.1 mg, 0.046 mmol, 51% yield). (m/z): [M+H]$^+$ calcd for $C_{20}H_{19}N_3O_2S$ 366.13 found 366.1.

Preparation 42: tert-butyl (3S)-3-((6-(4-hydroxyphenyl)-1-(tetrahydro-2H-pyran-2-yl)-1H-indazol-4-yl)sulfonyl)pyrrolidine-1-carboxylate

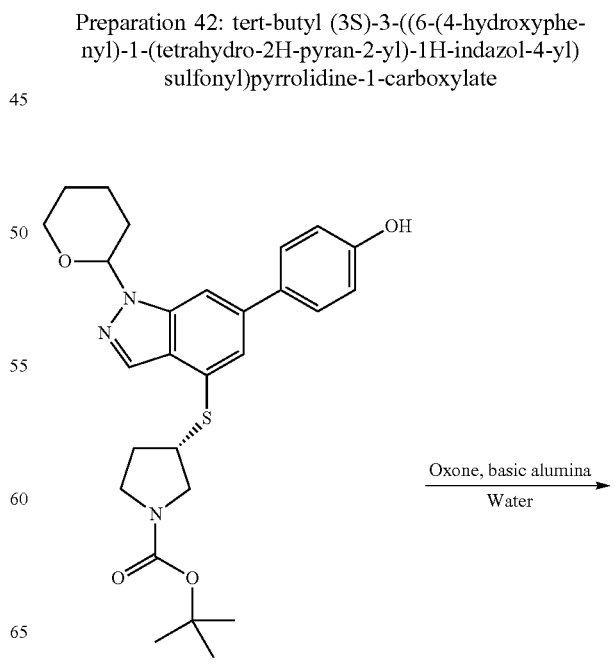

Oxone, basic alumina / Water

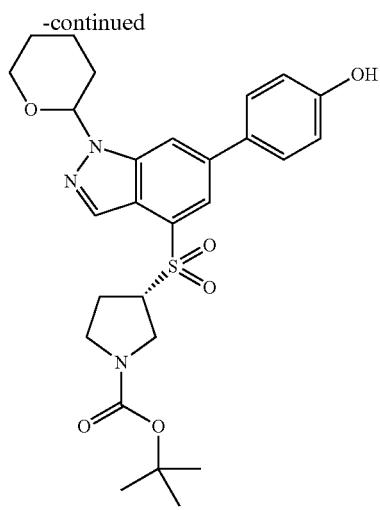

Basic alumina (200 mg) and Oxone (744 mg, 2.42 mmol) were added to a solution of tert-butyl (3S)-3-((6-(4-hydroxyphenyl)-1-(tetrahydro-2H-pyran-2-yl)-1H-indazol-4-yl)thio)pyrrolidine-1-carboxylate (400 mg, 0.80 mmol) in chloroform (50 mL) and water (1 mL) and the reaction mixture was stirred at 65° C. for 12 h. The reaction mixture was filtered through a bed of Celite, and the filtered material was washed with chloroform. The filtrates were combined, water was added and the mixture was extracted with chloroform (3×100 mL). The chloroform extracts were combined, washed with brine, dried over sodium sulfate and concentrated in vacuo. The crude liquid was purified via flash column chromatography using a 30% EtOAc in hexanes to yield tert-butyl (3S)-3-((6-(4-hydroxyphenyl)-1-(tetrahydro-2H-pyran-2-yl)-1H-indazol-4-yl)sulfonyl)pyrrolidine-1-carboxylate (200 mg, 0.379 mmol, 47% yield). (m/z): [M+H]+ calculated for $C_{27}H_{33}ClN_3O_6$ 528.22 found 528.48.

Preparation 43: (S)-4-(4-(pyrrolidin-3-ylsulfonyl)-1H-indazol-6-yl)phenol

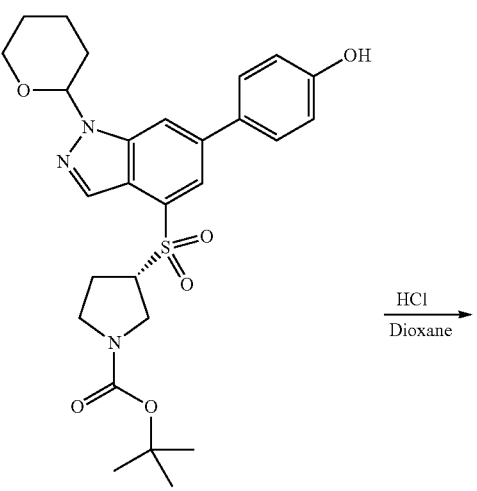

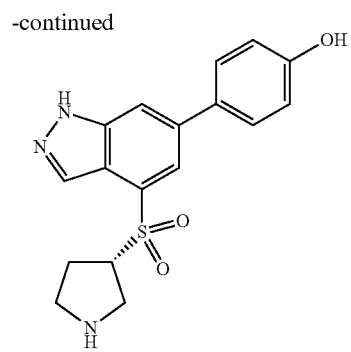

4.0N HCl in dioxane (10.0 ml, 40.0 mmol) was added to a solution of (3S)-3-((6-(4-hydroxyphenyl)-1-(tetrahydro-2H-pyran-2-yl)-1H-indazol-4-yl)sulfonyl)pyrrolidine-1-carboxylate (200 mg, 0.379 mmol) in methanol (2 ml), and the reaction mixture was stirred at rt for 8 h. The reaction mixture was concentrated in vacuo and the resulting residue was triturated with diethyl ether to yield ((S)-4-(4-(pyrrolidin-3-ylsulfonyl)-1H-indazol-6-yl)phenol as an HCl salt (140 mg, 0.369 mmol, 97% yield). (m/z): [M+H]+ calcd for $C_{17}H_{17}N_3O_3S$ 344.11 found 344.04.

Example 13: ((S)-1-(3-((6-(4-hydroxyphenyl)-1H-indazol-4-yl)sulfonyl)pyrrolidin-1-yl)prop-2-en-1-one

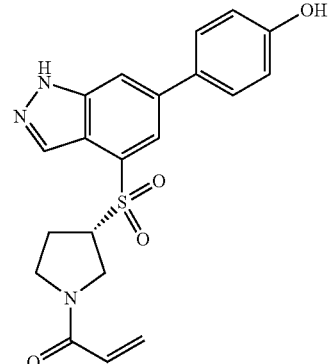

N,N-Diisopropylethylamine (0.079 ml, 0.450 mmol) was added to a solution of (((S)-4-(4-(pyrrolidin-3-ylsulfonyl)-1H-indazol-6-yl)phenol HCl salt (31.0 mg, 0.082 mmol) in DMF (0.2 ml) at 0° C., followed by acryloyl chloride (8.0 µL, 0.099 mmol). The reaction mixture was stirred at rt for 10 minutes and the crude liquid was purified via preparatory scale C18 column chromatography using a gradient of acetonitrile in water with 0.05% trifluoroacetic acid to yield ((S)-1-(3-((6-(4-hydroxyphenyl)-1H-indazol-4-yl)sulfonyl)pyrrolidin-1-yl)prop-2-en-1-one as a TFA salt (3.1 mg, 0.0061 mmol, 7% yield). (m/z): [M+H]$^+$ calcd for $C_{20}H_{19}N_3O_4S$ 398.12 found 398.0.

Preparation 44: tert-butyl 4-((6-chloro-1-(tetrahydro-2H-pyran-2-yl)-1H-indazol-4-yl)methyl)piperidine-1-carboxylate

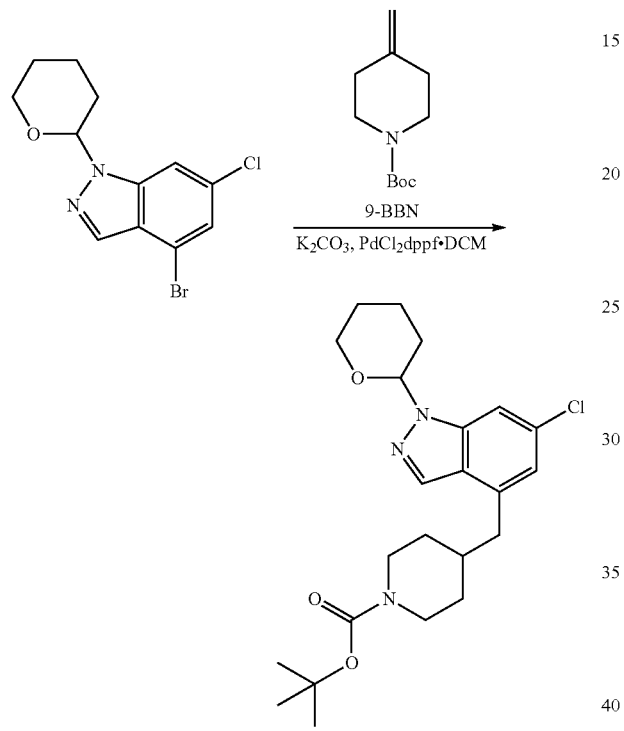

A 0.5 M solution of 9-BBN in THF (7.92 mL, 3.96 mmol) was added to tert-butyl 4-methylenepiperidine-1-carboxylate (468 mg, 2.37 mmol) and the reaction mixture was stirred at 80° C. for 2 h. The reaction mixture was cooled to rt and then cannulated into a preformed solution of 4-bromo-6-chloro-1-(tetrahydro-2H-pyran-2-yl)-1H-indazole (500 mg, 1.58 mmol), potassium carbonate (548 mg, 3.96 mmol) and Pd(dppf)Cl$_2$.DCM (129 mg, 0.15 mmol) in DMF (10.0 ml) & H2O (2.0 ml). The reaction mixture was stirred at 80° C. for 16 h. The reaction mixture was filtered through a bed of Celite, and the filtered material was washed with ethyl acetate. The filtrates were combined, water (100 mL) was added and the mixture was extracted with ethyl acetate (2×150 mL). The cethyl acetate extracts were combined, washed with brine, dried over sodium sulfate and concentrated in vacuo. The crude liquid was purified via flash column chromatography using a 30% EtOAc in hexanes to yield tert-butyl 4-((6-chloro-1-(tetrahydro-2H-pyran-2-yl)-1H-indazol-4-yl)methyl)piperidine-1-carboxylate (460 mg, 1.06 mmol, 67% yield). (m/z): [M+H]$^+$ calculated for $C_{23}H_{32}ClN_3O_3$ 434.22 found 434.47.

Preparation 45: tert-butyl 4-((6-(4-hydroxyphenyl)-1-(tetrahydro-2H-pyran-2-yl)-1H-indazol-4-yl)methyl)piperidine-1-carboxylate

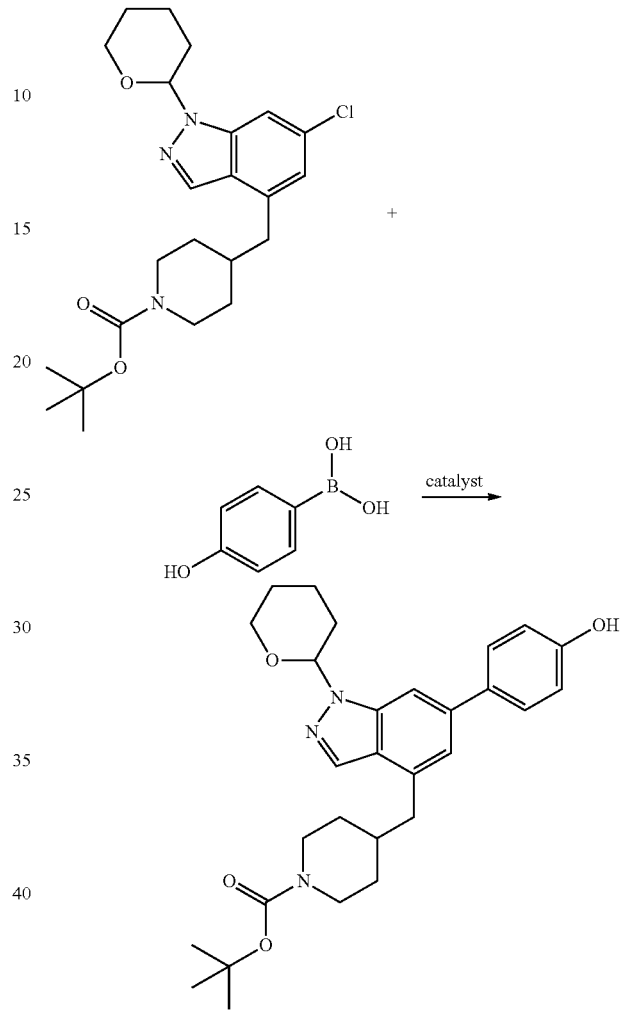

4-Hydroxyphenylboronic acid (195 mg, 1.41 mmol) was added to a suspension of tert-butyl 4-((6-chloro-1-(tetrahydro-2H-pyran-2-yl)-1H-indazol-4-yl)methyl)piperidine-1-carboxylate (410 mg, 0.94 mmol) in dioxane (10.0 mL) and water (2.0 mL), followed by potassium phosphate (401 mg, 1.88 mmol) and the reaction mixture was degassed with nitrogen for 15 minutes. 2'-(Dimethylamino)-2-biphenylylpalladium(II) chloride dinorbornylphosphine complex (52 mg, 0.07 mmol) was added and the reaction mixture was heated under microwave irradiation at 100° C. for 1 hour. The reaction mixture was cooled to rt and then filtered through a bed of Celite. Water (100 mL) was added to the filtrate, which was then extracted with ethyl acetate (3×100 mL). The ethyl acetate extracts were combined, washed with water, brine, dried over sodium sulfate and concentrated in vacuo. The crude liquid was purified via flash column chromatography using 50% EtOAc in hexanes to yield tert-butyl 4-((6-(4-hydroxyphenyl)-1-(tetrahydro-2H-pyran-2-yl)-1H-indazol-4-yl)methyl)piperidine-1-carboxylate (300 mg, 0.610 mmol, 65%). (m/z): [M+H]$^+$ calculated for $C_{29}H_{37}N_3O_4$ 492.29 found 492.46.

Preparation 46: 4-(4-(piperidin-4-ylmethyl)-1H-indazol-6-yl)phenol

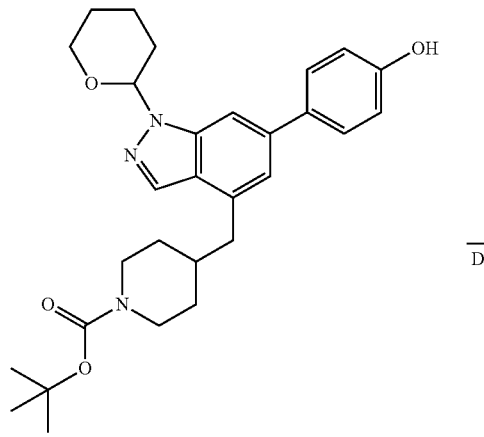

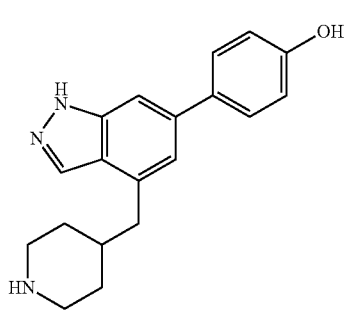

4.0N HCl in dioxane (10.0 ml, 40.0 mmol) was added to a solution of tert-butyl 4-((6-(4-hydroxyphenyl)-1-(tetrahydro-2H-pyran-2-yl)-1H-indazol-4-yl)methyl)piperidine-1-carboxylate (300 mg, 0.610 mmol) in methanol (2 ml), and the reaction mixture was stirred at rt for 8 h. The reaction mixture was concentrated in vacuo and the resulting residue was triturated with diethyl ether to yield 4-(4-(piperidin-4-ylmethyl)-1H-indazol-6-yl)phenol as an HCl salt (195 mg, 0.567 mmol, 93% yield). (m/z): [M+H]$^+$ calcd for $C_{19}H_{21}N_3O$ 308.18 found 308.10.

Example 14: 1-(4-((6-(4-hydroxyphenyl)-1H-indazol-4-yl)methyl)piperidin-1-yl)prop-2-en-1-one

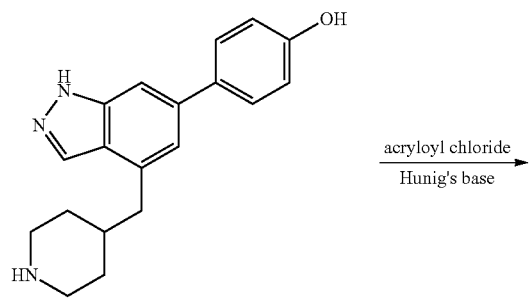

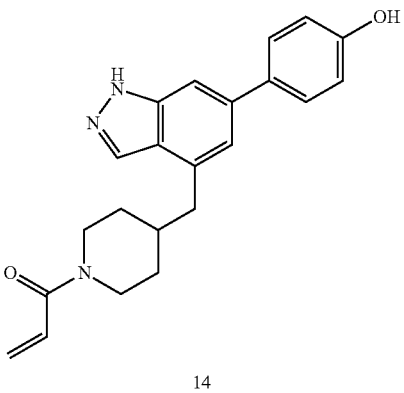

N,N-Diisopropylethylamine (0.079 ml, 0.450 mmol) was added to a solution of 4-(4-(piperidin-4-ylmethyl)-1H-indazol-6-yl)phenol HCl salt (27.5 mg, 0.080 mmol) in DMF (0.2 ml) at 0° C., followed by acryloyl chloride (8.00 μL, 0.099 mmol). The reaction mixture was stirred at rt for 10 minutes and the crude liquid was purified via preparatory scale C18 column chromatography using a gradient of acetonitrile in water with 0.05% trifluoroacetic acid to yield 1-(4-((6-(4-hydroxyphenyl)-1H-indazol-4-yl)methyl)piperidin-1-yl)prop-2-en-1-one as a TFA salt (7.2 mg, 0.015 mmol, 19% yield). (m/z): [M+H]$^+$ calcd for $C_{22}H_{23}N_3O_2$ 362.19 found 362.1.

Preparation 47: tert-butyl (R,E)-2-(3-ethoxy-3-oxoprop-1-en-1-yl)pyrrolidine-1-carboxylate

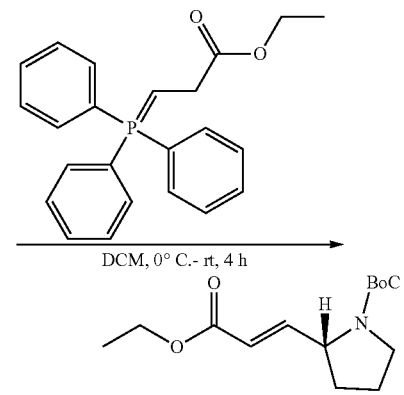

Ethyl 3-(triphenylphosphoranylidene)propanoate (3.64 g, 10.0 mmol) was added to a solution of tert-butyl (R)-2-formylpyrrolidine-1-carboxylate (2.0 g, 10.0 mmol) in methylene chloride (40 mL) at 0° C. and the reaction mixture was stirred at rt for 4 h. Water (200 mL) was added and the reaction mixture was extracted with methylene chloride (2×100 mL). The methylene chloride extracts were combined, dried over sodium sulfate and concentrated in vacuo. The crude liquid was purified via flash column chromatography using 5% ethyl acetate in hexanes to yield tert-butyl (R,E)-2-(3-ethoxy-3-oxoprop-1-en-1-yl)pyrrolidine-1-carboxylate (1.70 g, 6.31 mmol, 63% yield).

Preparation 48: ethyl (R,E)-3-(1-methylpyrrolidin-2-yl)acrylate

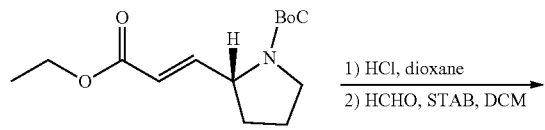

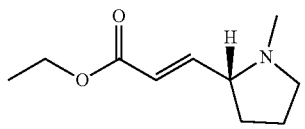

4M HCl in dioxane (7.20 mL, 28.8 mmol) was added to a solution of TFA (10.90 ml) was slowly added to a solution of tert-butyl (R,E)-2-(3-ethoxy-3-oxoprop-1-en-1-yl)pyrrolidine-1-carboxylate (1.70 g, 6.31 mmol) in dioxane (40 mL) and the reaction mixture was stirred at rt for 2 h. The reaction was concentrated in vacuo to yield the crude intermediate. A 37% solution of formaldehyde in water (4.19 mL, 41.4 mmol) was added to a solution of the crude intermediate in methylene chloride (50 mL) at 0° C., followed by sodium triacetoxyborohydride (5.26 g, 24.8 mmol), and the reaction mixture was stirred at rt for 16 h. Ice cold water (20 mL) was added and the reaction mixture was extracted with methylene chloride (2×100 mL). The methylene chloride extracts were combined, washed with brine, dried over sodium sulfate and concentrated in vacuo to yield ethyl (R,E)-3-(1-methylpyrrolidin-2-yl)acrylate (0.900 g, 4.915 mmol, 78% yield). (m/z): [M+H]$^+$ calcd for $C_{10}H_{17}NO_2$ 184.14 found 184.0.

Preparation 49: (R,E)-3-(1-methylpyrrolidin-2-yl)acrylic Acid

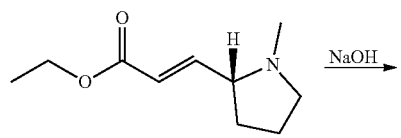

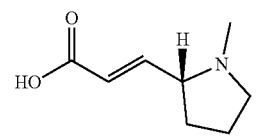

Sodium hydroxide (294 mg, 7.36 mmol) was added to a solution of ethyl (R,E)-3-(1-methylpyrrolidin-2-yl)acrylate (0.900 g, 4.915 mmol, 78% yield) in 2:1 THF/water (15 mL) and the reaction mixture was stirred at rt for 4 h. The reaction mixture was concentrated in vacuo to yield ethyl (R,E)-3-(1-methylpyrrolidin-2-yl)acrylic acid (668 mg, 4.30 mmol, 88% yield). (m/z): [M+H]$^+$ calcd for $C_8H_{13}NO_2$ 156.10 found 156.26.

Example 15: (E)-1-((S)-3-((6-(4-hydroxyphenyl)-1H-indazol-4-yl)oxy)pyrrolidin-1-yl)-3-((R)-1-methylpyrrolidin-2-yl)prop-2-en-1-one

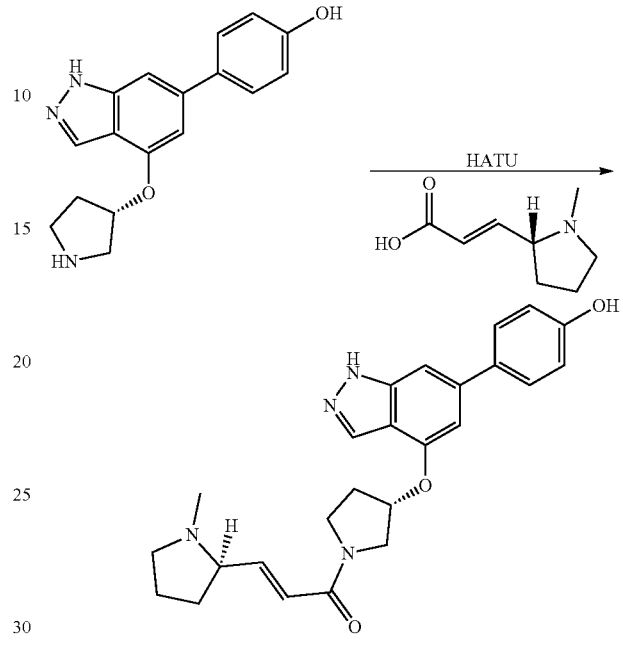

A solution of HATU (0.031 g, 0.083 mmol) in DMF (0.1 mL) was added to ethyl (R,E)-3-(1-methylpyrrolidin-2-yl) acrylic acid (14.0 mg, 0.090 mmol), followed by a solution of (S)-4-(4-(pyrrolidin-3-yloxy)-1H-indazol-6-yl)phenol hydrochloride (0.025 g, 0.075 mmol) and DIPEA (0.065 ml, 0.375 mmol), the reaction mixture was stirred at rt for 15 minutes and the crude liquid was purified via preparatory scale C18 column chromatography using a gradient of acetonitrile in water with 0.05% trifluoroacetic acid to yield ((E)-1-((S)-3-((6-(4-hydroxyphenyl)-1H-indazol-4-yl)oxy) pyrrolidin-1-yl)-3-((R)-1-methylpyrrolidin-2-yl)prop-2-en-1-one as a TFA salt (7.8 mg, 0.014 mmol, 19% yield). (m/z): [M+H]$^+$ calcd for $C_{25}H_{28}N_4O_3$ 433.23 found 433.1.

Preparation 50: tert-butyl 2-((dimethylamino)methyl)acrylate

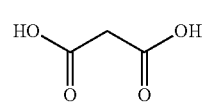

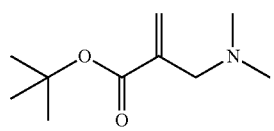

Paraformaldehyde (1.20 g, 43.2 mmol) was added to a solution of Malonic acid (2.0 g, 19.3 mmol) in 1,4-dioxane (20 mL), followed by a 2M solution of dimethylamine in THF (9.60 mL, 19.2 mmol) and the reaction mixture was stirred at 70° C. for 1 h. The reaction mixture was concentrated in vacuo and the crude product was recrystallized using diethyl ether and acetone to yield the intermediate as a white solid. The intermediate white solid was dissolved in t-BuOH (100 mL) and di-tert-butyl dicarbonate (4.60 mL, 20.7 mmol) was added to the reaction mixture followed by 4-dimethylaminopyridine (511 mg, 4.18 mmol) and the reaction mixture was stirred at rt for 4 h. Methylene chloride (500 mL) was added and the reaction mixture was washed with water (2×500 mL), dried over sodium sulfate and concentrated in vacuo. The crude residue was purified via flash column chromatography using 2% methanol in methylene chloride to yield tert-butyl 2-((dimethylamino)methyl) acrylate (220 mg, 1.19 mmol, 6% yield).

Preparation 51: 2-((dimethylamino)methyl)acrylic Acid

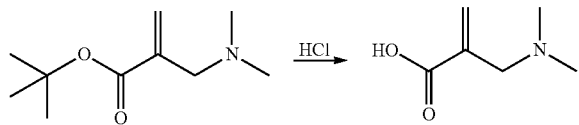

A 1N aqueous solution of HCl (5.0 mL, 5 mmol) was added to tert-butyl 2-((dimethylamino)methyl)acrylate (220 mg, 1.19 mmol) and the reaction mixture was stirred at 100° C. for 15 minutes. The reaction mixture was concentrated in vacuo and the resulting residue was azeotroped with toluene and further triturated with diethyl ether to yield 2-((dimethylamino)methyl)acrylic acid as a HCl salt (119 mg, 0.719 mmol, 60% yield). (m/z): [M+H]$^+$ calcd for $C_6H_{11}NO_2$ 130.09 found 130.22.

Example 16: (S)-2-((dimethylamino)methyl)-1-(3-((6-(4-hydroxyphenyl)-1H-indazol-4-yl)oxy)pyrrolidin-1-yl)prop-2-en-1-one

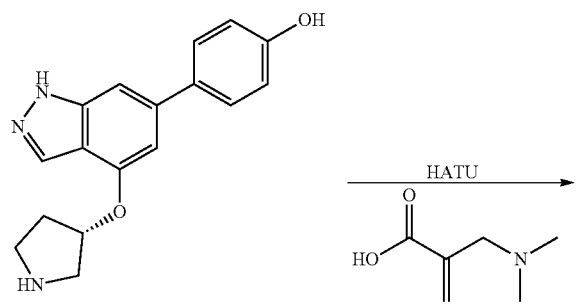

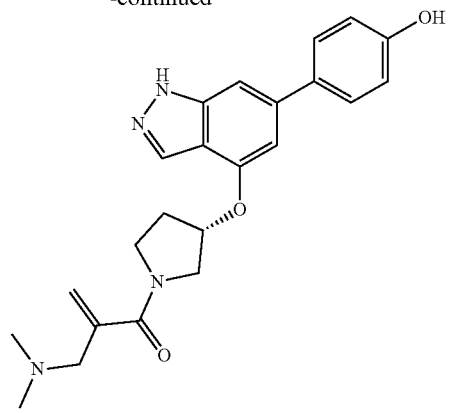

A solution of HATU (0.031 g, 0.083 mmol) in DMF (0.1 mL) was added to 2-((dimethylamino)methyl)acrylic acid hydrochloride (14.9 mg, 0.090 mmol), followed by a solution of (S)-4-(4-(pyrrolidin-3-yloxy)-1H-indazol-6-yl)phenol hydrochloride (0.025 g, 0.075 mmol) and DIPEA (0.065 ml, 0.375 mmol), the reaction mixture was stirred at rt for 15 minutes and the crude liquid was purified via preparatory scale C18 column chromatography using a gradient of acetonitrile in water with 0.05% trifluoroacetic acid to yield (S)-2-((dimethylamino)methyl)-1-(3-((6-(4-hydroxyphenyl)-1H-indazol-4-yl)oxy)pyrrolidin-1-yl)prop-2-en-1-one as a TFA salt (2.6 mg, 0.005 mmol, 7% yield). (m/z): [M+H]$^+$ calcd for $C_{23}H_{26}N_4O_3$ 407.21 found 407.1.

Example 17: (S)-1-(3-((6-(4-hydroxyphenyl)-1H-indazol-4-yl)oxy)pyrrolidin-1-yl)prop-2-yn-1-one

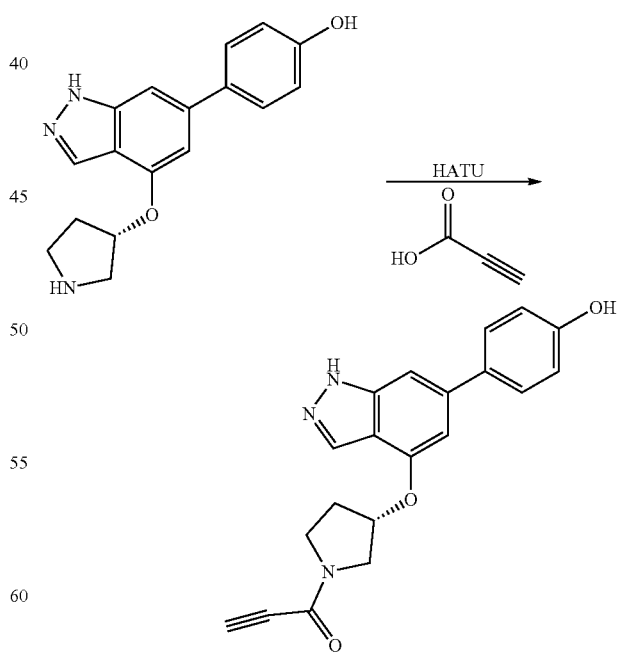

A solution of HATU (0.031 g, 0.083 mmol) in DMF (0.1 mL) was added to propiolic acid (6.0 mg, 0.090 mmol), followed by a solution of (S)-4-(4-(pyrrolidin-3-yloxy)-1H-indazol-6-yl)phenol hydrochloride (0.025 g, 0.075 mmol) and DIPEA (0.065 ml, 0.375 mmol), the reaction mixture was stirred at rt for 15 minutes and the crude liquid was purified via preparatory scale C18 column chromatography using a gradient of acetonitrile in water with 0.05% trifluoroacetic acid to yield (S)-1-(3-((6-(4-hydroxyphenyl)-1H-indazol-4-yl)oxy)pyrrolidin-1-yl)prop-2-yn-1-one as a TFA salt (2.4 mg, 0.005 mmol, 7% yield). (m/z): [M+H]$^+$ calcd for $C_{20}H_{17}N_3O_3$ 348.14 found 348.0.

Example 18: (S)-4-(4-((1-(vinylsulfonyl)pyrrolidin-3-yl)oxy)-1H-indazol-6-yl)phenol

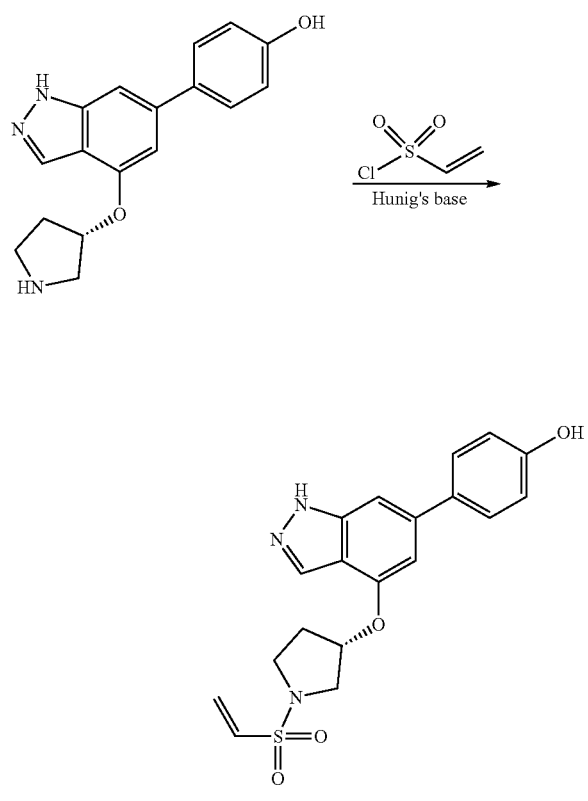

Preparation 52: tert-butyl 3-(2-((6-fluoro-1-(tetrahydro-2H-pyran-2-yl)-1H-indazol-4-yl)oxy)propan-2-yl)azetidine-1-carboxylate

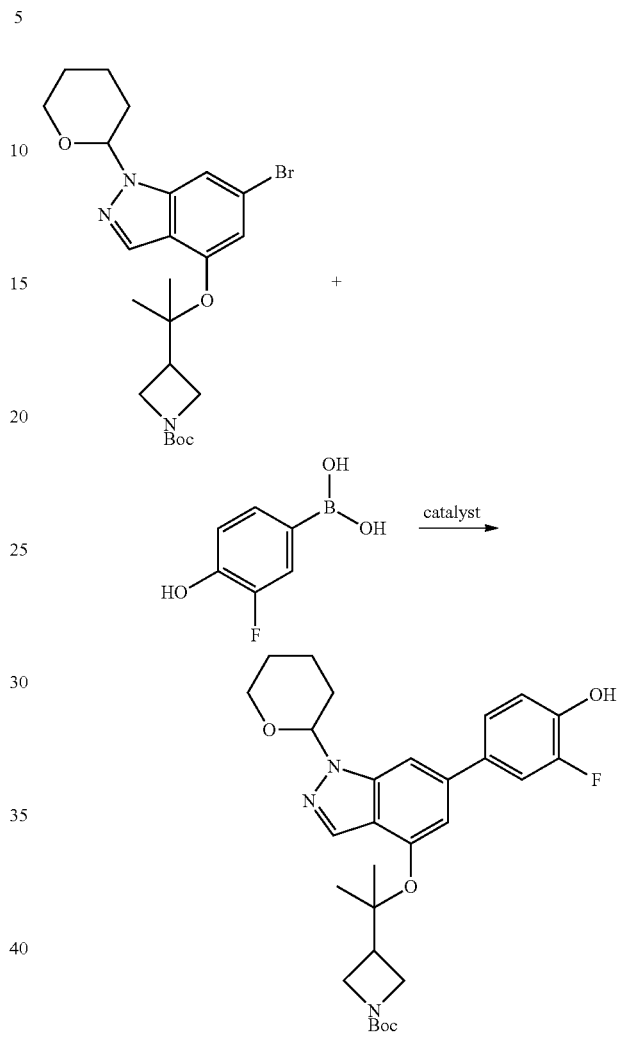

Cesium carbonate (6.33 g, 19.42 mmol) was added to a solution of tert-butyl 3-(2-((6-bromo-1-(tetrahydro-2H-pyran-2-yl)-1H-indazol-4-yl)oxy)propan-2-yl)azetidine-1-carboxylate (3.20 g, 6.47 mmol) and 3-fluoro-4-hydroxybenzeneboronic acid (1.514 g, 9.71 mmol) in 1,4-dioxane (20.71 ml) and water (5.18 ml) and the reaction mixture was degassed with nitrogen for 10 minutes.

Dichloro[1,1'-bis(diphenylphosphino)ferrocene]palladium(II) (0.793 g, 0.971 mmol) was added and the reaction mixture was stirred 110° C. for 2 hours. The reaction mixture was concentrated in vacuo to a volume of about 5 mL. A saturated aqueous solution of ammonium chloride (20 mL) was added and the mixture was extracted with methylene chloride (2×20 mL). The methylene chloride extracts were combined, dried over sodium sulfate and concentrated in vacuo to yield a brown liquid. The crude liquid was purified via flash column chromatography using 50% ethyl acetate in hexanes to yield tert-butyl 3-(2-((6-fluoro-1-(tetrahydro-2H-pyran-2-yl)-1H-indazol-4-yl)oxy)propan-2-yl)azetidine-1-carboxylate (2.30 g, 4.38 mmol, 68% yield). (m/z): [M+H]$^+$ calcd for $C_{29}H_{37}FN_3O_5$ 526.27 found 526.3.

N,N-Diisopropylethylamine (0.052 ml, 0.301 mmol) was added to a solution of (S)-4-(4-(pyrrolidin-3-yloxy)-1H-indazol-6-yl)phenol hydrochloride (0.020 g, 0.060 mmol) in DMF (0.2 ml) at 0° C., followed by ethenesulfonyl chloride (8.4 mL, 0.066 mmol). The reaction mixture was stirred at rt for 10 minutes and the crude liquid was purified via preparatory scale C18 column chromatography using a gradient of acetonitrile in water with 0.05% trifluoroacetic acid to yield (S)-4-(4-((1-(vinylsulfonyl)pyrrolidin-3-yl)oxy)-1H-indazol-6-yl)phenol as a TFA salt (8.2 mg, 0.016 mmol, 27% yield). (m/z): [M+H]$^+$ calcd for $C_{19}H_{19}N_3O_4$ 386.12 found 386.3.

Preparation 53: 4-(4-((2-azetidin-3-yl)propan-2-yl)oxy)-1-H-indazole-6-yl)-2-fluorophenol

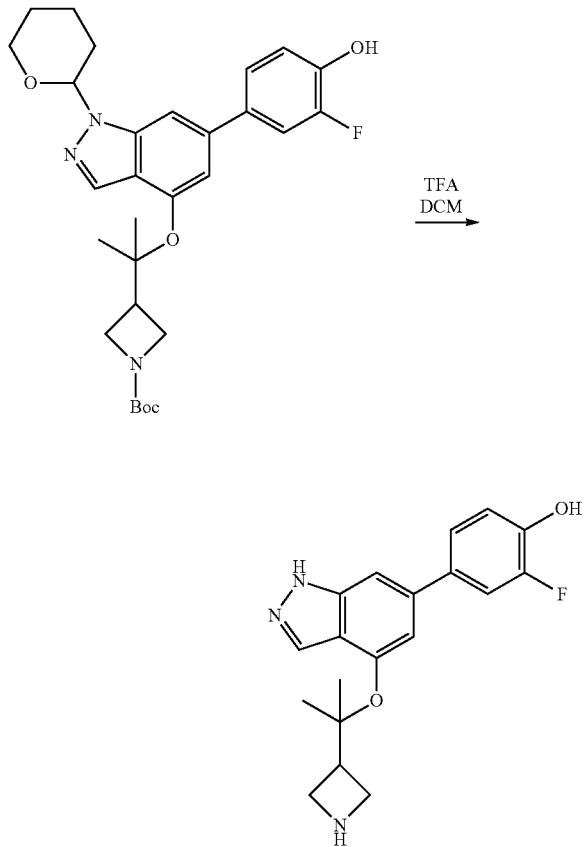 [SMILES: CC(C)(C)OC(=O)N1CC(COc2cc(-c3ccc(O)cc3)cc3c2cnn3C2CCCCO2)C1 ; Oc1ccc(-c2cc(OCC3CNC3)c3cn[nH]c3c2)cc1]

Tert-butyl 3-(2-((6-fluoro-1-(tetrahydro-2H-pyran-2-yl)-1H-indazol-4-yl)oxy)propan-2-yl)azetidine-1-carboxylate (3.10 g, 5.90 mmol) was dissolved in dichloromethane (10 ml) and TFA (10 ml) was slowly added. The clear solution was stirred at rt for 2 hours upon which LCMS indicated good conversion to the desired product. The reaction was concentrated down to provide 4-(4-((2-azetidin-3-yl)propan-2-yl)oxy)-1-H-indazole-6-yl)-2-fluorophenol as a TFA salt (100% yield). (m/z): [M+H]$^+$ calcd for C$_{19}$H$_{21}$FN$_3$O$_2$ 342.16 found 342.3.

Example 19: (E)-1-(3-(2-((6-(3-fluoro-4-hydroxyphenyl)-1H-indazol-4-yl)oxy)propan-2-yl)azetidin-1-yl)-4-(dimethylamino)but-2-en-1-one

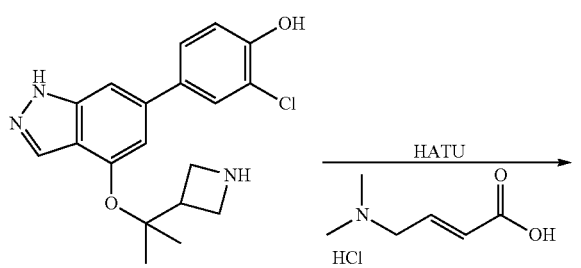

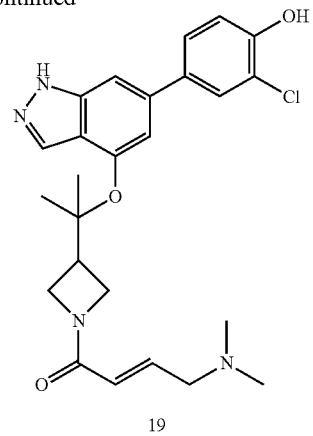

HATU (2-(7-aza-1H-benzotriazole-1-yl)-1,1,3,3-tetramethyluronium hexafluorophosphate, 2.92 g, 7.07 mmol) was added to a solution of (E)-4-(dimethylamino)but-2-enoic acid hydrochloride (1.07 g, 6.48 mmol) in DMF (10 mL). The reaction mixture was stirred at rt for 10 minutes then 4-(4-((2-azetidin-3-yl)propan-2-yl)oxy)-1-H-indazole-6-yl)-2-fluorophenol TFA salt (2.01 g, 5.89 mmol) was added, followed by DIPEA (3.08 ml, 17.7 mmol). The reaction mixture was stirred at rt for 15 minutes and then concentrated in vacuo to yield a yellow liquid. The crude liquid was purified via preparatory scale C18 column chromatography using a gradient of 20-80% acetonitrile in water with 0.05% trifluoroacetic acid to yield (E)-4-(dimethylamino)-1-(3-(2-((6-(3-fluoro-4-hydroxyphenyl)-1H-indazol-4-yl)oxy)propan-2-yl)cyclobutyl)but-2-en-1-one as a TFA salt (1.65 g, 3.65 mmol, 61.9% yield). (m/z): [M+H]$^+$ calcd for C$_{25}$H$_{30}$FN$_4$O$_3$ 453.23 found 453.3.

Preparation 54: tert-butyl 3-(2-((2,6-dichloropyridin-4-yl)oxy)propan-2-yl)azetidine-1-carboxylate

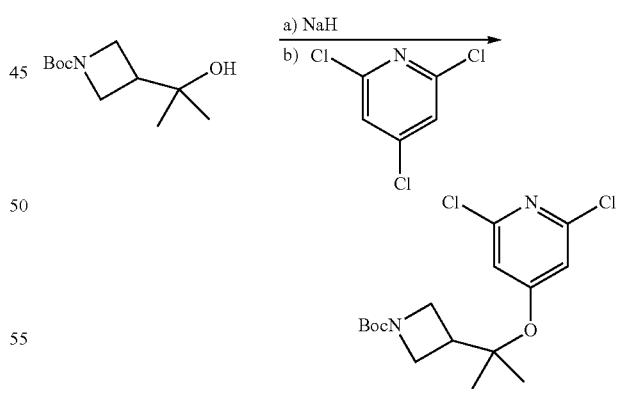

A solution of tert-butyl 3-(2-hydroxypropan-2-yl)azetidine-1-carboxylate (6.5 g, 30.21 mmol) in DMSO (10 mL) was added dropwise to a solution of 60% by weight sodium hydride in mineral oil (1.65 g, 41.20 mmol) in DMSO (15 mL) and the reaction mixture was stirred at rt for 10 minutes. A solution of 2,4,6-trichloropyridine (5.0 g, 27.62 mmol) in DMSO (25 mL) was added dropwise to the resulting suspension, and the reaction mixture was stirred at 60° C. for 16 h. The reaction mixture was quenched using a saturated aqueous solution of ammonium chloride and extracted with ethyl acetate. The ethyl acetate extracts were combined, washed with an aqueous saturated solution of sodium chloride, dried over sodium sulfate and concentrated in vacuo to yield the crude liquid. The crude liquid was purified via flash column chromatography using 5% ethyl acetate in hexanes to yield tert-butyl 3-(2-((2,6-dichloropyridin-4-yl)oxy)propan-2-yl)azetidine-1-carboxylate (2.10 g, 5.80 mmol, 21.1% yield). (m/z): [M+H]$^+$ calculated for $C_{16}H_{23}Cl_2N_2O_3$ 361.11 found 361.11.

Preparation 55: tert-butyl 3-(2-((6-chloro-1H-pyrazolo[3,4-b]pyridin-4-yl)oxy)propan-2-yl)azetidine-1-carboxylate

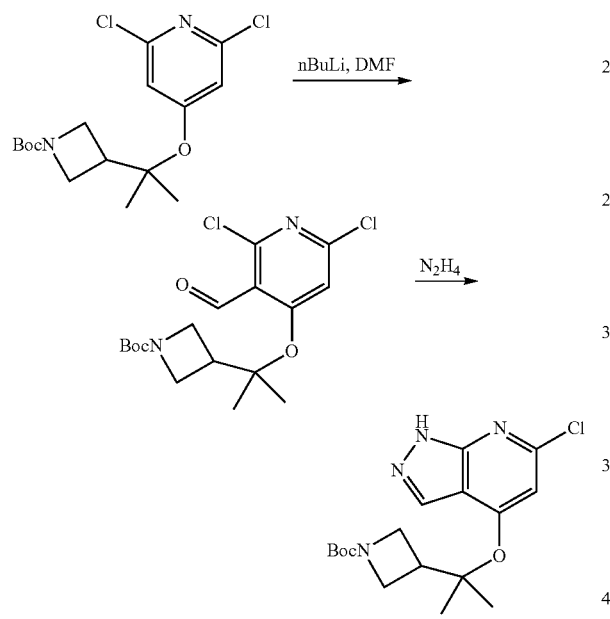

A 2M solution of nBuLi in hexanes (3.05 mL, 6.11 mmol) was added dropwise to a solution of tert-butyl 3-(2-((2,6-dichloropyridin-4-yl)oxy)propan-2-yl)azetidine-1-carboxylate (2.0 g, 5.55 mmol) in THF (40 mL) at −78° C. DMF (0.64 mL, 8.33 mmol) was added in one portion and the reaction mixture was stirred at −78° C. for 10 min. 5% Acetic acid in diethyl ether was added and the mixture was further diluted with water. The aqueous layer was extracted with ethyl acetate (3 times). The ethyl acetate extracts were combined, washed with an aqueous saturated solution of sodium chloride, dried over sodium sulfate and concentrated in vacuo to yield the crude intermediate tert-butyl 3-(2-((2,6-dichloro-3-formylpyridine-4-yl)oxy)propan-2-yl)azetidine-1-carboxylate. Hydrazine hydrate (1.0 mL, 20.56 mmol) was added dropwise to a solution of the crude tert-butyl 3-(2-((2,6-dichloro-3-formylpyridine-4-yl)oxy)propan-2-yl)azetidine-1-carboxylate in THF (40 mL) at 0° C., and the reaction mixture was stirred at rt for 2 h. Triethylamine (1.45 mL, 10.28 mmol) was added, and the reaction mixture was stirred at 60° C. for 16 h. The reaction mixture was concentrated in vacuo and the resulting residue was diluted with water and extracted with ethyl acetate. The ethyl acetate extracts were combined, washed with an aqueous saturated solution of sodium chloride, dried over sodium sulfate and concentrated in vacuo to yield the crude liquid. The crude liquid was purified via flash column chromatography using 20% ethyl acetate in hexanes to yield tert-butyl 3-(2-((6-chloro-1H-pyrazolo[3,4-b]pyridin-4-yl)oxy)propan-2-yl)azetidine-1-carboxylate (1.20 g, 3.27 mmol, 58.9% yield). (m/z): [M+H]$^+$ calculated for $C_{17}H_{23}ClN_4O_3$ 367.15 found 367.00.

Preparation 56: tert-butyl 3-(2-((6-(4-hydroxyphenyl)-1H-pyrazolo[3,4-b]pyridin-4-yl)oxy)propan-2-yl)azetidine-1-carboxylate

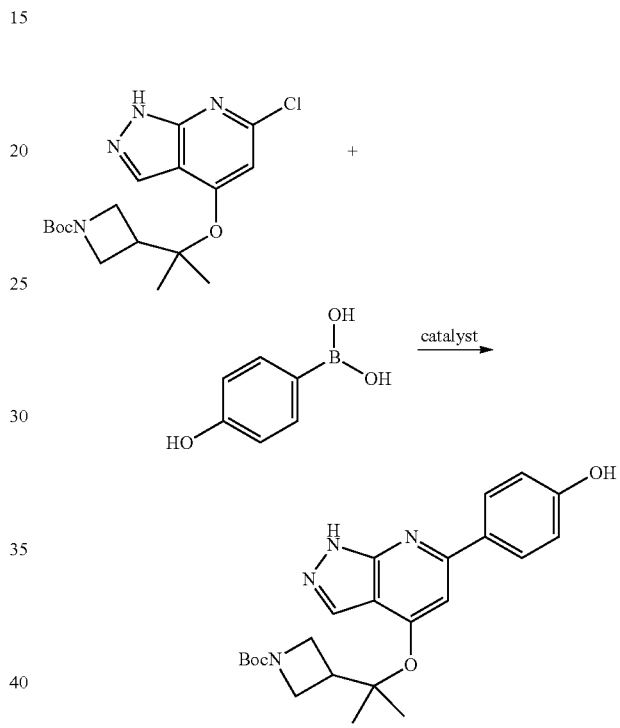

Sodium carbonate (636 mg, 6.00 mmol) was added to a solution of tert-butyl 3-(2-((6-chloro-1H-pyrazolo[3,4-b]pyridin-4-yl)oxy)propan-2-yl)azetidine-1-carboxylate (1.1 g, 3.00 mmol) in 4:1 dioxane/water (15 mL), followed by phenylboronic acid (496 mg, 3.60 mmol) and the reaction mixture was degassed with argon for 10 minutes. Dichloro[1,1'-bis(diphenylphosphino)ferrocene]palladium(II) dichloromethane adduct (245 mg, 0.3 mmol) was added, the reaction mixture was degassed further with argon for 5 minutes and the reaction mixture was stirred under microwave irradiation at 130° C. for 1 hour. The reaction mixture was diluted with water and extracted with ethyl acetate. The ethyl acetate extracts were combined, washed with a saturated aqueous solution of sodium chloride, dried over sodium sulfate and concentrated in vacuo to yield the crude liquid. The crude liquid was purified via flash column chromatography using 50% ethyl acetate in hexanes to yield tert-butyl 3-(2-((6-(4-hydroxyphenyl)-1H-pyrazolo[3,4-b]pyridin-4-yl)oxy)propan-2-yl)azetidine-1-carboxylate (650 mg, 1.53 mmol, 51.0% yield). (m/z): [M+H]$^+$ calcd for $C_{23}H_{29}N_4O_4$ 425.22 found 425.21.

Preparation 57: 4-(4-((2-(azetidin-3-yl)propan-2-yl)oxy)-1H-pyrazolo[3,4-b]pyridin-6-yl)phenol

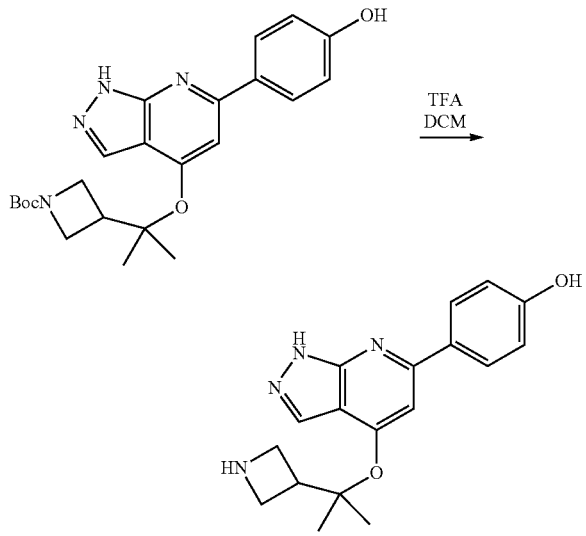

Tert-butyl 3-(2-((6-(4-hydroxyphenyl)-1H-pyrazolo[3,4-b]pyridin-4-yl)oxy)propan-2-yl)azetidine-1-carboxylate (630 mg, 1.48 mmol) was dissolved in dichloromethane (10 ml) and TFA (6.3 ml) was slowly added. The clear solution was stirred at rt for 4 hours upon which LCMS indicated good conversion to the desired product. The reaction was concentrated in vacuo and the residue was triturated with acetonitrile and diethyl ether to yield 4-(4-((2-(azetidin-3-yl)propan-2-yl)oxy)-1H-pyrazolo[3,4-b]pyridin-6-yl)phenol as a TFA salt (100% yield). (m/z): [M+H]$^+$ calcd for $C_{18}H_{21}N_4O_2$ 325.17 found 325.13.

Example 20: 1-(3-(2-((6-(4-hydroxyphenyl)-1H-pyrazolo[3,4-b]pyridin-4-yl)oxy)propan-2-yl)azetidin-1-yl)prop-2-en-1-one

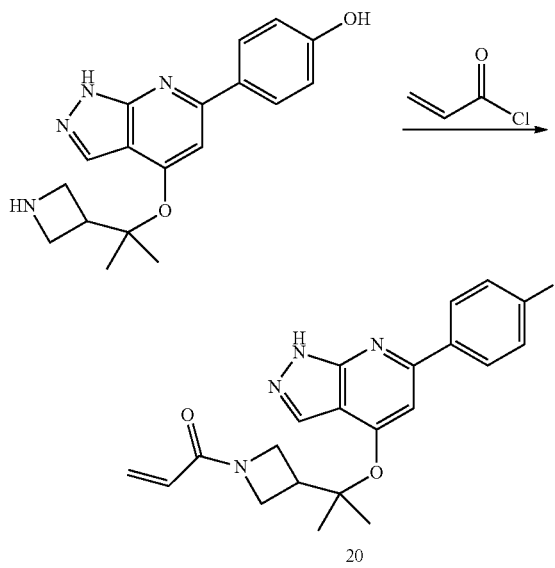

Diisopropylethylamine (0.298 ml, 1.711 mmol) was added to a solution of 4-(4-((2-(azetidin-3-yl)propan-2-yl)oxy)-1H-pyrazolo[3,4-b]pyridin-6-yl)phenol TFA salt (150 mg, 0.342 mmol) in DMF (3.00 ml) at 0° C., followed by acryloyl chloride (0.031 ml, 0.376 mmol) and the reaction mixture was stirred at rt for 15 min. The reaction mixture was concentrated in vacuo to yield a brown liquid. The crude liquid was purified via preparatory scale C18 column chromatography using a gradient of 10-70% acetonitrile in water with 0.05% trifluoroacetic acid to yield 1-(3-(2-((6-(4-hydroxyphenyl)-1H-pyrazolo[3,4-b]pyridin-4-yl)oxy)propan-2-yl)azetidin-1-yl)prop-2-en-1-one as a TFA salt (80.5 mg, 0.163 mmol, 47.8% yield). (m/z): [M+H]$^+$ calcd for $C_{21}H_{23}N_4O_3$ 379.18 found 379.3.

Preparation 58: tert-butyl 3-(((6-chloro-1-(tetrahydro-2H-pyran-2-yl)-1H-pyrazolo[3,4-d]pyrimidin-4-yl)oxy)methyl)-3-methylazetidine-1-carboxylate

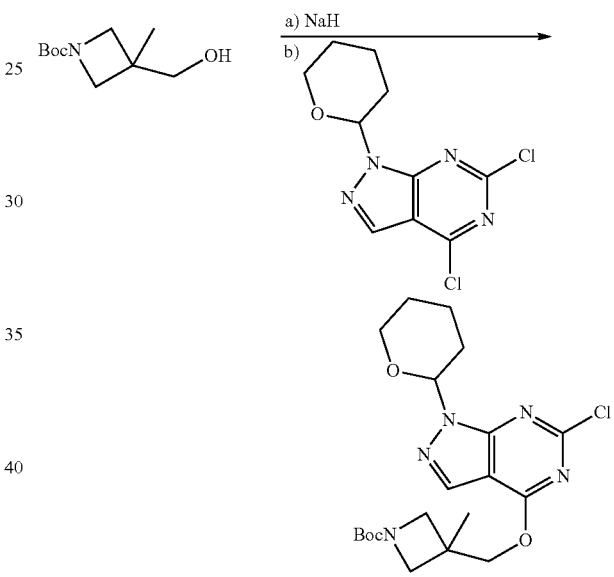

Sodium hydride (211 mg, 8.79 mmol) was added to a solution of tert-butyl 3-(hydroxymethyl)-3-methylazetidine-1-carboxylate (973 mg, 4.83 mmol) in DMF (4.4 mL) at 0° C. and the reaction mixture was stirred at rt for 30 minutes. The reaction mixture was then added dropwise to a solution of 4,6-dichloro-1-(tetrahydro-2H-pyran-2-yl)-1H-pyrazolo[3,4-d]pyrimidine (1.20 g, 4.39 mmol) in DMF (4.4 mL) at 0° C. and the reaction mixture was stirred at rt for 2 hours. The reaction was quenched with addition of water (1 mL) and the resulting mixture was concentrated in vacuo to yield a light brown liquid. Water (10 mL) was added and the mixture was extracted with ethyl acetate (3×20 mL). The ethyl acetate extracts were combined, washed with a saturated aqueous solution of sodium chloride (5 mL) and dried over sodium sulfate to yield a brown liquid. The crude liquid was purified via flash column chromatography using 40% ethyl acetate in hexanes to yield tert-butyl 3-(((6-chloro-1-(tetrahydro-2H-pyran-2-yl)-1H-pyrazolo[3,4-d]pyrimidin-4-yl)oxy)methyl)-3-methylazetidine-1-carboxylate (1.06 g, 4.39 mmol, 54.9% yield). (m/z): [M+H]$^+$ calcd for $C_{20}H_{29}ClN_5O_4$ 438.19 found 438.6.

Preparation 59: tert-butyl 3-(((6-(3-fluoro-4-hydroxyphenyl)-1-(tetrahydro-2H-pyran-2-yl)-1H-pyrazolo[3,4-d]pyrimidin-4-yl)oxy)methyl)-3-methylazetidine-1-carboxylate

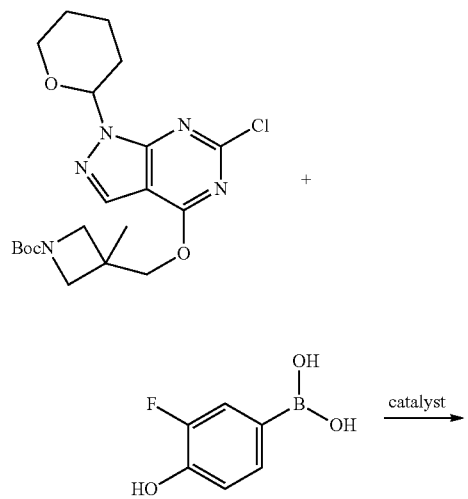

Preparation 60: 2-fluoro-4-(4-((3-methylazetidin-3-yl)methoxy)-1H-pyrazolo[3,4-d]pyrimidin-6-yl)phenol

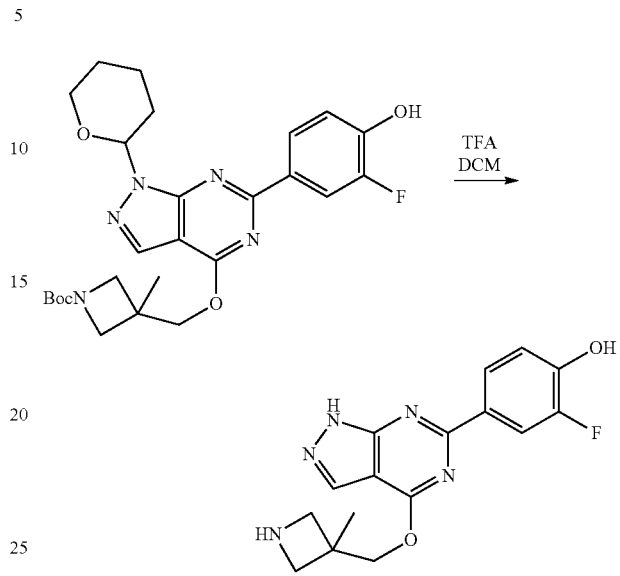

Potassium phosphate tribasic (218 mg, 1.03 mmol) was added to a solution of tert-butyl 3-(((6-chloro-1-(tetrahydro-2H-pyran-2-yl)-1H-pyrazolo[3,4-d]pyrimidin-4-yl)oxy)methyl)-3-methylazetidine-1-carboxylate (150 mg, 0.343 mmol) in 4:1 dioxane/water (1.71 mL), followed by 3-fluoro-4-hydroxyphenylboronic acid (80.0 mg, 0.514 mmol) and the reaction mixture was degassed with nitrogen for 10 minutes. Palladium acetate (15.4 mg, 0.069 mmol) and 1,1'-bis(di-t-butylphosphino)ferrocene (32.5 mg, 0.069 mmol) were added and the reaction mixture was stirred at 110° C. for overnight. The reaction mixture was concentrated in vacuo to a volume of about 5 mL. A saturated aqueous solution of ammonium chloride (20 mL) was added and the mixture was extracted with ethyl acetate (3×20 mL). The ethyl acetate extracts were combined, dried over sodium sulfate and concentrated in vacuo to yield a brown liquid. The crude liquid was purified via flash column chromatography using 40% ethyl acetate in hexanes to yield tert-butyl 3-(((6-(3-fluoro-4-hydroxyphenyl)-1-(tetrahydro-2H-pyran-2-yl)-1H-pyrazolo[3,4-d]pyrimidin-4-yl)oxy)methyl)-3-methylazetidine-1-carboxylate (65 mg, 0.343 mmol, 37.0% yield). (m/z): [M+H]$^+$ calcd for $C_{26}H_{33}FN_5O_5$ 514.25 found 514.7.

Tert-butyl 3-(((6-(3-fluoro-4-hydroxyphenyl)-1-(tetrahydro-2H-pyran-2-yl)-1H-pyrazolo[3,4-d]pyrimidin-4-yl)oxy)methyl)-3-methylazetidine-1-carboxylate (65 mg, 0.127 mmol) was dissolved in dichloromethane (0.56 ml) and TFA (0.56 ml) was added and the reaction mixture was stirred at rt for 4 hours. The reaction was concentrated in vacuo to yield 2-fluoro-4-(4-((3-methylazetidin-3-yl)methoxy)-1H-pyrazolo[3,4-d]pyrimidin-6-yl)phenol as a TFA salt (100% yield). (m/z): [M+H]$^+$ calcd for $C_{16}H_{17}FN_5O_2$ 330.14 found 330.3.

Example 21: 1-(3-(((6-(3-fluoro-4-hydroxyphenyl)-1H-pyrazolo[3,4-d]pyrimidin-4-yl)oxy)methyl)-3-methylazetidin-1-yl)prop-2-en-1-one

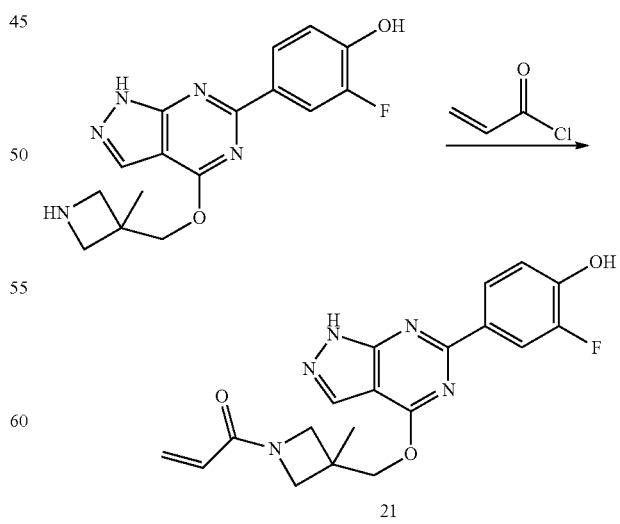

Diisopropylethylamine (0.210 ml, 1.20 mmol) was added to a solution of 2-fluoro-4-(4-((3-methylazetidin-3-yl)

methoxy)-1H-pyrazolo[3,4-d]pyrimidin-6-yl)phenol TFA salt (53.2 mg, 0.12 mmol) in DMF (0.60 ml) at 0° C., followed by acryloyl chloride (9.75 µl, 0.120 mmol) and the reaction mixture was stirred at rt for 15 min. The reaction mixture was concentrated in vacuo to yield the crude liquid. The crude liquid was purified via preparatory scale C18 column chromatography using a gradient of 10-60% acetonitrile in water with 0.05% trifluoroacetic acid to yield 1-(3-(((6-(3-fluoro-4-hydroxyphenyl)-1H-pyrazolo[3,4-d]pyrimidin-4-yl)oxy)methyl)-3-methylazetidin-1-yl)prop-2-en-1-one as a TFA salt (10.5 mg, 0.120 mmol, 21.7% yield). (m/z): [M+H]+ calcd for $C_{19}H_{19}FN_5O_3$ 384.15 found 384.3.

Preparation 61: tert-butyl 3-(((6-chloro-1-(tetrahydro-2H-pyran-2-yl)-1H-pyrazolo[3,4-b]pyridin-4-yl)oxy)methyl)-3-ethylazetidine-1-carboxylate

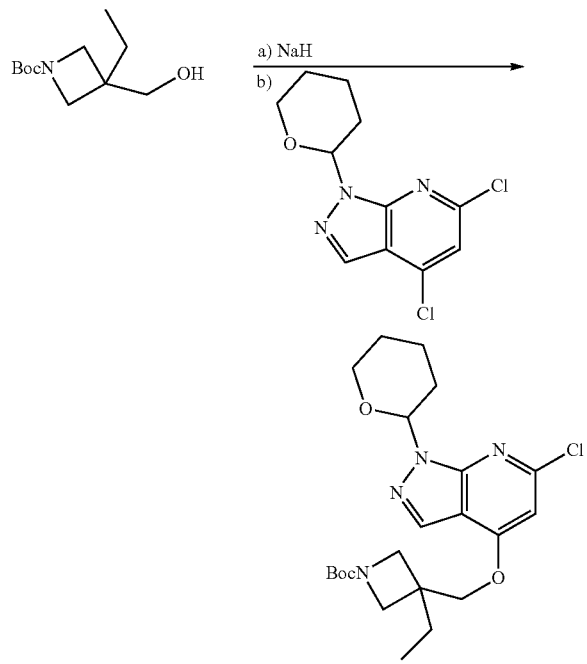

60% By weight sodium hydride in mineral oil (353 mg, 8.82 mmol) was added to a solution of tert-butyl 3-ethyl-3-(hydroxymethyl)azetidine-1-carboxylate (1.1 g, 4.85 mmol) in DMF (10 mL) at 0° C. and the reaction mixture was stirred at rt for 40 minutes. A solution of 4,6-dichloro-1-(tetrahydro-2H-pyran-2-yl)-1H-pyrazolo[3,4-b]pyridine (1.20 g, 4.41 mmol) in DMF (5 mL) at 0° C. and the reaction mixture was stirred at rt for 1 hour. The reaction was quenched with addition of water and the mixture was extracted with ethyl acetate. The ethyl acetate extracts were combined, washed with water and a saturated aqueous solution of sodium chloride and then dried over sodium sulfate to yield the crude residue. The crude residue was purified via flash column chromatography using 5% ethyl acetate in hexanes to yield tert-butyl 3-(((6-chloro-1-(tetrahydro-2H-pyran-2-yl)-1H-pyrazolo[3,4-b]pyridin-4-yl)oxy)methyl)-3-ethylazetidine-1-carboxylate (900 mg, 4.39 mmol, 45.2% yield). (m/z): [M+H]+ calcd for $C_{22}H_{32}ClN_4O_4$ 451.21 found 451.13.

Preparation 62: tert-butyl 3-ethyl-3-(((6-(4-hydroxyphenyl)-1-(tetrahydro-2H-pyran-2-yl)-1H-pyrazolo[3,4-b]pyridin-4-yl)oxy)methyl)azetidine-1-carboxylate

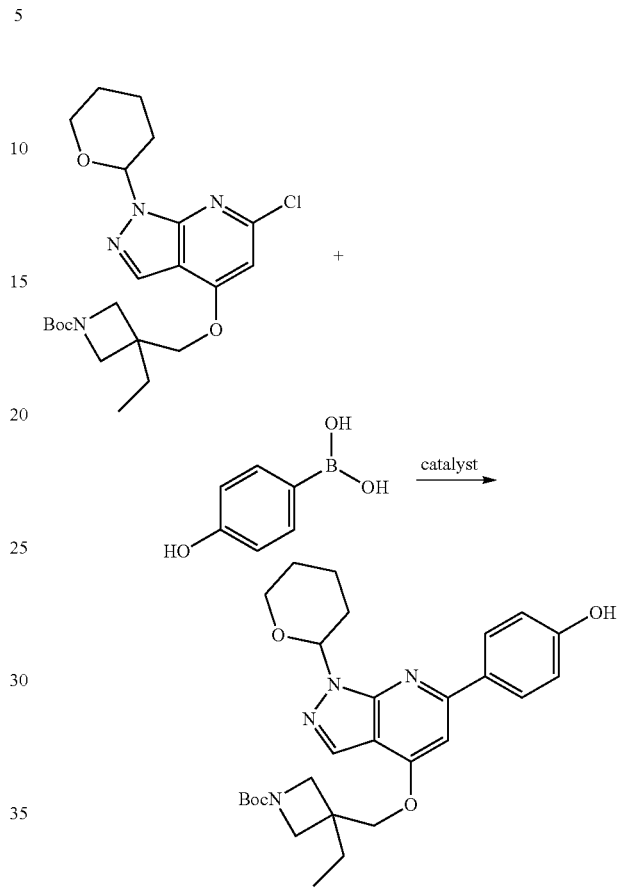

A solution of phenylboronic acid (413 mg, 2.99 mmol) and sodium carbonate (421 mg 3.98 mmol) in water (2 mL) was added to solution of tert-butyl 3-(((6-chloro-1-(tetrahydro-2H-pyran-2-yl)-1H-pyrazolo[3,4-b]pyridin-4-yl)oxy)methyl)-3-ethylazetidine-1-carboxylate (900 mg, 1.99 mmol) in dioxane (8 mL) and the reaction was degassed with argon for 5 minutes.

Dichloro[1,1'-bis(diphenylphosphino)ferrocene]palladium(II) dichloromethane adduct (162 mg, 0.19 mmol) was added, the reaction mixture was degassed further with argon for 5 minutes and the reaction mixture was stirred at 110° C. for 1 hour. The reaction mixture was diluted with ethyl acetate and filtered through Celite. Water was added, the ethyl acetate layer was separated and the aqueous layer was extracted with ethyl acetate. The ethyl acetate extracts were combined, washed with a saturated aqueous solution of sodium chloride, dried over sodium sulfate and concentrated in vacuo to yield the crude liquid. The crude liquid was purified via flash column chromatography using 30% ethyl acetate in hexanes to yield tert-butyl 3-ethyl-3-(((6-(4-hydroxyphenyl)-1-(tetrahydro-2H-pyran-2-yl)-1H-pyrazolo[3,4-b]pyridin-4-yl)oxy)methyl)azetidine-1-carboxylate (800 mg, 1.57 mmol, 79.0% yield). (m/z): [M+H]+ calcd for $C_{28}H_{37}N_4O_5$ 509.28 found 509.29.

Preparation 63: 4-(4-((3-ethylazetidin-3-yl)methoxy)-1H-pyrazolo[3,4-b]pyridin-6-yl)phenol

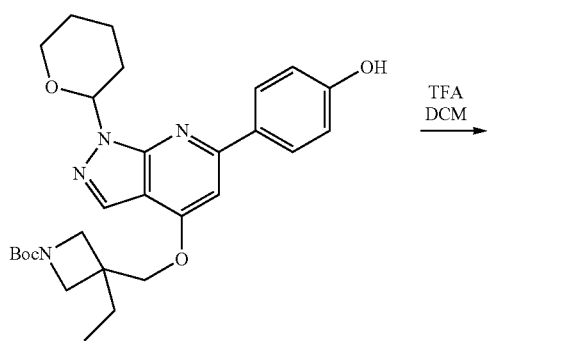

Tert-butyl 3-ethyl-3-(((6-(4-hydroxyphenyl)-1-(tetrahydro-2H-pyran-2-yl)-1H-pyrazolo[3,4-b]pyridin-4-yl)oxy)methyl)azetidine-1-carboxylate (800 mg, 1.57 mmol) was dissolved in dichloromethane (10 ml) and TFA (10 ml) was added at 0° C. and the reaction mixture was stirred at rt for 3 hours. The reaction was concentrated in vacuo and the resulting residue was triturated with diethyl ether. The crude residue was dissolved in a minimum of acetonitrile and precipitated with diethyl ether to yield 4-(4-((3-ethylazetidin-3-yl)methoxy)-1H-pyrazolo[3,4-b]pyridin-6-yl)phenol as a TFA salt (287 mg, 0.885 mmol, 56.3% yield). (m/z): [M+H]$^+$ calcd for $C_{18}H_{21}N_4O_2$ 325.17 found 325.07.

Example 22: 1-(3-ethyl-3-(((6-(4-hydroxyphenyl)-1H-pyrazolo[3,4-b]pyridin-4-yl)oxy)methyl)azetidin-1-yl)prop-2-en-1-one

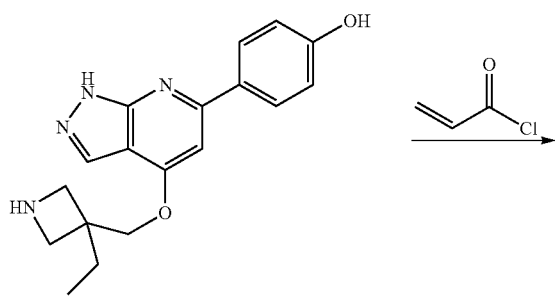

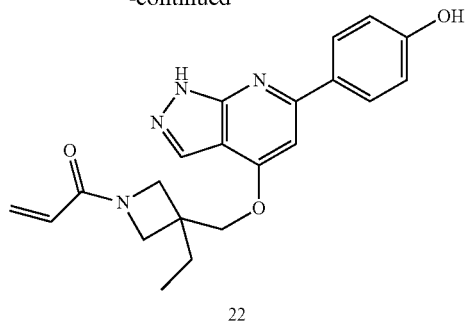

Diisopropylethylamine (0.246 ml, 1.41 mmol) was added to a solution of 4-(4-((3-ethylazetidin-3-yl)methoxy)-1H-pyrazolo[3,4-b]pyridin-6-yl)phenol TFA salt (124 mg, 0.283 mmol) in DMF (2.0 ml) at 0° C., followed by acryloyl chloride (25 µl, 0.311 mmol) and the reaction mixture was stirred at rt for 15 min. The reaction mixture was concentrated in vacuo to yield a brown liquid. The crude liquid was purified via preparatory scale C18 column chromatography using a gradient of 20-80% acetonitrile in water with 0.05% trifluoroacetic acid to yield 1-(3-ethyl-3-(((6-(4-hydroxyphenyl)-1H-pyrazolo[3,4-b]pyridin-4-yl)oxy)methyl)azetidin-1-yl)prop-2-en-1-one as a TFA salt (44.8 mg, 0.118 mmol, 41.9% yield). (m/z): [M+H]$^+$ calcd for $C_{11}H_{23}N_4O_3$ 379.18 found 379.3.

Preparation 64: 6-bromo-4-fluoro-1H-benzo[d][1,2,3]triazole

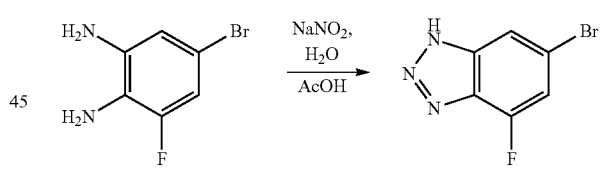

A solution of sodium nitrite (1.85 g, 26.8 mmol) in water (50 mL) was added to a solution of 5-bromo-3-fluorobenzene-1,2-diamine (5.00 g, 24.4 mmol) in water (50 mL) and acetic acid (18.0 mL) and the reaction mixture was stirred at rt for 15 minutes and then at 85° C. for 1 hour. The reaction mixture was concentrated in vacuo a water was added to the resulting residue. The mixture was extracted with ethyl acetate (2×300 mL), the ethyl acetate extracts were combined, dried over sodium sulfate and concentrated in vacuo to yield 6-bromo-4-fluoro-1H-benzo[d][1,2,3]triazole (5.0 g, 23.1 mmol, 94.0% yield). (m/z): [M–H]$^-$ calcd for $C_6H_3BrFN_3$ 213.94 found 213.94.

Preparation 65: 6-bromo-4-fluoro-1-(tetrahydro-2H-pyran-2-yl)-1H-benzo[d][1,2,3]triazole

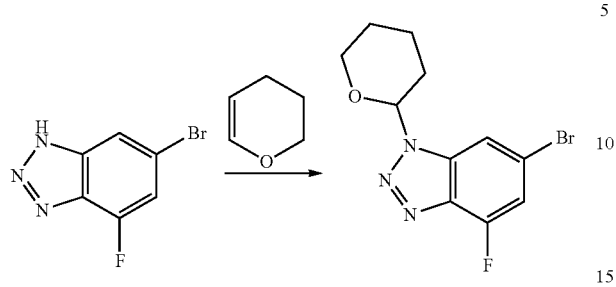

p-Toluenesulfonic acid (796 mg, 4.62 mmol) was added to a solution of 6-bromo-4-fluoro-1H-benzo[d][1,2,3]triazole (5.0 g, 23.1 mmol) in tetrahydrofuran (200 mL), followed by 3,4-dihydro-2H-pyran (7.7 g, 92.6 mmol) and the reaction mixture was stirred at rt for 4 hours. The reaction mixture was concentrated in vacuo and the resulting residue was purified via flash column chromatography using 10% ethyl acetate in hexanes to yield 6-bromo-4-fluoro-1-(tetrahydro-2H-pyran-2-yl)-1H-benzo[d][1,2,3]triazole (3.8 g, 12.7 mmol, 55.4% yield). (m/z): [M+H]$^+$ calcd for $C_{11}H_{12}BrFN_3O$ 300.01 found 300.09.

Preparation 66: tert-butyl (3S)-3-(((6-bromo-1-(tetrahydro-2H-pyran-2-yl)-1H-benzo[d][1,2,3]triazol-4-yl)oxy)methyl)pyrrolidine-1-carboxylate

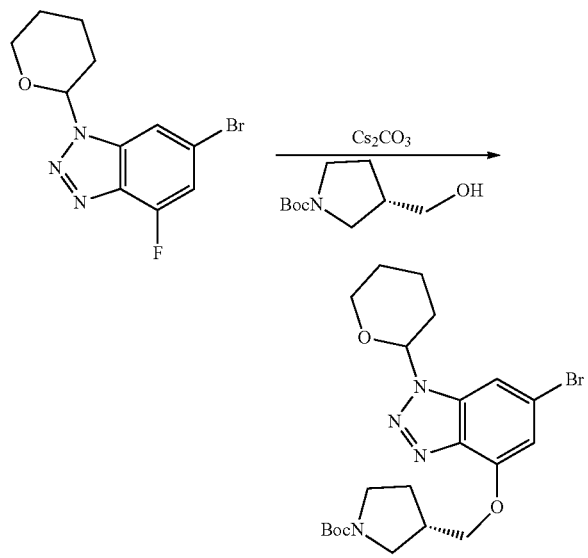

Cesium carbonate (1.50 g, 4.64 mmol) was added to a solution of tert-butyl (S)-3-(hydroxymethyl)pyrrolidine-1-carboxylate (564 mg, 2.80 mmol) in DMSO (15 ml) at 0° C., followed by 6-bromo-4-fluoro-1-(tetrahydro-2H-pyran-2-yl)-1H-benzo[d][1,2,3]triazole (700 mg, 2.34 mmol) and the reaction mixture was stirred at 80° C. for 3 hours. Water was added and the mixture was extracted with ethyl acetate (3×). The ethyl acetate extracts were combined, washed with water and an aqueous solution of sodium chloride, dried over sodium sulfate and concentrated in vacuo to yield the crude residue. The crude residue was purified via flash column chromatography using 30% ethyl acetate in hexanes to yield tert-butyl (3S)-3-(((6-bromo-1-(tetrahydro-2H-pyran-2-yl)-1H-benzo[d][1,2,3]triazol-4-yl)oxy)methyl)pyrrolidine-1-carboxylate (500 mg, 1.04 mmol, 45.6% yield). (m/z): [M+H]$^+$ calcd for $C_{21}H_{30}BrN_4O_4$ 481.15 found 481.2.

Preparation 67: tert-butyl (3S)-3-(((6-(4-hydroxyphenyl)-1-(tetrahydro-2H-pyran-2-yl)-1H-benzo[d][1,2,3]triazol-4-yl)oxy)methyl)pyrrolidine-1-carboxylate

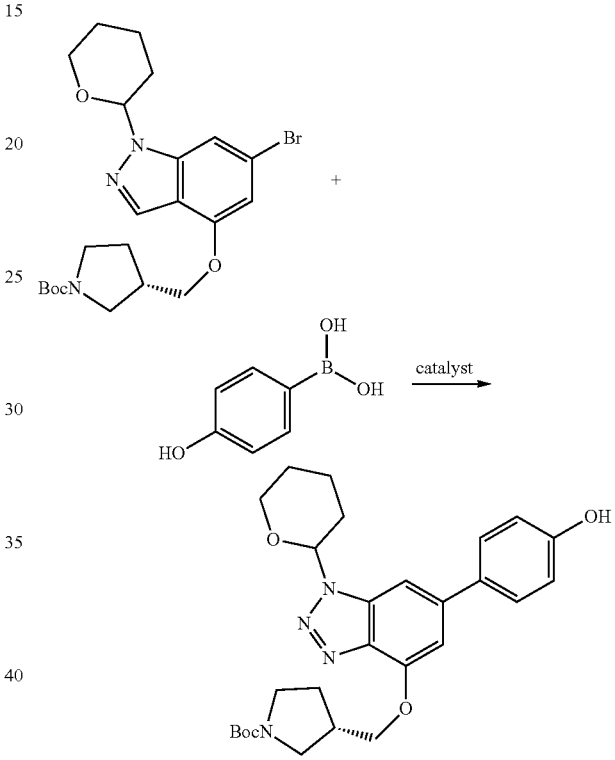

Phenolboronic acid (192 mg, 1.40 mmol) was added to solution of tert-butyl (3S)-3-(((6-bromo-1-(tetrahydro-2H-pyran-2-yl)-1H-benzo[d][1,2,3]triazol-4-yl)oxy)methyl)pyrrolidine-1-carboxylate (450 mg, 0.93 mmol) in dioxane (10 mL) and water (2 mL), followed by potassium phosphate (394 mg, 1.86 mmol) and the reaction was degassed with argon for 15 minutes. 2'-(Dimethylamino)-2-biphenylyl-palladium(II) chloride dinorbornylphosphine complex (52 mg, 0.093 mmol) was added and the reaction mixture was stirred at 110° C. for 40 minutes under microwave irradiation. The reaction mixture was filtered through Celite. Water was added and the mixture was extracted with ethyl acetate (3 x). The ethyl acetate extracts were combined, washed with a saturated aqueous solution of sodium chloride, dried over sodium sulfate and concentrated in vacuo to yield the crude residue. The crude residue was purified via flash column chromatography using 30% ethyl acetate in hexanes to yield tert-butyl (3S)-3-(((6-(4-hydroxyphenyl)-1-(tetrahydro-2H-pyran-2-yl)-1H-benzo[d][1,2,3]triazol-4-yl)oxy)methyl)pyrrolidine-1-carboxylate (300 mg, 0.607 mmol, 65.0% yield). (m/z): [M+H]$^+$ calcd for $C_{27}H_{35}N_4O_5$ 495.26 found 495.06.

Preparation 68: (S)-4-(4-(pyrrolidin-3-ylmethoxy)-1H-benzo[d][1,2,3]triazol-6-yl)phenol

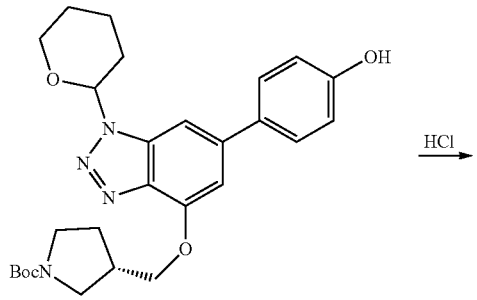

HCl →

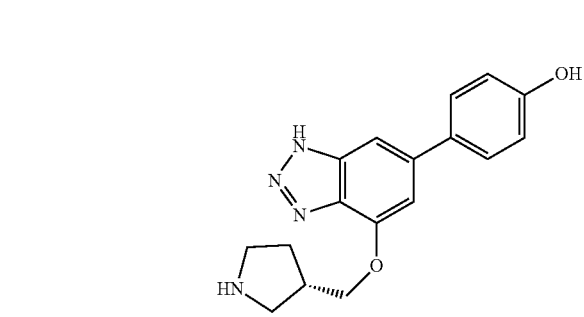

4M hydrochloric acid in dioxane (10.0 mL, 40 mmol) was added to a solution of ((3S)-3-(((6-(4-hydroxyphenyl)-1-(tetrahydro-2H-pyran-2-yl)-1H-benzo[d][1,2,3]triazol-4-yl)oxy)methyl)pyrrolidine-1-carboxylate (230 mg, 0.465 mmol) in methanol (2. mL) and the reaction mixture was stirred at rt for 5 hours. The reaction was concentrated in vacuo and the resulting residue was triturated with diethyl ether to yield (S)-4-(4-(pyrrolidin-3-ylmethoxy)-1H-benzo[d][1,2,3]triazol-6-yl)phenol as a hydrochloride salt (225 mg, 0.649 mmol, 85.0% yield). (m/z): [M+H]$^+$ calcd for $C_{17}H_{19}N_4O_2$ 311.15 found 311.06.

Example 23: (S)-1-(3-(((6-(4-hydroxyphenyl)-1H-benzo[d][1,2,3]triazol-4-yl)oxy)methyl)pyrrolidin-1-yl)prop-2-en-1-one

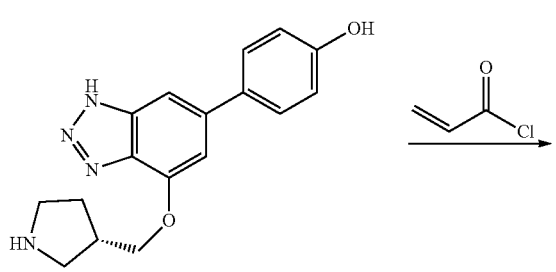

→

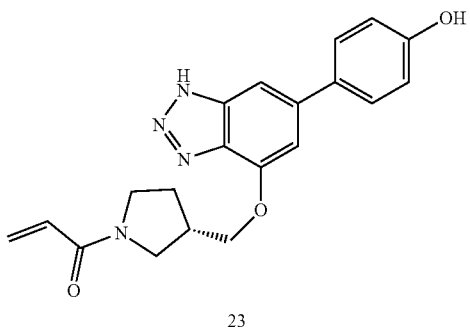

Diisopropylethylamine (0.083 ml, 0.475 mmol) was added to a solution of (S)-4-(4-(pyrrolidin-3-ylmethoxy)-1H-benzo[d][1,2,3]triazol-6-yl)phenol hydrochloride salt (32.9 mg, 0.095 mmol) in DMF (0.475 ml) at 0° C., followed by acryloyl chloride (7.7 μl, 0.095 mmol) and the reaction mixture was stirred at rt for 15 min. The reaction mixture was concentrated in vacuo to yield a brown liquid. The crude liquid was purified via preparatory scale C18 column chromatography using a gradient of 5-75% acetonitrile in water with 0.05% trifluoroacetic acid to yield (S)-1-(3-(((6-(4-hydroxyphenyl)-1H-benzo[d][1,2,3]triazol-4-yl)oxy)methyl)pyrrolidin-1-yl)prop-2-en-1-one as a TFA salt (2.5 mg, 0.068 mmol, 7.2% yield). (m/z): [M+H]$^+$ calcd for $C_{20}H_{21}N_4O_3$ 365.16 found 365.1.

Preparation 69: 6-bromo-4-fluoro-3-methyl-1-(tetrahydro-2H-pyran-2-yl)-1H-indazole

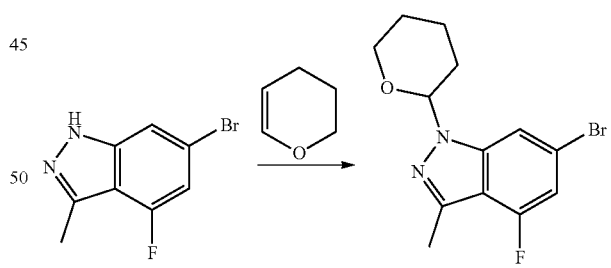

p-Toluenesulfonic acid (236 mg, 1.24 mmol) was added to a solution of 6-bromo-4-fluoro-3-methyl-1H-indazole (2.84 g, 12.4 mmol) in dichloromethane (41 mL), followed by 3,4-dihydro-2H-pyran (3.13 g, 37.2 mmol) and the reaction mixture was stirred at rt for 3 days. The reaction mixture filtered through a pad of silica gel and the filtrated was concentrated in vacuo to yield 6-bromo-4-fluoro-3-methyl-1-(tetrahydro-2H-pyran-2-yl)-1H-indazole (3.3 g, 10.5 mmol, 85% yield). (m/z): [M+Na]$^+$ calcd for $C_{13}H_{14}BrFN_2NaO$ 335.02 found 335.4.

Example 24: (S)-1-(3-((6-(3-chloro-4-hydroxyphenyl)-3-methyl-1H-indazol-4-yl)oxy)pyrrolidin-1-yl)prop-2-en-1-one

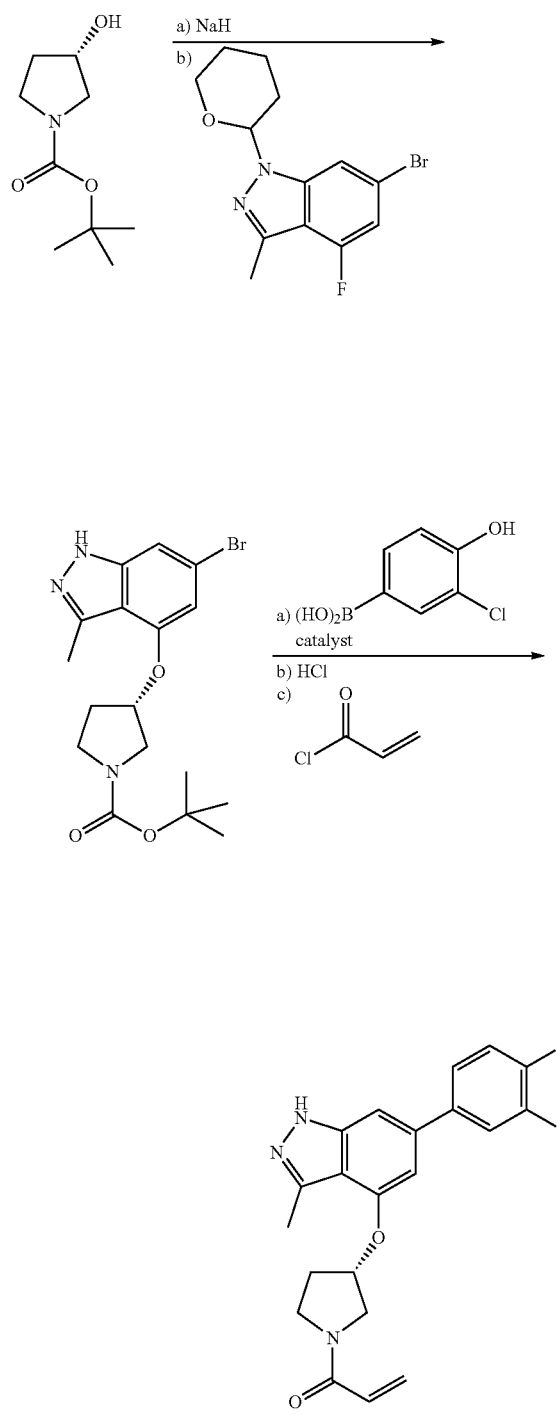

60% By weight sodium hydride in mineral oil (319 mg, 7.98 mmol) was added to a solution of (S)-1-boc-3-hydroxypyrrolidine (1.3 g, 6.94 mmol) in DMF (16 mL) at 0° C. and the reaction mixture was stirred at rt for 20 minutes. 6-Bromo-4-fluoro-3-methyl-1-(tetrahydro-2H-pyran-2-yl)-1H-indazole (1.00 g, 3.19 mmol) was added and the reaction mixture was stirred at rt for overnight. The reaction was quenched with addition of water and the mixture was concentrated in vacuo to yield the crude intermediate tert-butyl (3S)-3-((6-bromo-3-methyl-1-(tetrahydro-2H-pyran-2-yl)-1H-indazol-4-yl)oxy)pyrrolidine-1-carboxylate.

3-chloro-4-hydroxyphenylboronic acid (0.484 g, 2.81 mmol) and potassium phosphate tribasic (1.19 g, 5.62 mmol) were added to a solution of the crude tert-butyl (3S)-3-((6-bromo-3-methyl-1-(tetrahydro-2H-pyran-2-yl)-1H-indazol-4-yl)oxy)pyrrolidine-1-carboxylate in 2:1 dioxane/water (9.5 mL), and the reaction mixture was degassed with nitrogen for 10 minutes. (2-Dicyclohexylphosphino-2', 4',6'-triisopropyl-1,1'-biphenyl)[2-(2'-amino-1,1'-biphenyl)] palladium(II) methanesulfonate, XPhos-G3-Palladacycle (95 mg, 0.112 mmol) was added and the reaction mixture was stirred at 110° C. for 3 hours under microwave irradiation. Water was added and the mixture was extracted with ethyl acetate. The ethyl acetate extracts were combined and concentrated in vacuo to yield the crude intermediate tert-butyl (3S)-3-((6-(3-chloro-4-hydroxyphenyl)-3-methyl-1-(tetrahydro-2H-pyran-2-yl)-1H-indazol-4-yl)oxy)pyrrolidine-1-carboxylate.

4.0N HCl in dioxane (3.75 ml, 15.0 mmol) was added to a solution of the crude tert-butyl (3S)-3-((6-(3-chloro-4-hydroxyphenyl)-3-methyl-1-(tetrahydro-2H-pyran-2-yl)-1H-indazol-4-yl)oxy)pyrrolidine-1-carboxylate in methanol (0.5 mL), and the reaction mixture was stirred at 60° C. for 30 minutes. The reaction mixture was concentrated in vacuo to yield the crude intermediate (S)-2-chloro-4-(3-methyl-4-(pyrrolidin-3-yloxy)-1H-indazol-6-yl)phenol.

N,N-Diisopropylethylamine (4.59 ml, 26.3 mmol) was added to a solution of the crude intermediate (S)-2-chloro-4-(3-methyl-4-(pyrrolidin-3-yloxy)-1H-indazol-6-yl)phenol in methylene chloride (3.75 ml), followed by acryloyl chloride (60.9 µL, 0.750 mmol). The reaction mixture was stirred at rt for 30 minutes then concentrated in vacuo to yield the crude residue. The crude residue was purified via preparatory scale C18 column chromatography using a gradient of 0-40% acetonitrile in water with 0.05% trifluoroacetic acid to yield (S)-1-(3-((6-(3-chloro-4-hydroxyphenyl)-3-methyl-1H-indazol-4-yl)oxy)pyrrolidin-1-yl)prop-2-en-1-one as a TFA salt (7.6 mg, 0.015 mmol, 0.98% yield). (m/z): [M+H]+ calcd for $C_{21}H_{21}ClN_3O_3$ 398.13 found 398.3.

The compounds of Tables 1-12 were prepared using similar synthetic methods.

TABLE 1

[Structure: pyrazolo-fused bicyclic core with X¹, X², R⁶ substituents, phenol ring with R², R³, R⁴, R⁵, and pyrrolidine with R¹, R^k1, R^k2]

| Ex No. | R¹ | R² | R³ | R⁴ | R⁵ | R⁶ | X¹ | X² | R^k1 | R^k2 | Formula | Calc [M + H]⁺ | Found [M + H]⁺ |
|---|---|---|---|---|---|---|---|---|---|---|---|---|---|
| 1-1 | (E)-5-(dimethylamino)pent-3-en-2-one-yl [Me₂N-CH₂-CH=CH-C(O)-] | H | H | H | H | H | CH | CH | H | H | C₂₃H₂₆N₄O₃ | 407.20 | 407 |
| 1-2 | acryloyl (CH₂=CH-C(O)-) | H | H | H | H | H | CH | CH | H | H | C₂₀H₁₉N₃O₃ | 350.13 | 350 |
| 1-3 | (E)-5-(dimethylamino)pent-3-en-2-one-yl | Cl | H | H | H | H | CH | CH | H | H | C₂₃H₂₅ClN₄O₃ | 441.15 | 441.1 |
| 1-4 | (E)-5-(dimethylamino)pent-3-en-2-one-yl | F | H | H | H | H | CH | CH | H | H | C₂₃H₂₅FN₄O₃ | 425.18 | 425.1 |
| 1-5 | acryloyl | F | H | H | H | H | CH | CH | H | H | C₂₀H₁₈FN₃O₃ | 368.12 | 368 |
| 1-6 | acryloyl | H | H | H | H | H | N | N | H | H | C₁₈H₁₇N₅O₃ | 352.12 | 352.3 |
| 1-7 | (E)-5-(dimethylamino)pent-3-en-2-one-yl | H | H | H | H | H | CH | N | H | H | C₂₂H₂₅N₅O₃ | 408.18 | 408.2 |
| 1-8 | acryloyl | H | H | H | H | H | CH | N | H | H | C₁₉H₁₈N₄O₃ | 351.12 | 351.2 |
| 1-9 | acryloyl | H | H | H | H | H | N | CH | H | H | C₁₉H₁₈N₄O₃ | 351.12 | 351.1 |

TABLE 1-continued

[Structure: 1H-pyrazolo-fused bicyclic core with X1, X2 positions connected to a phenol ring bearing R2, R3, R4, R5 substituents; R6 on pyrazole; O-linked pyrrolidine with N-R1 and Rk1, Rk2 substituents]

| Ex No. | R1 | R2 | R3 | R4 | R5 | R6 | X1 | X2 | Rk1 | Rk2 | Formula | Calc [M + H]+ | Found [M + H]+ |
|---|---|---|---|---|---|---|---|---|---|---|---|---|---|
| 1-10 | Me2N-CH2-CH=CH-C(=O)- | H | H | H | H | H | CH | CH | Me | H | $C_{24}H_{28}N_4O_3$ | 421.20 | 421.3 |
| 1-11 | CH2=CH-C(=O)- | H | H | H | H | H | CH | CH | Me | H | $C_{21}H_{21}N_3O_3$ | 364.14 | 364.2 |
| 1-12 | CH2=CH-C(=O)- | H | H | H | H | H | CH | CH | H | Me | $C_{21}H_{21}N_3O_3$ | 364.14 | 364 |
| 1-13 | CH2=CH-C(=O)- | F | F | H | H | H | CH | CH | H | H | $C_{20}H_{17}F_2N_3O_4$ | 386.11 | 386 |
| 1-14 | CH2=CH-C(=O)- | F | H | F | H | H | CH | CH | H | H | $C_{20}H_{17}F_2N_3O_3$ | 386.11 | 386 |
| 1-15 | CH2=CH-C(=O)- | F | Cl | H | H | H | CH | CH | H | H | $C_{20}H_{17}ClFN_7O_3$ | 402.08 | 402 |
| 1-16 | CH2=CH-C(=O)- | F | H | H | Me | H | CH | CH | H | H | $C_{21}H_{20}FN_3O_3$ | 382.13 | 382.1 |
| 1-17 | CH2=CH-C(=O)- | H | F | H | H | H | CH | CH | H | H | $C_{20}H_{18}FN_3O_3$ | 368.12 | 368.0 |
| 1-18 | CH2=CH-C(=O)- | H | F | H | F | H | CH | CH | H | H | $C_{20}H_{17}F_2N_3O_3$ | 386.11 | 386.0 |

TABLE 1-continued

| Ex No. | R¹ | R² | R³ | R⁴ | R⁵ | R⁶ | X¹ | X² | R^{k1} | R^{k2} | Formula | Calc [M + H]⁺ | Found [M + H]⁺ |
|---|---|---|---|---|---|---|---|---|---|---|---|---|---|
| 1-19 | vinyl ketone | F | H | H | F | H | CH | CH | H | H | $C_{20}H_{17}F_2N_3O_3$ | 386.11 | 386.0 |
| 1-20 | vinyl ketone | H | H | H | H | Me | CH | CH | H | H | $C_{21}H_{21}N_3O_3$ | 364.14 | 364.0 |
| 1-21 | vinyl ketone | H | H | H | H | NHMe | CH | CH | H | H | $C_{21}H_{22}N_4O_3$ | 379.15 | 379.0 |
| 1-22 | vinyl ketone | H | H | H | H | CH₂—OMe | CH | CH | H | H | $C_{22}H_{23}N_3O_4$ | 394.15 | 394.0 |
| 1-23 | vinyl ketone | F | H | H | H | Me | CH | CH | H | H | $C_{21}H_{20}FN_3O_3$ | 382.13 | 382.0 |
| 1-24 | vinyl ketone | H | H | H | H | H | N | N | Me | H | $C_{19}H_{19}N_5O_3$ | 366.13 | 366.0 |
| 1-25 | vinyl ketone | H | H | H | H | CHF₂ | N | N | H | H | $C_{19}H_{17}F_2N_5O_3$ | 402.11 | 402.0 |
| 1-26 | vinyl ketone | H | H | H | H | H | N | CH | Me | H | $C_{20}H_{20}N_4O_3$ | 365.14 | 365.0 |
| 1-27 | vinyl ketone | F | H | H | H | H | CH | N | H | H | $C_{19}H_{17}FN_4O_3$ | 369.11 | 369.2 |

TABLE 1-continued

| Ex No. | R¹ | R² | R³ | R⁴ | R⁵ | R⁶ | X¹ | X² | R^{k1} | R^{k2} | Formula | Calc [M + H]⁺ | Found [M + H]⁺ |
|---|---|---|---|---|---|---|---|---|---|---|---|---|---|
| 1-28 | (E)-5-(dimethylamino)pent-3-en-2-one-yl | F | H | H | H | H | CH | N | H | H | $C_{22}H_{24}FN_5O_3$ | 426.17 | 426.1 |
| 1-29 | (E)-5-(dimethylamino)pent-3-en-2-one-yl | F | H | H | Me | H | CH | CH | H | H | $C_{24}H_{27}FN_4O_3$ | 439.19 | 439.1 |
| 1-30 | acryloyl | F | H | H | F | Me | CH | CH | H | H | $C_{21}H_{19}F_2N_3O_3$ | 400.12 | 400.4 |
| 1-31 | acryloyl | H | H | H | H | Me | N | CH | H | H | $C_{20}H_{20}N_4O_3$ | 365.14 | 365.0 |
| 1-32 | acryloyl | Cl | H | H | H | Me | N | CH | H | H | $C_{20}H_{19}ClN_4O_3$ | 399.10 | 399.0 |
| 1-33 | acryloyl | F | H | H | H | Me | N | CH | H | H | $C_{20}H_{19}FN_4O_3$ | 383.13 | 383.0 |
| 1-34 | acryloyl | H | H | H | H | Me | CH | N | H | H | $C_{20}H_{20}N_4O_3$ | 365.14 | 365.0 |
| 1-35 | acryloyl | Cl | H | H | H | Me | CH | N | H | H | $C_{20}H_{19}ClN_4O_3$ | 399.10 | 399.0 |
| 1-36 | acryloyl | F | H | H | H | Me | CH | N | H | H | $C_{20}H_{19}FN_4O_3$ | 383.13 | 383.0 |

TABLE 1-continued
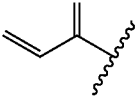
| Ex No. | R¹ | R² | R³ | R⁴ | R⁵ | R⁶ | X¹ | X² | R^{k1} | R^{k2} | Formula | Calc [M + H]⁺ | Found [M + H]⁺ |
|---|---|---|---|---|---|---|---|---|---|---|---|---|---|
| 1-37 | 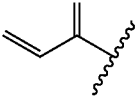 | Cl | H | H | H | Me | N | N | H | H | $C_{19}H_{18}ClN_5O_3$ | 400.09 | 400.0 |
| 1-38 | 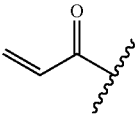 [SMILES: *C(=O)C=C] | F | H | H | H | Me | N | N | H | H | $C_{19}H_{18}FN_5O_3$ | 384.12 | 384.0 |
| 1-39 | 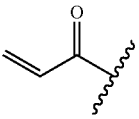 [SMILES: *C(=O)C=C] | H | H | H | H | SMe | CH | CH | H | H | $C_{21}H_{21}N_3O_3S$ | 396.11 | 396.4 |
| 1-40 | 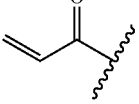 | F | H | H | H | SMe | CH | CH | H | H | $C_{21}H_{20}FN_3O_3S$ | 414.11 | 414.0 |
| 1-41 | 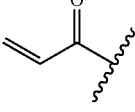 | Cl | H | H | H | SMe | CH | CH | H | H | $C_{21}H_{20}ClN_3O_3S$ | 430.08 | 430.0 |
| 1-42 | 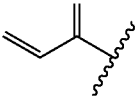 | H | H | H | H | NMe₂ | CH | CH | H | H | $C_{22}H_{24}N_4O_3$ | 393.17 | 393.0 |
| 1-43 | 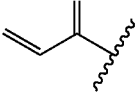 | H | H | H | H | CF₃ | CH | CH | H | H | $C_{21}H_{18}F_3N_3O_3$ | 418.11 | 418.4 |
| 1-44 | 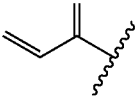 | H | H | H | H | OMe | CH | CH | H | H | $C_{21}H_{21}N_3O_4$ | 380.14 | 380.0 |
| 1-45 | 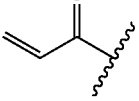 | H | H | H | H | CN | CH | CH | H | H | $C_{21}H_{18}N_4O_3$ | 375.12 | 375.0 |

TABLE 1-continued
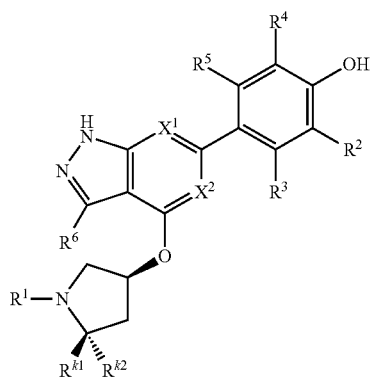
| Ex No. | $R^1$ | $R^2$ | $R^3$ | $R^4$ | $R^5$ | $R^6$ | $X^1$ | $X^2$ | $R^{k1}$ | $R^{k2}$ | Formula | Calc [M + H]$^+$ | Found [M + H]$^+$ |
|---|---|---|---|---|---|---|---|---|---|---|---|---|---|
| 1-46 | | Cl | H | H | H | OMe | CH | CH | H | H | $C_{21}H_{17}ClN_4O_3$ | 409.08 | 409.0 |
| 1-47 | | H | H | H | H | Cl | CH | CH | H | H | $C_{20}H_{18}ClN_3O_3$ | 384.09 | 384.1 |
| 1-48 | | H | H | H | H | Cl | CH | CH | H | H | $C_{23}H_{25}ClN_4O_3$ | 441.15 | 441.8 |
TABLE 2
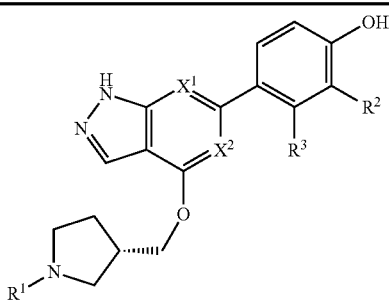
| Ex No. | $R^1$ | $R^2$ | $R^3$ | $X^1$ | $X^2$ | Formula | Calc [M + H]$^+$ | Found [M + H]$^+$ |
|---|---|---|---|---|---|---|---|---|
| 2-1 | | H | H | CH | CH | $C_{24}H_{28}N_4O_3$ | 421.20 | 421.2 |
| 2-2 | | Cl | H | CH | CH | $C_{24}H_{27}N_4O_3Cl$ | 455.16 | 455.1 |

TABLE 2-continued
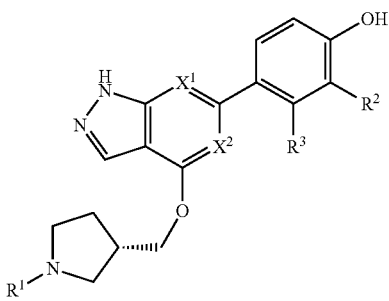
| Ex No. | R¹ | R² | R³ | X¹ | X² | Formula | Calc [M + H]⁺ | Found [M + H]⁺ |
|---|---|---|---|---|---|---|---|---|
| 2-3 | | Cl | H | CH | CH | $C_{21}H_{20}ClN_3O_3$ | 398.10 | 398.2 |
| 2-4 | | F | H | CH | CH | $C_{24}H_{27}FN_4O_3$ | 439.19 | 439.3 |
| 2-5 | | F | H | CH | CH | $C_{21}H_{20}FN_3O_3$ | 382.13 | 382.1 |
| 2-6 | | H | H | N | CH | $C_{20}H_{20}N_4O_3$ | 365.14 | 365.0 |
| 2-7 | | H | H | N | N | $C_{19}H_{19}N_5O_3$ | 366.13 | 366.0 |
| 2-8 | | H | H | CH | N | $C_{20}H_{20}N_4O_3$ | 365.14 | 365.0 |
| 2-9 | | Cl | H | CH | N | $C_{23}H_{26}ClN_5O_3$ | 456.16 | 456.2 |
| 2-10 | | F | H | CH | N | $C_{20}H_{19}FN_4O_3$ | 383.13 | 383.0 |
| 2-11 | | Cl | H | N | N | $C_{19}H_{18}ClN_5O_3$ | 400.09 | 400.1 |

TABLE 2-continued
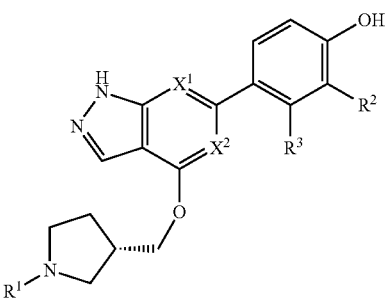
| Ex No. | R[1] | R[2] | R[3] | X[1] | X[2] | Formula | Calc [M + H]+ | Found [M + H]+ |
|---|---|---|---|---|---|---|---|---|
| 2-12 | (vinyl ketone) | H | H | N | CH | $C_{20}H_{20}N_4O_3$ | 365.14 | 365.0 |
| 2-13 | (dimethylamino crotonyl) | F | H | CH | N | $C_{23}H_{26}FN_5O_3$ | 440.19 | 440.3 |
| 2-14 | (vinyl ketone) | Cl | H | CH | N | $C_{20}H_{19}ClN_4O_3$ | 399.10 | 399.0 |
| 2-15 | (vinyl ketone) | F | H | N | N | $C_{19}H_{18}FN_5O_3$ | 384.12 | 384.1 |
| 2-16 | (vinyl ketone) | Cl | H | N | CH | $C_{20}H_{19}ClN_4O_3$ | 399.10 | 399.1 |
| 2-17 | (vinyl ketone) | F | H | N | CH | $C_{20}H_{19}FN_4O_3$ | 383.13 | 383.1 |

TABLE 3
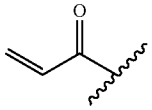 [SMILES: *C(=O)C=C]
| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-1 | 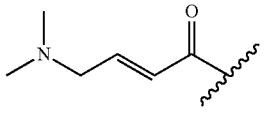 | H | H | CH | CH | H | H | H | H | $C_{20}H_{19}N_3O_3$ | 350.13 | 350.2 |
| 3-2 | 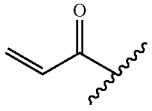 [SMILES: *C(=O)C=C] | Cl | H | CH | CH | H | H | H | H | $C_{23}H_{25}ClN_4O_3$ | 441.15 | 441.3 |
| 3-3 | 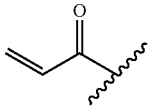 [SMILES: *C(=O)C=C] | Cl | H | CH | CH | H | H | H | H | $C_{20}H_{18}ClN_3O_3$ | 384.09 | 384.1 |
| 3-4 | 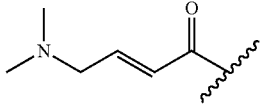 [SMILES: *C(=O)/C=C/CN(C)C] | F | H | CH | CH | H | H | H | H | $C_{20}H_{18}FN_3O_3$ | 368.12 | 368.2 |
| 3-5 | 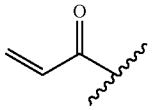 | H | H | CH | CH | F | H | H | H | $C_{23}H_{25}FN_4O_3$ | 425.18 | 425.1 |
| 3-6 | 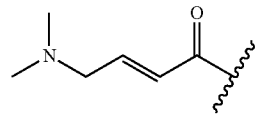 [SMILES: *C(=O)/C=C/CN(C)C] | H | H | CH | CH | F | H | H | H | $C_{20}H_{18}FN_3O_3$ | 368.12 | 368.2 |
| 3-7 | 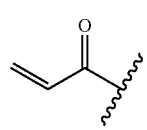 [SMILES: *C(=O)C=C] | H | H | CH | CH | Me | H | H | H | $C_{24}H_{28}N_4O_3$ | 421.20 | 421.1 |
| 3-8 | 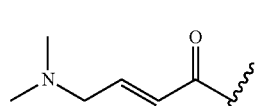 | H | H | CH | CH | Me | H | H | H | $C_{21}H_{21}N_3O_3$ | 364.14 | 364.1 |
| 3-9 | 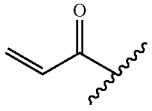 [SMILES: *C(=O)C=C] | Cl | H | CH | CH | Me | H | H | H | $C_{24}H_{27}ClN_4O_3$ | 455.16 | 456.1 |

TABLE 3-continued
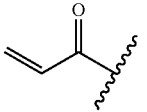 [SMILES: *C(=O)C=C]
| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-10 | 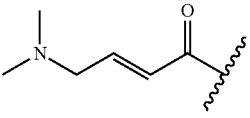 [SMILES: *C(=O)/C=C/CN(C)C] | Cl | H | CH | CH | Me | H | H | H | $C_{21}H_{20}ClN_3O_3$ | 398.10 | 398.1 |
| 3-11 | 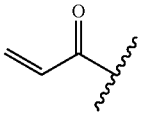 [SMILES: *C(=O)C=C] | F | H | CH | CH | Me | H | H | H | $C_{24}H_{27}FN_4O_3$ | 439.19 | 439.2 |
| 3-12 | 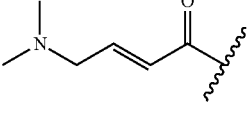 | F | H | CH | CH | Me | H | H | H | $C_{21}H_{20}FN_3O_3$ | 382.13 | 382.1 |
| 3-13 | 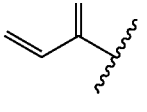 | H | H | CH | CH | Et | H | H | H | $C_{25}H_{30}N_4O_3$ | 435.22 | 435.1 |
| 3-14 | 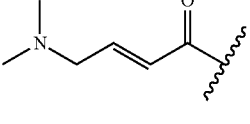 | H | H | CH | CH | Et | H | H | H | $C_{22}H_{23}N_3O_3$ | 378.16 | 378.1 |
| 3-15 | 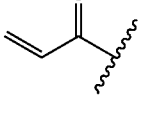 | Cl | H | CH | CH | Et | H | H | H | $C_{25}H_{29}ClN_4O_3$ | 469.18 | 469.1 |
| 3-16 | 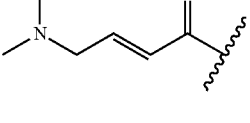 | Cl | H | CH | CH | Et | H | H | H | $C_{22}H_{22}ClN_3O_3$ | 412.12 | 412.1 |
| 3-17 | 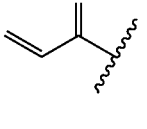 | F | H | CH | CH | Et | H | H | H | $C_{25}H_{29}FN_4O_3$ | 453.21 | 453.3 |
| 3-18 |  | F | H | CH | CH | Et | H | H | H | $C_{22}H_{22}FN_3O_3$ | 396.15 | 396.1 |

TABLE 3-continued
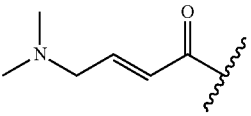 [SMILES: *C(=O)/C=C/CN(C)C]
| Ex No. | R¹ | R² | R³ | X¹ | X² | $R^{k1}$ | $R^{k2}$ | $R^d$ | $R^e$ | Formula | Calc [M + H]⁺ | Found [M + H]⁺ |
|---|---|---|---|---|---|---|---|---|---|---|---|---|
| 3-19 | 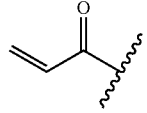 [SMILES: *C(=O)C=C] | H | H | CH | CH | CN | H | H | H | $C_{24}H_{25}N_5O_3$ | 432.18 | 432.1 |
| 3-20 | 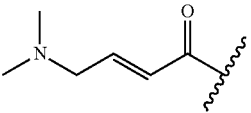 [SMILES: *C(=O)/C=C/CN(C)C] | H | H | CH | CH | CN | H | H | H | $C_{21}H_{18}N_4O_3$ | 375.12 | 375.1 |
| 3-21 | 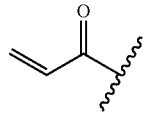 [SMILES: *C(=O)C=C] | Cl | H | CH | CH | CN | H | H | H | $C_{24}H_{24}ClN_5O_3$ | 466.14 | 466.2 |
| 3-22 | 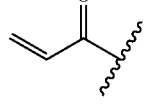 | Cl | H | CH | CH | CN | H | H | H | $C_{21}H_{17}ClN_4O_3$ | 409.08 | 409.1 |
| 3-23 | 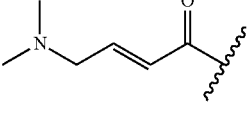 | F | H | CH | CH | CN | H | H | H | $C_{21}H_{17}FN_4O_3$ | 393.11 | 393.1 |
| 3-24 | 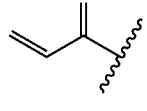 | H | H | CH | CH | H | H | Me | Me | $C_{25}H_{30}N_4O_3$ | 435.22 | 435.0 |
| 3-25 | 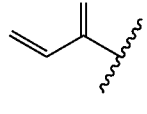 | H | H | CH | CH | H | H | Me | Me | $C_{22}H_{23}N_3O_3$ | 378.16 | 378.1 |
| 3-26 | 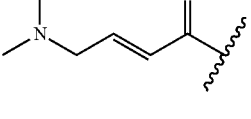 | Cl | H | CH | CH | H | H | Me | Me | $C_{22}H_{22}ClN_3O_3$ | 412.12 | 412.2 |
| 3-27 |  | F | H | CH | CH | H | H | Me | Me | $C_{25}H_{29}FN_4O_3$ | 453.21 | 453.2 |

TABLE 3-continued
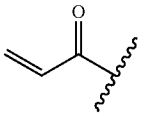 [SMILES: *C(=O)C=C]
| Ex No. | R[1] | R[2] | R[3] | X[1] | X[2] | R[k1] | R[k2] | R[d] | R[e] | Formula | Calc [M + H]+ | Found [M + H]+ |
|---|---|---|---|---|---|---|---|---|---|---|---|---|
| 3-28 | 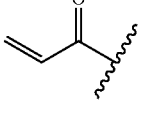 | F | H | CH | CH | H | H | Me | Me | $C_{22}H_{22}FN_3O_3$ | 393.15 | 396.3 |
| 3-29 | 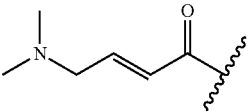 [SMILES: *C(=O)/C=C/CN(C)C] | H | H | CH | N | H | H | H | H | $C_{19}H_{18}N_4O_3$ | 351.12 | 351.0 |
| 3-30 | 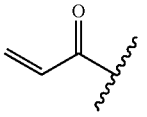 [SMILES: *C(=O)C=C] | H | H | CH | CH | H | Me | H | H | $C_{24}H_{28}N_4O_3$ | 421.20 | 421.2 |
| 3-31 | 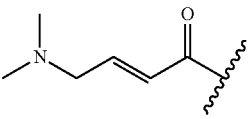 [SMILES: *C(=O)/C=C/CN(C)C] | H | H | N | N | H | Me | H | H | $C_{19}H_{19}N_5O_3$ | 366.13 | 366.1 |
| 3-32 | 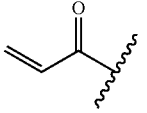 [SMILES: *C(=O)C=C] | H | H | CH | CH | OMe | H | H | H | $C_{24}H_{28}N_4O_4$ | 437.20 | 437.3 |
| 3-33 | 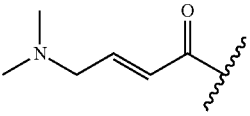 [SMILES: *C(=O)/C=C/CN(C)C] | H | H | CH | CH | OMe | H | H | H | $C_{21}H_{21}N_3O_4$ | 380.14 | 380.2 |
| 3-34 | 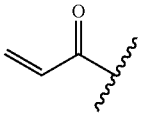 [SMILES: *C(=O)C=C] | Cl | H | CH | N | H | H | H | H | $C_{22}H_{24}ClN_5O_3$ | 442.14 | 442.1 |
| 3-35 | 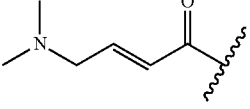 | Cl | H | CH | N | H | H | H | H | $C_{19}H_{17}ClN_4O_3$ | 385.08 | 385.0 |
| 3-36 |  | F | H | CH | N | H | H | H | H | $C_{22}H_{24}FN_5O_3$ | 426.17 | 426.0 |

TABLE 3-continued

| Ex No. | R¹ | R² | R³ | X¹ | X² | $R^{k1}$ | $R^{k2}$ | $R^d$ | $R^e$ | Formula | Calc [M + H]⁺ | Found [M + H]⁺ |
|---|---|---|---|---|---|---|---|---|---|---|---|---|
| 3-37 | vinyl ketone | F | H | CH | N | H | H | H | H | $C_{19}H_{17}FN_4O_3$ | 369.11 | 369.1 |
| 3-38 | vinyl ketone | Cl | H | N | N | H | H | H | H | $C_{18}H_{16}ClN_5O_3$ | 386.08 | 386.2 |
| 3-39 | vinyl ketone | F | H | N | N | H | H | H | H | $C_{18}H_{16}FN_5O_3$ | 370.11 | 370.1 |
| 3-40 | dimethylamino enone | F | H | CH | CH | F | H | H | H | $C_{23}H_{24}F_2N_4O_3$ | 443.17 | 443.1 |
| 3-41 | vinyl ketone | F | H | CH | CH | F | H | H | H | $C_{20}H_{17}F_2N_3O_3$ | 386.11 | 386.2 |
| 3-42 | dimethylamino enone | Cl | H | CH | CH | F | H | H | H | $C_{23}H_{24}ClFN_4O_3$ | 459.14 | 459.1 |
| 3-43 | vinyl ketone | Cl | H | CH | CH | F | H | H | H | $C_{20}H_{17}ClFN_3O_3$ | 402.08 | 402.0 |
| 3-44 | dimethylamino enone | H | H | CH | N | F | H | H | H | $C_{22}H_{24}FN_5O_3$ | 426.17 | 426.2 |
| 3-45 | vinyl ketone | H | H | N | N | F | H | H | H | $C_{18}H_{16}FN_5O_3$ | 370.11 | 370.1 |

TABLE 3-continued
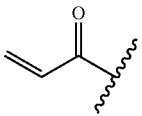 [SMILES: *C(=O)C=C]
| Ex No. | R¹ | R² | R³ | X¹ | X² | $R^{k1}$ | $R^{k2}$ | $R^d$ | $R^e$ | Formula | Calc [M + H]⁺ | Found [M + H]⁺ |
|---|---|---|---|---|---|---|---|---|---|---|---|---|
| 3-46 | 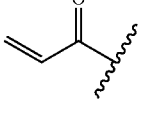 | H | H | N | CH | F | H | H | H | $C_{19}H_{17}FN_4O_3$ | 369.11 | 369.3 |
| 3-47 | 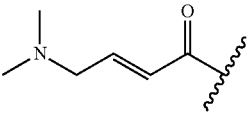 [SMILES: *C(=O)/C=C/CN(C)C] | Cl | H | CH | N | F | H | H | H | $C_{19}H_{16}ClFN_4O_3$ | 403.07 | 403.0 |
| 3-48 | 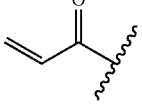 | F | H | CH | N | F | H | H | H | $C_{22}H_{23}F_2N_5O_3$ | 444.16 | 444.0 |
| 3-49 | 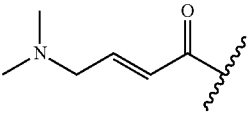 [SMILES: *C(=O)/C=C/CN(C)C] | F | H | CH | N | F | H | H | H | $C_{19}H_{16}F_2N_4O_3$ | 387.10 | 387.0 |
| 3-50 | 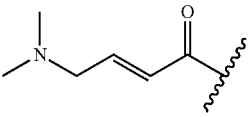 [SMILES: *C(=O)/C=C/CN(C)C] | Cl | H | N | N | F | H | H | H | $C_{21}H_{22}ClFN_6O_3$ | 461.13 | 461.1 |
| 3-51 | 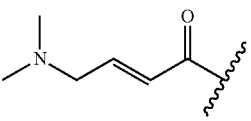 [SMILES: *C(=O)/C=C/CN(C)C] | F | H | N | N | F | H | H | H | $C_{21}H_{22}F_2N_6O_3$ | 445.16 | 445.2 |
| 3-52 | 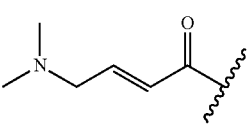 [SMILES: *C(=O)/C=C/CN(C)C] | Cl | H | N | CH | F | H | H | H | $C_{22}H_{23}ClFN_5O_3$ | 460.13 | 460.1 |
| 3-53 | 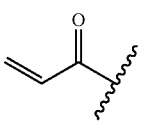 [SMILES: *C(=O)C=C] | F | H | N | CH | F | H | H | H | $C_{22}H_{23}F_2N_5O_3$ | 444.16 | 444.2 |
| 3-54 |  | F | H | N | CH | F | H | H | H | $C_{19}H_{16}F_2N_4O_3$ | 387.10 | 387.1 |

TABLE 3-continued

| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-55 | (dimethylamino-butenone) | H | H | CH | N | Me | H | H | H | $C_{23}H_{27}N_5O_3$ | 422.20 | 422.2 |
| 3-56 | (vinyl ketone) | H | H | CH | N | Me | H | H | H | $C_{20}H_{20}N_4O_3$ | 365.14 | 365.2 |
| 3-57 | (vinyl ketone) | H | H | N | N | Me | H | H | H | $C_{19}H_{19}N_5O_3$ | 366.13 | 366.1 |
| 3-58 | (vinyl ketone) | H | H | N | CH | Me | H | H | H | $C_{20}H_{20}N_4O_3$ | 365.14 | 365.2 |
| 3-59 | (vinyl ketone) | F | H | CH | N | Me | H | H | H | $C_{20}H_{19}FN_4O_3$ | 383.13 | 383.3 |
| 3-60 | (dimethylaminomethyl acrylketone) | Cl | H | N | N | H | H | H | H | $C_{21}H_{23}ClN_6O_3$ | 443.14 | 443.1 |
| 3-61 | (dimethylamino-butenone) | H | H | CH | N | Et | H | H | H | $C_{24}H_{29}N_5O_3$ | 436.21 | 436.1 |
| 3-62 | (vinyl ketone) | H | H | CH | N | Et | H | H | H | $C_{21}H_{22}N_4O_3$ | 379.15 | 379.0 |
| 3-63 | (vinyl ketone) | H | H | N | N | Et | H | H | H | $C_{20}H_{21}N_5O_3$ | 380.15 | 380.2 |

TABLE 3-continued
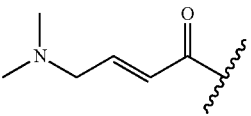 [SMILES: *C(=O)/C=C/CN(C)C]
| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-64 | 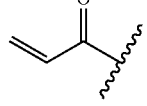 | H | H | CH | N | Et | H | H | H | $C_{24}H_{29}N_5O_3$ | 436.21 | 436.1 |
| 3-65 | 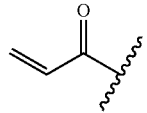 [SMILES: *C(=O)C=C] | H | H | CH | N | Et | H | H | H | $C_{21}H_{22}N_4O_3$ | 379.15 | 379.0 |
| 3-66 | 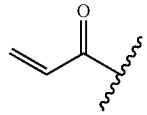 [SMILES: *C(=O)C=C] | Cl | H | CH | N | Et | H | H | H | $C_{21}H_{21}ClN_4O_3$ | 413.11 | 413.1 |
| 3-67 | 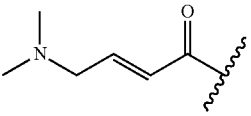 [SMILES: *C(=O)/C=C/CN(C)C] | F | H | N | N | Et | H | H | H | $C_{20}H_{20}FN_5O_3$ | 398.14 | 398.1 |
| 3-68 | 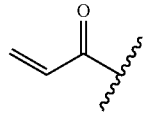 [SMILES: *C(=O)C=C] | Cl | H | N | CH | Et | H | H | H | $C_{24}H_{28}ClN_5O_3$ | 470.17 | 470.2 |
| 3-69 | 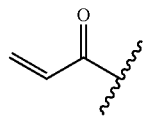 [SMILES: *C(=O)C=C] | Cl | H | N | CH | Et | H | H | H | $C_{21}H_{21}ClN_4O_3$ | 413.11 | 413.2 |
| 3-70 | 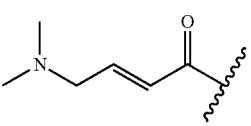 [SMILES: *C(=O)/C=C/CN(C)C] | F | H | N | CH | Et | H | H | H | $C_{21}H_{21}FN_4O_3$ | 397.14 | 397.2 |
| 3-71 | 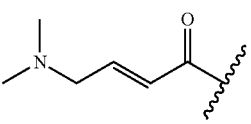 [SMILES: *C(=O)/C=C/CN(C)C] | Cl | H | CH | N | CN | H | H | H | $C_{23}H_{23}ClN_6O_3$ | 467.14 | 467.0 |
| 3-72 | 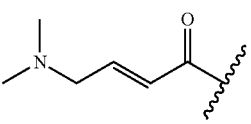 [SMILES: *C(=O)/C=C/CN(C)C] | Cl | H | CH | CH | OMe | H | H | H | $C_{24}H_{27}ClN_4O_4$ | 471.16 | 471.2 |

TABLE 3-continued
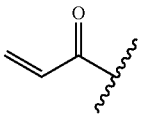 [SMILES: *C(=O)C=C]
| Ex No. | R¹ | R² | R³ | X¹ | X² | R$^{k1}$ | R$^{k2}$ | R$^d$ | R$^e$ | Formula | Calc [M + H]⁺ | Found [M + H]⁺ |
|---|---|---|---|---|---|---|---|---|---|---|---|---|
| 3-73 | 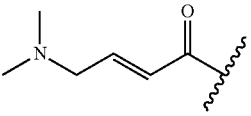 [SMILES: *C(=O)/C=C/CN(C)C] | Cl | H | CH | CH | OMe | H | H | H | $C_{21}H_{20}ClN_3O_4$ | 414.10 | 414.2 |
| 3-74 | 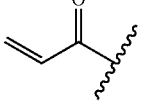 | F | H | CH | CH | OMe | H | H | H | $C_{24}H_{27}FN_4O_4$ | 455.19 | 455.1 |
| 3-75 | 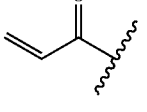 | F | H | CH | CH | OMe | H | H | H | $C_{21}H_{20}FN_3O_4$ | 398.13 | 398.2 |
| 3-76 | 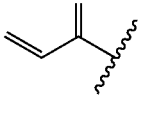 | H | H | N | N | OMe | H | H | H | $C_{19}H_{19}N_5O_4$ | 382.13 | 382.1 |
| 3-77 | 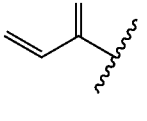 | H | H | N | N | H | H | H | Me | $C_{19}H_{19}N_5O_3$ | 366.13 | 366.1 |
| 3-78 | 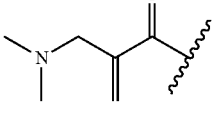 | H | H | N | N | H | H | H | Me (S) | $C_{19}H_{19}N_5O_3$ | 366.13 | 366.1 |
| 3-79 | 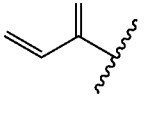 | H | H | N | CH | H | H | H | H | $C_{22}H_{25}N_5O_3$ | 408.18 | 408.1 |
| 3-80 | 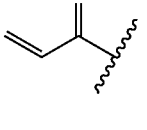 | Cl | H | N | CH | H | H | Me | Me | $C_{21}H_{21}ClN_4O_3$ | 413.11 | 413.2 |
| 3-81 | 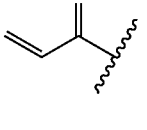 | F | H | N | CH | H | H | Me | Me | $C_{21}H_{21}FN_4O_3$ | 397.14 | 397.1 |

TABLE 3-continued

| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-82 | (CH₃)₂N-CH₂-CH=CH-C(O)- | F | F | CH | CH | H | H | H | H | $C_{23}H_{24}F_2N_4O_3$ | 443.17 | 443.7 |
| 3-83 | CH₂=CH-C(O)- | OMe | H | CH | CH | H | H | H | H | $C_{21}H_{21}N_3O_4$ | 380.14 | 380.0 |
| 3-84 | HC≡C-C(O)- | H | H | CH | CH | H | H | H | H | $C_{20}H_{17}N_3O_3$ | 348.11 | 348.1 |
| 3-85 | (N-methylpyrrolidin-2-yl)-CH=CH-C(O)- | H | H | CH | CH | H | H | H | H | $C_{25}H_{28}N_4O_3$ | 433.20 | 433.1 |
| 3-86 | CH₂=CH-C(O)- | Cl | H | N | CH | H | H | H | H | $C_{19}H_{17}ClN_4O_3$ | 385.08 | 385.1 |
| 3-87 | CH₂=CH-C(O)- | F | H | N | CH | H | H | H | H | $C_{19}H_{17}FN_4O_3$ | 369.11 | 369.1 |
| 3-88 | (CH₃)₂N-CH₂-CH=CH-C(O)- | H | H | N | N | F | H | H | H | $C_{21}H_{23}FN_6O_3$ | 427.17 | 427.2 |
| 3-89 | (CH₃)₂N-CH₂-CH=CH-C(O)- | H | H | N | CH | F | H | H | H | $C_{22}H_{24}FN_5O_3$ | 426.17 | 426.2 |
| 3-90 | CH₂=CH-C(O)- | H | H | CH | N | F | H | H | H | $C_{19}H_{17}FN_4O_3$ | 369.11 | 369.1 |

TABLE 3-continued

| Ex No. | R¹ | R² | R³ | X¹ | X² | R$^{k1}$ | R$^{k2}$ | R$^d$ | R$^e$ | Formula | Calc [M + H]⁺ | Found [M + H]⁺ |
|---|---|---|---|---|---|---|---|---|---|---|---|---|
| 3-91 | (E)-Me₂N-CH₂-CH=CH-C(O)- | Cl | H | CH | N | F | H | H | H | $C_{22}H_{23}ClFN_5O_3$ | 460.13 | 460.0 |
| 3-92 | CH₂=CH-C(O)- | Cl | H | N | N | F | H | H | H | $C_{18}H_{15}ClFN_5O_3$ | 404.07 | 404.1 |
| 3-93 | CH₂=CH-C(O)- | F | H | N | N | F | H | H | H | $C_{18}H_{15}F_2N_5O_3$ | 388.10 | 388.1 |
| 3-94 | CH₂=CH-C(O)- | Cl | H | N | CH | F | H | H | H | $C_{19}H_{16}ClFN_4O_3$ | 403.07 | 403.1 |
| 3-95 | (E)-Me₂N-CH₂-CH=CH-C(O)- | Cl | H | CH | N | Me | H | H | H | $C_{23}H_{26}ClN_5O_3$ | 456.16 | 456.2 |
| 3-96 | (E)-Me₂N-CH₂-CH=CH-C(O)- | F | H | CH | N | Me | H | H | H | $C_{23}H_{26}FN_5O_3$ | 440.19 | 440.2 |
| 3-97 | CH₂=CH-C(O)- | Cl | H | CH | N | Me | H | H | H | $C_{20}H_{19}ClN_4O_3$ | 399.10 | 399.2 |
| 3-98 | CH₂=CH-C(O)- | F | H | N | CH | Me | H | H | H | $C_{20}H_{19}FN_4O_3$ | 383.13 | 383.2 |
| 3-99 | (E)-Me₂N-CH₂-CH=CH-C(O)- | Cl | H | CH | N | Et | H | H | H | $C_{24}H_{28}ClN_5O_3$ | 470.17 | 470.1 |

TABLE 3-continued

| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-100 | (E)-4-(dimethylamino)but-2-enoyl | F | H | CH | N | Et | H | H | H | $C_{24}H_{28}FN_5O_3$ | 454.20 | 454.2 |
| 3-101 | acryloyl | F | H | CH | N | Et | H | H | H | $C_{21}H_{21}FN_4O_3$ | 397.14 | 397.2 |
| 3-102 | (E)-4-(dimethylamino)but-2-enoyl | H | H | CH | N | CN | H | H | H | $C_{23}H_{24}N_6O_3$ | 433.18 | 433.2 |
| 3-103 | acryloyl | H | H | CH | N | CN | H | H | H | $C_{20}H_{17}N_5O_3$ | 376.12 | 376.2 |
| 3-104 | acryloyl | H | H | N | N | CN | H | H | H | $C_{19}H_{16}N_6O_3$ | 377.11 | 377.0 |
| 3-105 | acryloyl | H | H | CH | N | CN | H | H | H | $C_{20}H_{17}N_5O_3$ | 376.12 | 376.2 |
| 3-106 | (E)-4-(dimethylamino)but-2-enoyl | F | H | CH | N | CN | H | H | H | $C_{23}H_{23}FN_6O_3$ | 451.17 | 451.1 |
| 3-107 | acryloyl | Cl | H | CH | N | CN | H | H | H | $C_{20}H_{16}ClN_5O_3$ | 410.08 | 410.1 |
| 3-108 | acryloyl | F | H | CH | N | CN | H | H | H | $C_{20}H_{16}FN_5O_3$ | 394.11 | 394.2 |

TABLE 3-continued
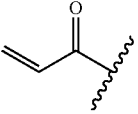 [SMILES: *C(=O)C=C]
| Ex No. | R¹ | R² | R³ | X¹ | X² | R$^{k1}$ | R$^{k2}$ | R$^d$ | R$^e$ | Formula | Calc [M + H]⁺ | Found [M + H]⁺ |
|---|---|---|---|---|---|---|---|---|---|---|---|---|
| 3-109 | 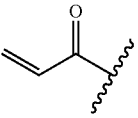 [SMILES: *C(=O)C=C] | Cl | H | N | N | CN | H | H | H | $C_{19}H_{15}ClN_6O_3$ | 411.07 | 411.1 |
| 3-110 | 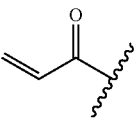 [SMILES: *C(=O)C=C] | F | H | N | N | CN | H | H | H | $C_{19}H_{15}FN_6O_3$ | 395.10 | 395.1 |
| 3-111 | 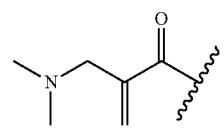 [SMILES: *C(=O)C(=C)CN(C)C] | F | H | N | CH | CN | H | H | H | $C_{20}H_{16}FN_5O_3$ | 394.11 | 394.1 |
| 3-112 | 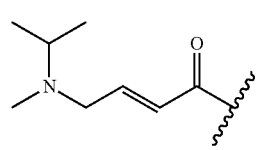 [SMILES: *C(=O)/C=C/CN(C)C(C)C] | H | H | N | N | H | H | H | H | $C_{21}H_{24}N_6O_3$ | 409.18 | 409.1 |
| 3-113 | 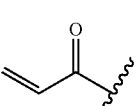 | H | H | CH | CH | H | H | H | H | $C_{25}H_{30}N_4O_3$ | 435.22 | 435.1 |
| 3-114 | 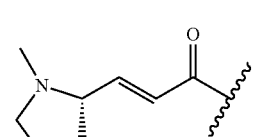 | H | H | CH | CH | H | Me | H | H | $C_{21}H_{21}N_3O_3$ | 364.14 | 364.1 |
| 3-115 | 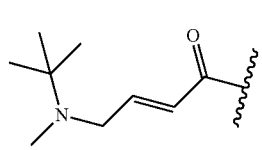 [SMILES: *C(=O)/C=C/CN(C)C(C)(C)C] | H | H | CH | CH | H | H | H | H | $C_{25}H_{28}N_4O_3$ | 433.20 | 433.1 |
| 3-116 |  | H | H | CH | CH | H | H | H | H | $C_{26}H_{32}N_4O_3$ | 449.23 | 449.2 |

TABLE 3-continued

| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-117 | (N-methyl-N-cyclobutyl-aminomethyl-CH=CH-C(O)-) | H | H | CH | CH | H | H | H | H | $C_{26}H_{30}N_4O_3$ | 447.22 | |
| 3-118 | (N-methyl-N-isobutyl-aminomethyl-CH=CH-C(O)-) | H | H | CH | CH | H | H | H | H | $C_{26}H_{32}N_4O_3$ | 449.23 | 449.2 |
| 3-119 | (N-methyl-N-(2-methoxyethyl)aminomethyl-CH=CH-C(O)-) | H | H | CH | CH | H | H | H | H | $C_{25}H_{30}N_4O_4$ | 451.21 | 451.1 |
| 3-120 | (N,N-bis(2-methoxyethyl)aminomethyl-CH=CH-C(O)-) | H | H | CH | CH | H | H | H | H | $C_{27}H_{34}N_4O_5$ | 495.24 | |
| 3-121 | (N-methyl-N-(2,2-dimethoxyethyl)aminomethyl-CH=CH-C(O)-) | H | H | CH | CH | H | H | H | H | $C_{26}H_{32}N_4O_5$ | 481.22 | |
| 3-122 | (N,N-dimethylaminomethyl-CH=CH-C(O)-) | Cl | H | CH | CH | H | H | H | H | $C_{23}H_{25}ClN_4O_3$ | 441.15 | 441.1 |
| 3-123 | (azetidin-1-yl-methyl-CH=CH-C(O)-) | H | H | CH | CH | H | H | H | H | $C_{24}H_{26}N_4O_3$ | 419.18 | 419.1 |
| 3-124 | (pyrrolidin-1-yl-methyl-CH=CH-C(O)-) | H | H | CH | CH | H | H | H | H | $C_{25}H_{28}N_4O_3$ | 433.20 | |

TABLE 3-continued
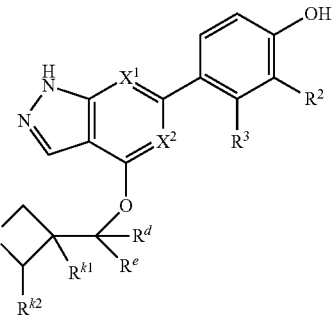
| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-125 | | H | H | CH | CH | H | H | H | H | $C_{26}H_{30}N_4O_3S$ | 479.19 | 479.2 |
| 3-126 | | H | H | CH | CH | H | H | H | H | $C_{25}H_{30}N_4O_3S$ | 467.18 | |
| 3-127 | | H | H | CH | CH | H | H | H | H | $C_{27}H_{32}N_4O_4$ | 477.23 | |
| 3-128 | | H | H | CH | CH | H | H | H | H | $C_{27}H_{32}N_4O_4$ | 477.23 | 477.2 |
| 3-129 | | H | H | CH | CH | H | H | H | H | $C_{25}H_{28}N_4O_4$ | 449.20 | 449.1 |
| 3-130 | | H | H | CH | CH | H | H | H | H | $C_{25}H_{28}N_4O_3S$ | 465.17 | 465.1 |
| 3-131 | | H | H | CH | CH | H | H | H | H | $C_{27}H_{32}N_4O_3S$ | 493.20 | 493.2 |
| 3-132 | | H | H | CH | CH | H | H | H | H | $C_{25}H_{28}N_4O_4$ | 449.20 | |

TABLE 3-continued

[Structure: pyrazolopyridine core with OH-phenyl and azetidine-O linker, substituents R¹, R², R³, X¹, X², R^{k1}, R^{k2}, R^d, R^e]

| Ex No. | R¹ | R² | R³ | X¹ | X² | R^{k1} | R^{k2} | R^d | R^e | Formula | Calc [M + H]⁺ | Found [M + H]⁺ |
|---|---|---|---|---|---|---|---|---|---|---|---|---|
| 3-133 | 3-methoxy-3-methyl-azetidine with CH=CH-C(O)- linker | H | H | CH | CH | H | H | H | H | $C_{26}H_{30}N_4O_4$ | 463.21 | 463.2 |
| 3-134 | (3R)-3-(methoxymethyl)pyrrolidine with CH=CH-C(O)- linker | H | H | CH | CH | H | H | H | H | $C_{27}H_{32}N_4O_4$ | 477.23 | |

TABLE 4

[Structure: pyrazolopyridine core with OH-phenyl and azetidine-CH₂-N(R^b) linker]

| Ex No. | R¹ | R² | R³ | R^b | R^k | X¹ | X² | Formula | Calc [M + H]⁺ | Found [M + H]⁺ |
|---|---|---|---|---|---|---|---|---|---|---|
| 4-1 | vinyl ketone (acryloyl) | H | H | Me | H | CH | CH | $C_{21}H_{22}N_4O_2$ | 363.15 | 363.1 |
| 4-2 | vinyl ketone (acryloyl) | H | H | H | Me | CH | CH | $C_{21}H_{22}N_4O_2$ | 363.15 | 363 |
| 4-3 | vinyl ketone (acryloyl) | H | H | H | H | CH | CH | $C_{20}H_{20}N_4O_2$ | 349.14 | 349.1 |
| 4-4 | (E)-4-(dimethylamino)but-2-enoyl | Cl | H | Me | H | CH | CH | $C_{24}H_{28}ClN_5O_2$ | 454.18 | 454.1 |

TABLE 4-continued
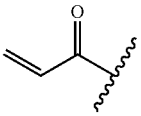 [SMILES: *C(=O)C=C]
| Ex No. | R¹ | R² | R³ | R$^b$ | R$^k$ | X¹ | X² | Formula | Calc [M + H]⁺ | Found [M + H]⁺ |
|---|---|---|---|---|---|---|---|---|---|---|
| 4-5 | 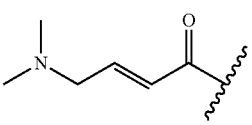 [SMILES: *C(=O)/C=C/CN(C)C] | Cl | H | Me | H | CH | CH | $C_{21}H_{21}ClN_4O_2$ | 397.12 | 397.0 |
| 4-6 | 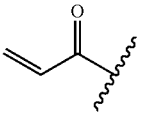 | F | H | Me | H | CH | CH | $C_{24}H_{28}FN_5O_2$ | 438.21 | 438.1 |
| 4-7 | 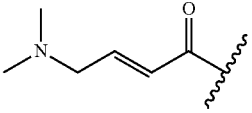 [SMILES: *C(=O)/C=C/CN(C)C] | F | H | Me | H | CH | CH | $C_{21}H_{21}FN_4O_2$ | 481.15 | 381.0 |
| 4-8 | 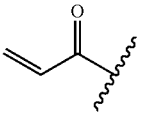 | H | H | Me | H | CH | N | $C_{23}H_{28}N_6O_2$ | 421.21 | 421.2 |
TABLE 5
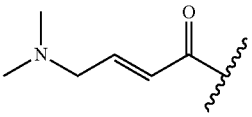 [SMILES: *C(=O)/C=C/CN(C)C]
| Ex No. | R¹ | R² | R³ | X¹ | X² | R$^k$ | L | Formula | Calc [M + H]⁺ | Found [M + H]⁺ |
|---|---|---|---|---|---|---|---|---|---|---|
| 5-1 | 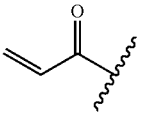 | H | H | CH | CH | H | O | $C_{22}H_{24}N_4O_3$ | 393.17 | 393.4 |

TABLE 5-continued
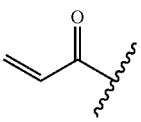 [SMILES: *C(=O)C=C]
| Ex No. | R¹ | R² | R³ | X¹ | X² | R^k | L | Formula | Calc [M + H]⁺ | Found [M + H]⁺ |
|---|---|---|---|---|---|---|---|---|---|---|
| 5-2 | 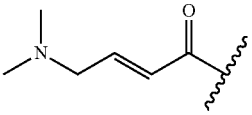 [SMILES: *C(=O)/C=C/CN(C)C] | H | H | CH | CH | H | O | $C_{19}H_{17}N_3O_3$ | 336.11 | 336.2 |
| 5-3 | 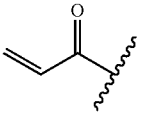 [SMILES: *C(=O)C=C] | Cl | H | CH | CH | H | O | $C_{22}H_{23}ClN_4O_3$ | 427.13 | 427.1 |
| 5-4 | 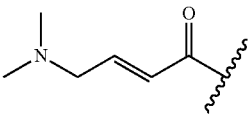 [SMILES: *C(=O)/C=C/CN(C)C] | Cl | H | CH | CH | H | O | $C_{19}H_{16}ClN_3O_3$ | 370.07 | 370.1 |
| 5-5 | 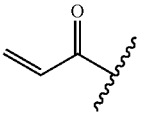 [SMILES: *C(=O)C=C] | F | H | CH | CH | H | O | $C_{22}H_{23}FN_4O_3$ | 411.16 | 411.3 |
| 5-6 | 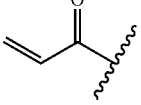 | F | H | CH | CH | H | O | $C_{19}H_{16}FN_3O_3$ | 354.10 | 354.2 |
| 5-7 | 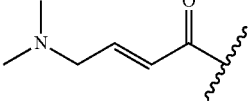 | H | H | CH | CH | H | NH | $C_{19}H_{18}N_4O_2$ | 335.12 | 335.2 |
| 5-8 | 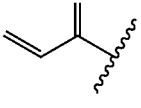 | H | H | CH | CH | H | NMe | $C_{23}H_{27}N_5O_2$ | 406.20 | 406.1 |
| 5-9 | 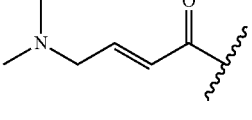 | H | H | CH | CH | H | NMe | $C_{20}H_{20}N_4O_2$ | 349.14 | 349.1 |
| 5-10 |  | H | H | CH | CH | CHF₂ | O | $C_{23}H_{24}F_2N_4O_3$ | 443.17 | 443.1 |

TABLE 5-continued

| Ex No. | R¹ | R² | R³ | X¹ | X² | R^k | L | Formula | Calc [M + H]⁺ | Found [M + H]⁺ |
|---|---|---|---|---|---|---|---|---|---|---|
| 5-11 | Me₂N-CH₂-CH=CH-C(O)- | H | H | CH | CH | Me | O | $C_{23}H_{26}N_4O_3$ | 407.18 | 407.1 |
| 5-12 | CH₂=CH-C(O)- | H | H | CH | CH | Me | O | $C_{20}H_{19}N_3O_3$ | 350.13 | 350.1 |
| 5-13 | Me₂N-CH₂-CH=CH-C(O)- | H | H | CH | CH | cyclopropyl | O | $C_{25}H_{28}N_4O_3$ | 433.20 | 433.2 |
| 5-14 | CH₂=CH-C(O)- | H | H | CH | CH | CHF₂ | O | $C_{20}H_{17}F_2N_3O_3$ | 386.11 | 386.0 |
| 5-15 | CH₂=CH-C(O)- | H | H | N | CH | H | O | $C_{18}H_{16}N_4O_3$ | 337.11 | 337.1 |
| 5-16 | Me₂N-CH₂-CH=CH-C(O)- | Cl | H | CH | CH | CHF₂ | O | $C_{23}H_{23}ClF_2N_4O_3$ | 477.13 | 477.1 |
| 5-17 | Me₂N-CH₂-CH=CH-C(O)- | F | H | CH | CH | CHF₂ | O | $C_{23}H_{23}F_3N_4O_3$ | 461.16 | 461.2 |
| 5-18 | Me₂N-CH₂-CH=CH-C(O)- | Cl | H | CH | CH | Me | O | $C_{23}H_{25}ClN_4O_3$ | 441.15 | 441.2 |
| 5-19 | Me₂N-CH₂-CH=CH-C(O)- | F | H | CH | CH | Me | O | $C_{23}H_{25}FN_4O_3$ | 425.18 | 425.3 |

TABLE 5-continued

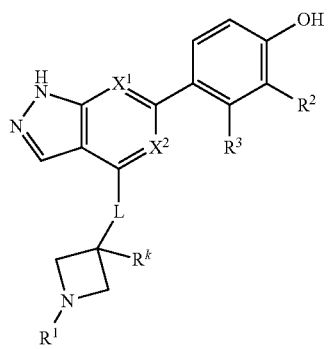

| Ex No. | R$^1$ | R$^2$ | R$^3$ | X$^1$ | X$^2$ | R$^k$ | L | Formula | Calc [M + H]$^+$ | Found [M + H]$^+$ |
|---|---|---|---|---|---|---|---|---|---|---|
| 5-20 | vinyl ketone | H | H | N | N | H | O | C$_{17}$H$_{15}$N$_5$O$_3$ | 338.10 | 338.2 |
| 5-21 | vinyl ketone | Cl | H | CH | CH | CHF$_2$ | O | C$_{20}$H$_{16}$ClF$_2$N$_3$O$_3$ | 420.07 | 420.0 |
| 5-22 | vinyl ketone | F | H | CH | CH | CHF$_2$ | O | C$_{20}$H$_{16}$F$_3$N$_3$O$_3$ | 404.10 | 404.1 |
| 5-23 | vinyl ketone | Cl | H | CH | CH | Me | O | C$_{20}$H$_{18}$ClN$_3$O$_3$ | 384.09 | 384.2 |
| 5-24 | vinyl ketone | F | H | CH | CH | Me | O | C$_{20}$H$_{18}$FN$_3$O$_3$ | 368.12 | 368.1 |
| 5-25 | dimethylamino enone | H | H | CH | CH | CF$_3$ | O | C$_{23}$H$_{23}$F$_3$N$_4$O$_3$ | 461.16 | 461.2 |
| 5-26 | vinyl ketone | H | H | CH | CH | CF$_3$ | O | C$_{20}$H$_{16}$F$_3$N$_3$O$_3$ | 404.10 | 404.1 |

TABLE 6

| Ex No. | R¹ | R² | R³ | X¹ | X² | R^k1 | R^k2 | R^k3 | Formula | Calc [M + H]⁺ | Found [M + H]⁺ |
|---|---|---|---|---|---|---|---|---|---|---|---|
| 6-1 | (E)-Me₂N-CH₂-CH=CH-C(O)- | H | H | CH | CH | H | H | H | $C_{24}H_{28}N_4O_3$ | 421.20 | 421.2 |
| 6-2 | CH₂=CH-C(O)- | H | H | CH | CH | H | H | H | $C_{21}H_{21}N_3O_3$ | 364.14 | 364.2 |
| 6-3 | CH₂=CH-C(O)- | H | H | CH | CH | Me | H | H | $C_{22}H_{23}N_3O_3$ | 378.16 | 378.1 |
| 6-4 | (E)-Me₂N-CH₂-CH=CH-C(O)- | Cl | H | CH | CH | Me | H | H | $C_{25}H_{29}ClN_4O_3$ | 469.18 | 469.2 |
| 6-5 | CH₂=CH-C(O)- | Cl | H | CH | CH | Me | H | H | $C_{22}H_{22}ClN_3O_3$ | 412.12 | 412.2 |
| 6-6 | (E)-Me₂N-CH₂-CH=CH-C(O)- | F | H | CH | CH | Me | H | H | $C_{25}H_{29}FN_4O_3$ | 453.21 | 453.2 |
| 6-7 | CH₂=CH-C(O)- | F | H | CH | CH | Me | H | H | $C_{22}H_{22}FN_3O_3$ | 396.15 | 396.1 |
| 6-8 | CH₂=CH-C(O)- | H | H | CH | CH | H | F | F | $C_{21}H_{19}F_2N_3O_3$ | 400.12 | 400.0 |
| 6-9 | (E)-Me₂N-CH₂-CH=CH-C(O)- | H | H | CH | CH | Me | H | H | $C_{25}H_{30}N_4O_3$ | 435.22 | 435.2 |

TABLE 6-continued
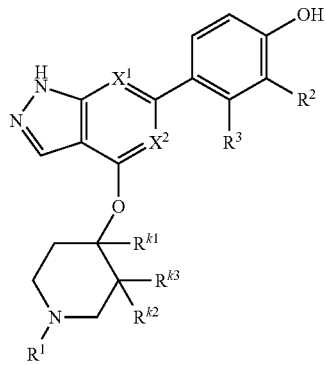
| Ex No. | R¹ | R² | R³ | X¹ | X² | R^{k1} | R^{k2} | R^{k3} | Formula | Calc [M + H]⁺ | Found [M + H]⁺ |
|---|---|---|---|---|---|---|---|---|---|---|---|
| 6-10 | (CH₂=CHC(O)-) | H | H | CH | CH | Me | H | H | $C_{22}H_{23}N_3O_3$ | 378.16 | 378.1 |
| 6-11 | (CH₂=CHC(O)-) | H | H | N | CH | H | H | H | $C_{20}H_{20}N_4O_3$ | 365.14 | 365.0 |
| 6-12 | (CH₂=CHC(O)-) | H | H | N | N | H | H | H | $C_{19}H_{19}N_5O_3$ | 366.13 | 366.1 |
| 6-13 | (CH₂=CHC(O)-) | Cl | H | CH | CH | H | H | H | $C_{21}H_{20}ClN_3O_3$ | 398.10 | 398.1 |
| 6-14 | (CH₂=CHC(O)-) | F | H | CH | CH | H | H | H | $C_{21}H_{20}FN_3O_3$ | 382.13 | 382.1 |
| 6-15 | (CH₂=CHC(O)-) | H | H | CH | N | H | H | H | $C_{21}H_{20}N_4O_3$ | 365.14 | 365.1 |
| 6-16 | (CH₂=CHC(O)-) | F | H | CH | N | H | H | H | $C_{20}H_{19}FN_4O_3$ | 383.13 | 383.0 |
| 6-17 | (CH₂=CHC(O)-) | Cl | H | N | CH | H | H | H | $C_{20}H_{19}ClN_4O_3$ | 399.10 | 399.3 |
| 6-18 | (CH₂=CHC(O)-) | F | H | N | CH | H | H | H | $C_{20}H_{19}FN_4O_3$ | 383.13 | 383.0 |

TABLE 6-continued

| Ex No. | R¹ | R² | R³ | X¹ | X² | R^{k1} | R^{k2} | R^{k3} | Formula | Calc [M + H]⁺ | Found [M + H]⁺ |
|---|---|---|---|---|---|---|---|---|---|---|---|
| 6-19 | (CH₃)₂N-CH₂-CH=CH-C(O)- | Cl | H | CH | CH | H | H | H | $C_{24}H_{27}ClN_4O_3$ | 455.16 | 455.2 |
| 6-20 | (CH₃)₂N-CH₂-CH=CH-C(O)- | F | H | CH | CH | H | H | H | $C_{24}H_{27}FN_4O_3$ | 439.19 | 439.1 |
| 6-21 | CH₂=CH-C(O)- | Cl | H | CH | N | H | H | H | $C_{20}H_{19}ClN_4O_3$ | 399.10 | 399.1 |
| 6-22 | CH₂=CH-C(O)- | Cl | H | N | N | H | H | H | $C_{19}H_{18}ClN_5O_3$ | 400.09 | 400.1 |
| 6-23 | CH₂=CH-C(O)- | F | H | N | N | H | H | H | $C_{19}H_{18}FN_5O_3$ | 384.12 | 384.0 |

TABLE 7

| Ex. No. | R¹ | R² | R³ | X¹ | X² | $R^{k1}$ | $R^{k2}$ | $R^{k3}$ | $R^b$ | Formula | Calc [M + H]⁺ | Found [M +H]⁺ |
|---|---|---|---|---|---|---|---|---|---|---|---|---|
| 7-1 | (E)-5-(dimethylamino)pent-3-en-1-on-1-yl | H | H | CH | CH | Me | H | H | H | $C_{25}H_{31}N_5O_2$ | 434.22 | 434.2 |
| 7-2 | acryloyl | H | H | CH | CH | Me | H | H | H | $C_{22}H_{24}N_4O_2$ | 377.17 | 377.3 |
| 7-3 | acryloyl | H | H | CH | CH | H | H | H | Me | $C_{22}H_{24}N_4O_2$ | 377.17 | 377 |
| 7-4 | acryloyl | H | H | CH | CH | H | H | H | H | $C_{21}H_{22}N_4O_2$ | 363.15 | 363 |
| 7-5 | (E)-5-(dimethylamino)pent-3-en-1-on-1-yl | H | H | CH | CH | H | F | F | H | $C_{24}H_{27}F_2N_5O_2$ | 456.19 | 456.2 |
| 7-6 | acryloyl | H | H | CH | CH | H | F | F | H | $C_{21}H_{20}F_2N_4O_2$ | 399.13 | 399.2 |
| 7-7 | acryloyl | Cl | H | CH | CH | H | H | H | Me | $C_{22}H_{23}ClN_4O_2$ | 411.14 | 411.2 |
| 7-8 | (E)-5-(dimethylamino)pent-3-en-1-on-1-yl | Cl | H | CH | CH | Me | H | H | H | $C_{25}H_{30}ClN_5O_2$ | 468.19 | 468.2 |
| 7-9 | acryloyl | F | H | CH | CH | Me | H | H | H | $C_{22}H_{23}FN_4O_2$ | 395.16 | 395.1 |

TABLE 7-continued
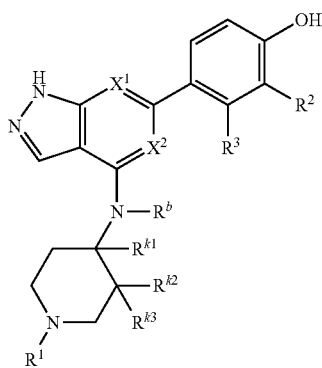
| Ex. No. | R$^1$ | R$^2$ | R$^3$ | X$^1$ | X$^2$ | R$^{k1}$ | R$^{k2}$ | R$^{k3}$ | R$^b$ | Formula | Calc [M + H]$^+$ | Found [M +H]$^+$ |
|---|---|---|---|---|---|---|---|---|---|---|---|---|
| 7-10 | ![](vinyl ketone) | F | H | CH | CH | H | H | H | Me | C$_{22}$H$_{23}$FN$_4$O$_2$ | 395.16 | 395.3 |
| 7-11 | ![](vinyl ketone) | Cl | H | CH | CH | Me | H | H | H | C$_{22}$H$_{23}$ClN$_4$O$_2$ | 411.13 | 411.2 |
| 7-12 | ![](dimethylamino enone) | F | H | CH | CH | Me | H | H | H | C$_{25}$H$_{30}$FN$_5$O$_2$ | 452.21 | 452.2 |
| 7-13 | ![](vinyl ketone) | H | H | CH | N | Me | H | H | H | C$_{21}$H$_{23}$N$_5$O$_2$ | 378.16 | 378.2 |
| 7-14 | ![](vinyl ketone) | Cl | H | CH | N | Me | H | H | H | C$_{21}$H$_{22}$ClN$_5$O$_2$ | 412.12 | 412.2 |

TABLE 8

| Ex No. | R¹ | R² | R³ | X¹ | X² | Formula | Calc [M + H]⁺ | Found [M + H]⁺ |
|---|---|---|---|---|---|---|---|---|
| 8-1 | vinyl ketone | H | H | CH | CH | $C_{21}H_{21}N_3O_3$ | 364.14 | 364 |
| 8-2 | (E)-4-(dimethylamino)but-2-enoyl | Cl | H | CH | CH | $C_{24}H_{27}ClN_4O_3$ | 455.16 | 455.1 |
| 8-3 | vinyl ketone | Cl | H | CH | CH | $C_{21}H_{20}ClN_3O_3$ | 398.10 | 398.0 |
| 8-4 | (E)-4-(dimethylamino)but-2-enoyl | F | H | CH | CH | $C_{24}H_{27}FN_4O_3$ | 439.19 | 439.2 |
| 8-5 | vinyl ketone | F | H | CH | CH | $C_{21}H_{20}FN_3O_3$ | 382.13 | 382.0 |
| 8-6 | vinyl ketone | H | H | N | CH | $C_{20}H_{20}FN_4O_3$ | 365.14 | 365.1 |
| 8-7 | vinyl ketone | H | H | CH | N | $C_{20}H_{20}N_4O_3$ | 365.14 | 365.1 |
| 8-8 | vinyl ketone | F | H | N | CH | $C_{20}H_{19}FN_4O_3$ | 383.13 | 383.0 |
| 8-9 | (E)-4-(dimethylamino)but-2-enoyl | F | H | CH | N | $C_{23}H_{26}FN_5O_3$ | 440.19 | 440.2 |

TABLE 8-continued
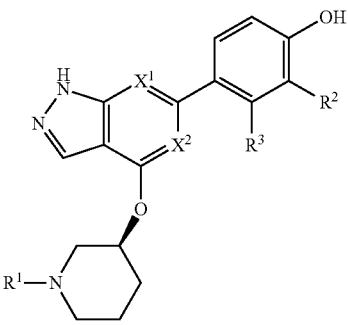
| Ex No. | R¹ | R² | R³ | X¹ | X² | Formula | Calc [M + H]⁺ | Found [M + H]⁺ |
|---|---|---|---|---|---|---|---|---|
| 8-10 | (acryloyl) | Cl | H | CH | N | $C_{20}H_{19}ClN_4O_3$ | 399.10 | 399.1 |
| 8-11 | (acryloyl) | F | H | CH | N | $C_{20}H_{19}FN_4O_3$ | 383.13 | 383.1 |
| 8-12 | (acryloyl) | Cl | H | N | N | $C_{19}H_{18}ClN_5O_3$ | 400.09 | 400.2 |
| 8-13 | (acryloyl) | F | H | N | N | $C_{19}H_{18}FN_5O_3$ | 384.12 | 384.0 |
| 8-14 | (acryloyl) | Cl | H | N | CH | $C_{20}H_{19}ClN_4O_3$ | 399.10 | 399.0 |
TABLE 9
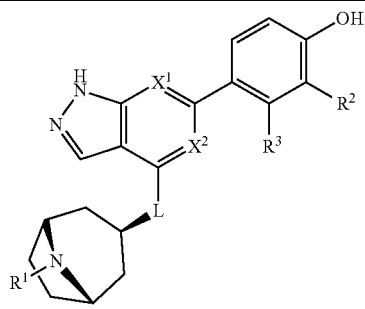
| Ex No. | R¹ | R² | R³ | X¹ | X² | L | Formula | Calc [M + H]⁺ | Found [M + H]⁺ |
|---|---|---|---|---|---|---|---|---|---|
| 9-1 | (acryloyl) | H | H | CH | CH | O | $C_{23}H_{23}N_3O_3$ | 390.16 | 390.1 |

TABLE 9-continued
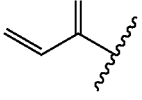
| Ex No. | R¹ | R² | R³ | X¹ | X² | L | Formula | Calc [M + H]⁺ | Found [M + H]⁺ |
|---|---|---|---|---|---|---|---|---|---|
| 9-2 | 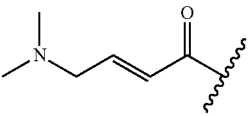 [SMILES: *C(=O)/C=C/CN(C)C] | Cl | H | CH | CH | O | $C_{23}H_{22}ClN_3O_3$ | 424.12 | 424.0 |
| 9-3 | 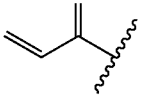 | Cl | H | CH | CH | O | $C_{26}H_{29}ClN_4O_3$ | 481.18 | 481.1 |
| 9-4 | 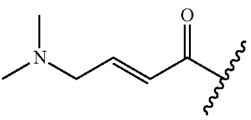 [SMILES: *C(=O)/C=C/CN(C)C] | F | H | CH | CH | O | $C_{23}H_{22}FN_3O_3$ | 408.15 | 408.1 |
| 9-5 | 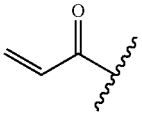 [SMILES: *C(=O)C=C] | F | H | CH | CH | O | $C_{26}H_{29}FN_4O_3$ | 465.21 | 465.1 |
| 9-6 | 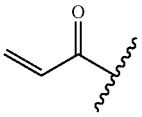 [SMILES: *C(=O)C=C] | H | H | CH | N | O | $C_{22}H_{22}N_4O_3$ | 391.15 | 391.1 |
| 9-7 | 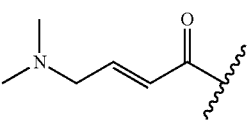 [SMILES: *C(=O)/C=C/CN(C)C] | Cl | H | CH | N | O | $C_{22}H_{21}ClN_4O_3$ | 425.11 | 425.0 |
| 9-8 | 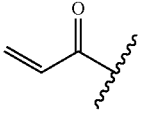 [SMILES: *C(=O)C=C] | Cl | H | CH | N | O | $C_{25}H_{28}ClN_5O_3$ | 482.17 | 482.1 |
| 9-9 | 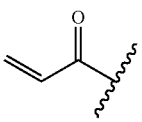 [SMILES: *C(=O)C=C] | H | H | CH | CH | NH | $C_{23}H_{24}N_4O_2$ | 389.17 | 389.2 |
| 9-10 |  | F | H | CH | N | O | $C_{22}H_{21}FN_4O_3$ | 409.14 | 409.0 |

TABLE 9-continued

| Ex No. | R$^1$ | R$^2$ | R$^3$ | X$^1$ | X$^2$ | L | Formula | Calc [M + H]$^+$ | Found [M + H]$^+$ |
|---|---|---|---|---|---|---|---|---|---|
| 9-11 | (vinyl ketone) | H | H | N | N | O | C$_{22}$H$_{21}$N$_5$O$_3$ | 392.15 | 392.2 |

TABLE 10

| Ex No. | R$^1$ | R$^2$ | R$^3$ | X$^1$ | X$^2$ | L | Formula | Calc [M + H]$^+$ | Found [M + H]$^+$ |
|---|---|---|---|---|---|---|---|---|---|
| 10-1 | (dimethylamino enone) | H | H | CH | CH | O | C$_{26}$H$_{30}$N$_4$O$_3$ | 447.22 | 447.2 |
| 10-2 | (vinyl ketone) | H | H | CH | CH | O | C$_{23}$H$_{23}$N$_3$O$_3$ | 390.16 | 390.2 |
| 10-3 | (dimethylamino enone) | Cl | H | CH | CH | O | C$_{26}$H$_{29}$ClN$_4$O$_3$ | 481.18 | 481.3 |
| 10-4 | (vinyl ketone) | Cl | H | CH | CH | O | C$_{23}$H$_{22}$ClN$_3$O$_3$ | 424.12 | 424.2 |
| 10-5 | (dimethylamino enone) | F | H | CH | CH | O | C$_{26}$H$_{29}$FN$_4$O$_3$ | 465.21 | 465.2 |

TABLE 10-continued
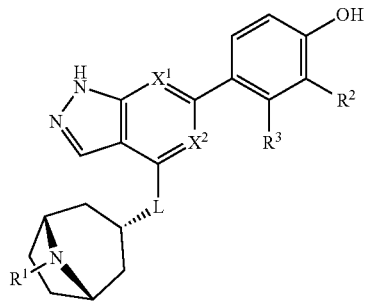
| Ex No. | R¹ | R² | R³ | X¹ | X² | L | Formula | Calc [M + H]⁺ | Found [M + H]⁺ |
|---|---|---|---|---|---|---|---|---|---|
| 10-6 | (CH₂=CH-C(O)-) | F | H | CH | CH | O | $C_{23}H_{22}FN_3O_3$ | 408.15 | 408.1 |
| 10-7 | (CH₂=CH-C(O)-) | H | H | CH | CH | NH | $C_{23}H_{24}N_4O_2$ | 389.17 | 389.3 |
TABLE 11
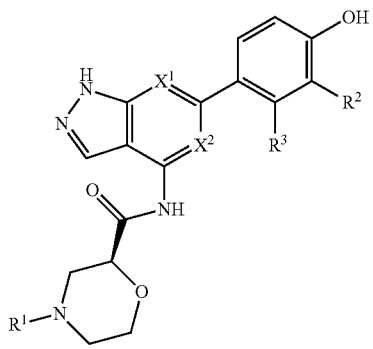
| Ex No. | R¹ | R² | R³ | X¹ | X² | Formula | Calc [M + H]⁺ | Found [M + H]⁺ |
|---|---|---|---|---|---|---|---|---|
| 11-1 | (CH₂=CH-C(O)-) | H | H | CH | CH | $C_{21}H_{20}N_4O_4$ | 393.12 | 393.1 |
| 11-2 | (Me₂N-CH₂-CH=CH-C(O)-) | H | H | CH | CH | $C_{24}H_{27}N_5O_4$ | 450.18 | 450.2 |

TABLE 12

| Ex No. | R | R¹ | Formula | Calc [M + H]⁺ | Found [M + H]⁺ |
|---|---|---|---|---|---|
| 12-1 | R¹-N(pyrrolidine)-S- | Me₂N-CH₂-CH=CH-C(O)- | $C_{23}H_{26}N_4O_2S$ | 423.16 | 423.1 |
| 12-2 | R¹-N(pyrrolidine)-S- | CH₂=CH-C(O)- | $C_{20}H_{19}N_3O_2S$ | 366.10 | 366.2 |
| 12-3 | R¹-N(pyrrolidine)-S- | Me₂N-CH₂-CH=CH-C(O)- | $C_{23}H_{26}N_4O_2S$ | 423.16 | 423.2 |
| 12-4 | R¹-N(piperidine)-S- | CH₂=CH-C(O)- | $C_{21}H_{21}N_3O_2S$ | 380.12 | 380.3 |
| 12-5 | R¹-N(piperidine)-S- | Me₂N-CH₂-CH=CH-C(O)- | $C_{24}H_{28}N_4O_2S$ | 437.18 | 437.2 |
| 12-6 | R¹-N(piperidine-3-yl)-S- | CH₂=CH-C(O)- | $C_{21}H_{21}N_3O_2S$ | 380.12 | 380.2 |
| 12-7 | R¹-N(piperidine-3-yl)-S- | Me₂N-CH₂-CH=CH-C(O)- | $C_{24}H_{28}N_4O_2S$ | 437.18 | 437.2 |
| 12-8 | R¹-N(piperidine)-SO₂- | CH₂=CH-C(O)- | $C_{21}H_{21}N_3O_4S$ | 412.11 | 412.1 |

TABLE 12-continued

| Ex No. | R | R¹ | Formula | Calc [M + H]⁺ | Found [M + H]⁺ |
|---|---|---|---|---|---|
| 12-9 | | | $C_{21}H_{21}N_3O_4S$ | 412.11 | 412.1 |
| 12-10 (racemic) | | | $C_{21}H_{21}N_3O_2$ | 348.15 | 348.2 |
| 12-11 (racemic) | | | $C_{24}H_{28}N_4O_2$ | 405.21 | 405.2 |
| 12-12 (racemic) | | | $C_{22}H_{23}N_3O_2$ | 362.16 | 362.3 |
| 12-13 (racemic) | | | $C_{25}H_{30}N_4O_2$ | 419.22 | 419.2 |
| 12-14 | | | $C_{25}H_{30}N_4O_2$ | 149.22 | 419.2 |
| 12-15 | | | $C_{22}H_{24}N_4O_2$ | 377.17 | 377 |

TABLE 12-continued

[Structure: 6-(4-hydroxyphenyl)-1H-indazole with R substituent at position 4]

| Ex No. | R | R¹ | Formula | Calc [M + H]⁺ | Found [M + H]⁺ |
|---|---|---|---|---|---|
| 12-16 | 4-(NH-)-3-methyl-1-R¹-piperidine | vinyl ketone | $C_{22}H_{24}N_4O_2$ | 377.17 | 377.2 |
| 12-17 | 4-(N-)-3-methyl-1-R¹-piperidine | vinyl ketone | $C_{22}H_{24}N_4O_2$ | 377.17 | 377.3 |
| 12-18 | 3-(N-)-1-R¹-pyrrolidine | vinyl ketone | $C_{20}H_{20}N_4O_2$ | 349.14 | 349.2 |
| 12-19 | 3-(CH₂O-)-1-R¹-pyrrolidine | (E)-4-(dimethylamino)but-2-enoyl | $C_{24}H_{28}N_4O_3$ | 421.20 | 421.3 |
| 12-20 | 3-(CH₂O-)-1-R¹-pyrrolidine | vinyl ketone | $C_{21}H_{21}N_3O_3$ | 364.14 | 364.2 |
| 12-21 | 6-(O-)-2-R¹-2-azaspiro[3.3]heptane | vinyl ketone | $C_{22}H_{21}N_3O_3$ | 376.14 | 376.4 |
| 12-22 | 2-(CH₂O-)-1-R¹-azetidine | (E)-4-(dimethylamino)but-2-enoyl | $C_{23}H_{26}N_4O_3$ | 407.18 | 407.1 |
| 12-23 | 2-(CH₂O-)-1-R¹-azetidine | vinyl ketone | $C_{20}H_{19}N_3O_3$ | 350.13 | 350.1 |
| 12-24 | 2-(CH₂O-)-1-R¹-azetidine | (E)-4-(dimethylamino)but-2-enoyl | $C_{23}H_{26}N_4O_3$ | 407.18 | 407.2 |

TABLE 12-continued

| Ex No. | R | R¹ | Formula | Calc [M + H]⁺ | Found [M + H]⁺ |
|---|---|---|---|---|---|
| 12-25 | | | $C_{20}H_{19}N_3O_3$ | 350.13 | 350.2 |
| 12-26 | | | $C_{25}H_{30}N_4O_3$ | 435.22 | 435.1 |
| 12-27 | | | $C_{22}H_{23}N_3O_3$ | 378.16 | 378.1 |
| 12-28 | | | $C_{25}H_{30}N_4O_3$ | 435.22 | 435.2 |
| 12-29 | | | $C_{22}H_{23}N_3O_3$ | 378.16 | 378.2 |
| 12-30 | | | $C_{22}H_{23}N_3O_3$ | 378.16 | 378.2 |
| 12-31 | | | $C_{22}H_{23}N_3O_3$ | 378.16 | 378.2 |

TABLE 12-continued

| Ex No. | R | R¹ | Formula | Calc [M + H]⁺ | Found [M + H]⁺ |
|---|---|---|---|---|---|
| 12-32 | piperidine-O- (2-methyl) | vinyl ketone | $C_{22}H_{23}N_3O_3$ | 378.16 | 378.1 |
| 12-33 | piperidine-O- (6-methyl) | vinyl ketone | $C_{22}H_{23}N_3O_3$ | 378.16 | 378.2 |
| 12-34 | azetidine-CH₂-S- | vinyl ketone | $C_{20}H_{19}N_3O_2S$ | 366.10 | 366.1 |
| 12-35 | azetidine-S- | vinyl ketone | $C_{19}H_{17}N_3O_2S$ | 352.09 | 352.3 |
| 12-36 | azetidine-F-cyclopropyl-O- | dimethylamino crotonyl | $C_{25}H_{27}FN_4O_3$ | 451.19 | 451.2 |
| 12-37 | azetidine-F-cyclopropyl-O- | vinyl ketone | $C_{22}H_{20}FN_3O_3$ | 394.13 | 394.2 |
| 12-38 | azetidine-O-CH₂- | dimethylamino crotonyl | $C_{23}H_{26}N_4O_3$ | 407.18 | 407.3 |

TABLE 12-continued

| Ex No. | R | R¹ | Formula | Calc [M + H]⁺ | Found [M + H]⁺ |
|---|---|---|---|---|---|
| 12-39 | azetidine-O-CH2CH2- | vinyl ketone | $C_{20}H_{19}N_3O_3$ | 350.13 | 350.1 |
| 12-40 | piperidine-3-C(O)NH- | vinyl ketone | $C_{22}H_{22}N_4O_3$ | 391.15 | 391.1 |
| 12-41 | 4-cyanopiperidine-4-C(O)NH- | vinyl ketone | $C_{23}H_{21}N_5O_3$ | 416.14 | 416.1 |
| 12-42 | thiomorpholine-2-C(O)NH- | vinyl ketone | $C_{21}H_{20}N_4O_3S$ | 409.10 | 409.1 |
| 12-43 | thiomorpholine-2-C(O)NH- | vinyl ketone | $C_{21}H_{20}N_4O_3S$ | 409.10 | 409.3 |
| 12-44 | thiomorpholine-2-C(O)NH- | vinyl ketone | $C_{21}H_{20}N_4O_3S$ | 409.10 | 409.3 |

TABLE 12-continued

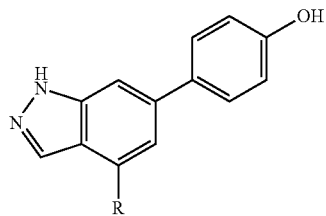

| Ex No. | R | R¹ | Formula | Calc [M + H]⁺ | Found [M + H]⁺ |
|---|---|---|---|---|---|
| 12-45 | ![R group with thiomorpholine dioxide carboxamide] | ![vinyl ketone] | $C_{21}H_{20}N_4O_5S$ | 441.09 | 441.1 |
| 12-46 | ![azetidine carboxamide] | ![vinyl ketone] | $C_{20}H_{18}N_4O_3$ | 363.11 | 363.1 |
| 12-47 | ![CN-azetidine carboxamide] | ![vinyl ketone] | $C_{21}H_{17}N_5O_3$ | 388.11 | 388.0 |
| 12-48 | ![F-azetidine carboxamide] | ![vinyl ketone] | $C_{20}H_{17}FN_4O_3$ | 381.10 | 381.0 |
| 12-49 | ![azetidine sulfonyl] | ![dimethylamino enone] | $C_{22}H_{24}N_4O_4S$ | 441.14 | 441.2 |
| 12-50 | ![azetidine sulfonyl] | ![vinyl ketone] | $C_{19}H_{17}N_3O_4S$ | 384.08 | 384.0 |
| 12-51 | ![azetidine thio] | ![dimethylamino enone] | $C_{22}H_{24}N_4O_2S$ | 409.15 | 409.3 |

TABLE 12-continued

| Ex No. | R | R¹ | Formula | Calc [M + H]⁺ | Found [M + H]⁺ |
|---|---|---|---|---|---|
| 12-52 | | | $C_{25}H_{28}N_4O_3$ | 433.20 | 433.2 |
| 12-53 | | | $C_{25}H_{28}N_4O_3$ | 433.20 | 433.5 |
| 12-54 | | | $C_{22}H_{21}N_3O_3$ | 376.14 | 376.5 |
| 12-55 | | | $C_{22}H_{22}N_4O_3$ | 391.15 | 391.1 |
| 12-56 | | | $C_{22}H_{22}N_4O_3$ | 391.15 | 391.0 |
| 12-57 | | | $C_{23}H_{24}N_4O_3$ | 405.16 | 405.2 |

TABLE 12-continued

| Ex No. | R | R¹ | Formula | Calc [M + H]⁺ | Found [M + H]⁺ |
|---|---|---|---|---|---|
| 12-58 | 4-fluoro-piperidine-4-carboxamide (N-R¹) | vinyl ketone | $C_{22}H_{21}FN_4O_3$ | 409.14 | 409.3 |
| 12-59 | piperidine-4-carboxamide (N-R¹) | vinyl ketone | $C_{22}H_{22}N_4O_3$ | 391.15 | 391.1 |
| 12-60 | 5-methyl-morpholine-2-carboxamide (N-R¹) | vinyl ketone | $C_{22}H_{22}N_4O_4$ | 407.14 | 407.1 |
| 12-61 | 6-methyl-morpholine-2-carboxamide (N-R¹) | vinyl ketone | $C_{22}H_{22}N_4O_4$ | 407.14 | 407.1 |
| 12-62 | 6,6-dimethyl-morpholine-2-carboxamide (N-R¹) | vinyl ketone | $C_{23}H_{24}N_4O_4$ | 421.16 | 421.1 |

TABLE 12-continued

| Ex No. | R | R¹ | Formula | Calc [M + H]⁺ | Found [M + H]⁺ |
|---|---|---|---|---|---|
| 12-63 | (morpholine-3-carboxamide) | (vinyl ketone) | $C_{21}H_{20}N_4O_4$ | 393.12 | 393.1 |
| 12-64 | (thiomorpholine-3-carboxamide) | (vinyl ketone) | $C_{21}H_{20}N_4O_3S$ | 409.10 | 409.1 |
| 12-65 | (thiomorpholine-3-carboxamide) | (dimethylamino enone) | $C_{24}H_{27}N_5O_3S$ | 466.16 | 466.1 |
| 12-66 | (thiomorpholine-3-carboxamide) | (vinyl ketone) | $C_{21}H_{20}N_4O_3S$ | 409.10 | 409.1 |
| 12-67 | (3-fluoroazetidine-3-carboxamide) | (dimethylamino enone) | $C_{23}H_{24}FN_5O_3$ | 438.16 | 438.1 |
| 12-68 | (3-methylazetidine-3-carboxamide) | (vinyl ketone) | $C_{21}H_{20}N_4O_3$ | 377.13 | 377.1 |
| 12-69 | (azetidine-2-carboxamide) | (vinyl ketone) | $C_{20}H_{18}N_4O_3$ | 363.11 | 363.0 |

TABLE 13

| Ex No. | R | R¹ | R² | R³ | X¹ | X² | Formula | Calc [M + H]⁺ | Found [M + H]⁺ |
|---|---|---|---|---|---|---|---|---|---|
| 13-1 | azetidinylmethyl-S- | vinyl ketone | Cl | H | N | CH | $C_{19}H_{17}ClN_4O_2S$ | 401.06 | 401.1 |
| 13-2 | morpholine-2-carboxamide | vinyl ketone | Cl | H | CH | CH | $C_{21}H_{19}ClN_4O_4$ | 427.09 | 427.0 |
| 13-3 | morpholine-2-carboxamide | vinyl ketone | F | H | CH | CH | $C_{21}H_{19}FN_4O_4$ | 411.12 | 411.0 |
| 13-4 | azetidinylmethyl-S- | dimethylamino crotonyl | H | H | CH | CH | $C_{23}H_{26}N_4O_2S$ | 423.16 | 423.1 |
| 13-5 | azetidinylmethyl-S- | dimethylamino crotonyl | F | H | CH | CH | $C_{23}H_{25}FN_4O_2S$ | 441.15 | 441.2 |
| 13-6 | azetidinylmethyl-S- | dimethylamino crotonyl | Cl | H | CH | CH | $C_{23}H_{25}ClN_4O_2S$ | 457.12 | 457.1 |
| 13-7 | azetidinylmethyl-S- | vinyl ketone | F | H | CH | CH | $C_{20}H_{18}FN_3O_2S$ | 384.09 | 384.1 |

TABLE 13-continued

| Ex No. | R | R¹ | R² | R³ | X¹ | X² | Formula | Calc [M + H]⁺ | Found [M + H]⁺ |
|---|---|---|---|---|---|---|---|---|---|
| 13-8 | azetidine-CH₂-S- | vinyl ketone | Cl | H | CH | CH | $C_{20}H_{18}ClN_3O_2S$ | 400.07 | 400.1 |
| 13-9 | azetidine-CH₂-S- | vinyl ketone | H | H | N | CH | $C_{19}H_{18}N_4O_2S$ | 367.10 | 367.0 |
| 13-10 | 2-methylpiperidin-4-yloxy | vinyl ketone | H | H | CH | CH | $C_{20}H_{21}N_5O_3$ | 380.15 | 380.2 |
| 13-11 | 2-methylpiperidin-4-yloxy | vinyl ketone | H | H | N | CH | $C_{21}H_{22}N_4O_3$ | 379.15 | 379.0 |
| 13-12 | 2-methylpiperidin-4-yloxy | vinyl ketone | H | H | N | CH | $C_{21}H_{22}N_4O_3$ | 379.15 | 379.0 |
| 13-13 | 2-methylpiperidin-4-yloxy | vinyl ketone | H | H | N | CH | $C_{21}H_{22}N_4O_3$ | 379.15 | 379.0 |

TABLE 13-continued

| Ex No. | R | R¹ | R² | R³ | X¹ | X² | Formula | Calc [M + H]⁺ | Found [M + H]⁺ |
|---|---|---|---|---|---|---|---|---|---|
| 13-14 | (racemic) methyl-pyrrolidinyl-O- | vinyl ketone | H | Cl | CH | CH | $C_{21}H_{20}ClN_3O_3$ | 398.10 | 398.3 |
| 13-15 | (racemic) methyl-pyrrolidinyl-O- | vinyl ketone | H | H | CH | CH | $C_{21}H_{21}N_3O_3$ | 364.14 | 364.5 |
| 13-16 | azaspiro-O- | vinyl ketone | H | H | N | N | $C_{20}H_{19}N_5O_3$ | 378.13 | 378.5 |
| 13-17 | azaspiro-O- | vinyl ketone | Cl | H | N | N | $C_{20}H_{18}ClN_5O_3$ | 412.09 | 412.4 |
| 13-18 | azaspiro-O- | vinyl ketone | F | H | N | N | $C_{20}H_{18}FN_5O_3$ | 396.12 | 396.2 |
| 13-19 | morpholine carboxamide | vinyl ketone | H | H | N | CH | $C_{20}H_{19}N_5O_4$ | 394.12 | 394.1 |

TABLE 13-continued

[Structure: 1H-pyrazolo fused ring with X1, X2 positions, connected to phenol ring with R2, R3 substituents, and R group at bottom]

| Ex No. | R | R¹ | R² | R³ | X¹ | X² | Formula | Calc [M + H]⁺ | Found [M + H]⁺ |
|---|---|---|---|---|---|---|---|---|---|
| 13-20 | morpholine-2-carboxamide (S) | vinyl ketone | Cl | H | CH | N | $C_{20}H_{18}ClN_5O_4$ | 428.08 | 428.0 |
| 13-21 | morpholine-2-carboxamide (S) | vinyl ketone | F | H | CH | N | $C_{20}H_{18}FN_5O_4$ | 412.11 | 412.1 |
| 13-22 | morpholine-2-carboxamide (S) | vinyl ketone | Cl | H | N | CH | $C_{20}H_{18}ClN_5O_4$ | 428.08 | 428 |

TABLE 14

[Structure: 1H-pyrazolo fused ring with X1, X2, connected to phenol with R2, R3 and piperidinylmethoxy group with R¹-N]

| Ex No. | R¹ | R² | R³ | X¹ | X² | Formula | Calc [M + H]⁺ | Found [M + H]⁺ |
|---|---|---|---|---|---|---|---|---|
| 14-1 | vinyl ketone | Cl | H | CH | CH | $C_{22}H_{22}ClN_3O_3$ | 412.12 | 412.0 |
| 14-2 | vinyl ketone | H | H | N | CH | $C_{21}H_{22}N_4O_3$ | 379.15 | 379.1 |

TABLE 14-continued
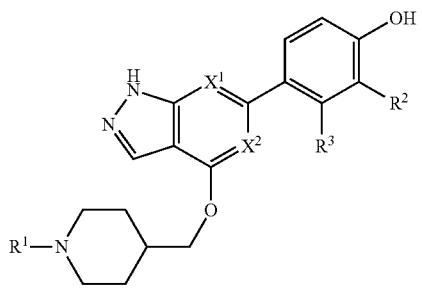
| Ex No. | R¹ | R² | R³ | X¹ | X² | Formula | Calc [M + H]⁺ | Found [M + H]⁺ |
|---|---|---|---|---|---|---|---|---|
| 14-3 | (CH₃)₂N-CH₂-CH=CH-C(O)- | Cl | H | CH | CH | $C_{25}H_{29}ClN_4O_3$ | 469.18 | 469.1 |
| 14-4 | (CH₃)₂N-CH₂-CH=CH-C(O)- | F | H | CH | CH | $C_{25}H_{29}FN_4O_3$ | 453.21 | 453.1 |
| 14-5 | CH₂=CH-C(O)- | F | H | CH | CH | $C_{22}H_{22}FN_3O_3$ | 396.15 | 396.1 |
| 14-6 | CH₂=CH-C(O)- | H | H | CH | N | $C_{21}H_{22}N_4O_3$ | 379.15 | 379.1 |
| 14-7 | CH₂=CH-C(O)- | Cl | H | CH | N | $C_{21}H_{21}ClN_4O_3$ | 413.11 | 413.0 |
| 14-8 | CH₂=CH-C(O)- | F | H | CH | N | $C_{21}H_{21}FN_4O_3$ | 397.14 | 397.1 |
| 14-9 | CH₂=CH-C(O)- | F | H | N | CH | $C_{21}H_{21}FN_4O_3$ | 397.14 | 397.1 |
| 14-10 | (CH₃)₂N-CH₂-CH=CH-C(O)- | Cl | H | CH | N | $C_{24}H_{28}ClN_5O_3$ | 470.17 | 470.1 |
| 14-11 | (CH₃)₂N-CH₂-CH=CH-C(O)- | F | H | CH | N | $C_{24}H_{28}FN_5O_3$ | 454.20 | 454.1 |

TABLE 14-continued
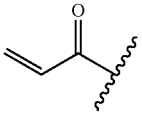 [SMILES: *C(=O)C=C]
| Ex No. | R¹ | R² | R³ | X¹ | X² | Formula | Calc [M + H]⁺ | Found [M + H]⁺ |
|---|---|---|---|---|---|---|---|---|
| 14-12 | ![acryloyl] | H | H | N | N | $C_{20}H_{21}N_5O_3$ | 380.15 | 380.2 |
TABLE 15
| Ex No. | R¹ | R² | R³ | X¹ | X² | Formula | Calc [M + H]⁺ | Found [M + H]⁺ |
|---|---|---|---|---|---|---|---|---|
| 15-1 | ![acryloyl] | Cl | H | CH | CH | $C_{22}H_{20}ClN_3O_3$ | 410.10 | 409.9 |
| 15-2 | ![acryloyl] | F | H | CH | CH | $C_{22}H_{20}FN_3O_3$ | 394.13 | 393.4 |
| 15-3 | ![acryloyl] | H | H | N | N | $C_{20}H_{19}N_5O_3$ | 378.13 | 378.1 |
| 15-4 | ![dimethylaminocrotonoyl] | Cl | H | CH | CH | $C_{25}H_{27}ClN_4O_3$ | 467.16 | 467.1 |
| 15-5 | ![dimethylaminocrotonoyl] | F | H | CH | CH | $C_{25}H_{27}FN_4O_3$ | 451.19 | 451.1 |

TABLE 15-continued
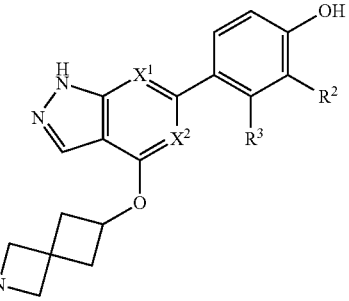
| Ex No. | R¹ | R² | R³ | X¹ | X² | Formula | Calc [M + H]⁺ | Found [M + H]⁺ |
|---|---|---|---|---|---|---|---|---|
| 15-6 | 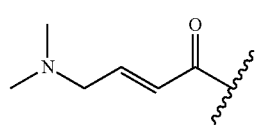 [SMILES: *C(=O)/C=C/CN(C)C] | H | H | CH | N | $C_{24}H_{27}N_5O_3$ | 434.20 | 434.1 |
| 15-7 | 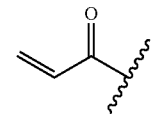 [SMILES: *C(=O)C=C] | H | H | CH | N | $C_{21}H_{20}N_4O_3$ | 377.14 | 377.2 |
| 15-8 | 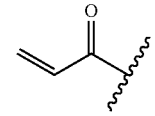 | H | H | N | CH | $C_{21}H_{20}N_4O_3$ | 377.14 | 377.0 |
| 15-9 | 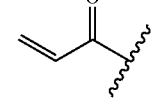 | Cl | H | N | N | $C_{20}H_{18}ClN_5O_3$ | 412.09 | 412.2 |
| 15-10 | 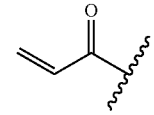 [SMILES: *C(=O)C=C] | F | H | N | N | $C_{20}H_{18}FN_5O_3$ | 396.12 | 396.1 |
TABLE 16
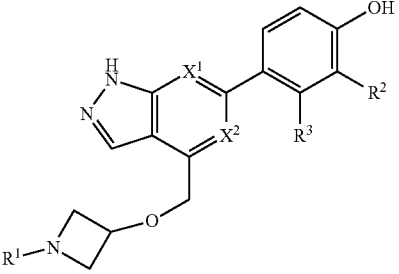
| Ex No. | R¹ | R² | R³ | X¹ | X² | Formula | Calc [M + H]⁺ | Found [M + H]⁺ |
|---|---|---|---|---|---|---|---|---|
| 16-1 | 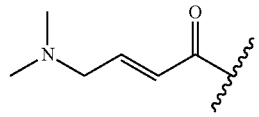 [SMILES: *C(=O)/C=C/CN(C)C] | Cl | H | CH | CH | $C_{23}H_{25}ClN_4O_3$ | 441.15 | 441.2 |

TABLE 16-continued
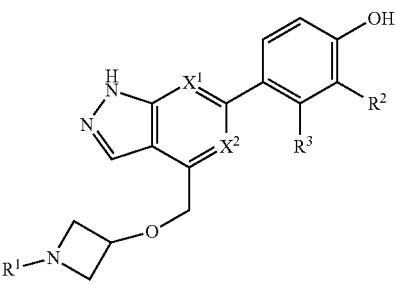
| Ex No. | R¹ | R² | R³ | X¹ | X² | Formula | Calc [M + H]⁺ | Found [M + H]⁺ |
|---|---|---|---|---|---|---|---|---|
| 16-2 | | Cl | H | CH | CH | $C_{20}H_{18}ClN_3O_3$ | 384.09 | 384.1 |
| 16-3 | | F | H | CH | CH | $C_{20}H_{18}FN_3O_3$ | 368.12 | 368.2 |
| 16-4 | | H | H | N | CH | $C_{19}H_{18}N_4O_3$ | 351.12 | 351.0 |
| 16-5 | | H | H | CH | N | $C_{19}H_{18}N_4O_3$ | 351.12 | 351.0 |
| 16-6 | | H | H | CH | N | $C_{22}H_{25}N_5O_3$ | 408.18 | 408.1 |
| 16-7 | | F | H | CH | CH | $C_{23}H_{25}FN_4O_3$ | 425.18 | 425.2 |

TABLE 17
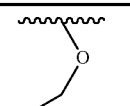
| Ex. No. | R | R¹ | R² | R³ | X¹ | X² | Formula | Calc [M + H]⁺ | Found [M + H]⁺ |
|---|---|---|---|---|---|---|---|---|---|
| 17-1 | 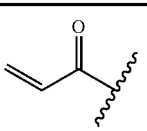 | 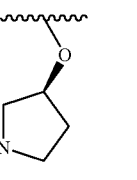 | H | H | CH | CH | $C_{19}H_{18}N_4O_3$ | 351.12 | 351.0 |
| 17-2 | 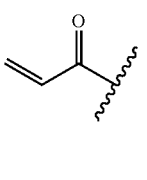 [SMILES: *C(=O)C=C] | 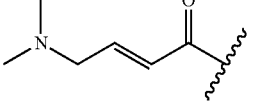 | H | H | CH | CH | $C_{19}H_{18}N_4O_3$ | 351.12 | 351.2 |
TABLE 18
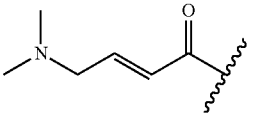 [SMILES: *C(=O)/C=C/CN(C)C]
| Ex. No. | R¹ | R² | R³ | R⁴ | R⁵ | R⁶ | X¹ | X² | Formula | Calc [M + H]⁺ | Found [M + H]⁺ |
|---|---|---|---|---|---|---|---|---|---|---|---|
| 18-1 | 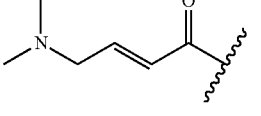 | Cl | H | H | H | Me | CH | CH | $C_{24}H_{27}ClN_4O_3$ | 455.16 | 455.0 |
| 18-2 | 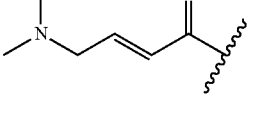 | H | F | H | F | H | CH | CH | $C_{23}H_{24}F_2N_4O_3$ | 443.17 | 443.2 |
| 18-3 | 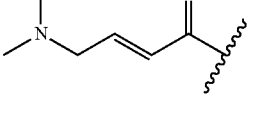 | F | H | H | F | H | CH | CH | $C_{23}H_{24}F_2N_4O_3$ | 443.17 | 443.0 |
| 18-4 | 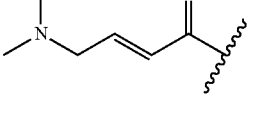 | H | H | H | H | Me | CH | CH | $C_{24}H_{28}N_4O_3$ | 421.2 | 421.0 |

TABLE 18-continued
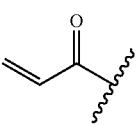 [SMILES: *C(=O)C=C]
| Ex. No. | R¹ | R² | R³ | R⁴ | R⁵ | R⁶ | X¹ | X² | Formula | Calc [M + H]⁺ | Found [M + H]⁺ |
|---|---|---|---|---|---|---|---|---|---|---|---|
| 18-5 | 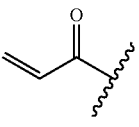 [SMILES: *C(=O)C=C] | H | H | H | H | Me | CH | CH | $C_{21}H_{21}N_3O_3$ | 364.14 | 364 |
| 18-6 | 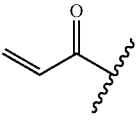 [SMILES: *C(=O)C=C] | Cl | H | H | H | Me | CH | CH | $C_{21}H_{20}ClN_3O_3$ | 398.10 | 398.0 |
| 18-7 | 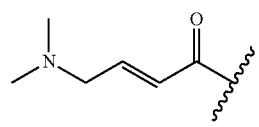 [SMILES: *C(=O)/C=C/CN(C)C] | F | H | H | H | Me | CH | CH | $C_{21}H_{20}FN_3O_3$ | 382.13 | 382.0 |
| 18-8 | 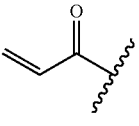 [SMILES: *C(=O)C=C] | Me | H | H | H | H | CH | CH | $C_{24}H_{28}N_4O_3$ | 421.2 | 421.0 |
| 18-9 | 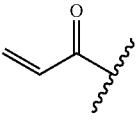 [SMILES: *C(=O)C=C] | Me | H | H | H | H | CH | CH | $C_{21}H_{21}N_3O_3$ | 364.14 | 364.0 |
| 18-10 | 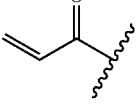 | H | H | H | H | SMe | CH | CH | $C_{21}H_{21}N_3O_3S$ | 396.11 | 396.0 |
| 18-11 | 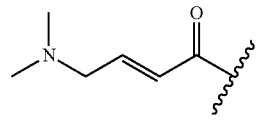 [SMILES: *C(=O)/C=C/CN(C)C] | H | H | H | H | NMe₂ | CH | CH | $C_{22}H_{24}N_4O_3$ | 393.17 | 393.0 |
| 18-12 | 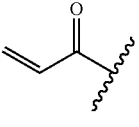 [SMILES: *C(=O)C=C] | H | H | H | H | CF₃ | CH | CH | $C_{24}H_{25}F_3N_4O_3$ | 475.17 | 475.0 |
| 18-13 |  | H | H | H | H | CF₃ | CH | CH | $C_{21}H_{18}F_3N_3O_3$ | 418.11 | 418.0 |

TABLE 18-continued

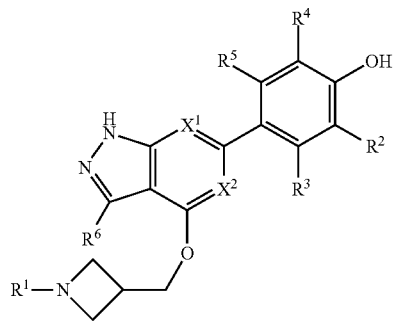

| Ex. No. | $R^1$ | $R^2$ | $R^3$ | $R^4$ | $R^5$ | $R^6$ | $X^1$ | $X^2$ | Formula | Calc [M + H]+ | Found [M + H]+ |
|---|---|---|---|---|---|---|---|---|---|---|---|
| 18-14 | ![acryloyl] | H | H | H | H | Cl | CH | CH | $C_{20}H_{18}ClN_3O_3$ | 384.09 | 384.2 |

Biological Assays

The compounds of the disclosure have been characterized in one or more of the following biological assays.

Assay 1: Biochemical JAK and Tyk2 Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially or discretely diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to pKi (negative logarithm of dissociation constant, Ki) using the Cheng-Prusoff equation.

Assay 2: Cellular JAK3 Potency Assay: Inhibition of IL-2 Stimulated pSTAT5 in Tall-1 T Cells The potency of test compounds for inhibition of interleukin-2 (IL-2) stimulated STAT5 phosphorylation was measured in the Tall-1 human T cell line (DSMZ) using AlphaLisa. Because IL-2 signals through JAK3, this assay provides a measure of JAK3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1× Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 µL/well) and plates shaken at 900 rpm for 10 mins. Cells were seeded at 45,000 cells/well in assay media (4 µL/well), and incubated at 37° C., 5% $CO_2$ for 1 hour, followed by the addition of IL-2 (R&D Systems; final concentration 300 ng/ml) in pre-warmed assay media (4 µL) for 30 minutes. After cytokine stimulation, cells were lysed with 6 ul of 3× AlphaLisa Lysis Buffer (PerkinElmer) containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 µL) under green filtered <100 lux light. Plates were shaken at 900 rpm for 2 mins, briefly spun down, and incubated for 2 hrs at RT in the dark. Donor beads were dispensed (5 µL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean±standard deviation).

Assay 3: Inhibition of IL-2 Stimulated pSTAT5 in CD4+ T Cells Isolated from Murine Splenocytes The potency of test compounds for inhibition of interleukin-2 (IL-2) stimulated STAT5 phosphorylation was measured in the CD4+ T cells isolated from murine splenocytes using AlphaLisa. Because IL-2 signals through JAK3, this assay provides a measure of JAK3 cellular potency in mouse.

Phosphorylated STAT5 was measured via the AlphaLISA SureFire Ultra pSTAT5 (Tyr694/699) kit (PerkinElmer).

CD4+ T cells were isolated from murine splenocytes via negative selection on a magnetic column (Miltnyi Biotec) and re-suspended in assay media (phenol red-free DMEM (Life Technologies) supplemented with 10% FBS (ATCC)). Cells were seeded at 50,000 cells/well in assay media (2 µL/well). Compounds were serially diluted in DMSO and diluted to 2× final concentration in assay media. Compound was added (4 µl/well) and the cells incubated at 37° C., 5% $CO_2$ for 1 hour, followed by the addition of IL-2 (R&D Systems; final concentration 7 ng/ml) in pre-warmed assay media (2 µL) for 30 minutes. After cytokine stimulation, cells were lysed with 2 µl of 5× AlphaLisa Lysis Buffer (PerkinElmer). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 ul) under green filtered <100 lux light. Plates were shaken at 900 rpm for 2 mins, briefly spun down, and incubated for 2 hrs at RT in the dark. Donor beads were dispensed (5 µl) under green filtered <100 lux light. Plates were shaken at 900 rpm for 2 mins, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in primary CD4+ T cells isolated from murine splenocytes. $IC_{50}$ values were determined from analysis of the inhibition curves of signal intensity vs compound concentration. Data are expressed as $pIC_{50}$ (negative decadic logarithm $IC_{50}$) values (mean±standard deviation).

Compounds 1-10, 19, 20, 21, and 22 all had $pIC_{50}$ values over 6.0 in this assay.

Assay 4: Inhibition of IL-2 Stimulated pSTAT5 in Human PBMC CD4+ T Cells

The potency of test compounds for inhibition of interleukin-2 (IL-2) stimulated STAT5 phosphorylation was measured in human peripheral blood mononuclear cell (PBMC) CD4+ T cells using flow cytometry. Because IL-2 signals through JAK3, this assay provides a measure of JAK3 cellular potency in human primary cells.

Phosphorylated STAT5 was measured via flow cytometry by measuring pSTAT5 response in CD4+ T cells (Becton Disckinson, AlexaFluor 647 Mouse anti-Human STAT5 (pY694) and PE Mouse anti-Human CD4).

Human PBMCs were isolated from donors via Ficoll gradient and frozen at −80° C. Frozen PBMCs were thawed and cultured for one hour in a 37° C., 5% $CO_2$ humidified incubator in RPMI (Life Technologies) supplemented with 10% Heat Inactivated Fetal Bovine Serum (FBS, Life Technologies), 2 mM Glutamax (Life Technologies), 25 mM HEPES (Life Technologies) and 1× Pen/Strep (Life Technologies). Cells were seeded into 2 ml deep well plates at 4e6 cells/ml (50 µl/well). Compounds were serially diluted in DMSO and diluted to 2× final concentration in assay media. Compound was added (100 µl/well) and the cells incubated at 37° C., 5% $CO_2$ for 1 hr, followed by the addition of IL-2 (R&D Systems; final assay concentration 100 ng/ml) in pre-warmed assay media (50 µL/well) for 30 minutes. After cytokine stimulation, cells were fixed for 10 mins at 37° C. (Becton Dickinson). Cells were washed and re-suspended in Dulbecco's phosphate buffered saline (DPBS, Life Technologies). Cells were permeabilized for 30 mins with ice cold Perm Buffer III (Becton Dickinson), and then washed and re-suspended with DPBS containing 2% fetal bovine serum (staining buffer, Life Technologies). Cells were stained for 1 hr with a 50× dilution of CD4 surface marker (PE Mouse anti-Human CD4) and 5× dilution of pSTAT5 antibody (Becton Disckinson, AlexaFluor 647 Mouse anti-Human STAT5 (pY694)) in staining buffer. Cells were washed and re-suspended in staining buffer before storage at 4° C.

To determine the inhibitory potency of test compounds in response to IL-2, the median fluorescence intensity of pSTAT5 in CD4+ gated cells was measured in human PBMCs with a BD LSRII with analysis in FCS Express 6. $IC_{50}$ values were determined from analysis of the inhibition curves of signal intensity vs compound concentration. Data are expressed as $pIC_{50}$ (negative decadic logarithm $IC_{50}$) values (mean±standard deviation).

Compounds 1-6, 8 and 9 were tested in this assay and exhibited values very similar to the ones obtained in assay 2 (IL-2 Stimulated pSTAT5 in Tall-1 T cells assay).

Assay 5: JAK Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µL of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the disclosure tested in this assay typically exhibited $pCC_{15}$ values between 5 and about 6.

Assay 6: Caco-2 Permeation Assay

The Caco-2 permeation assay was performed to model the ability of test compounds to pass through the intestine and get into the blood stream after oral administration. The rate at which test compounds in solution permeate a cell monolayer designed to mimic the tight junction of human small intestinal monolayers was determined.

CacoReady 24-well transwell plates were obtained from ADMEcell (Alameda, Calif.). The compounds were evaluated at a concentration of 5 µM from 10 mM DMSO stock solutions in duplicate (n=2). The passive permeability of the compounds tested was evaluated using Caco-2 cell monolayers along with Verapamil (25 µM) to inhibit P-gp transport proteins in the apical to basolateral (A-B) direction. The experiment was conducted in a 37° C., 5% $CO_2$ incubator. Caco-2 culture media consisted of standard filtered DMEM, FCS 10%, L-Glutamine 1% and PenStrep 1%. Basal assay plate was prepared by adding 750 µL, of transport buffer to A-B wells. A CacoReady™ plate was prepared by removing the Caco-2 media from the apical wells and replacing with fresh transport media (200 µL repeated for a total of 3 washes). Blank media (200 µL) was then replaced with diluted compound for A-B wells. To begin the incubation, the basal plate was removed from the incubator and the apical section was added on top of it. Samples (40 µL) were collected from the apical and basal compartments for time zero (t0). Samples were collected again after 120 minutes (t120) from the apical and basal compartments. All samples were diluted and prepared for bioanalysis by LC-MS/MS. The permeation coefficient ($K_p$, mean A to B+Verapamil Papparent) in cm/sec was calculated as dQ (flux)/(dt×Area× concentration).

In this assay, a $K_p$ value less than about $5 \times 10^{-6}$ cm/sec is considered favorable to minimize systemic exposure and target the colon. A $K_p$ value less than about $10 \times 10^{-6}$ cm/sec may also be sufficient to minimize systemic exposure and target the colon. By comparison, PF-06651600, a JAK3 inhibitor available systemically (2-propen-1-one, 1-[(2S,5R)-2-methyl-5-(7H-pyrrolo[2,3-d]pyrimidin-4-ylamino)-1-piperidinyl]) exhibited a Kp value of 25.

In Vitro Assay Results

All of the compounds of Examples 1 to 18 and Tables 1 to 12 were tested in one or more of the assays described above.

In Table 13 below, for the JAK1, JAK 2, JAK3, and TYK2 enzyme assays, A represents a $pK_i$ value ≥10 ($K_i$≤0.1 nM), B represents a $pK_i$ value between 9 and 10 ($K_i$ between 1 nM and 0.1 nM), C represents a $pK_i$ value between 8 and 9 ($K_i$ between 10 nM and 1 nM), D represents a $pK_i$ value between 7 and 8 ($K_i$ between 100 nM and 10 nM), and E represents a $pK_i$ value of 7 or below ($K_i$ of 100 nM or above). For the Tall-1 Potency assay, A represents a $pIC_{50}$ value ≥7.5 ($IC_{50}$≤32 nM), B represents a $pIC_{50}$ value between 6.7 (included) and 7.5 ($IC_{50}$ between 200 nM and 32 nM), and C represents a $pIC_{50}$ value between 6 and 6.7 ($IC_{50}$ between 1 µM and 200 nM). For the JAK3 (pKi)-JAK1 (pKi) values, A represents a value of 3 or above, B represents a value of 2.3 to 3 and C represents a value of 1.8 to 2.3. For the Caco assay, A represents a value below $5 \times 10^{-6}$ cm/sec, B represents a value between $5 \times 10^{-6}$ and $10 \times 10^{-6}$ cm/sec, C represents a value between $10 \times 10^{-6}$ and $22 \times 10^{-6}$ cm/sec.

TABLE 13

| Example Number | JAK 1 (pKi) | JAK 2 (pKi) | JAK 3 (pKi) | Tyk 2 (pKi) | Tall-1 ($pIC_{50}$) | JAK3 (pKi)-JAK1 (pKi) | Caco $K_p$ $10^{-6}$ cm/sec |
|---|---|---|---|---|---|---|---|
| 1 | E | D | A | E | B | A | A |
| 2 | E | E | A | E | A | A | A |
| 3 | E | E | B | E | B | A | A |
| 4 | E | E | A | E | B | A | A |
| 5 | E | D | A | E | B | A | A |
| 6 | E | D | A | E | A | A | A |
| 7 | E | D | B | E | B | A | B |
| 8 | E | D | A | E | A | A | A |
| 9 | E | | B | | B | A | A |
| 10 | E | E | A | E | B | A | A |
| 11 | E | E | B | E | B | A | A |
| 12 | E | E | B | E | B | B | A |
| 13 | E | E | A | E | B | A | A |
| 14 | E | E | B | E | B | A | C |
| 15 | E | | B | | C | A | A |
| 16 | E | | B | | B | A | A |
| 17 | E | | B | | C | B | |
| 18 | E | D | B | E | A | A | C |
| 19 | E | E | A | E | B | A | A |
| 20 | E | E | A | E | A | A | A |
| 21 | E | E | A | E | B | A | B |
| 22 | E | E | A | E | B | A | A |
| 23 | E | D | A | E | B | A | A |
| 24 | E | E | B | E | A | A | A |
| 1-1 | E | D | B | E | A | A | |
| 1-2 | E | D | A | E | A | A | C |
| 1-3 | E | | B | | B | A | |
| 1-4 | E | | B | | C | A | |
| 1-5 | E | D | A | E | A | A | B |
| 1-6 | E | | B | | C | A | |
| 1-7 | E | | B | | C | B | |
| 1-8 | E | E | B | E | B | A | B |
| 1-9 | E | | A | | C | A | |
| 1-10 | E | | B | | C | A | |
| 1-11 | E | E | A | E | A | A | C |
| 1-12 | E | | B | | B | A | |
| 1-13 | E | | B | | B | B | A |
| 1-14 | E | | A | | B | A | A |
| 1-15 | E | E | A | E | B | A | A |
| 1-16 | E | D | B | E | B | B | A |
| 1-17 | E | D | B | E | A | A | A |
| 1-18 | D | D | B | E | A | B | A |
| 1-19 | E | D | B | E | B | A | A |
| 1-20 | E | D | B | E | A | B | A |
| 1-21 | E | E | B | E | B | A | A |
| 1-22 | E | D | A | E | B | A | A |
| 1-23 | D | | B | | A | B | A |
| 1-24 | E | E | B | E | C | A | C |
| 1-25 | E | | B | | B | A | C |
| 1-26 | E | E | A | E | B | A | B |
| 1-27 | E | D | A | E | B | A | |
| 1-28 | E | | B | | C | B | |
| 1-29 | D | D | B | E | B | B | |
| 1-30 | D | | A | | B | B | |
| 1-31 | E | E | A | E | B | A | |
| 1-32 | E | | B | | C | A | |
| 1-33 | E | E | B | E | B | A | |
| 1-34 | E | D | B | E | A | A | |
| 1-35 | D | | A | | A | A | |
| 1-36 | D | D | B | E | A | B | |
| 1-37 | E | | B | | C | A | |
| 1-38 | E | E | A | E | B | A | |
| 1-39 | E | | B | | B | A | B |
| 1-40 | E | E | B | E | B | B | |
| 1-41 | E | E | B | E | B | A | |
| 1-42 | E | | B | | C | A | B |
| 1-43 | E | | A | | A | A | |
| 1-44 | E | E | A | E | A | A | C |
| 1-45 | E | E | A | E | A | A | |
| 1-46 | E | E | B | E | C | A | |
| 1-47 | E | E | B | E | B | B | C |
| 1-48 | E | | C | | B | B | |
| 2-1 | D | | A | | C | B | |
| 2-2 | E | D | B | E | B | A | A |
| 2-3 | E | D | B | E | B | A | B |
| 2-4 | E | | B | | C | B | |
| 2-5 | E | D | B | E | B | A | B |
| 2-6 | E | | A | | C | A | C |
| 2-7 | E | | B | | B | A | A |
| 2-8 | E | D | B | E | B | A | A |
| 2-9 | E | | B | | B | B | A |
| 2-10 | E | D | B | E | A | A | A |
| 2-11 | E | E | B | E | B | A | B |
| 2-12 | E | | A | | C | A | C |
| 2-13 | E | | B | | C | B | |
| 2-14 | E | | A | | A | A | |
| 2-15 | E | E | A | E | B | A | C |

TABLE 13-continued

| Example Number | JAK 1 (pKi) | JAK 2 (pKi) | JAK 3 (pKi) | Tyk 2 (pKi) | Tall-1 (pIC$_{50}$) | JAK3 (pKi)-JAK1 (pKi) | Caco K$_p$ 10$^{-6}$ cm/sec |
|---|---|---|---|---|---|---|---|
| 2-16 | E |   | B |   | C | A |   |
| 2-17 | E | E | A | E | B | A |   |
| 3-1  | E | E | B | E | A | A | A |
| 3-2  | E | E | B | E | B | A | A |
| 3-3  | E | E | B | E | A | A | B |
| 3-4  | E | D | B | E | A | A | B |
| 3-5  | D | D | B | E | A | B | A |
| 3-6  | D |   | A |   | A | A |   |
| 3-7  | E | D | A | E | B | A | A |
| 3-8  | E | E | B | E | A | A | A |
| 3-9  | E |   | B |   | B | B | A |
| 3-10 | E |   | B |   | A | A | A |
| 3-11 | E | D | A | E | B | A | A |
| 3-12 | E |   | B |   | B | B | A |
| 3-13 | E | D | B | E | A | A | A |
| 3-14 | E |   | B |   | B | A |   |
| 3-15 | E | E | A | E | B | A | A |
| 3-16 | E |   | A |   | B | A | A |
| 3-17 | E | D | A | E | A | A | A |
| 3-18 | E |   | A |   | B | A | A |
| 3-19 | E | E | B | E | B | A | A |
| 3-20 | E | D | B | E | B | B | A |
| 3-21 | E | E | B | E | A | A | A |
| 3-22 | E | E | A | E | B | A | A |
| 3-23 | E | D | A | E | B | A | A |
| 3-24 | E | E | B | E | B | A | A |
| 3-25 | E | C |   |   | B | B | A |
| 3-26 | E |   | B |   | B | A | A |
| 3-27 | E | E | A | E | B | A | A |
| 3-28 | E |   | A |   | A | A | B |
| 3-29 | E |   | B |   | A | A | A |
| 3-30 | E | D | A | E | B | A | A |
| 3-31 | E | E | B | E | B | A | B |
| 3-32 | E | E | B | E | A | A | A |
| 3-33 | E | E | B | E | B | B | A |
| 3-34 | E | E | A | E | B | A | A |
| 3-35 | E | E | B | E | A | A | A |
| 3-36 | E | E | A | E | B | A | A |
| 3-37 | E | D | A | E | A | A | A |
| 3-38 | E | E | A | E | B | A | A |
| 3-39 | E | E | A | E | A | A | A |
| 3-40 | B | D | A | E | A | A | A |
| 3-41 | B | C | B | E | A | B | A |
| 3-42 | B | D | B | E | A | B | A |
| 3-43 | E | D | B | E | A | A | A |
| 3-44 | D | D | B | E | A | B | A |
| 3-45 | E | E | B | E | A | A | A |
| 3-46 | E | E | A | E | A | A | A |
| 3-47 | E | D | B | E | A | B | A |
| 3-48 | D | D | A | E | A | A | A |
| 3-49 | E | D | B | E | A | B | A |
| 3-50 | E | E | B | E | B | A | A |
| 3-51 | E | E | B | E | C | A | A |
| 3-52 | E | E | B | E | B | A | A |
| 3-53 | E | E | B | E | B | A | A |
| 3-54 | E | E | B | E | A | A | A |
| 3-55 | E | E | A | E | B | A | A |
| 3-56 | E | D | A | E | A | A | A |
| 3-57 | E | E | A | E | B | A | A |
| 3-58 | E | E | A | E | B | A | A |
| 3-59 | E | D | B | E | A | B | A |
| 3-60 | E | E | A | E | B | A |   |
| 3-61 | E | D | A | E | A | A | A |
| 3-62 | E | D | B | E | A | A | A |
| 3-63 | E | E | A | E | B | A | A |
| 3-64 | E | D | A | E | A | A | A |
| 3-65 | E | D | B | E | A | A | A |
| 3-66 | E | E | B | E | A | A | A |
| 3-67 | E | E | B | E | B | A | A |
| 3-68 | D | E | B | E | C | B | A |
| 3-69 | E | E | A | E | A | A | A |
| 3-70 | E | E | A | E | B | A | A |
| 3-71 | E | E | A | E | A | A | A |
| 3-72 | E | E | B | E | A | A | A |
| 3-73 | E | E | A | E | A | A | A |
| 3-74 | E | E | A | E | A | A | A |
| 3-75 | E | E | B | E | A | A | A |
| 3-76 | E |   | A |   | B | A | A |
| 3-77 | E | E | A | E | B | A | A |
| 3-78 | E | E | B | E | B | A | A |
| 3-79 | E | E | B | E | B | A |   |
| 3-80 | E | E | A | E | B | A | A |
| 3-81 | E | E | A | E | A | A | A |
| 3-82 | D |   | A |   | A | B | A |
| 3-83 | E | E | A | E | A | A | B |
| 3-84 | E |   | A |   | B | A |   |
| 3-85 | E | D | A | E | A | A | A |
| 3-86 | E | E | A | E | B | A |   |
| 3-87 | E | E | B | E | B | A |   |
| 3-88 | E | E | B | E | A | A |   |
| 3-89 | E | E | A | E | B | A |   |
| 3-90 | D |   | A |   | A | B |   |
| 3-91 | D | D | A | E | A | A |   |
| 3-92 | E | E | A | E | A | A |   |
| 3-93 | E | E | A | E | A | A |   |
| 3-94 | E | E | A | E | A | A |   |
| 3-95 | E | E | A | E | A | A |   |
| 3-96 | E | E | B | E | B | A |   |
| 3-97 | E | E | B | E | A | B |   |
| 3-98 | E | E | A | E | B | A |   |
| 3-99 | E | E | A | E | A | A |   |
| 3-100 | E | E | B | E | A | A |   |
| 3-101 | E | D | A | E | A | A |   |
| 3-102 | E | E | B | E | B | A |   |
| 3-103 | E | D | A | E | A | A |   |
| 3-104 | E | E | A | E | A | A |   |
| 3-105 | E | D | A | E | A | A |   |
| 3-106 | E | E | B | E | B | A |   |
| 3-107 | E | E | A | E | A | A |   |
| 3-108 | E | D | A | E | A | A |   |
| 3-109 | E | E | B | E | B | A |   |
| 3-110 | E | E | B | E | B | A |   |
| 3-111 | E | E | B | E | C | A |   |
| 3-112 | E | E | B | E | B | A | A |
| 3-113 | E | D | A | E | A | A | A |
| 3-114 | E | E | B | E | A | A |   |
| 3-115 | E | B | B | E | B | A | A |
| 3-116 | E | D | B | E | B | B |   |
| 3-117 | E | D | B | E | B | B |   |
| 3-118 | E | E | B | E | A | A |   |
| 3-119 | E | D | A | E | B | B | A |
| 3-120 | E | D | A | E | B | A | A |
| 3-121 | E | D | B | E | B | A | A |
| 3-122 | E | D | A | E | A | A |   |
| 3-123 | E |   | A |   | C | A |   |
| 3-124 | E |   | B |   | B | A |   |
| 3-125 | E | E | B | E | B | A |   |
| 3-126 | E | D | A | E | C | A |   |
| 3-127 | E | D | A | E | B | A |   |
| 3-128 | E | B | A | E | B | A |   |
| 3-129 | E |   | B |   | C | A | A |
| 3-130 | E |   | B |   | B | A | A |
| 3-131 | E | B | B | E | A | B |   |
| 3-132 | E | E | B | E | C | A |   |
| 3-133 | E | D | A | E | C | A |   |
| 3-134 | E |   | B |   | B | A |   |
| 4-1 | E | E | B | E | B | A |   |
| 4-2 | D | D | B | E | B | B | A |
| 4-3 | E |   | B |   | B | B | A |
| 4-4 | E | E | A | E | A | A | A |
| 4-5 | E | E | B | E | B | A | A |
| 4-6 | E | E | B | E | B | A | A |
| 4-7 | E | E | C | E | B | B | A |
| 4-8 | E |   | B |   | B | B |   |
| 5-1 | E |   | B |   | C | A |   |
| 5-2 | E | E | B | E | B | A | A |
| 5-3 | E | E | A | E | A | A | A |
| 5-4 | E | E | B | E | A | A | A |
| 5-5 | E | D | A | E | B | A | A |
| 5-6 | E | E | B | E | B | A | A |

TABLE 13-continued

| Example Number | JAK 1 (pKi) | JAK 2 (pKi) | JAK 3 (pKi) | Tyk 2 (pKi) | Tall-1 (pIC$_{50}$) | JAK3 (pKi)-JAK1 (pKi) | Caco K$_p$ 10$^{-6}$ cm/sec |
|---|---|---|---|---|---|---|---|
| 5-7 | E | D | A | E | B | A | A |
| 5-8 | E |  | B |  | C | A |  |
| 5-9 | E |  | B |  | C | A | A |
| 5-10 | E |  | B |  | B | A | A |
| 5-11 | E |  | B |  | B | A | A |
| 5-12 | E | E | B | E | B | A | A |
| 5-13 | E |  | B |  | B | B | A |
| 5-14 | E | E | A | E | A | A | A |
| 5-15 | E |  | A |  | B | A | A |
| 5-16 | E | 6 | A | E | A | A | A |
| 5-17 | E | E | B | E | A | A | A |
| 5-18 | E | E | A | E | A | A | A |
| 5-19 | E | E | B | E | B | A | A |
| 5-20 | E |  | B |  | C | A |  |
| 5-21 | E | E | B | E | A | A |  |
| 5-22 | E | E | B | E | B | A |  |
| 5-23 | E | E | B | E | B | A |  |
| 5-24 | E |  | B |  | B | A |  |
| 5-25 | E |  | B |  | A | A |  |
| 5-26 | E |  | B |  | C | B |  |
| 6-1 | D |  | A |  | B | B |  |
| 6-2 | D | D | A | E | A | B | C |
| 6-3 | E | D | B | E | A | A | C |
| 6-4 | E | D | A | E | B | A | A |
| 6-5 | E |  | B |  | A | A | A |
| 6-6 | E | D | B | E | A | A | A |
| 6-7 | E |  | B |  | A | A | B |
| 6-8 | D |  | A |  | A | B |  |
| 6-9 | E |  | B |  | B | A | A |
| 6-10 | E | D | B | E | A | A | C |
| 6-11 | E |  | A |  | B | A | B |
| 6-12 | E |  | B |  | B | A | A |
| 6-13 | E | D | B | E | A | B | A |
| 6-14 | D |  | A |  | A | B | B |
| 6-15 | E | D | B | E | B | A | B |
| 6-16 | E | D | B | E | B | A | A |
| 6-17 | E | E | A | E | B | A | A |
| 6-18 | E | E | A | E | B | A | B |
| 6-19 | D |  | B |  | B | B |  |
| 6-20 | D | C | B | E | B | B | A |
| 6-21 | D | D | B | E | B | B |  |
| 6-22 | E |  | B |  | C | A |  |
| 6-23 | E |  | B |  | C | A |  |
| 7-1 | E |  | B |  | C | A |  |
| 7-2 | E | D | B | E | A | A | A |
| 7-3 | E | E | B | E | B | A | C |
| 7-4 | D | C | B | E | A | B | C |
| 7-5 | D |  | B |  | B | C |  |
| 7-6 | D |  | A |  | A | B |  |
| 7-7 | E | D | B | E | B | A | A |
| 7-8 | E | E | A | E | B | A | A |
| 7-9 | E | D | A | E | A | A | A |
| 7-10 | E | D | B | E | B | A | C |
| 7-11 | E | D | B | E | A | A |  |
| 7-12 | E | D | B | E | B | A |  |
| 7-13 | E | D | A | E | A | A |  |
| 7-14 | E | D | B | E | A | B |  |
| 8-1 | E | D | B | E | A | B | C |
| 8-2 | E | D | B | E | A | A | A |
| 8-3 | E | D | B | E | A | A | A |
| 8-4 | E | D | B | E | B | B | A |
| 8-5 | E | D | A | E | A | A | A |
| 8-6 | E |  | B |  | B | A | B |
| 8-7 | E | D | B | E | B | A | B |
| 8-8 | E |  | A |  | B | A | B |
| 8-9 | E |  | B |  | C | B |  |
| 8-10 | D |  | A |  | A | A |  |
| 8-11 | D | D | A | E | A | B |  |
| 8-12 | E |  | B |  | C | A |  |
| 8-13 | E |  | B |  | C | A |  |
| 8-14 | E | E | A | E | B | A | C |
| 9-1 | E | D | A | E | A | A | C |
| 9-2 | E | E | B | E | A | A | B |
| 9-3 | E |  | B |  | C | C |  |
| 9-4 | E | C | A | E | A | A | C |
| 9-5 | D |  | B |  | C | C |  |
| 9-6 | E |  | B |  | A | A | C |
| 9-7 | E |  | A |  | B | A |  |
| 9-8 | D |  | B |  | C | C |  |
| 9-9 | D | C | A | D | A | B |  |
| 9-10 | E |  | B |  | A | A | C |
| 9-11 | E |  | A |  | B | A | C |
| 10-1 | D |  | A |  | B | B | A |
| 10-2 | D | C | A | D | A | B | C |
| 10-3 | D |  | B |  | B | B |  |
| 10-4 | E | D | B | E | B | A | A |
| 10-5 | D |  | B |  | B | C |  |
| 10-6 | D |  | B |  | A | B |  |
| 10-7 | E | D | B | E | B | A | B |
| 11-1 | E |  | B |  | A | A | A |
| 11-2 | E |  | B |  | C | A |  |
| 12-1 | E | D | B | E | B | A |  |
| 12-2 | E |  | B |  | B | B |  |
| 12-3 | D |  | B |  | C | B |  |
| 12-4 | E | E | B | E | B | A | B |
| 12-5 | E |  | B |  | B | B |  |
| 12-6 | D |  | B |  | B | B |  |
| 12-7 | D |  | B |  | C | C |  |
| 12-8 | E |  | B |  | C | A | A |
| 12-9 | E |  | B |  | C | A | A |
| 12-10 | E |  | C |  | B | B |  |
| 12-11 | E |  | B |  | C | A |  |
| 12-12 | E |  | B |  | B | A |  |
| 12-13 | E |  | B |  | C | A |  |
| 12-14 | E |  | B |  | C | C |  |
| 12-15 | E |  | B |  | B | B |  |
| 12-16 | D | C | B | E | A | B |  |
| 12-17 | D | C | A | E | A | B |  |
| 12-18 | D |  | A |  | B | B |  |
| 12-19 | E |  | A |  | C | A |  |
| 12-20 | E | D | B | E | A | A | B |
| 12-21 | E |  | B |  | A | B | A |
| 12-22 | E |  | B |  | C | A | A |
| 12-23 | E |  | B |  | B | A | B |
| 12-24 | E |  | B |  | C | A | A |
| 12-25 | E |  | B |  | C | B | A |
| 12-26 | E | D | B | E | C | B |  |
| 12-27 | E | D | A | E | A | A | C |
| 12-28 | E | C | A | E | B | A | C |
| 12-29 | E | D | B | E | A | A | C |
| 12-30 | E | C | A | E | A | A | C |
| 12-31 | E | C | A | E | B | A | C |
| 12-32 | E | D | A | E | A | A | C |
| 12-33 | E | E | B | E | B | A | A |
| 12-34 | E | E | B | E | A | B | A |
| 12-35 | E | E | B | E | B | B | A |
| 12-36 | D | E | A | E | A | A | A |
| 12-37 | D |  | B |  | B | B | A |
| 12-38 | E | E | A | E | B | A | A |
| 12-39 | E | E | B | E | A | A | B |
| 12-40 | E |  | B |  | C | B | A |
| 12-41 | E | E | B | E | A | A | A |
| 12-42 | E | D | B | E | B | B | A |
| 12-43 | E | D | A | E | A | A | A |
| 12-44 | E | D | A | E | A | A | A |
| 12-45 | E | E | A | E | C | A | A |
| 12-46 | E | D | A | E | B | A | A |
| 12-47 | E | E | B | E | A | A | A |
| 12-48 | E | E | B | E | A | A | A |
| 12-49 | E | E | B | E | C | A |  |
| 12-50 | E | E | A | E | B | A |  |
| 12-51 | D | D | A | E | B | A |  |
| 12-52 | D |  | B |  | C | B |  |
| 12-53 | E | C | B | E | A | B |  |
| 12-54 | E | D | B | E | A | B |  |
| 12-55 | E |  | A |  | B | A |  |
| 12-56 | E |  | A |  | B | A |  |
| 12-57 | E | D | B | E | B | A |  |
| 12-58 | E | D | A | E | B | A |  |
| 12-59 | E |  | A |  | B | A |  |

TABLE 13-continued

| Example Number | JAK 1 (pKi) | JAK 2 (pKi) | JAK 3 (pKi) | Tyk 2 (pKi) | Tall-1 (pIC$_{50}$) | JAK3 (pKi)-JAK1 (pKi) | Caco K$_p$ 10$^{-6}$ cm/sec |
|---|---|---|---|---|---|---|---|
| 12-60 | E | E | B | E | B | A | |
| 12-61 | E | E | A | E | B | A | |
| 12-62 | E |   | A |   | B | A | |
| 12-63 | E | E | B | E | B | A | |
| 12-64 | E | E | A | E | A | A | |
| 12-65 | E | E | B | E | C | A | |
| 12-66 | E | E | B | E | B | A | |
| 12-67 | E | E | B | E | B | A | |
| 12-68 | E | E | B | E | C | A | |
| 12-69 | E |   | A |   | B | A | |
| 13-1 | E | E | B | E | B | A | A |
| 13-2 | E | E | B | E | A | A | A |
| 13-3 | E |   | A |   | A | A | A |
| 13-4 | E | D | A | E | B | A | |
| 13-5 | E | D | A | E | B | A | |
| 13-6 | E | E | A | E | A | A | |
| 13-7 | E | D | A | E | B | A | |
| 13-8 | E | E | B | E | A | A | |
| 13-9 | E | E | B | E | B | A | |
| 13-10 | E | E | B | E | B | A | |
| 13-11 | E | E | A | E | A | A | C |
| 13-12 | E | E | B | E | B | A | C |
| 13-13 | E | E | B | E | C | A | C |
| 13-14 | E | D | A | E | A | A | |
| 13-15 | E | D | B | E | B | A | |
| 13-16 | E | E | B | E | B | A | C |
| 13-17 | E |   | A |   | B | A | |
| 13-18 | E |   | B |   | B | A | |
| 13-19 | E | E | A | E | B | A | |
| 13-20 | E | E | B | E | B | B | |
| 13-21 | E | D | B | E | A | B | |
| 13-22 | E | E | B | E | B | A | |
| 14-1 | E | E | B | E | A | A | A |
| 14-2 | E | E | A | E | B | A | A |
| 14-3 | E |   | B |   | B | B | |
| 14-4 | D |   | B |   | B | B | |
| 14-5 | D |   | B |   | A | B | |
| 14-6 | D |   | A |   | A | B | |
| 14-7 | D |   | A |   | A | B | |
| 14-8 | D |   | A |   | A | B | |
| 14-9 | E | E | B | E | B | A | |
| 14-10 | D |   | B |   | C | C | |
| 14-11 | D |   | B |   | C | B | |
| 14-12 | E | E | B | E | C | A | |
| 15-1 | E | E | B | E | A | A | A |
| 15-2 | D | D | A | E | A | B | A |
| 15-3 | E | E | A | E | A | A | A |
| 15-4 | E |   | A |   | B | A | |
| 15-5 | D | D | B | E | B | B | |
| 15-6 | D |   | A |   | C | B | |
| 15-7 | E | D | B | E | A | B | |
| 15-8 | D |   | B |   | B | B | |
| 15-9 | E | E | A | E | B | A | |
| 15-10 | E | E | A | E | A | A | |
| 16-1 | E | E | A | E | B | A | A |
| 16-2 | E | E | A | E | A | A | A |
| 16-3 | E | E | B | E | A | A | A |
| 16-4 | E |   | B |   | B | A | A |
| 16-5 | E | E | A | E | A | A | A |
| 16-6 | E | E | B | E | C | A | |
| 16-7 | E | E | A | E | B | A | |
| 17-1 | E | E | B | E | B | A | A |
| 17-2 | E |   | A |   | C | A | A |
| 18-1 | E | D | B | E | A | B | A |
| 18-2 | D |   | A |   | A | C | |
| 18-3 | D | D | A | E | A | B | |
| 18-4 | D |   | A |   | B | B | |
| 18-5 | D |   | B |   | A | B | |
| 18-6 | D |   | A |   | A | B | |
| 18-7 | D |   | B |   | A | C | |
| 18-8 | E | E | B | E | B | A | |
| 18-9 | E | E | A | E | A | A | |
| 18-10 | E | D | A | E | B | A | |
| 18-11 | E |   | B |   | C | A | |
| 18-12 | D | D | B | E | B | B | |
| 18-13 | E | D | A | E | A | A | |
| 18-14 | E |   | B |   | B | A | |

Assay 7: Colon and Plasma Mouse Pharmacokinetics 6 male Balb/c mice were administered 10 mg/kg of compound in 1% HPMC+0.1% Tween-80 by PO administration. At 0.5, 2 and 6 hours after dose administration, animals were anesthetized, and terminal blood samples were collected by cardiac puncture, followed by collection of colon contents and colon tissue.

Blood samples were collected into K$_2$EDTA and stored on wet ice until processed to plasma by centrifugation (12000 rpm at 4° C.). Plasma samples were transferred to cluster tubes and placed on dry ice prior to freezer storage. The colon contents from each animal were collected at each terminal blood collection time point. The colon tissues were flushed with saline and patted dry. The colon and colon content tissues were homogenized using sterile water containing 0.1% formic acid 9:1 (water:tissue, v/w). The homogenized tissues and colon contents were transferred to cluster tubes and placed on dry ice prior to freezer storage. All samples were analyzed using LC/MS/MS against analytical standards.

The composite pharmacokinetic parameters of the compounds were determined by non-compartmental analysis using Phoenix WinNonlin Version 6 (Certara, St. Louis, Mo.) and using mean values from 2 animals/time point. For plasma concentrations below the quantification limit (BQL), the lowest concentration measurable or the BLOQ (below limit of quantification) was used.

A colon to plasma ratio was determined as the ratio of the colon AUC to the plasma AUC. Compounds 1, 2, 3, 4, 6, 7, 8, 21 and 22 exhibited a colon to plasma ratio in excess of about 1250. Compounds 9, 5, 19, and 20 exhibited a colon to plasma ratio in excess of about 200.

In contrast, the reference compound (PF-06651600, a JAK3 inhibitor available systemically) 2-propen-1-one, 1-[(2S,5R)-2-methyl-5-(7H-pyrrolo[2,3-d]pyrimidin-4-ylamino)-1-piperidinyl], exhibited a colon to plasma ratio of 2.8.

Assay 8: Mouse Model of Oxazolone-Induced Colitis

Oxazolone-induced colitis is an experimental model that has a histological resemblance to human ulcerative colitis (Heller et al. *Immunology*, 2002, 17, 629-638). Adult BALB/C mice from Harlan were used in the assay. On day 1, animals were lightly anesthetized with isoflurane and the hairs between the shoulder were carefully removed before oxazolone (4%, 150 µL, 4:1 acetone: olive oil formulation) or vehicle solution was slowly applied for skin sensitization. Seven days after skin sensitization, the mice were fasted around 6 hours prior, anesthetized with ketamine/xylazine injection, and a 1 mL syringe equipped with a 3.5-F catheter, filled with oxazolone solution, was inserted carefully about 4 cm into the colon of the mouse. Following insertion, 50 µL of the oxazolone solution (0.8% in 1:1 ethanol:water formulation) was injected very slowly (over 30 sec using an injection pump) into the colon. Drug treatment (PO, QD or BID or TID) or vehicle was initiated a day prior to the oxazolone intrarectal (IR) challenge. Two-day post oxazolone intrarectal challenge, the disease was assessed by treatment-blinded experimenters for each mouse according to the criteria score: stool consistency score (0, normal; 2, loose; 4, diarrhea), gross bleeding score (0, absence; 2, blood tinged; 4, presence); Combined stool score endpoint=stool consistency score+stool blood score.

Select compounds were tested in the assay. Efficacy in the model is evidenced by a statistically significant decrease in combined stool score endpoint as compared with the score from vehicle treated animals.

The compounds 1, 2, 3, 4, 5, 6, 7, 8, 3-11, 5-10, 19, 15-1, 3-55, 3-34, 15-3, 21, 3-80, 3-81, 3-72 and 3-57 exhibited a statistically significant decrease in combined stool score endpoint as compared with vehicle treated animals in the oxazolone model at a dose of 3 mg/kg (PO, BID). The compounds 3-113 and 3-74 exhibited a statistically significant decrease in the combined stool score endpoint as compared with vehicle treated animals in the oxazolone model at a dose of 1 and 10 mg/kg only (PO, BID).

Assay 9: Immunosuppression Effects in Mouse Splenic Natural Killer (NK) Cells

Depletion of mouse splenic cells is an experimental model of immunosuppression (Kudlacz et al., *Am. J. of Transplantation*, 2004, 4, 51-57). Select compounds were assessed in the mouse splenic cell model following the same treatment paradigm used in the oxazolone-induced colitis model (assay 8).

Adult male Balb/C mice from Harlan were used for the study. The test compound and a Jak3 covalent inhibitor standard 2-proper-1-one, 1-[(2S,5R)-2-methyl-5-(7H-pyrrolo[2,3-d]pyrimidin-4-ylamino)-1-piperidinyl] (30 mg/kg, BID) as a positive control, were dosed orally for three days to naïve mice. Spleens were harvested up to 4 hours post last dose and crushed immediately for cell subtype staining. Prior to fixation, fluorophore-labelled antibodies for CD19 (FITC; B cells), CD3e (PE; pan T cells) and CD49e (APC; NK cells) were incubated with splenocyte samples from each animal to allow for simultaneous, multiple subtype % analysis on the flow cytometer. The number of total spleen cells for each animal was measured by Scepter™ 2.0 Handheld Automated Cell Counter.

The absolute number of lymphocyte subtype population (e.g., splenic B, T and NK cells) was calculated from the percentage of each subtype times the total spleen cells for each animal. A one-way ANOVA, with Fisher's LSD post hoc test, was used to compare the splenic lymphocytes number of the vehicle and test compound groups. The a level was set at $p<0.05$. Data were presented as the mean±SEM for each group.

The positive control PF-06651600, a JAK3 inhibitor available systemically (2-propen-1-one, 1-[(2S,5R)-2-methyl-5-(7H-pyrrolo[2,3-d]pyrimidin-4-ylamino-1-piperidinyl]) (30 mg/kg PO, BID), significantly decreased splenic NK cell counts. Splenic NK cell counts were unaffected by compound 1 at (PO, BID) doses up to 300 mg/kg (the maximum dose tested). Splenic NK cell counts were unaffected by compounds 4, 6 and 8 at (PO, BID) doses up to 100 mg/kg (the maximum dose tested). Splenic NK cell counts were unaffected by compound 3 at (PO, BID) doses up to 85 mg/kg (the maximum dose tested). Splenic NK cell counts were unaffected by compound 2 at (PO, BID) doses up to 30 mg/kg (the maximum dose tested). Splenic NK cell counts were unaffected by compound 5 at (PO, BID) doses up to 80 mg/kg (the maximum dose tested). No treatment effects were observed for the B and T cell populations with any of the compounds tested.

Assay 10: Systemic Target Engagement Assay: Murine Model of IL-2 Induced pSTAT5 Induction in Thymus IL-2 is an important cytokine underlying the pathophysiology of gastro-intestinal diseases such as irritable bowel disease (IBD; Guan and Zhang. *Mediators Inflamm*, 2017; 4810258). IL-2 binds to cell surface receptors activating members of the Janus family of kinases (JAK), specifically JAK3, which then phosphorylates STAT5 and subsequently activates further transcription pathways. In this model, a dose of IL-2 was delivered systemically to mice to induce the phosphorylation of STAT5 (pSTAT5) which was then measured as the endpoint. The compounds tested in this assay which do not exhibit significant inhibition of IL-2 induced pSTAT5 compared to the vehicle-treated; IL-2 challenged control animals, demonstrate lack of systemic activity.

Adult male Balb/c mice from Harlan were used in the assay. Animals were administered test compound via oral gavage (PO, 10 or 30 mg/kg for single dose studies; 10-60 mg/kg for dose response studies) on the afternoon of the day prior to study and then in the morning on the day of study. Two hours after the second PO dose administration, mice were injected intraperitoneally (i.p.) with 100 µl of an appropriate IL-2 dose (for a total of 1-5 µg/mouse depending upon IL-2 batch; R&D Systems). 90-120 minutes after IL-2 insult, thymus samples were harvested. Phosphorylated STAT5 (pSTAT5) levels were determined in the thymus using AlphaLISA (AlphaLISA® SureFire® Ultra™ p-STAT5 (Tyr694/699) HV (high volume). Activity in the model is evidenced by a lack of significant inhibition in the level of pSTAT5 present in the thymus of treated animals at 1.5-2 hours following IL-2 challenge.

Compounds 6 and 7 were tested at 10 mg/kg and exhibited no significant inhibition of IL-2 induced pSTAT5 compared to the vehicle-treated; IL-2 challenged control animals, therefore demonstrating lack of systemic activity. Compound 1 was tested at 10, 30, 60 and 100 mg/kg and exhibited no significant inhibition of IL-2 induced pSTAT5 compared to the vehicle. Compound 2 was tested at 10, 30 and 60 mg/kg and exhibited no significant inhibition of IL-2 induced pSTAT5 compared to the vehicle. Compound 3 was tested at 30 and 100 mg/kg and exhibited no significant inhibition of IL-2 induced pSTAT5 compared to the vehicle. Compounds 8, 5 and 4 were tested at 30 mg/kg and exhibited no significant inhibition of IL-2 induced pSTAT5 compared to the vehicle.

In contrast, the reference compound (PF-06651600, a JAK3 inhibitor available systemically) 2-propen-1-one, 1-[(2S,5R)-2-methyl-5-(7H-pyrrolo[2,3-d]pyrimidin-4-ylamino)-1-piperidinyl], exhibited significant inhibition of pSTAT5 induction in the thymus at 10, 30 and 50 mg/kg, demonstrating systemic activity.

Crystal Structures

Co-crystal structures were obtained for compounds 1, 3 and 4 each bound to human JAK3. The resolutions for the complex structures were at 2.73 Å, 2.80 Å, and 2.64 Å respectively for compound 1, compound 3 and compound 4. In each case, the ligands were observed to bind in the ATP binding site. Based on a distance of less than 3.5 Å of the donor and acceptor atoms four specific hydrogen bonds were identified for each of the ligands, namely to the main chain atoms of Glu903, Leu905 and Phe968 as well as the side chain atoms of Glu871. An additional hydrogen bond was identified for compound 1 to the side chain atoms of Asp 912. Of particular note, the ligands are each covalently bound to Cys909 of JAK3 located shortly after the hinge region. The S—H moiety of the cysteine residue performs an addition reaction to the Michael system. The observed results of the covalent binding interaction in the crystal structures confirms the irreversible binding nature for each of these ligands to JAK3.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A pharmaceutical composition comprising a compound of formula:

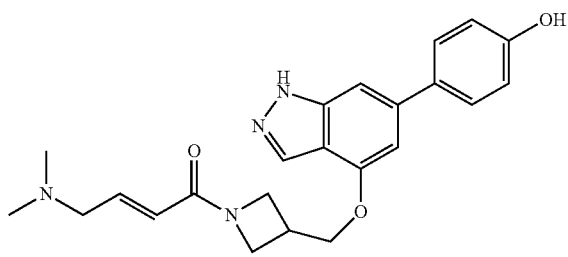 [SMILES: CN(C)C/C=C/C(=O)N1CC(COc2cc(-c3ccc(O)cc3)cc3[nH]ncc23)C1]

or a pharmaceutically acceptable salt thereof, and a pharmaceutically-acceptable carrier.

2. The pharmaceutical composition of claim 1, wherein the pharmaceutical composition is suitable for oral administration.

3. The pharmaceutical composition of claim 1, wherein the pharmaceutical composition is in the form of a capsule, a tablet, or a pill.

4. The pharmaceutical composition of claim 1, further comprising one or more other therapeutic agents useful for treating a gastrointestinal inflammatory disease.

5. A pharmaceutical composition comprising a compound of formula:

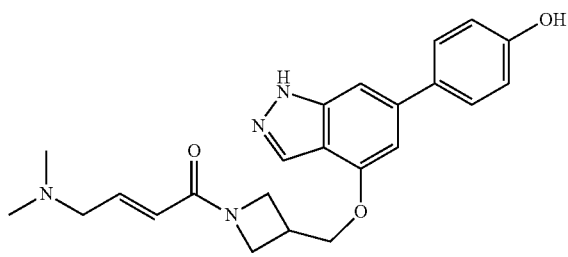 [SMILES: CN(C)C/C=C/C(=O)N1CC(COc2cc(-c3ccc(O)cc3)cc3[nH]ncc23)C1]

and a pharmaceutically-acceptable carrier.

6. The pharmaceutical composition of claim 5, wherein the pharmaceutical composition is suitable for oral administration.

7. The pharmaceutical composition of claim 5, wherein the pharmaceutical composition is in the form of a capsule, a tablet, or a pill.

8. The pharmaceutical composition of claim 5, further comprising one or more other therapeutic agents useful for treating a gastrointestinal inflammatory disease.

9. A pharmaceutical composition comprising a pharmaceutically-acceptable carrier and a crystalline form of the compound of formula:

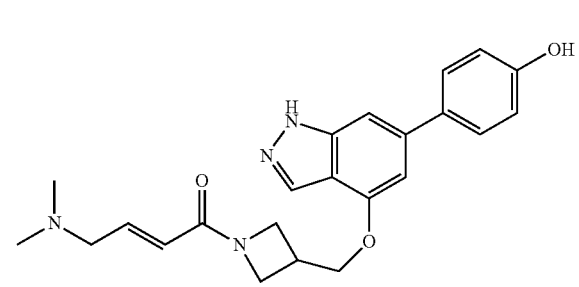 [SMILES: CN(C)C/C=C/C(=O)N1CC(COc2cc(-c3ccc(O)cc3)cc3[nH]ncc23)C1]

wherein the crystalline form is characterized by a powder X-ray diffraction pattern comprising diffraction peaks at 2θ values of 9.67±0.20, 11.61±0.20, 17.61±0.20, 18.88±0.20, and 23.33±0.20.

10. The pharmaceutical composition of claim 9, wherein the powder X-ray diffraction pattern further comprises additional diffraction peaks at 2θ values of 4.82±0.20, 15.69±0.20, and 16.19±0.20.

11. The pharmaceutical composition of claim 9, wherein the powder X-ray diffraction pattern further comprises two or more additional diffraction peaks at 2θ values selected from 11.92±0.20, 12.98±0.20, 13.23±0.20, 16.45±0.20, 16.67±0.20, 19.39±0.20, 19.96±0.20, 20.14±0.20, 22.14±0.20, 23.84±0.20, 24.06±0.20, 24.29±0.20, 25.31±0.20, 25.63±0.20, 27.06±0.20, 27.31±0.20, 30.10±0.20, and 30.53±0.20.

12. The pharmaceutical composition of claim 9, wherein the crystalline form is characterized by a powder X-ray diffraction pattern in which the peak positions are substantially in accordance with the peak positions of the pattern shown in FIG. 9.

13. The pharmaceutical composition of claim 9, wherein the crystalline form is characterized by a differential scanning calorimetry trace recorded at a heating rate of 10° C. per minute which shows a maximum in endothermic heat flow with a peak at 201.3° C.±2° C.

14. The pharmaceutical composition of claim 9, wherein the crystalline form is characterized by a differential scanning calorimetry trace recorded at a heating rate of 10° C. per minute which shows a maximum in endothermic heat flow at a temperature between 198° C. and 204° C.

15. The pharmaceutical composition of claim 9, wherein the crystalline form is characterized by a differential scanning calorimetry trace substantially in accordance with that shown in FIG. 10.

16. The pharmaceutical composition of claim 9, further comprising one or more other therapeutic agents useful for treating a gastrointestinal inflammatory disease.

* * * * *